(12) United States Patent
Han et al.

(10) Patent No.: US 11,566,015 B2
(45) Date of Patent: Jan. 31, 2023

(54) MELANOCORTIN SUBTYPE-2 RECEPTOR (MC2R) ANTAGONISTS AND USES THEREOF

(71) Applicant: Crinetics Pharmaceuticals, Inc., San Diego, CA (US)

(72) Inventors: Sangdon Han, San Diego, CA (US); Yunfei Zhu, San Diego, CA (US); Sun Hee Kim, San Diego, CA (US); Jian Zhao, San Diego, CA (US); Shimiao Wang, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/170,396

(22) Filed: Feb. 8, 2021

(65) Prior Publication Data
US 2021/0238164 A1  Aug. 5, 2021

Related U.S. Application Data

(60) Continuation of application No. 16/931,156, filed on Jul. 16, 2020, now Pat. No. 10,981,894, which is a division of application No. 16/713,601, filed on Dec. 13, 2019, now Pat. No. 10,766,877, which is a division of application No. 16/432,228, filed on Jun. 5, 2019, now Pat. No. 10,562,884.

(60) Provisional application No. 62/734,873, filed on Sep. 21, 2018, provisional application No. 62/681,011, filed on Jun. 5, 2018.

(51) Int. Cl.
*C07D 401/14* (2006.01)
*C07D 295/04* (2006.01)
*C07D 401/10* (2006.01)
*C07D 407/14* (2006.01)

(52) U.S. Cl.
CPC ......... *C07D 401/14* (2013.01); *C07D 295/04* (2013.01); *C07D 401/10* (2013.01); *C07D 407/14* (2013.01)

(58) Field of Classification Search
CPC .. C07D 401/14; C07D 401/10; C07D 407/14; C07D 295/04
USPC .................................................. 514/210.2
See application file for complete search history.

(56) References Cited

U.S. PATENT DOCUMENTS

| | | |
|---|---|---|
| 10,562,884 B2 | 2/2020 | Han et al. |
| 10,604,507 B2 | 3/2020 | Han et al. |
| 10,766,877 B2 | 9/2020 | Han et al. |
| 10,981,894 B2 | 4/2021 | Han et al. |
| 2003/0158209 A1 | 8/2003 | Dyck et al. |
| 2004/0053933 A1 | 3/2004 | Pontillo et al. |
| 2004/0192676 A1 | 9/2004 | Chen et al. |
| 2005/0119252 A1 | 6/2005 | Tucci et al. |
| 2005/0192286 A1 | 9/2005 | Tran et al. |

FOREIGN PATENT DOCUMENTS

| | | |
|---|---|---|
| EP | 3199156 A1 | 8/2017 |
| WO | WO-03009847 A1 | 2/2003 |
| WO | WO-03009850 A1 | 2/2003 |
| WO | WO-03031410 A1 | 4/2003 |
| WO | WO-03068738 A1 | 8/2003 |
| WO | WO-03094918 A1 | 11/2003 |
| WO | WO-2004058735 A2 | 7/2004 |
| WO | WO-2005014563 A1 | 2/2005 |
| WO | WO-2005023260 A1 | 3/2005 |
| WO | WO-2005040109 A1 | 5/2005 |
| WO | WO-2005040136 A1 | 5/2005 |
| WO | WO-2005042516 A2 | 5/2005 |
| WO | WO-2019236699 A1 | 12/2019 |

OTHER PUBLICATIONS

Arasasingham et al. Structure-activity relationship of (1-aryl-2-piperazinylethyl)piperazines: antagonists for the AGRP/melanocortin receptor binding. J Med Chem 46:9-11 (2003).
Berge et al. Pharmaceutical Salts. Journal of Pharmaceutical Sciences 66(1):1-19 (Jan. 1977).
Bundgaard. Design and Application of Prodrugs. Textbook of Drug Design and Development. Krosgaard-Larsen and Bundgaard. Chapters, pp. 113-191 (1991).
Bundgaard. Means to Enhance Penetration: Prodrugs as a Means to Improve the Delivery of Peptide Drugs. Advanced Drug Delivery Review 8:1-38 (1992).
Chen et al. Identification and characterization of pyrrolidine diastereoisomers as potent functional agonists and antagonists of the human melanocortin-4 receptor. Bioorg Med Chem Lett 18:129-136 (2008).
Chen et al. Pharmacological and pharmacokinetic characterization of 2-piperazine-a-isopropyl benzylamine derivatives as melanocortin-4 receptor antagonists. Bioorg Med Chem 16:5606-5618 (2008).
Gantz et al. The melanocortin system. Am. J. Physiol. Endocrinol. Metab. 284:E468-E474 (2003).
PCT/US2019/035572 International Search Report dated Sep. 17, 2019.
Richardson et al. Synthesis and structure-activity relationships of novel arylpiperazines as potent and selective agonists of the melanocortin subtype-4 receptor. J Med Chem 47:744-755 (2004).
Science IP Report dated Mar. 29, 2018 (129 pgs).
Tian et al. Design, Synthesis, and Evaluation of Proline and Pyrrolidine Based Melanocortin Receptor Agonists. A Conformationally Restricted Dipeptide Mimic Approach. J Med Chem 49:4745-4761 (2006).
Tran et al. Syntheses of tetrahydrothiophenes and tetrahydrofurans and studies of their derivatives as melanocortin-4 receptor ligands. Bioorg Med Chem Lett 18:1124-1130 (2008).

*Primary Examiner* — Kahsay Habte
(74) *Attorney, Agent, or Firm* — Wilson Sonsini Goodrich & Rosati

(57) ABSTRACT

Described herein are compounds that are melanocortin subtype-2 receptor (MC2R) modulators, methods of making such compounds, pharmaceutical compositions and medicaments comprising such compounds, and methods of using such compounds in the treatment of conditions, diseases, or disorders that would benefit from modulation of MC2R activity.

36 Claims, No Drawings

MELANOCORTIN SUBTYPE-2 RECEPTOR (MC2R) ANTAGONISTS AND USES THEREOF

RELATED APPLICATIONS

This application is a continuation of U.S. application Ser. No. 16/931,156, filed Jul. 16, 2020, which is a divisional of U.S. application Ser. No. 16/713,601, filed Dec. 13, 2019, now U.S. Pat. No. 10,766,877, issued Sep. 8, 2020, which is a divisional application of U.S. application Ser. No. 16/432,228, filed Jun. 5, 2019, now U.S. Pat. No. 10,562,884, issued Feb. 18, 2020, which claims the benefit of U.S. Provisional Patent Application No. 62/681,011 filed on Jun. 5, 2018, and U.S. Provisional Patent Application No. 62/734,873 filed on Sep. 21, 2018, each of which is herein incorporated by reference in its entirety.

STATEMENT AS TO FEDERALLY SPONSORED RESEARCH

This invention was made with government support under DK115245 awarded by the National Institutes of Health. The government has certain rights in the invention.

FIELD OF THE INVENTION

Described herein are compounds that modulate the activity of one or more melanocortin receptors, methods of making such compounds, pharmaceutical compositions and medicaments comprising such compounds, and methods of using such compounds in the treatment of conditions, diseases, or disorders that would benefit from modulating melanocortin subtype-2 receptor (MC2R) activity.

BACKGROUND OF THE INVENTION

The melanocortin receptors form a family of G protein-coupled receptor (GPCRs) (MC1R, MC2R, MC3R, MC4R, and MC5R) that are selectively activated by different melanocortin peptides adrenocorticotropic hormone (ACTH), and the melanocortin peptides α-, β-, and γ-melanocyte-stimulating hormone (α-MSH, β-MSH, and γ-MSH) that are all derived proteolytically from proopiomelanocortin hormone, or POMC. ACTH is a 39 amino acid peptide that is the primary regulator of adrenal glucocorticoid synthesis and secretion and only has affinity for MC2R. As the central actor in this hypothalamic-pituitary-adrenal (HPA) axis, ACTH is secreted by the pituitary in response to stressful stimuli and acts at the adrenal gland to stimulate the synthesis and secretion of cortisol. Modulation of MC2R is attractive for the treatment of conditions, diseases, or disorders that would benefit from modulating melanocortin receptor activity.

SUMMARY OF THE INVENTION

Compounds described herein are melanocortin receptor modulator compounds. In some embodiments, compounds described herein modulate one or more of the subtype melanocortin receptor proteins. In some embodiments, compounds described herein modulate two or more of the subtype melanocortin receptor proteins. In some embodiments, compounds described herein modulate MC2R.

In one aspect, described herein is a compound of Formula (I), or a pharmaceutically acceptable salt, or solvate thereof:

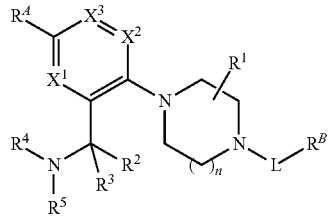

Formula (I)

wherein:
$R^A$ is unsubstituted or substituted phenyl, unsubstituted or substituted monocyclic heteroaryl, wherein if $R^A$ is substituted then $R^A$ is substituted with $R^a$, $R^b$ and $R^c$;
$R^a$, $R^b$ and $R^c$ are independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^a$, $R^b$ and $R^c$ is substituted with one or more $R^9$ groups;
L is absent, —C(=O)—, —C(=O)$NR^7$—, or —$SO_2$—;
$R^B$ is unsubstituted or substituted carbocycle, unsubstituted or substituted heterocycle, unsubstituted or substituted $C_1$-$C_7$ alkyl, unsubstituted or substituted $C_1$-$C_7$ fluoroalkyl, unsubstituted or substituted $C_1$-$C_6$ heteroalkyl, wherein if $R^B$ is substituted then $R^B$ is substituted with $R^d$, $R^e$ and $R^f$;
or $R^B$ and $R^7$ are taken together with the nitrogen atom to which they are attached to form an unsubstituted or substituted 3- to 7-membered heterocycle, wherein if the 3- to 7-membered heterocyle is substituted then the 3- to 7-membered heterocyle is substituted with $R^d$, $R^e$ and $R^f$;
$R^d$, $R^e$ and $R^f$ are independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^d$, $R^e$ and $R^f$ is substituted with one or more $R^9$ groups;
$X^1$ is $CR^6$ or N;
$X^2$ is $CR^6$ or N;
$X^3$ is $CR^6$ or N;
$R^1$ is an unsubstituted or substituted $C_1$-$C_6$ alkyl, or unsubstituted or substituted $C_3$-$C_6$ cycloalkyl, wherein if $R^1$ is substituted then $R^1$ is substituted with hydrogen, —$OR^8$, halogen, —$N(R^7)_2$, or —CN;
$R^2$ and $R^3$ are independently hydrogen, unsubstituted or substituted $C_1$-$C_6$ alkyl, or unsubstituted or substituted $C_3$-$C_6$cycloalkyl, wherein any substituted group of $R^2$ and $R^3$ is substituted with hydrogen, —$OR^8$, —$N(R^7)_2$, halogen, or —CN;
or $R^2$ and $R^3$ are taken together with the carbon atom to which they are attached to form —C(=O)—;
or $R^2$ and $R^3$ are taken together with the carbon atom to which they are attached to form an unsubstituted or substituted 3- to 6-membered monocyclic carbocycle;

R$^4$ and R$^5$ are independently selected from the group consisting of hydrogen, unsubstituted or substituted C$_1$-C$_6$ alkyl, unsubstituted or substituted monocyclic carbocycle, unsubstituted or substituted monocyclic heterocycle, unsubstituted or substituted —(C$_1$-C$_6$ alkyl)-carbocycle, or unsubstituted or substituted —(C$_1$-C$_6$ alkyl)-heterocycle, wherein any substituted group of R$^4$ and R$^5$ is substituted with one or more halogen, unsubstituted or substituted C$_1$-C$_6$ alkyl, unsubstituted or substituted monocyclic heterocycle, —N(R$^7$)$_2$, —OR$^8$, —CN, —CO$_2$R$^8$, —C(=O)N(R$^7$)$_2$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$;

or R$^4$ and R$^5$ are taken together with the nitrogen atom to which they are attached to form a substituted or unsubstituted 3- to 6-membered heterocycle, wherein if the 3- to 6-membered heterocycle is substituted then the 3- to 6-membered heterocycle is substituted with one or more halogen, unsubstituted or substituted C$_1$-C$_6$ alkyl, unsubstituted or substituted monocyclic heterocycle, —N(R$^7$)$_2$, —OR$^8$, —CN, —CO$_2$R$^8$, —C(=O)N(R$^7$)$_2$, —SR$^8$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$;

or R$^2$ and R$^4$ are taken together with the intervening atoms to which they are attached to form a substituted or unsubstituted 5- to 6-membered N-containing heterocycle;

each R$^6$ is independently selected from the group consisting of hydrogen, halogen, unsubstituted or substituted C$_1$-C$_6$ alkyl, unsubstituted or substituted C$_3$-C$_6$cycloalkyl, unsubstituted or substituted C$_1$-C$_6$fluoroalkyl, —CN, —OR$^8$, —CO$_2$R$^8$, —C(=O)N(R$^7$)$_2$, or —N(R$^7$)$_2$;

each R$^7$ is independently selected from the group consisting of hydrogen, substituted C$_1$-C$_6$ alkyl, unsubstituted or substituted C$_3$-C$_6$ cycloalkyl, unsubstituted or substituted C$_1$-C$_6$fluoroalkyl, unsubstituted or substituted aryl, unsubstituted or substituted heteroaryl;

or two R$^7$ are taken together with the nitrogen atom to which they are attached to form an unsubstituted or substituted 3- to 6-membered monocyclic heterocycle;

each R$^8$ is independently selected from the group consisting of hydrogen, substituted or substituted C$_1$-C$_6$ alkyl, unsubstituted or substituted C$_3$-C$_6$ cycloalkyl, unsubstituted or substituted C$_1$-C$_6$fluoroalkyl, unsubstituted or substituted aryl, and unsubstituted or substituted heteroaryl;

each R$^9$ is independently hydrogen, halogen, unsubstituted or substituted C$_1$-C$_4$alkyl, unsubstituted or substituted C$_1$-C$_4$alkoxy, unsubstituted or substituted C$_1$-C$_4$fluoroalkyl, unsubstituted or substituted C$_1$-C$_4$fluoroalkoxy, unsubstituted or substituted monocyclic carbocycle, unsubstituted or substituted monocyclic heterocycle, —CN, —OH, —CO$_2$R$^8$, —CH$_2$CO$_2$R$^8$, —C(=O)N(R$^7$)$_2$, —C(=O)N(R$^7$)OR$^8$, —CH$_2$C(=O)N(R$^7$)$_2$, —N(R$^7$)$_2$, —CH$_2$N(R$^7$)$_2$, —C(R$^8$)$_2$N(R$^7$)$_2$, —NR$^7$C(=O)R$^8$, —CH$_2$NR$^7$C(=O)1e, —NR$^7$C(=O)N(R$^7$)$_2$, —NR$^7$C(=O)N(R$^7$)$_2$, C(R$^8$)=N(R$^7$)—OR$^8$, —SR$^8$, —S(=O)R$^{10}$, —SO$_2$R$^{10}$, or —SO$_2$N(R$^7$)$_2$;

each R$^{10}$ is independently selected from the group consisting substituted or substituted C$_1$-C$_6$ alkyl, unsubstituted or substituted C$_3$-C$_6$ cycloalkyl, unsubstituted or substituted C$_1$-C$_6$fluoroalkyl, unsubstituted or substituted phenyl, and unsubstituted or substituted heteroaryl;

n is 1 or 2.

Also described herein are pharmaceutical compositions comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype melanocortin receptor proteins, or for the treatment, prevention or amelioration of one or more symptoms of a disease or condition that would benefit from modulating one or more subtype melanocortin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Adrenocorticotropic hormone (ACTH) is a 39 amino acid peptide synthesized by anterior pituitary corticotrophic cells by proteolytic cleavage of the proopiomelanocortin hormone (POMC). ACTH is the primary regulator of adrenal glucocorticoid (GC; cortisol in humans and most other species; corticosterone in rodents) synthesis and secretion. As the central actor in this hypothalamic-pituitary-adrenal (HPA) axis, ACTH is secreted by the pituitary in response to stressful stimuli and acts at the adrenal gland to stimulate the synthesis and secretion of cortisol. This stimulation is mediated through a highly specific G protein-coupled receptor (GPCR) which is expressed almost uniquely in the adrenal cortex. The receptor is the melanocortin 2 receptor (MC2R), and, along with ACTH, is part of the larger melanocortin system.

The melanocortin system comprises a family of five GPCRs (MC1R, MC2R, MC3R, MC4R, and MC5R); their natural agonists, the melanocortin peptides α-, β-, and γ-melanocyte-stimulating hormone (α-MSH, β-MSH, and γ-MSH) and ACTH; and endogenous melanocortin antagonists agouti and agouti-related protein (AGRP). The melanocortin receptors (MCRs) have different selectivities for endogenous agonist and antagonist peptides and are expressed in diverse tissues where they serve varied and discreet physiological functions (Gantz, I. and T. M. Fong, *Am. J. Physiol. Endocrinol. Metab.*, 284: E468E474, 2003).

It is possible to selectively modulate any one of the MCRs, or combinations thereof. In some embodiments, selectively modulating any one of the MCRs relative to the other MCRs, or combinations thereof, is useful in a variety of clinical applications. In some embodiments, selectively modulating any one of the MCRs relative to the other MCRs, or combinations thereof, reduces unwanted side effects in a variety of clinical applications. In one aspect, compounds described herein are antagonists of MC2R. In some embodiments, compounds described herein are selective antagonists for MC2R relative or other MCRs.

MC2R is a highly selective receptor for ACTH. Although ACTH can activate all five MCRs, at physiological levels, the sensitivity of the other receptors is not high enough to be activated, and ACTH selectively activates MC2R. Importantly, the other naturally occurring agonists α-MSH, β-MSH, and γ-MSH have no affinity for MC2R (Gantz, I. and T. M. Fong, *Am. J. Physiol. Endocrinol. Metab.*, 284: E468E474, 2003). The major function of MC2R is to stimulate the *fasciculata* cells of the adrenal cortex to synthesize and secret cortisol. MC2R requires the GPCR accessory protein MRAP (melanocortin 2 receptor protein) to be successfully secreted to the cell surface and as well as to function. MRAP is a small protein with a single transmembrane domain that forms an antiparallel homodimer in stable complex with MC2R and is necessary for both cell surface expression of MC2R and its ability to bind ACTH. MRAP can bind to any of the MCRs and affect their activities, but is only essential for MC2R activity. Binding of ACTH to the MC2R/MRAP complex on adrenal cortical cells activates Gs to elevate intracellular cAMP levels which in turn stimulates cortisol synthesis and secretion by regulating multiple steps in the steroidogenic pathway.

Cushing's syndrome is a rare disorder characterized by chronic, excess glucocorticoid exposure. Clinical signs of Cushing's syndrome include growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, and a range of other metabolic disturbances resulting in high morbidity. If inadequately controlled in its severe forms, Cushing's syndrome is associated with high mortality. Although glucocorticoid excess can sometimes be ACTH independent, for example from excessive autonomous secretion of cortisol from a hyperfunctioning adrenal adenoma, carcinoma, or steroid abuse, about 60-80% of all cases are ACTH dependent Cushing's syndrome, known as Cushing's disease. Cushing's disease is caused by microadenomas of pituitary corticotropic cells that secrete excess ACTH. Corticotroph adenomas are small, usually slow growing, benign tumors that normally come to clinical attention as a result of the effects of glucocorticoid excess, rather than because of the physical effects of an expanding tumor. First line treatments for Cushing's disease are surgical and involve removal of either the ACTH-secreting tumor in the pituitary or the adrenal glands themselves. As surgery is often unsuccessful, contraindicated, or delayed, medical therapy for these patients becomes necessary. Current treatment options include inhibitors of steroid synthesis enzymes that can prevent the production of cortisol and improve symptoms, but these treatments also induce a host of unwanted side effects due to the accumulation of other steroid products. In one aspect, an MC2R antagonist is used in the treatment of Cushing's syndrome. In some embodiments, an MC2R antagonist is used in the treatment of Cushing's disease. In some embodiments, glucocorticoid excess is ACTH independent. In some embodiments, glucocorticoid excess is ACTH dependent.

Ectopic ACTH syndrome, or ectopic Cushing's syndrome or disease, is essentially the same as Cushing's disease, except that the underlying tumor expressing ACTH is outside the pituitary gland. In some embodiments, the tumors are small carcinoid tumors that occur anywhere in the lungs or gastrointestinal tract. In some embodiments, an MC2R antagonist is used in the treatment of ectopic ACTH syndrome.

Congenital adrenal hyperplasia (CAH) is characterized by a reduction or loss of cortisol synthesis and excessive ACTH and corticotropin-releasing hormone. CAH can result from a variety of genetic defects in the adrenal steroidal biosynthesis pathway. In some embodiments, CAH is due to a mutation in 21β-hydroxylase. The lack of cortisol removes the negative feedback to the pituitary which leads to excessive ACTH secretion. The resulting excessive adrenal stimulation causes overproduction of steroid precursors which also have negative consequences (e.g., hyperandrogenism). Administration of replacement glucocorticoids typically does not adequately suppress ACTH without also causing Cushing's-like symptoms. In some embodiments, an MC2R antagonist is used in the treatment of CAH.

In addition to Cushing's disease and CAH it has also been hypothesized that there might be a role for an MC2R antagonist in the treatment of depressive illness and septic shock. In some embodiments, an MC2R antagonist is used in the treatment of depressive illness. In some embodiments, an MC2R antagonist is used in the treatment of septic shock.

In some embodiments, compounds described herein are amenable to administration to a mammal in need of treatment with an MC2R antagonist.

Compounds

Compounds of Formula (I), including pharmaceutically acceptable salts, prodrugs, active metabolites and pharmaceutically acceptable solvates thereof, are melanocortin receptor modulators. In some embodiments, the compounds of Formula (I), including pharmaceutically acceptable salts, prodrugs, active metabolites and pharmaceutically acceptable solvates thereof, are MC2R modulators. In some embodiments, the MC2R modulators are MC2R antagonists.

Provided in one aspect is a compound of Formula (I), or a pharmaceutically acceptable salt, or solvate thereof:

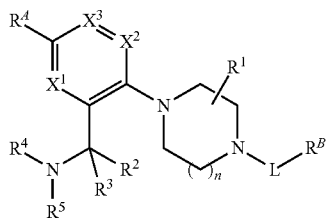

Formula (I)

wherein:

$R^A$ is unsubstituted or substituted phenyl, unsubstituted or substituted monocyclic heteroaryl, wherein if $R^A$ is substituted then $R^A$ is substituted with $R^a$, $R^b$ and $R^c$;

$R^a$, $R^b$ and $R^c$ are independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^a$, $R^b$ and $R^c$ is substituted with one or more $R^9$ groups;

L is absent, —C(=O)—, —C(=O)$NR^7$—, or —$SO_2$—;

$R^B$ is unsubstituted or substituted carbocycle, unsubstituted or substituted heterocycle, unsubstituted or substituted $C_1$-$C_7$ alkyl, unsubstituted or substituted $C_1$-$C_7$ fluoroalkyl, unsubstituted or substituted $C_1$-$C_6$ heteroalkyl, wherein if $R^B$ is substituted then $R^B$ is substituted with $R^d$, $R^e$ and $R^f$;

or $R^B$ and $R^7$ are taken together with the nitrogen atom to which they are attached to form an unsubstituted or substituted 3- to 7-membered heterocycle, wherein if the 3- to 7-membered heterocyle is substituted then the 3- to 7-membered heterocyle is substituted with $R^d$, $R^e$ and $R^f$;

$R^d$, $R^e$ and $R^f$ are independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^d$, $R^e$ and $R^f$ is substituted with one or more $R^9$ groups;

$X^1$ is $CR^6$ or N;

$X^2$ is $CR^6$ or N;

$X^3$ is $CR^6$ or N;

$R^1$ is an unsubstituted or substituted $C_1$-$C_6$ alkyl, or unsubstituted or substituted $C_3$-$C_6$ cycloalkyl, wherein if $R^1$ is substituted then $R^1$ is substituted with hydrogen, —$OR^8$, halogen, —$N(R^7)_2$, or —CN;

$R^2$ and $R^3$ are independently hydrogen, unsubstituted or substituted $C_1$-$C_6$ alkyl, or unsubstituted or substituted $C_3$-$C_6$ cycloalkyl, wherein any substituted group of $R^2$ and $R^3$ is substituted with hydrogen, —$OR^8$, —$N(R^7)_2$, halogen, or —CN;

or $R^2$ and $R^3$ are taken together with the carbon atom to which they are attached to form —C(=O)—;

or $R^2$ and $R^3$ are taken together with the carbon atom to which they are attached to form an unsubstituted or substituted 3- to 6-membered monocyclic carbocycle;

$R^4$ and $R^5$ are independently selected from the group consisting of hydrogen, unsubstituted or substituted $C_1$-$C_6$ alkyl, unsubstituted or substituted monocyclic carbocycle, unsubstituted or substituted monocyclic heterocycle, unsubstituted or substituted —($C_1$-$C_6$ alkyl)-carbocycle, or unsubstituted or substituted —($C_1$-$C_6$ alkyl)-heterocycle, wherein any substituted group of $R^4$ and $R^5$ is substituted with one or more halogen, unsubstituted or substituted $C_1$-$C_6$ alkyl, unsubstituted or substituted monocyclic heterocycle, —$N(R^7)_2$, —CN, —$CO_2R^8$, —C(=O)$N(R^7)_2$, —S(=O)$R^{10}$, —S(=O)$_2R^{10}$, —$NR^7$C(=O)$R^8$, —$NR^7SO_2R^{10}$, —$SO_2R^{10}$, or —$SO_2N(R^7)_2$;

or $R^4$ and $R^5$ are taken together with the nitrogen atom to which they are attached to form a substituted or unsubstituted 3- to 6-membered heterocycle, wherein if the 3- to 6-membered heterocycle is substituted then the 3- to 6-membered heterocycle is substituted with one or more halogen, unsubstituted or substituted $C_1$-$C_6$ alkyl, unsubstituted or substituted monocyclic heterocycle, —$N(R^7)_2$, —CN, —$CO_2R^8$, —C(=O)$N(R^7)_2$, —$SR^8$, —S(=O)$R^{10}$, —S(=O)$_2R^{10}$, —$NR^7$C(=O)$R^8$, —$NR^7SO_2R^{10}$, —$SO_2R^{10}$, or —$SO_2N(R^7)_2$;

or $R^2$ and $R^4$ are taken together with the intervening atoms to which they are attached to form a substituted or unsubstituted 5- to 6-membered N-containing heterocycle;

each $R^6$ is independently selected from the group consisting of hydrogen, halogen, unsubstituted or substituted $C_1$-$C_6$ alkyl, unsubstituted or substituted $C_3$-$C_6$cycloalkyl, unsubstituted or substituted $C_1$-$C_6$fluoroalkyl, —CN, —$OR^8$, —$SR^8$, —$CO_2R^8$, —C(=O)$N(R^7)_2$, or —$N(R^7)_2$;

each $R^7$ is independently selected from the group consisting of hydrogen, substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, unsubstituted or substituted heteroaryl;

or two $R^7$ are taken together with the nitrogen atom to which they are attached to form an unsubstituted or substituted 3- to 6-membered monocyclic heterocycle;

each $R^8$ is independently selected from the group consisting of hydrogen, substituted or unsubstituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

each $R^9$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^8$, —$CH_2CO_2R^8$, —C(=O)$N(R^7)_2$, —C(=O)$N(R^7)OR^8$, —$CH_2C$(=O)$N(R^7)_2$, —$N(R^7)_2$, —$CH_2N(R^7)_2$, —$C(R^8)_2N(R^7)_2$, —$NR^7C$(=O)$R^8$, —$CH_2NR^7C$(=O)$R^8$, —$NR^7C$(=O)$N(R^7)_2$, —$NR^7C$(=O)$N(R^7)_2$, $C(R^8)$=$N(R^7)$—$OR^8$, —S(=O)$R^{10}$, —$SO_2R^{10}$, or —$SO_2N(R^7)_2$;

each $R^{10}$ is independently selected from the group consisting substituted or substituted $C_1$-$C_6$ alkyl, unsubstituted or substituted $C_3$-$C_6$ cycloalkyl, unsubstituted or substituted $C_1$-$C_6$ fluoroalkyl, unsubstituted or substituted phenyl, and unsubstituted or substituted heteroaryl;

n is 1 or 2.

In some embodiments, L is absent, —C(=O)—, —C(=O)NR$^7$—, or —SO$_2$—. In some embodiments, L is absent, —C(=O)—, or —C(=O)NR$^7$—. In some embodiments, L is —C(=O)— or —C(=O)NR$^7$—. In some embodiments, L is —C(=O)—. In some embodiments, L is —C(=O)NR$^7$—.

In some embodiments, L is —C(=O)—; R$^2$ and R$^3$ are independently hydrogen, —CH$_3$, —CH$_2$CH$_3$, —CH$_2$CH$_2$CH$_3$, —CH$_2$OR$^8$, or —CH$_2$NHR$^7$; or R$^2$ and R$^3$ are taken together with the carbon atom to which they are attached to form —C(=O)—. In some embodiments, R$^2$ and R$^3$ are hydrogen; or R$^2$ and R$^3$ are taken together with the carbon atom to which they are attached to form —C(=O)—. In some embodiments, R$^2$ and R$^3$ are hydrogen. In some embodiments, R$^2$ and R$^3$ are taken together with the carbon atom to which they are attached to form —C(=O)—.

In some embodiments, L is —C(=O)—; R$^2$ and R$^3$ are independently hydrogen or —CH$_3$; or R$^2$ and R$^3$ are taken together with the carbon atom to which they are attached to form —C(=O)—; or R$^2$ and R$^3$ are taken together with the carbon atom to which they are attached to form a cyclopropyl.

In some embodiments, R$^4$ is unsubstituted or substituted phenyl, unsubstituted or substituted monocyclic 6-membered heteroaryl, unsubstituted or substituted monocyclic 5-membered heteroaryl, wherein if R$^4$ is substituted then R$^4$ is substituted with R$^a$, R$^b$ and R$^c$.

In some embodiments, R$^4$ is unsubstituted or substituted phenyl, unsubstituted or substituted pyridinyl, unsubstituted or substituted pyrimidinyl, unsubstituted or substituted pyrazinyl, unsubstituted or substituted pyridazinyl, unsubstituted or substituted triazinyl, unsubstituted or substituted furanyl, unsubstituted or substituted thienyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, or unsubstituted or substituted thiadiazolyl; wherein if R$^4$ is substituted then R$^4$ is substituted with R$^a$, R$^b$ and R$^c$.

In some embodiments, R$^4$ is unsubstituted or substituted phenyl, unsubstituted or substituted pyridinyl, unsubstituted or substituted pyrimidinyl, unsubstituted or substituted pyrazinyl, or unsubstituted or substituted pyridazinyl; wherein if R$^4$ is substituted then R$^4$ is substituted with R$^a$, R$^b$ and R$^c$.

In some embodiments, R$^4$ is unsubstituted or substituted phenyl, or unsubstituted or substituted pyridinyl, wherein if R$^4$ is substituted then R$^4$ is substituted with R$^a$, R$^b$ and R$^c$.

In some embodiments, R$^4$ is

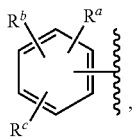, 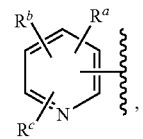, 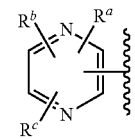,

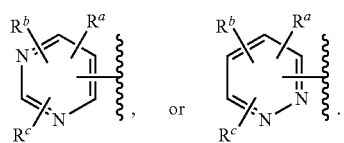

In some embodiments, R$^4$ is

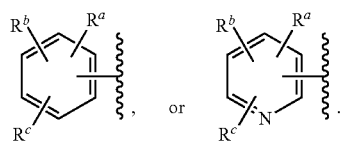

In some embodiments, R$^4$ is

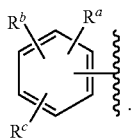

In some embodiments, R$^4$ is

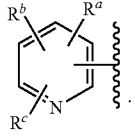

In some embodiments, R$^4$ is

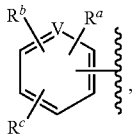

where V is CH or N.

In some embodiments, R$^4$ is

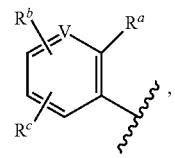

where V is CH or N. In some embodiments, $R^A$ is

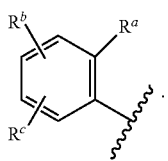

In some embodiments, $R^A$ is

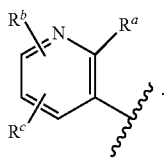

In some embodiments, n is 1. In some embodiments, n is 2.

In some embodiments, the compound has the structure of Formula (II), or a pharmaceutically acceptable salt, or solvate thereof:

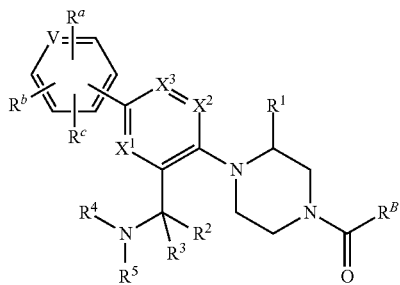

Formula (II)

wherein,
V is CH or N.

In some embodiments, $R^B$ is an unsubstituted or substituted monocyclic carbocycle, unsubstituted or substituted bicyclic carbocycle, unsubstituted or substituted polycyclic carbocycle, unsubstituted or substituted monocyclic heterocycle, unsubstituted or substituted bicyclic heterocycle, unsubstituted or substituted polycyclic heterocycle, wherein if $R^B$ is substituted then $R^B$ is substituted with $R^d$, $R^e$ and $R^f$.

In some embodiments, $R^B$ is an unsubstituted or substituted monocyclic carbocycle, unsubstituted or substituted bridged carbocycle, unsubstituted or substituted spiro carbocycle, unsubstituted or substituted monocyclic heterocycle, unsubstituted or substituted bridged heterocycle, unsubstituted or substituted spiro heterocycle, wherein if $R^B$ is substituted then $R^B$ is substituted with $R^d$, $R^e$ and $R^f$.

In some embodiments, $R^B$ is an unsubstituted or substituted phenyl, unsubstituted or substituted naphthyl, unsubstituted or substituted monocyclic 6-membered heteroaryl, unsubstituted or substituted monocyclic 5-membered heteroaryl, unsubstituted or substituted bicyclic heteroaryl, monocyclic $C_3$-$C_8$cycloalkyl, unsubstituted or substituted bridged $C_5$-$C_{10}$cycloalkyl, unsubstituted or substituted spiro $C_5$-$C_{10}$cycloalkyl, unsubstituted or substituted monocyclic $C_2$-$C_8$heterocycloalkyl, unsubstituted or substituted bridged $C_5$-$C_{10}$heterocycloalkyl, or unsubstituted or substituted spiro $C_5$-$C_{10}$heterocycloalkyl, wherein if $R^B$ is substituted then $R^B$ is substituted with $R^d$, $R^e$ and $R^f$.

In some embodiments, $R^B$ is an unsubstituted or substituted carbocycle that is an unsubstituted or substituted phenyl, unsubstituted or substituted naphthyl, unsubstituted or substituted indanyl, unsubstituted or substituted indenyl, unsubstituted or substituted tetrahyodronaphthyl, unsubstituted or substituted cyclopropyl, unsubstituted or substituted cyclobutyl, unsubstituted or substituted cyclopentyl, unsubstituted or substituted cyclopentenyl, unsubstituted or substituted cyclohexyl, unsubstituted or substituted cyclohexenyl, unsubstituted or substituted cycloheptyl, unsubstituted or substituted cyclooctyl, unsubstituted or substituted spiro[2.2]pentyl, unsubstituted or substituted spiro[3.3]heptyl, unsubstituted or substituted spiro[3.5]nonyl, unsubstituted or substituted spiro[4.4]nonyl, unsubstituted or substituted spiro[4.5]decyl, unsubstituted or substituted norbornyl, unsubstituted or substituted norbornenyl, unsubstituted or substituted bicyclo[1.1.1]pentyl, unsubstituted or substituted adamantyl, or unsubstituted or substituted decalinyl.

In some embodiments, $R^B$ is an unsubstituted or substituted furanyl, unsubstituted or substituted thienyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, unsubstituted or substituted triazinyl, unsubstituted or substituted quinolinyl, unsubstituted or substituted isoquinolinyl, unsubstituted or substituted cinnolinyl, unsubstituted or substituted phthalazinyl, unsubstituted or substituted quinazolinyl, unsubstituted or substituted quinoxalinyl, unsubstituted or substituted naphthyridinyl, unsubstituted or substituted pteridinyl, unsubstituted or substituted indolizinyl, unsubstituted or substituted azaindolizinyl, unsubstituted or substituted indolyl, unsubstituted or substituted azaindolyl, unsubstituted or substituted indazolyl, unsubstituted or substituted azaindazolyl, unsubstituted or substituted benzimidazolyl, unsubstituted or substituted azabenzimidazolyl, unsubstituted or substituted benzotriazolyl, unsubstituted or substituted azabenzotriazolyl, unsubstituted or substituted benzoxazolyl, unsubstituted or substituted azabenzoxazolyl, unsubstituted or substituted benzisoxazolyl, unsubstituted or substituted azabenzisoxazolyl, unsubstituted or substituted benzofuranyl, unsubstituted or substituted azabenzofuranyl, unsubstituted or substituted benzothienyl, unsubstituted or substituted azabenzothienyl, unsubstituted or substituted benzothiazolyl, unsubstituted or substituted azabenzothiazolyl, or unsubstituted or substituted purinyl. In some embodiments, $R^B$ is an unsubstituted or substituted indolyl, wherein if $R^B$ is substituted then $R^B$ is substituted with $R^d$, $R^e$ and $R^f$.

In some embodiments, $R^B$ is an unsubstituted or substituted aziridinyl, unsubstituted or substituted azetidinyl, unsubstituted or substituted oxetanyl, unsubstituted or substituted thietanyl, unsubstituted or substituted pyrrolidinyl, unsubstituted or substituted tetrahydrofuranyl, unsubstituted or substituted tetrahydrothienyl, unsubstituted or substituted oxazolidinonyl, unsubstituted or substituted tetrahydropyranyl, unsubstituted or substituted piperidinyl, unsubstituted or substituted morpholinyl, unsubstituted or substituted thiomorpholinyl, unsubstituted or substituted piperazinyl, unsubstituted or substituted homopiperidinyl, unsubstituted or substituted oxepanyl, unsubstituted or substituted thiepanyl, unsubstituted or substituted oxazepinyl, unsubstituted or substituted diazepinyl, unsubstituted or substituted thiazepinyl, unsubstituted or substituted azaspiro[3.3]heptanyl, unsubstituted or substituted azaspiro[3.4]octanyl, unsubstituted or substituted azaspiro[3.4]octanyl, or unsubstituted or substituted azaspiro[4.4]nonyl.

In some embodiments, $R^B$ is unsubstituted or substituted phenyl, unsubstituted or substituted pyridinyl, unsubstituted or substituted pyrimidinyl, unsubstituted or substituted pyrazinyl, or unsubstituted or substituted pyridazinyl, wherein if $R^B$ is substituted then $R^B$ is substituted with $R^d$, $R^e$ and $R^f$.

In some embodiments, $R^B$ is unsubstituted or substituted cyclopropyl, unsubstituted or substituted cyclobutyl, unsubstituted or substituted cyclopentyl, unsubstituted or substituted cyclopentenyl, or unsubstituted or substituted cyclohexyl, wherein if $R^B$ is substituted then $R^B$ is substituted with $R^d$, $R^e$ and $R^f$. In some embodiments, $R^B$ is unsubstituted or substituted cyclobutyl, wherein if $R^B$ is substituted then $R^B$ is substituted with $R^d$, $R^e$ and $R^f$.

In some embodiments, $R^B$ is an unsubstituted or substituted aziridinyl, unsubstituted or substituted azetidinyl, unsubstituted or substituted oxetanyl, unsubstituted or substituted thietanyl, unsubstituted or substituted pyrrolidinyl, unsubstituted or substituted tetrahydrofuranyl, unsubstituted or substituted tetrahydrothienyl, unsubstituted or substituted oxazolidinonyl, unsubstituted or substituted tetrahydropyranyl, unsubstituted or substituted piperidinyl, unsubstituted or substituted morpholinyl, unsubstituted or substituted thiomorpholinyl, or unsubstituted or substituted piperazinyl, wherein if $R^B$ is substituted then $R^B$ is substituted with $R^d$, $R^e$ and $R^f$. In some embodiments, $R^B$ is an unsubstituted or substituted aziridinyl, unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, or unsubstituted or substituted piperazinyl, wherein if $R^B$ is substituted then $R^B$ is substituted with $R^d$, $R^e$ and $R^f$. In some embodiments, $R^B$ is an unsubstituted or substituted pyrrolidinyl, wherein if $R^B$ is substituted then $R^B$ is substituted with $R^d$, $R^e$ and $R^f$.

In some embodiments, $R^B$ is

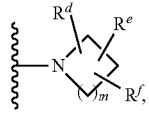

where m is 0, 1, 2, or 3. In some embodiments, m is 2 or 3. In some embodiments, m is 0. In some embodiments, m is 1. In some embodiments, m is 2. In some embodiments, m is 3.

In some embodiments, $R^B$ is unsubstituted or substituted phenyl, or unsubstituted or substituted pyridinyl, wherein if $R^B$ is substituted then $R^B$ is substituted with $R^d$, $R^e$ and $R^f$.

In some embodiments, $R^B$ is

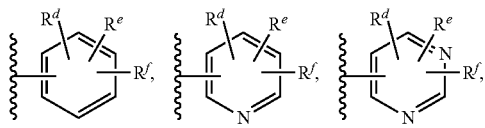

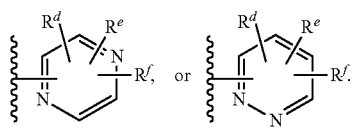

In some embodiments, $R^B$ is

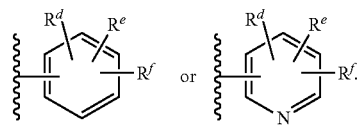

In some embodiments, $R^B$ is

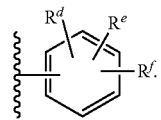

In some embodiments, $R^B$ is

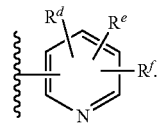

In some embodiments, $R^B$ is

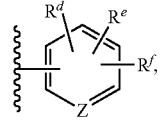

where Z is CH or N. In some embodiments, $R^B$ is

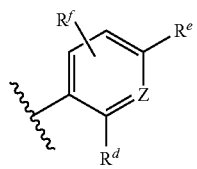

where Z is CH or N.

In some embodiments, the compound has the structure of Formula (III), or a pharmaceutically acceptable salt, or solvate thereof:

Formula (III)

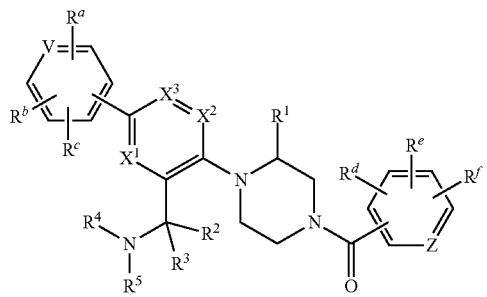

wherein,
V is CH or N;
Z is CH or N.

In some embodiments, the compound has the structure of Formula (IV), or a pharmaceutically acceptable salt, or solvate thereof:

Formula (IV)

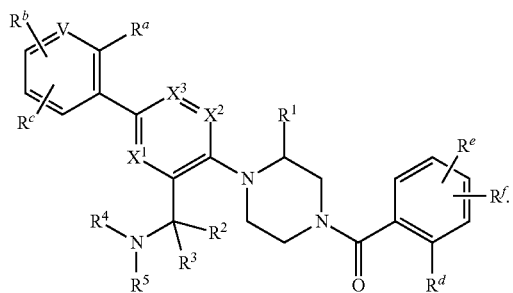

In some embodiments, the compound has the structure of Formula (V), or a pharmaceutically acceptable salt, or solvate thereof:

Formula (V)

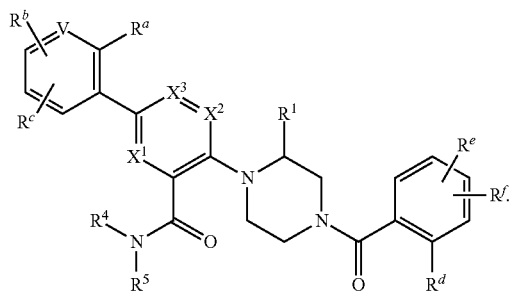

In some embodiments, $R^1$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, cyclopropyl, cyclobutyl, cyclopentyl, or cyclohexyl.

In some embodiments, $R^1$ is —$CH_3$, —$CH_2CH_3$, or —$CH_2CH_2CH_3$.

In some embodiments, $R^4$ is selected from the group consisting of hydrogen, unsubstituted or substituted $C_1$-$C_6$ alkyl, unsubstituted or substituted monocyclic carbocycle, unsubstituted or substituted monocyclic heterocycle, unsubstituted or substituted —($C_1$-$C_6$ alkyl)-carbocycle, or unsubstituted or substituted —($C_1$-$C_6$ alkyl)-heterocycle, wherein any substituted group of $R^4$ is substituted with one or more halogen, unsubstituted or substituted $C_1$-$C_6$ alkyl, unsubstituted or substituted monocyclic heterocycle, —$N(R^7)_2$, —$OR^8$, —$CN$, —$CO_2R^8$, —$C(=O)N(R^7)_2$, —$S(=O)R^{10}$, —$S(=O)_2R^{10}$, —$NR^7C(=O)R^8$, —$NR^7SO_2R^{10}$, —$SO_2R^{10}$, or —$SO_2N(R^7)_2$; $R^5$ is selected from the group consisting of hydrogen, and $C_1$-$C_6$ alkyl; or $R^4$ and $R^5$ are taken together with the nitrogen atom to which they are attached to form a substituted or unsubstituted 3- to 6-membered heterocycle, wherein if the 3- to 6-membered heterocycle is substituted then the 3- to 6-membered heterocycle is substituted with one or more halogen, unsubstituted or substituted $C_1$-$C_6$ alkyl, unsubstituted or substituted monocyclic heterocycle, —$N(R^7)_2$, —$OR^8$, —$CN$, —$CO_2R^8$, —$C(=O)N(R^7)_2$, —$S(=O)R^{10}$, —$S(=O)_2R^{10}$, —$NR^7C(=O)R^8$, —$NR^7SO_2R^{10}$, —$SO_2R^{10}$, or —$SO_2N(R^7)_2$.

In some embodiments, $R^4$ is selected from the group consisting of hydrogen, unsubstituted or substituted $C_1$-$C_6$ alkyl, unsubstituted or substituted monocyclic carbocycle, or unsubstituted or substituted monocyclic 4-, 5- or 6-membered heterocycle containing 1-4 N atoms and 0 or 1 O or S atoms, wherein any substituted group of $R^4$ is substituted with one or more halogen, unsubstituted or substituted $C_1$-$C_6$ alkyl, unsubstituted or substituted monocyclic 4-, 5- or 6-membered heterocycle containing 1-4 N atoms and 0 or 1 O or S atoms, —$N(R^7)_2$, —$OR^8$, —$CN$, —$CO_2R^8$, —$C(=O)N(R^7)_2$, —$S(=O)R^{10}$, —$S(=O)_2R^{10}$, —$NR^7C(=O)R^8$, —$NR^7SO_2R^{10}$, —$SO_2R^{10}$, or —$SO_2N(R^7)_2$; $R^5$ is selected from the group consisting of hydrogen, —$CH_3$, —$CH_2CH_3$, and —$CH_2CH_2CH_3$.

In some embodiments, $R^4$ is selected from the group consisting of hydrogen, unsubstituted or substituted $C_1$-$C_6$ alkyl, unsubstituted or substituted monocyclic carbocycle, or unsubstituted or substituted monocyclic 4-, 5- or 6-membered heterocycle containing 1-4 N atoms and 0 or 1 O or S atoms, wherein any substituted group of $R^4$ is substituted with one or more halogen, $C_1$-$C_6$ alkyl that is unsubstituted or substituted with a heterocycle, unsubstituted or substituted monocyclic 4-, 5- or 6-membered heterocycle containing 1-4 N atoms and 0 or 1 O or S atoms, —$N(R^7)_2$, —$CN$, —$CO_2R^8$, —$C(=O)N(R^7)_2$, —$SR^8$, —$S(=O)R^{10}$, —$S(=O)_2R^{10}$, —$NR^7C(=O)R^8$, —$NR^7SO_2R^{10}$, —$SO_2R^{10}$, or —$SO_2N(R^7)_2$; $R^5$ is selected from the group consisting of hydrogen, —$CH_3$, —$CH_2CH_3$, and —$CH_2CH_2CH_3$. In some embodiments, $R^4$ is unsubstituted or substituted monocyclic 4-, 5- or 6-membered heterocycle containing 1-4 N atoms and 0 or 1 O or S atoms, wherein any substituted group of $R^4$ is substituted with one or more halogen, $C_1$-$C_6$ alkyl that is unsubstituted or substituted with a heterocycle, unsubstituted or substituted monocyclic 4-, 5- or 6-membered heterocycle containing 1-4 N atoms and 0 or 1 O or S atoms, —$N(R^7)_2$, —$OR^8$, —$CN$, —$CO_2R^8$, —$C(=O)N(R^7)_2$, —$S(=O)R^{10}$, —$S(=O)_2R^{10}$, —$NR^7C(=O)R^8$, —$NR^7SO_2R^{10}$, —$SO_2R^{10}$, or —$SO_2N(R^7)_2$; $R^5$ is selected from the group consisting of hydrogen, —$CH_3$, —$CH_2CH_3$, and —$CH_2CH_2CH_3$. In some embodiments, $R^4$ is unsubstituted or substituted monocyclic 4-, 5- or 6-membered heterocycle containing 1-4 N atoms and 0 or 1 O or S atoms, wherein any substituted group of $R^4$ is substituted with one or more halogen, $C_1$-$C_6$ alkyl that is unsubstituted or substituted with a 1,3-dioxol-2-one group, unsubstituted or substituted monocyclic 4-, 5- or 6-membered heterocycle containing 1-4 N atoms and 0 or 1 O or S atoms, —N(R$^7$)$_2$, —OR$^8$, —CN, —CO$_2$R$^8$, —C(=O)N(R$^7$)$_2$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$; R$^5$ is selected from the group consisting of hydrogen, —CH$_3$, —CH$_2$CH$_3$, and —CH$_2$CH$_2$CH$_3$.

In some embodiments, the compound has the structure of Formula (VI), or a pharmaceutically acceptable salt, or solvate thereof:

Formula (VI)

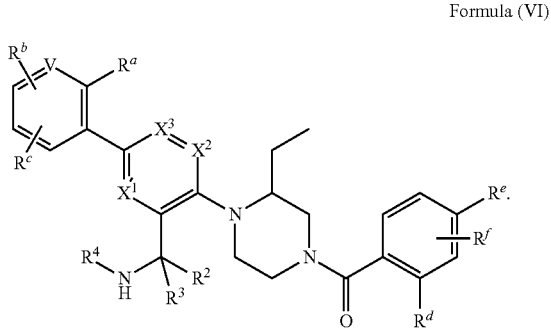

In some embodiments, the compound has the structure of Formula (VII), or a pharmaceutically acceptable salt, or solvate thereof:

Formula (VII)

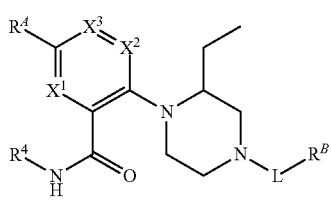

wherein:
R$^A$ is unsubstituted or substituted phenyl, or unsubstituted or substituted pyridinyl, wherein if
R$^A$ is substituted then R$^A$ is substituted with R$^a$, R$^b$ and R$^c$;
L is absent, —C(=O)—, or —C(=O)NR$^7$—;
R$^B$ is unsubstituted or substituted carbocycle, unsubstituted or substituted heterocycle, wherein if R$^B$ is substituted then R$^B$ is substituted with R$^d$, R$^e$ and R$^f$;
or R$^B$ and R$^7$ are taken together with the nitrogen atom to which they are attached to form an unsubstituted or substituted 3- to 7-membered heterocycle, wherein if the 3- to 7-membered heterocyle is substituted then the 3- to 7-membered heterocyle is substituted with R$^d$, R$^e$ and R$^f$.

In some embodiments, R$^A$ is

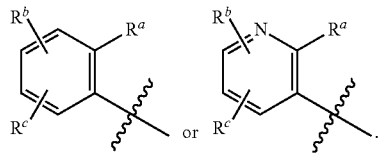

In some embodiments, R$^A$ is

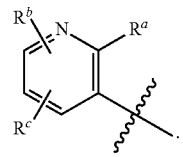

In some embodiments, R$^A$ is

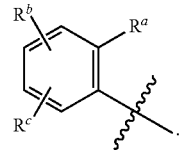

In some embodiments, X$^1$ is CR$^6$; X$^2$ is CR$^6$; X$^3$ is CR$^6$.
In some embodiments, X$^1$ is N; X$^2$ is CR$^6$; X$^3$ is CR$^6$.
In some embodiments, X$^1$ is CR$^6$; X$^2$ is N; X$^3$ is CR$^6$.
In some embodiments, X$^1$ is CR$^6$; X$^2$ is CR$^6$; X$^3$ is N.
In some embodiments, each R$^6$ is independently selected from the group consisting of hydrogen, halogen, unsubstituted or substituted C$_1$-C$_6$ alkyl, unsubstituted or substituted C$_1$-C$_6$fluoroalkyl, —CN, and —OR$^8$. In some embodiments, each R$^6$ is independently selected from the group consisting of hydrogen, halogen, and unsubstituted or substituted C$_1$-C$_6$ alkyl. In some embodiments, each R$^6$ is independently selected from the group consisting of hydrogen and halogen. In some embodiments, each R$^6$ is independently selected from the group consisting of hydrogen and fluorine.
In some embodiments, X$^1$ is CH, CF, or N; X$^2$ is CH, CF, or N; and X$^3$ is CH, CF, or N.
In some embodiments, R$^4$ is an unsubstituted or substituted C$_1$-C$_6$ alkyl or unsubstituted or substituted monocyclic 4-, 5- or 6-membered heterocycle containing 1-2 N atoms and 0 or 1 O or S atoms, wherein any substituted group of R$^4$ is substituted with one or more halogen, unsubstituted or substituted C$_1$-C$_6$ alkyl, or unsubstituted or substituted monocyclic 4-, 5- or 6-membered heterocycle containing 1-4 N atoms and 0 or 1 O or S atoms, —N(R$^7$)$_2$, —CN, —CO$_2$R$^8$, —C(=O)N(R$^7$)$_2$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$.
In some embodiments, R$^4$ is an unsubstituted or substituted C$_1$-C$_6$ alkyl, wherein any substituted group of R$^4$ is substituted with one or more halogen, unsubstituted or substituted C$_1$-C$_6$ alkyl, or unsubstituted or substituted monocyclic 4-, 5- or 6-membered heterocycle containing 1-4 N atoms and 0 or 1 O or S atoms, —N(R$^7$)$_2$, —CN, —CO$_2$R$^8$, —C(=O)N(R$^7$)$_2$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$.
In some embodiments, R$^4$ is an unsubstituted or substituted monocyclic 4-, 5- or 6-membered heterocycle containing 1-2 N atoms and 0 or 1 O or S atoms, wherein any substituted group of R$^4$ is substituted with one or more halogen, unsubstituted or substituted C$_1$-C$_6$ alkyl, —N(R$^7$)$_2$, —CN, —CO$_2$R$^8$, —C(=O)N(R$^7$)$_2$, —SR$^8$, —S(=O)R$^{10}$, —S(=O)$_2$R$^{10}$, —NR$^7$C(=O)R$^8$, —NR$^7$SO$_2$R$^{10}$, —SO$_2$R$^{10}$, or —SO$_2$N(R$^7$)$_2$. In some embodiments, R$^4$ is an unsubstituted or substituted monocyclic 4-, 5- or 6-membered heterocycle containing 1-2 N atoms and 0 or 1 O or S atoms, wherein any substituted group of R$^4$ is substituted with one or more halogen, unsubstituted or substituted $C_1$-$C_6$ alkyl, —N($R^7$)$_2$, —OR$^8$, or —CN. In some embodiments, $R^4$ is an unsubstituted or substituted monocyclic 4-, 5- or 6-membered heterocycle containing 1 atom, wherein any substituted group of $R^4$ is substituted with one or more halogen, unsubstituted or substituted $C_1$-$C_6$ alkyl, —N($R^7$)$_2$, —OR$^8$, or —CN.

In some embodiments, IV is selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, wherein any substituted group of IV is substituted with one or more $R^9$ groups; $R^b$ and $R^c$ are independently selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, unsubstituted or substituted $C_1$-$C_6$heteroalkyl, wherein any substituted group of $R^b$ and $R^c$ is substituted with one or more $R^9$ groups.

In some embodiments, IV is hydrogen, Cl, Br, —CN, —OH, —OCH$_3$, —OCH$_2$CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CH$_2$CH$_2$OH, —CH$_2$CH$_2$CN, —CH$_2$CH$_2$F, —CH$_2$CHF$_2$, —CH$_2$CF$_3$, —CH$_2$OCH$_3$, —CH$_2$CH$_2$OCH$_3$, —CH$_2$NH$_2$, —CH$_2$NHCH$_3$, —CH$_2$N(CH$_3$)$_2$, —CH$_2$CH$_2$NH$_2$, —CH$_2$CH$_2$NHCH$_3$, —CH$_2$CH$_2$N(CH$_3$)$_2$, cyclopropyl, cyclobutyl, cyclopentyl, or cyclohexyl; $R^b$ and $R^c$ are independently selected from the group consisting of hydrogen, Cl, Br, —CN, —OH, —OCH$_3$, —OCH$_2$CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CH$_2$CH$_2$OH, —CH$_2$CH$_2$CN, —CH$_2$CH$_2$F, —CH$_2$CHF$_2$, —CH$_2$CF$_3$, —CH$_2$OCH$_3$, —CH$_2$CH$_2$OCH$_3$, —CH$_2$NH$_2$, —CH$_2$NHCH$_3$, —CH$_2$N(CH$_3$)$_2$, —CH$_2$CH$_2$NH$_2$, —CH$_2$CH$_2$NHCH$_3$, or —CH$_2$CH$_2$N(CH$_3$)$_2$.

In some embodiments, $R^d$ is selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^d$ is substituted with one or more $R^9$ groups; $R^e$ and $R^f$ are independently selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, wherein any substituted group of $R^e$ and $R^f$ is substituted with one or more $R^9$ groups. In some embodiments, $R^d$ is selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of $R^d$ is substituted with one or more $R^9$ groups; and $R^e$ and $R^f$ are each independently selected from the group consisting of hydrogen, halogen, —OR$^8$, —CN, —N($R^7$)$_2$, and unsubstituted or substituted $C_1$-$C_6$ alkyl, wherein any substituted group of $R^e$ and $R^f$ is substituted with one or more $R^9$ groups.

In some embodiments, $R^d$ is selected from the group consisting of hydrogen, $C_1$, Br, —CN, —OH, —OCH$_3$, —OCH$_2$CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CH$_2$CH$_2$OH, —CH$_2$CH$_2$CN, —CH$_2$CH$_2$F, —CH$_2$CHF$_2$, —CH$_2$CF$_3$, —CH$_2$OCH$_3$, —CH$_2$CH$_2$OCH$_3$, —CH$_2$NH$_2$, —CH$_2$NHCH$_3$, —CH$_2$N(CH$_3$)$_2$, —CH$_2$CH$_2$NH$_2$, —CH$_2$CH$_2$NHCH$_3$, —CH$_2$CH$_2$N(CH$_3$)$_2$, unsubstituted or substituted cyclopropyl, unsubstituted or substituted cyclobutyl, unsubstituted or substituted cyclopentyl, unsubstituted or substituted cyclohexyl, unsubstituted or substituted $C_2$-$C_7$ heterocycloalkyl, unsubstituted or substituted phenyl or unsubstituted or substituted monocyclic heteroaryl, wherein any substituted group of $R^d$ is substituted with one or more $R^9$ groups; $R^e$ and $R^f$ are independently selected from the group consisting of F, $C_1$, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, and —OCH$_2$CH$_3$.

In some embodiments, the compound has the structure of Formula (VIII), or a pharmaceutically acceptable salt, or solvate thereof:

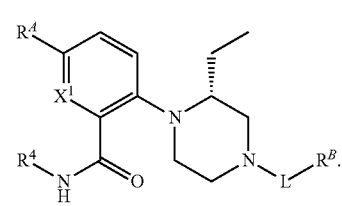

Formula (VIII)

In some embodiments, $R^A$, $R^B$, $R^4$, and $X^1$ are as described in Table 1, Table 2 or Table 3.

In some embodiments, the compound of Formula (I) or Formula (II) has the structure of Formula (IX), or a pharmaceutically acceptable salt, or solvate thereof:

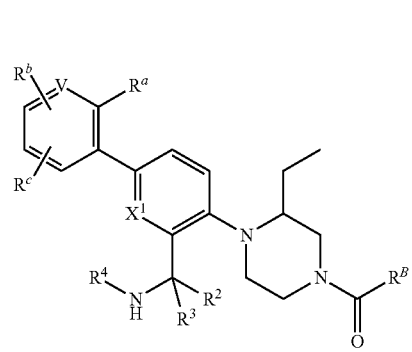

Formula (IX)

wherein,
V is CH or N.

In some embodiments, the compound has the structure of Formula (IX), or a pharmaceutically acceptable salt, or solvate thereof, wherein:

V is CH or N;

$R^a$ is selected from the group consisting of hydrogen, halogen, —OR$^8$, —CN, —N($R^7$)$_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, wherein any substituted group of IV is substituted with one or more $R^9$ groups;

$R^b$ and $R^c$ are each independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, wherein any substituted group of $R^b$ and $R^c$ is substituted with one or more $R^9$ groups;

$R^B$ is unsubstituted or substituted carbocycle, unsubstituted or substituted heterocycle, unsubstituted or substituted $C_1$-$C_7$ alkyl, unsubstituted or substituted $C_1$-$C_7$ fluoroalkyl, unsubstituted or substituted $C_1$-$C_6$ heteroalkyl, wherein if $R^B$ is substituted then $R^B$ is substituted with $R^d$, $R^e$ and $R^f$;

$R^d$ is selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, unsubstituted or substituted $C_3$-$C_6$ cycloalkyl, unsubstituted or substituted $C_2$-$C_7$ heterocycloalkyl, unsubstituted or substituted phenyl or unsubstituted or substituted monocyclic heteroaryl, wherein any substituted group of $R^d$ is substituted with one or more $R^9$ groups;

$R^e$ and $R^f$ are each independently selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, unsubstituted or substituted $C_1$-$C_6$ heteroalkyl, wherein any substituted group of $R^e$ and $R^f$ is substituted with one or more $R^9$ groups;

$X^1$ is $CR^6$ or N;

$R^2$ and $R^3$ are hydrogen;

or $R^2$ and $R^3$ are taken together with the carbon atom to which they are attached to form —C(=O)—;

$R^4$ is selected from the group consisting of hydrogen, unsubstituted or substituted $C_1$-$C_6$ alkyl, unsubstituted or substituted monocyclic carbocycle, unsubstituted or substituted monocyclic heterocycle, unsubstituted or substituted —($C_1$-$C_6$ alkyl)-carbocycle, or unsubstituted or substituted —($C_1$-$C_6$ alkyl)-heterocycle, wherein any substituted group of $R^4$ is substituted with one or more halogen, unsubstituted or substituted $C_1$-$C_6$ alkyl, unsubstituted or substituted monocyclic heterocycle, —$N(R^7)_2$, —$OR^8$, —CN, —$CO_2R^8$, —C(=O)$N(R^7)_2$, —S(=O)$R^{10}$, —S(=O)$_2R^{10}$, —$NR^7C$(=O)$R^8$, —$NR^7SO_2R^{10}$, —$SO_2R^{10}$, or —$SO_2N(R^7)_2$;

$R^6$ is H or F;

each $R^7$ is independently selected from the group consisting of hydrogen, substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, unsubstituted or substituted heteroaryl;

or two $R^7$ are taken together with the nitrogen atom to which they are attached to form an unsubstituted or substituted 3- to 6-membered monocyclic heterocycle;

each $R^8$ is independently selected from the group consisting of hydrogen, substituted or substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted aryl, and unsubstituted or substituted heteroaryl;

each $R^9$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^8$, —$CH_2CO_2R^8$, —C(=O)$N(R^7)_2$, —C(=O)$N(R^7)OR^8$, —$CH_2C$(=O)$N(R^7)_2$, —$N(R^7)_2$, —$CH_2N(R^7)_2$, —$C(R^8)_2N(R^7)_2$, —$NR^7C$(=O)$R^8$, —$CH_2NR^7C$(=O)$R^8$, —$NR^7C$(=O)$N(R^7)_2$, —$NR^7C$(=O)$N(R^7)_2$, $C(R^8)$=$N(R^7)$—$OR^8$, —$SR^8$, —S(=O)$R^{10}$, —$SO_2R^{10}$, or —$SO_2N(R^7)_2$; and each $R^{10}$ is independently selected from the group consisting substituted or substituted $C_1$-$C_6$ alkyl, unsubstituted or substituted $C_3$-$C_6$ cycloalkyl, unsubstituted or substituted $C_1$-$C_6$fluoroalkyl, unsubstituted or substituted phenyl, and unsubstituted or substituted heteroaryl.

In some embodiments, V is CH. In some embodiments, V is N.

In some embodiments, IV is selected from the group consisting of hydrogen, halogen, —$OR^8$, —CN, —$N(R^7)_2$, unsubstituted or substituted $C_1$-$C_6$ alkyl, unsubstituted or substituted $C_1$-$C_6$ fluoroalkyl, and unsubstituted or substituted $C_1$-$C_6$ heteroalkyl, wherein any substituted group of IV is substituted with one or more $R^9$ groups; and $R^b$ and $R^c$ are each independently selected from the group consisting of hydrogen, halogen, —$OR^8$, —$N(R^7)_2$, and unsubstituted or substituted $C_1$-$C_6$ alkyl, wherein any substituted group of $R^b$ and $R^c$ is substituted with one or more $R^9$ groups. In some embodiments, IV is hydrogen, Cl, Br, —CN, —OH, —$OCH_3$, —$OCH_2CH_3$, —$CH_3$, —$CH_2CH_3$, —$CH_2CH_2CH_3$, —CH($CH_3$)$_2$, —$CH_2CH_2CH_2CH_3$, —$CH_2CH(CH_3)_2$, —CH($CH_3$)($CH_2CH_3$), —C($CH_3$)$_3$, —$CH_2OH$, —$CH_2CN$, —$CH_2F$, —$CHF_2$, —$CF_3$, —$CH_2CH_2OH$, —$CH_2CH_2CN$, —$CH_2CH_2F$, —$CH_2CHF_2$, —$CH_2CF_3$, —$CH_2OCH_3$, —$CH_2CH_2OCH_3$, —$CH_2NH_2$, —$CH_2NHCH_3$, —$CH_2N(CH_3)_2$, —$CH_2CH_2NH_2$, —$CH_2CH_2NHCH_3$, —$CH_2CH_2N(CH_3)_2$, cyclopropyl, cyclobutyl, cyclopentyl, or cyclohexyl; $R^b$ and $R^c$ are hydrogen. In some embodiments, $R^a$ is —$OR^8$; and $R^b$ and $R^c$ are hydrogen. In some embodiments, $R^a$ is —OH, —$OCH_3$, or —$OCH_2CH_3$; and $R^b$ and $R^c$ are hydrogen.

In some embodiments, $X^1$ is CH, CF or N; V is CH or N; $R^2$ and $R^3$ are hydrogen; or $R^2$ and $R^3$ are taken together with the carbon atom to which they are attached to form —C(=O)—; $R^a$ is —$OCH_2CH_3$; $R^b$ and $R^c$ are hydrogen.

In some embodiments, $X^1$ is CH, CF or N; V is CH or N; $R^2$ and $R^3$ are hydrogen; or $R^2$ and $R^3$ are taken together with the carbon atom to which they are attached to form —C(=O)—; $R^a$ is —$OCH_2CH_3$; $R^b$ and $R^c$ are hydrogen; $R^B$ is as described in Table 1 and/or Table 2. $R^4$ is as described in Table 1 and/or Table 2.

In some embodiments, each $R^7$ is independently selected from the group consisting of hydrogen, substituted $C_1$-$C_6$ alkyl, unsubstituted or substituted $C_3$-$C_6$ cycloalkyl, and unsubstituted or substituted $C_1$-$C_6$fluoroalkyl; or two $R^7$ are taken together with the nitrogen atom to which they are attached to form an unsubstituted or substituted 3- to 6-membered monocyclic heterocycle. In some embodiments, each $R^7$ is independently selected from the group consisting of hydrogen, and substituted $C_1$-$C_6$ alkyl; or two $R^7$ are taken together with the nitrogen atom to which they are attached to form an unsubstituted or substituted 3- to 6-membered monocyclic heterocycle.

In some embodiments, each $R^8$ is independently selected from the group consisting of hydrogen, substituted or substituted $C_1$-$C_6$ alkyl, unsubstituted or substituted $C_3$-$C_6$ cycloalkyl, and unsubstituted or substituted $C_1$-$C_6$fluoroalkyl. In some embodiments, each $R^8$ is independently selected from the group consisting of hydrogen, substituted or substituted $C_1$-$C_6$ alkyl, and unsubstituted or substituted $C_3$-$C_6$ cycloalkyl. In some embodiments, each $R^8$ is independently selected from the group consisting of hydrogen and substituted or substituted $C_1$-$C_6$ alkyl.

In some embodiments, each $R^9$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —CO$_2$R$^8$, —CH$_2$CO$_2$R$^8$, —C(=O)N(R$^7$)$_2$, —CH$_2$C(=O)N(R$^7$)$_2$, —N(R$^7$)$_2$, —CH$_2$N(R$^7$)$_2$, —NR$^7$C(=O)R$^8$, or —CH$_2$NR$^7$C(=O)R$^8$. In some embodiments, each $R^9$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, —CN, —OH, —CO$_2$R$^8$, —C(=O)N(R$^7$)$_2$, —N(R$^7$)$_2$, or —CH$_2$N(R$^7$)$_2$.

In some embodiments, each $R^{10}$ is independently selected from the group consisting substituted or substituted $C_1$-$C_6$ alkyl, unsubstituted or substituted $C_3$-$C_6$ cycloalkyl, unsubstituted or substituted $C_1$-$C_6$fluoroalkyl, and unsubstituted or substituted phenyl. In some embodiments, each $R^{10}$ is independently selected from the group consisting substituted or substituted $C_1$-$C_6$ alkyl and unsubstituted or substituted phenyl.

In some embodiments, the compound of Formula (IX) has the structure of Formula (IXa), or a pharmaceutically acceptable salt, or solvate thereof:

Formula (IXa)

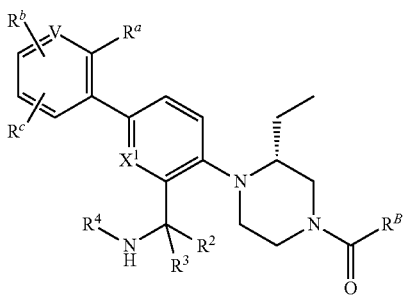

wherein,
V is CH or N.

In some embodiments, $R^B$, $R^4$, and $X^1$ are as described in Table 1 and/or Table 2.

In some embodiments, compounds described herein have the following structure:

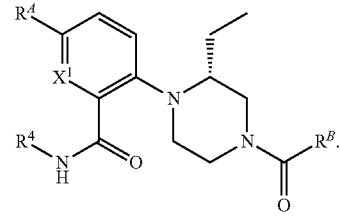

In some embodiments, $R^A$, $R^B$, $R^4$, and $X^1$ are as described herein.

In some embodiments, $R^A$, $R^B$, $R^4$, and $X^1$ are as described in Table 1.

In some embodiments, compounds described herein have the following structure:

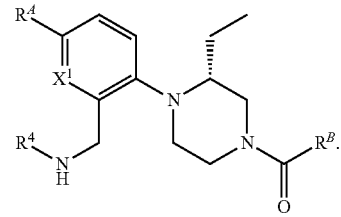

In some embodiments, $R^A$, $R^B$, $R^4$, and $X^1$ are as described herein.

In some embodiments, $R^A$, $R^B$, $R^4$, and $X^1$ are as described in Table 2.

In some embodiments, compounds described herein have the following structure:

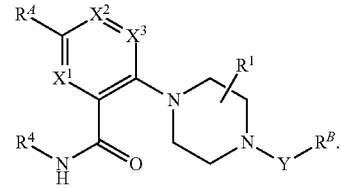

In some embodiments, $R^A$, $R^B$, $R^1$, $R^4$, and $X^1$, $X^2$, $X^3$ are as described herein.

In some embodiments, $R^A$, $R^B$, $R^1$, $R^4$ and $X^1$, $X^2$, $X^3$ are as described in Table 3.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in the following Tables:

TABLE 1

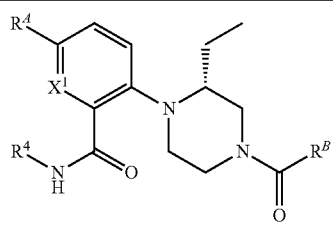

| Compound No. | $R^A$ | $R^B$ | $X^1$ | $R^4$ |
|---|---|---|---|---|
| 1-1 | 2,3-difluorophenyl | 2-chloro-4-(trifluoromethyl)phenyl | CH | —CH$_2$CH$_2$NH$_2$ |
| 1-2 | 2-methoxyphenyl | 2-chloro-4-(trifluoromethyl)phenyl | CH | —CH$_2$CH$_2$NH$_2$ |
| 1-3 | 2-ethoxyphenyl | 2-chloro-4-(trifluoromethyl)phenyl | CH | —CH$_2$CH$_2$NH$_2$ |
| 1-4 | 2-fluorophenyl | 2-chloro-4-(trifluoromethyl)phenyl | CH | —CH$_2$CH$_2$NH$_2$ |
| 1-5 | 2-ethylphenyl | 2-chloro-4-(trifluoromethyl)phenyl | CH | —CH$_2$CH$_2$NH$_2$ |
| 1-6 | 2-chlorophenyl | 2-chloro-4-(trifluoromethyl)phenyl | CH | —CH$_2$CH$_2$NH$_2$ |
| 1-7 | 2-cyanophenyl | 2-chloro-4-(trifluoromethyl)phenyl | CH | —CH$_2$CH$_2$NH$_2$ |
| 1-8 | 2-methylphenyl | 2-chloro-4-(trifluoromethyl)phenyl | CH | —CH$_2$CH$_2$NH$_2$ |

TABLE 1-continued

| Compound No. | $R^A$ | $R^B$ | $X^1$ | $R^4$ |
|---|---|---|---|---|
| 1-9 | 2-chloro-3-fluorophenyl | 2-chloro-4-(trifluoromethyl)phenyl | CH | —CH$_2$CH$_2$NH$_2$ |
| 1-10 | 3-ethoxyphenyl | 2-chloro-4-(trifluoromethyl)phenyl | CH | —CH$_2$CH$_2$NH$_2$ |
| 1-11 | 2-propoxyphenyl | 2-chloro-4-(trifluoromethyl)phenyl | CH | —CH$_2$CH$_2$NH$_2$ |
| 1-12 | 2-isopropoxyphenyl | 2-chloro-4-(trifluoromethyl)phenyl | CH | —CH$_2$CH$_2$NH$_2$ |
| 1-13 | 2-hydroxyphenyl | 2-chloro-4-(trifluoromethyl)phenyl | CH | —CH$_2$CH$_2$NH$_2$ |
| 1-14 | 2-cyclopropoxyphenyl | 2-chloro-4-(trifluoromethyl)phenyl | CH | —CH$_2$CH$_2$NH$_2$ |
| 1-15 | 2-ethoxyphenyl | 2,4-dichlorophenyl | CH | —CH$_2$CH$_2$NH$_2$ |
| 1-16 | 2-(methoxymethyl)phenyl | 2-chloro-4-(trifluoromethyl)phenyl | CH | —CH$_2$CH$_2$NH$_2$ |

TABLE 1-continued
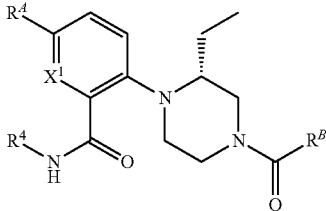
| Compound No. | $R^A$ | $R^B$ | $X^1$ | $R^4$ |
|---|---|---|---|---|
| 1-17 | 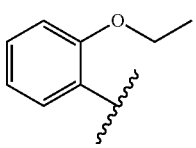 | 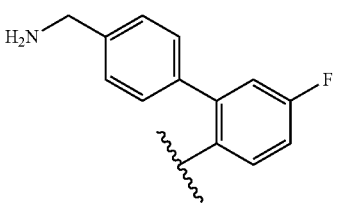 [SMILES: *c1ccc(F)cc1-c1ccc(CN)cc1] | CH | —CH$_2$CH$_2$NH$_2$ |
| 1-18 | 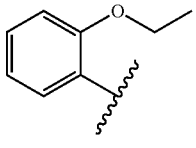 [SMILES: *c1ccccc1OCC] | 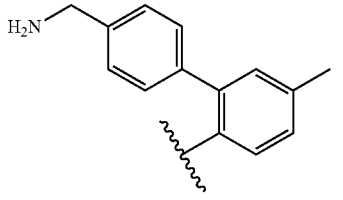 [SMILES: *c1ccc(C)cc1-c1ccc(CN)cc1] | CH | —CH$_2$CH$_2$NH$_2$ |
| 1-19 | 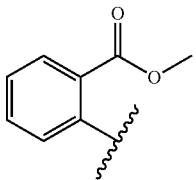 [SMILES: *c1ccccc1C(=O)OC] | 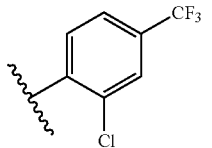 [SMILES: *c1ccc(C(F)(F)F)cc1Cl] | CH | —CH$_2$CH$_2$NH$_2$ |
| 1-20 | 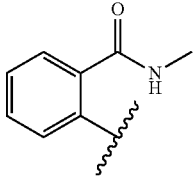 | 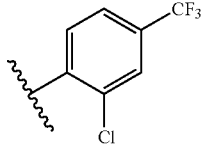 [SMILES: *c1ccc(C(F)(F)F)cc1Cl] | CH | —CH$_2$CH$_2$NH$_2$ |
| 1-21 | 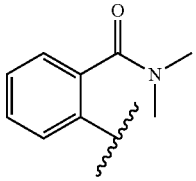 [SMILES: *c1ccccc1C(=O)N(C)C] | 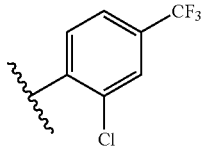 | CH | —CH$_2$CH$_2$NH$_2$ |
| 1-22 | 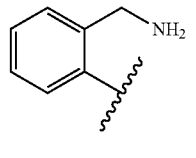 [SMILES: *c1ccccc1CN] | 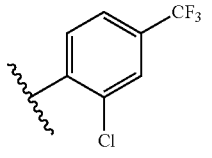 [SMILES: *c1ccc(C(F)(F)F)cc1Cl] | CH | —CH$_2$CH$_2$NH$_2$ |

TABLE 1-continued

| Compound No. | $R^A$ | $R^B$ | $X^1$ | $R^4$ |
|---|---|---|---|---|
| 1-23 | 2-ethoxyphenyl | 2-chloro-4-(trifluoromethyl)phenyl | CH | —CH$_2$(CH$_2$)$_2$NH$_2$ |
| 1-24 | 2-ethoxyphenyl | 4'-(aminomethyl)biphenyl-2-yl | CH | —CH$_2$(CH$_2$)$_2$NH$_2$ |
| 1-25 | 2-ethoxyphenyl | 4-chloro-2-(trifluoromethyl)phenyl | CH | —CH$_2$CH$_2$NH$_2$ |
| 1-26 | 2-ethoxyphenyl | 4'-(aminomethyl)-3'-fluorobiphenyl-2-yl | CH | —CH$_2$CH$_2$NH$_2$ |
| 1-27 | 2-ethoxyphenyl | 4'-(aminomethyl)-3,5'-difluoro-biphenyl-2-yl | CH | —CH$_2$CH$_2$NH$_2$ |
| 1-28 | 2-ethylphenyl | 2-chloro-4-(trifluoromethyl)phenyl | CH | —CH$_2$CH$_2$NH$_2$ |
| 1-29 | 4-ethylphenyl | 2-chloro-4-(trifluoromethyl)phenyl | CH | —CH$_2$CH$_2$NH$_2$ |

TABLE 1-continued
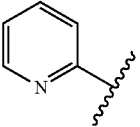 [SMILES: *c1ccccn1]
| Compound No. | R^A | R^B | X^1 | R^4 |
|---|---|---|---|---|
| 1-30 | 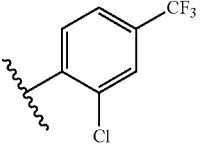 [SMILES: *c1ccc(C(F)(F)F)cc1Cl] | 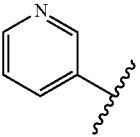 [SMILES: *c1cccnc1] | CH | —$CH_2CH_2NH_2$ |
| 1-31 | 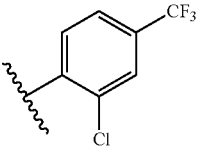 | 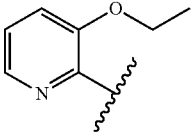 [SMILES: *c1ncccc1OCC] | CH | —$CH_2CH_2NH_2$ |
| 1-32 | 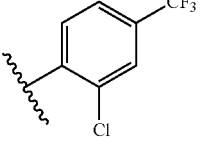 | 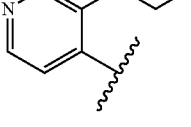 | CH | —$CH_2CH_2NH_2$ |
| 1-33 | 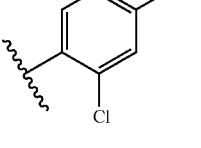 | 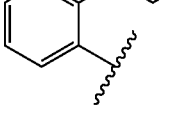 | CH | —$CH_2CH_2NH_2$ |
| 1-34 | 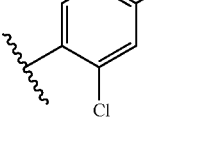 | 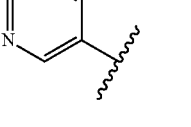 | CH | —$CH_2CH_2NH_2$ |
| 1-35 | 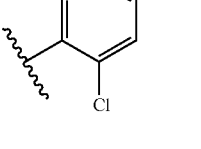 | 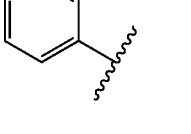 | CH | —$CH_2CH_2NH_2$ |
| 1-36 | 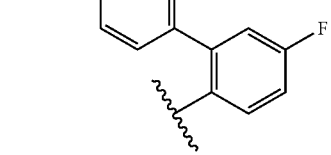 | | CH | —$CH_2CH_2NH_2$ |

TABLE 1-continued

| Compound No. | $R^A$ | $R^B$ | $X^1$ | $R^4$ |
|---|---|---|---|---|
| 1-37 | 2-ethoxypyridin-3-yl | 2-chloro-4-chloro-5-trifluoromethylphenyl (4-Cl, 2-CF₃-phenyl) | CH | —CH₂CH₂NH₂ |
| 1-38 | 2-ethoxypyridin-3-yl | 2-chloro-4-fluorophenyl | CH | —CH₂CH₂NH₂ |
| 1-39 | 2-ethoxypyridin-3-yl | 5-fluoro-2-(pyridin-4-yl)phenyl | CH | —CH₂CH₂NH₂ |
| 1-40 | 2-ethoxypyridin-3-yl | 2-[3-(aminomethyl)pyrrolidin-1-yl]-4-chlorophenyl | CH | —CH₂CH₂NH₂ |
| 1-41 | 2-ethoxypyridin-3-yl | 2-[(3R)-3-(aminomethyl)pyrrolidin-1-yl]-4-chlorophenyl | CH | —CH₂CH₂NH₂ |
| 1-42 | 2-ethoxypyridin-3-yl | 2-chloro-4-(trifluoromethyl)phenyl | CH | —CH₂CH₂NH₂ |
| 1-43 | 2-ethoxypyridin-3-yl | 2-chloro-4-methylphenyl | CH | —CH₂CH₂NH₂ |

TABLE 1-continued
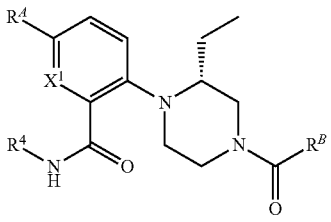
| Compound No. | $R^A$ | $R^B$ | $X^1$ | $R^4$ |
|---|---|---|---|---|
| 1-44 | 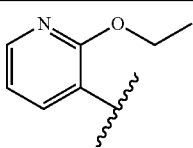 | 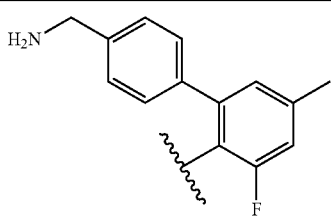 | CH | —CH$_2$CH$_2$NH$_2$ |
| 1-45 | 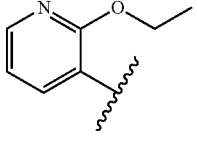 [SMILES: *c1cccnc1OCC] | 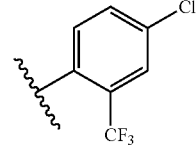 [SMILES: *c1ccc(Cl)cc1C(F)(F)F] | CH | 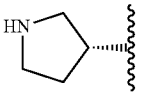 |
| 1-46 | 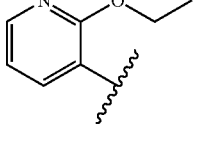 | 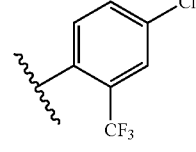 | CH | 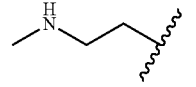 [SMILES: *CCNC] |
| 1-47 | 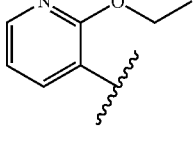 | 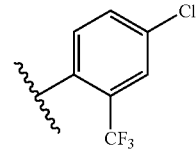 [SMILES: *c1ccc(Cl)cc1C(F)(F)F] | CH | 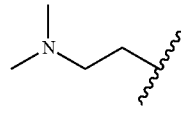 [SMILES: *CCN(C)C] |
| 1-48 | 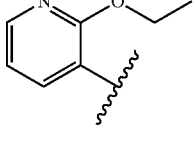 | 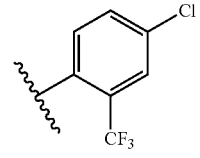 [SMILES: *c1ccc(Cl)cc1C(F)(F)F] | CH | 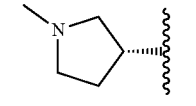 [SMILES: *[C@@H]1CCN(C)C1] |
| 1-49 | 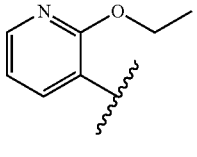 [SMILES: *c1cccnc1OCC] | 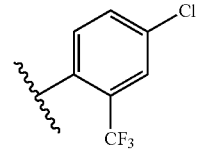 [SMILES: *c1ccc(Cl)cc1C(F)(F)F] | CH | 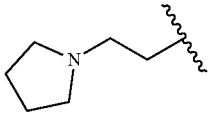 [SMILES: *CCN1CCCC1] |
| 1-50 | 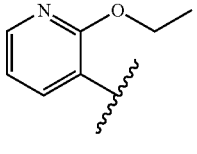 [SMILES: *c1cccnc1OCC] | 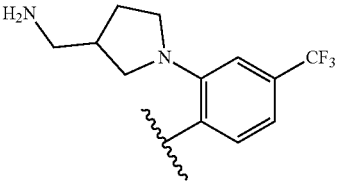 [SMILES: *c1ccc(C(F)(F)F)cc1N1CCC(CN)C1] | CH | —CH$_2$CH$_2$NH$_2$ |

TABLE 1-continued

| Compound No. | R^A | R^B | X^1 | R^4 |
|---|---|---|---|---|
| 1-51 | 2-ethoxypyridin-3-yl | (1-(5-fluoro-2-yl-phenyl)pyrrolidin-3-yl)methanamine | CH | —CH$_2$CH$_2$NH$_2$ |
| 1-52 | 2-ethoxypyridin-3-yl | 1-(5-chloro-2-yl-phenyl)piperidin-4-amine | CH | —CH$_2$CH$_2$NH$_2$ |
| 1-53 | 2-ethoxypyridin-3-yl | 3,5-dichloropyridin-2-yl | CH | —CH$_2$CH$_2$NH$_2$ |
| 1-54 | 2-ethoxypyridin-3-yl | 4-chloro-2-methoxyphenyl | CH | —CH$_2$CH$_2$NH$_2$ |
| 1-55 | 2-ethoxypyridin-3-yl | 2,4-dichlorophenyl | CH | —CH$_2$CH$_2$NH$_2$ |
| 1-56 | 2-ethoxypyridin-3-yl | (1-(3-fluoro-4-yl-phenyl)pyrrolidin-3-yl)methanamine | CH | —CH$_2$CH$_2$NH$_2$ |
| 1-57 | 2-ethoxypyridin-3-yl | (S)-1-(5-chloro-2-yl-phenyl)pyrrolidin-3-amine | CH | —CH$_2$CH$_2$NH$_2$ |

TABLE 1-continued

| Compound No. | $R^A$ | $R^B$ | $X^1$ | $R^4$ |
|---|---|---|---|---|
| 1-58 | 2-ethoxypyridin-3-yl | 4-fluoro-2-(trifluoromethyl)phenyl | CH | —CH$_2$CH$_2$NH$_2$ |
| 1-59 | 2-ethoxypyridin-3-yl | 4-methyl-2-(trifluoromethyl)phenyl | CH | —CH$_2$CH$_2$NH$_2$ |
| 1-60 | 2-ethoxypyridin-3-yl | 2,4-dimethylphenyl | CH | —CH$_2$CH$_2$NH$_2$ |
| 1-61 | 2-ethoxypyridin-3-yl | 4-chloro-2-(pyrrolidin-1-yl)phenyl | CH | —CH$_2$CH$_2$NH$_2$ |
| 1-62 | 2-ethoxypyridin-3-yl | 2-(trifluoromethyl)phenyl | CH | —CH$_2$CH$_2$NH$_2$ |
| 1-63 | 2-ethoxypyridin-3-yl | 2-cyclopropylphenyl | CH | —CH$_2$CH$_2$NH$_2$ |
| 1-64 | 2-ethoxypyridin-3-yl | 4-chloro-2-(trifluoromethyl)phenyl | CH | pyridin-2-ylmethyl |

TABLE 1-continued
| Compound No. | $R^A$ | $R^B$ | $X^1$ | $R^4$ |
|---|---|---|---|---|
| 1-65 | 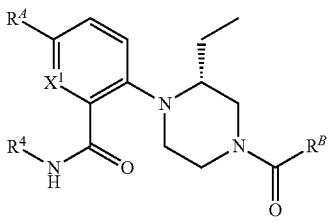 | 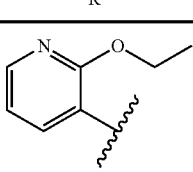 | CH | 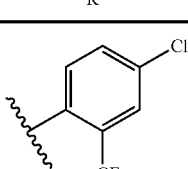 |
| 1-66 | 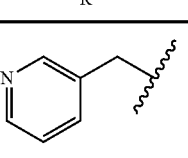 | 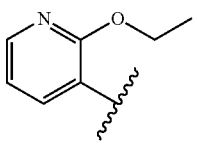 [SMILES: *c1cccnc1OCC] | CH | 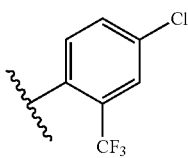 [SMILES: *c1ccc(Cl)cc1C(F)(F)F] |
| 1-67 | 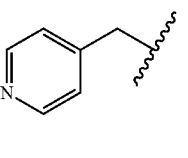 [SMILES: *Cc1ccncc1] | 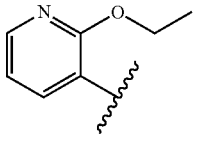 [SMILES: *c1cccnc1OCC] | CH | —CH$_2$CH$_2$NH$_2$ |
| 1-68 | 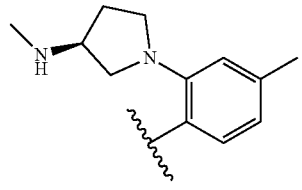 | 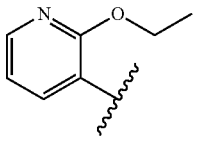 [SMILES: *c1cccnc1OCC] | CH | —CH$_2$CH$_2$NH$_2$ |
| 1-69 | 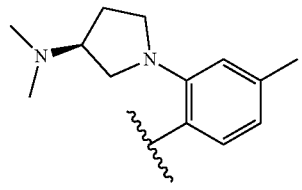 | 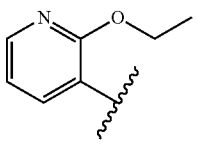 [SMILES: *c1cccnc1OCC] | CF | —CH$_2$CH$_2$NH$_2$ |
| 1-70 | 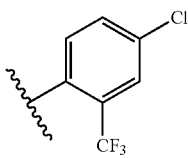 | 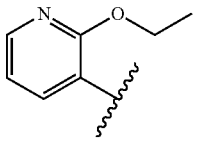 [SMILES: *c1cccnc1OCC] | CH | 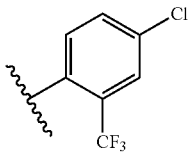 [SMILES: *c1ccc(Cl)cc1C(F)(F)F] |
| 1-71 | 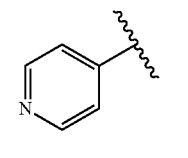 [SMILES: *c1ccncc1] | 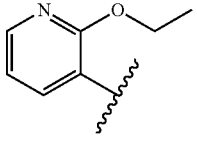 [SMILES: *c1cccnc1OCC] | CH | —CH$_2$CH$_2$NH$_2$ |

TABLE 1-continued

| Compound No. | R^A | R^B | X^1 | R^4 |
|---|---|---|---|---|
| 1-72 | 2-ethoxypyridin-3-yl | 4-chloro-2-(trifluoromethyl)phenyl | CF | (R)-pyrrolidin-3-yl |
| 1-73 | 2-ethoxypyridin-3-yl | 2-chloro-4-fluorophenyl | CF | (R)-pyrrolidin-3-yl |
| 1-74 | 2-ethoxypyridin-3-yl | 4-fluoro-2-(piperidin-4-yl)phenyl | CH | —CH$_2$CH$_2$NH$_2$ |
| 1-75 | 2-ethoxypyridin-3-yl | 2-(6-aminopyridin-3-yl)-4-fluorophenyl | CH | —CH$_2$CH$_2$NH$_2$ |
| 1-76 | 2-ethoxypyridin-3-yl | 2-(dimethylamino)-6-(trifluoromethyl)pyridin-3-yl | CH | —CH$_2$CH$_2$NH$_2$ |
| 1-77 | 2-ethoxypyridin-3-yl | 2,6-dimethylpyridin-3-yl | CH | —CH$_2$CH$_2$NH$_2$ |
| 1-78 | 2-ethoxypyridin-3-yl | 4-fluoro-2-methylphenyl | CH | —CH$_2$CH$_2$NH$_2$ |

TABLE 1-continued

| Compound No. | R^A | R^B | X^1 | R^4 |
|---|---|---|---|---|
| 1-79 | 2-ethoxypyridin-3-yl | 4-fluoro-2-methoxyphenyl | CH | —CH$_2$CH$_2$NH$_2$ |
| 1-80 | 2-ethoxypyridin-3-yl | 4-methyl-2-methoxyphenyl | CH | —CH$_2$CH$_2$NH$_2$ |
| 1-81 | 2-ethoxypyridin-3-yl | 4-tert-butylphenyl | CH | —CH$_2$CH$_2$NH$_2$ |
| 1-82 | 2-ethoxypyridin-3-yl | 2-chloro-4-fluorophenyl | CH | (R)-pyrrolidin-3-yl |
| 1-83 | 2-ethoxypyridin-3-yl | 4-chloro-2-(trifluoromethyl)phenyl | CH | (1H-imidazol-4-yl)methyl |
| 1-84 | 2-ethoxypyridin-3-yl | 4-chloro-2-(trifluoromethyl)phenyl | CH | 2-(1H-imidazol-4-yl)ethyl |
| 1-85 | 2-ethoxypyridin-3-yl | 2-amino-4-(5-fluoro-2-yl)pyridin-4-yl | CH | —CH$_2$CH$_2$NH$_2$ |

TABLE 1-continued

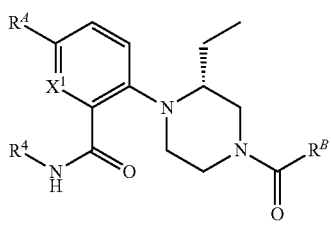

| Compound No. | R^A | R^B | X^1 | R^4 |
|---|---|---|---|---|
| 1-86 | 2-ethoxypyridin-3-yl | 2,6-dimethylpyridin-3-yl | CH | —CH$_2$CH$_2$NH$_2$ |
| 1-87 | 2-ethoxypyridin-3-yl | 4-chloro-2-methylphenyl | CH | —CH$_2$CH$_2$NH$_2$ |
| 1-88 | 2-ethoxypyridin-3-yl | 4-cyclopropyl-2-methylphenyl | CH | —CH$_2$CH$_2$NH$_2$ |
| 1-89 | 2-ethoxypyridin-3-yl | 3-chloro-5-fluoropyridin-2-yl | CH | —CH$_2$CH$_2$NH$_2$ |
| 1-90 | 2-ethoxypyridin-3-yl | 4-chloro-2-(piperazin-1-yl)phenyl | CH | pyrrolidin-3-yl |
| 1-91 | 2-ethoxypyridin-3-yl | 4-chloro-2-(dimethylamino)phenyl | CH | pyrrolidin-3-yl |
| 1-92 | 2-ethoxypyridin-3-yl | 4-chloro-2-(trifluoromethyl)phenyl | CH | (R)-pyrrolidin-3-yl |

US 11,566,015 B2
TABLE 1-continued
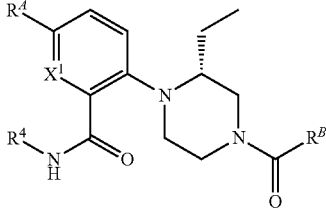
| Compound No. | R^A | R^B | X^1 | R^4 |
|---|---|---|---|---|
| 1-93 | 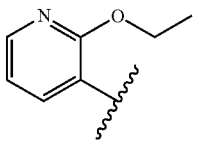 [SMILES: *c1cccnc1OCC] | 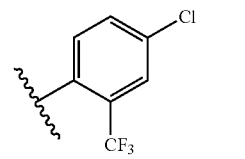 [SMILES: *c1ccc(Cl)cc1C(F)(F)F] | CH | 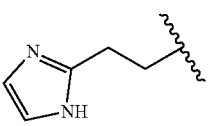 [SMILES: *CCc1ncc[nH]1] |
| 1-94 | 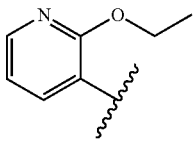 [SMILES: *c1cccnc1OCC] | 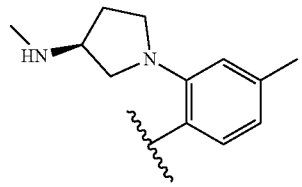 | CH | 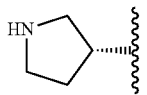 |
| 1-95 | 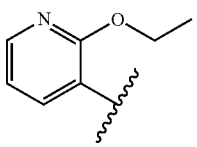 [SMILES: *c1cccnc1OCC] | 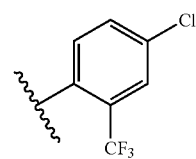 [SMILES: *c1ccc(Cl)cc1C(F)(F)F] | CF | 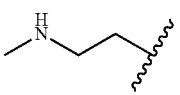 |
| 1-96 | 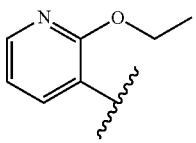 | 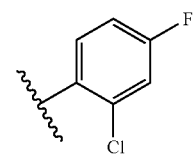 [SMILES: *c1ccc(F)cc1Cl] | CF | 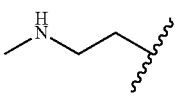 |
| 1-97 | 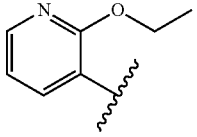 [SMILES: *c1cccnc1OCC] | 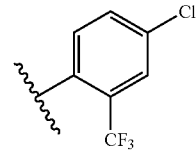 [SMILES: *c1ccc(Cl)cc1C(F)(F)F] | CH | 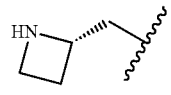 |
| 1-98 | 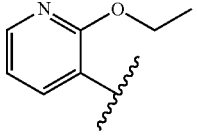 [SMILES: *c1cccnc1OCC] | 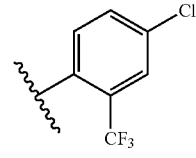 | CH | 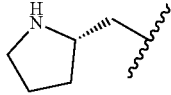 |
| 1-99 | 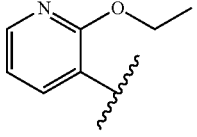 [SMILES: *c1cccnc1OCC] | 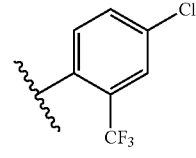 | CH | 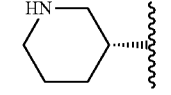 |

TABLE 1-continued

| Compound No. | R^A | R^B | X^1 | R^4 |
|---|---|---|---|---|
| 1-100 | 2-ethoxypyridin-3-yl | 4-chloro-2-(trifluoromethyl)phenyl | CH | piperidin-3-yl (HN) |
| 1-101 | 2-ethoxypyridin-3-yl | 2-[(3S)-3-(methylamino)pyrrolidin-1-yl]-4-fluorophenyl | CH | pyrrolidin-3-yl (HN) |
| 1-102 | 2-ethoxypyridin-3-yl | 4-chloro-2-(trifluoromethyl)phenyl | CH | azetidin-2-ylmethyl (HN) |
| 1-103 | 2-ethoxypyridin-3-yl | 4-[(3R)-3-(methylamino)pyrrolidin-1-yl]-2-fluorophenyl | CH | pyrrolidin-3-yl (HN) |
| 1-104 | 2-ethoxypyridin-3-yl | 2-[3-(aminomethyl)pyrrolidin-1-yl]-4-methylphenyl | CH | —CH₂CH₂NH₂ |
| 1-105 | 2-ethoxypyridin-3-yl | 2-morpholino-6-(trifluoromethyl)pyridin-3-yl | CH | —CH₂CH₂NH₂ |
| 1-106 | 2-ethoxypyridin-3-yl | 3-(dimethylamino)-5-(trifluoromethyl)pyridin-2-yl | CH | —CH₂CH₂NH₂ |

TABLE 1-continued

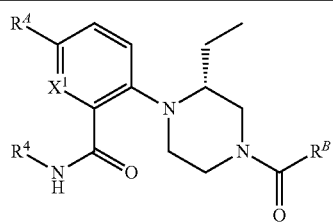

| Compound No. | R^A | R^B | X^1 | R^4 |
|---|---|---|---|---|
| 1-107 | 2-ethoxypyridin-3-yl | 2-(dimethylamino)-5-(trifluoromethyl)phenyl | CH | —CH₂CH₂NH₂ |
| 1-108 | 2-ethoxypyridin-3-yl | 4-chloro-2-(trifluoromethyl)phenyl | CH | (pyrrolidin-2-yl)methyl |
| 1-109 | 2-ethoxypyridin-3-yl | 4-chloro-2-(trifluoromethyl)phenyl | CH | (morpholin-2-yl)methyl |
| 1-110 | 2-ethoxypyridin-3-yl | 2-chloro-4-methylphenyl | CF | pyrrolidin-3-yl |
| 1-111 | 2-ethoxypyridin-3-yl | 4-fluoro-2-(trifluoromethyl)phenyl | CF | pyrrolidin-3-yl |
| 1-112 | 2-ethoxypyridin-3-yl | 4-chloro-2-(trifluoromethyl)phenyl | CF | (azetidin-2-yl)methyl |
| 1-113 | 2-ethoxypyridin-3-yl | 2-chloro-4-methylphenyl | CF | 3-(methylamino)propyl |
| 1-114 | 2-ethoxypyridin-3-yl | 4-fluoro-2-(trifluoromethyl)phenyl | CF | 3-(methylamino)propyl |

TABLE 1-continued

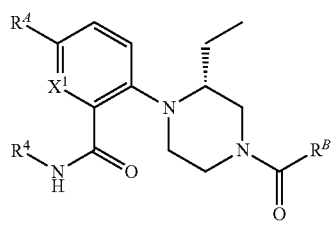

| Compound No. | $R^A$ | $R^B$ | $X^1$ | $R^4$ |
|---|---|---|---|---|
| 1-115 | 2-ethoxypyridin-3-yl | 5-chloro-2-(3-(dimethylamino)pyrrolidin-1-yl)phenyl | CH | (R)-pyrrolidin-3-yl |
| 1-116 | 2-ethoxypyridin-3-yl | 4-chloro-2-(trifluoromethyl)phenyl | CF | 2-(1H-imidazol-2-yl)ethyl |
| 1-117 | 2-ethoxypyridin-3-yl | 4-chloro-2-cyanophenyl | CH | —CH$_2$CH$_2$NH$_2$ |
| 1-118 | 2-ethoxypyridin-3-yl | 5-fluoro-3-(trifluoromethyl)pyridin-2-yl | CH | —CH$_2$CH$_2$NH$_2$ |
| 1-119 | 2-ethoxypyridin-3-yl | 2-(methylamino)-6-(trifluoromethyl)pyridin-3-yl | CH | —CH$_2$CH$_2$NH$_2$ |
| 1-120 | 2-ethoxypyridin-3-yl | 2-(pyrrolidin-1-yl)-6-(trifluoromethyl)pyridin-3-yl | CH | —CH$_2$CH$_2$NH$_2$ |
| 1-121 | 2-ethoxypyridin-3-yl | 2-(trifluoromethyl)phenyl | CF | 2-(methylamino)ethyl |

TABLE 1-continued

| Compound No. | R^A | R^B | X^1 | R^4 |
|---|---|---|---|---|
| 1-122 | 2-ethoxypyridin-3-yl | 2-(trifluoromethyl)phenyl | CF | (R)-pyrrolidin-3-yl |
| 1-123 | 2-ethoxypyridin-3-yl | 4-chloro-2-(trifluoromethyl)phenyl | CF | (S)-azetidin-2-ylmethyl |
| 1-124 | 2-ethoxypyridin-3-yl | 4-chloro-2-(trifluoromethyl)phenyl | CF | imidazolidin-2-ylmethyl |
| 1-125 | 2-ethoxypyridin-3-yl | 4-chloro-2-(trifluoromethyl)phenyl | CH | 4,5-dihydro-1H-imidazol-2-ylmethyl |
| 1-126 | 2-ethoxypyridin-3-yl | 2-amino-6-(trifluoromethyl)pyridin-3-yl | CH | —CH$_2$CH$_2$NH$_2$ |
| 1-127 | 2-ethoxypyridin-3-yl | 6-(dimethylamino)-2-(trifluoromethyl)pyridin-3-yl | CH | —CH$_2$CH$_2$NH$_2$ |
| 1-128 | 2-ethoxypyridin-3-yl | 4-chloro-2-(difluoromethyl)phenyl | CH | N-methyl-aminopropyl |

TABLE 1-continued

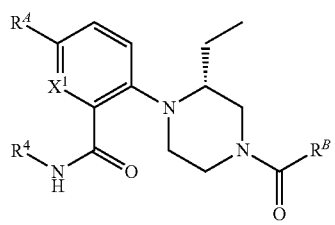

| Compound No. | $R^A$ | $R^B$ | $X^1$ | $R^4$ |
|---|---|---|---|---|
| 1-129 | 2-ethoxypyridin-3-yl | 2-(1H-imidazol-1-yl)-4-fluorophenyl | CH | 3-(dimethylamino)propyl |
| 1-130 | 2-ethoxypyridin-3-yl | 4-fluoro-2-(1H-pyrrol-1-yl)phenyl | CH | 3-(dimethylamino)propyl |
| 1-131 | 2-ethoxypyridin-3-yl | 4-fluoro-2-(1H-pyrazol-1-yl)phenyl | CH | 3-(dimethylamino)propyl |
| 1-132 | 2-ethoxypyridin-3-yl | 4-chloro-2-(trifluoromethyl)phenyl | CH | (1H-imidazol-2-yl)methyl |
| 1-133 | 2-ethoxypyridin-3-yl | 5-(trifluoromethyl)pyridin-2-yl | CH | (S)-pyrrolidin-3-yl |
| 1-134 | 2-ethoxypyridin-3-yl | 3-chloro-5-(trifluoromethyl)pyridin-2-yl | CH | (S)-pyrrolidin-3-yl |
| 1-135 | 2-ethoxypyridin-3-yl | 4-chloro-2-(trifluoromethyl)phenyl | N | 3-(methylamino)propyl |

Note: The R^A, R^B, and R^4 columns contain structural drawings; descriptions above are approximate representations of the depicted substituents.

TABLE 1-continued
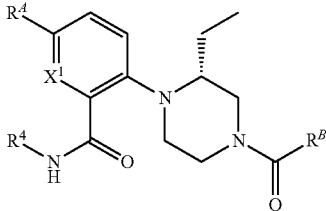
| Compound No. | R<sup>A</sup> | R<sup>B</sup> | X<sup>1</sup> | R<sup>4</sup> |
|---|---|---|---|---|
| 1-136 | 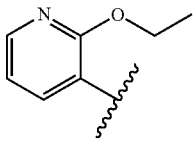 | 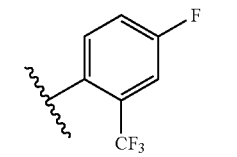 [SMILES: *c1ccc(F)cc1C(F)(F)F] | N | 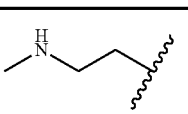 |
| 1-137 | 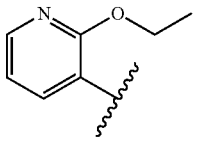 [SMILES: *c1cccnc1OCC] | 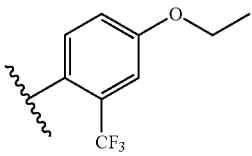 [SMILES: *c1ccc(OCC)cc1C(F)(F)F] | N | 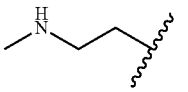 |
| 1-138 | 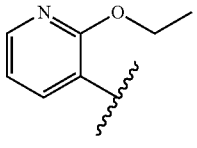 [SMILES: *c1cccnc1OCC] | 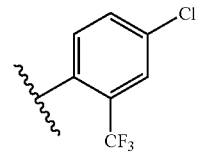 [SMILES: *c1ccc(Cl)cc1C(F)(F)F] | CH | 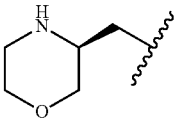 [SMILES: *C[C@H]1COCCN1] |
| 1-139 | 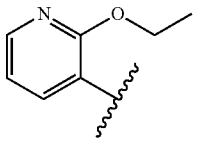 [SMILES: *c1cccnc1OCC] | 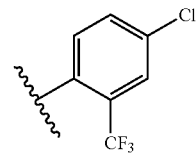 [SMILES: *c1ccc(Cl)cc1C(F)(F)F] | CH | 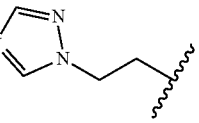 |
| 1-140 | 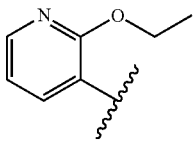 | 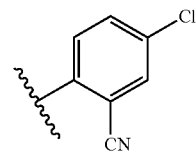 | CF | 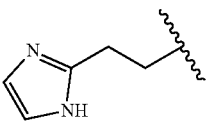 |
| 1-141 | 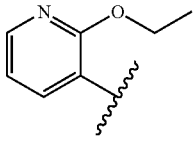 [SMILES: *c1cccnc1OCC] | 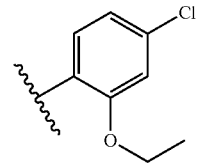 [SMILES: *c1ccc(Cl)cc1OCC] | CF | 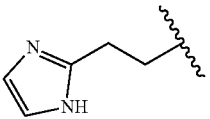 [SMILES: *CCc1ncc[nH]1] |
| 1-142 | 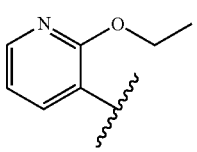 [SMILES: *c1cccnc1OCC] | 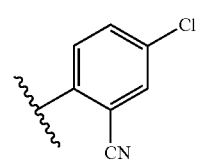 [SMILES: *c1ccc(Cl)cc1C#N] | CH | 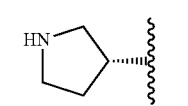 |

TABLE 1-continued

| Compound No. | $R^A$ | $R^B$ | $X^1$ | $R^4$ |
|---|---|---|---|---|
| 1-143 | 2-ethoxypyridin-3-yl | 4-methoxy-2-(trifluoromethyl)phenyl | CH | (R)-pyrrolidin-3-yl |
| 1-144 | 2-ethoxypyridin-3-yl | 4-cyano-2-(trifluoromethyl)phenyl | CH | (R)-pyrrolidin-3-yl |
| 1-145 | 2-ethoxypyridin-3-yl | 6-amino-2-(trifluoromethyl)pyridin-3-yl | CH | —CH$_2$CH$_2$NH$_2$ |
| 1-146 | 2-ethoxypyridin-3-yl | 4-(dimethylamino)-2-(trifluoromethyl)pyridin-5-yl | CH | —CH$_2$CH$_2$NH$_2$ |
| 1-147 | 2-ethoxypyridin-3-yl | 5-fluoro-2-(dimethylamino)phenyl | CH | N,N-dimethylaminoethyl |
| 1-148 | 2-ethoxypyridin-3-yl | 2-(3-amino-azetidin-1-yl)-4-fluorophenyl | CH | N,N-dimethylaminoethyl |
| 1-149 | 2-ethoxyphenyl | 4-chloro-2-(trifluoromethyl)phenyl | N | N,N-dimethylaminoethyl |

TABLE 1-continued

| Compound No. | R^A | R^B | X^1 | R^4 |
|---|---|---|---|---|
| 1-150 | 2-ethoxypyridin-3-yl | 4-chloro-2-(trifluoromethyl)phenyl | N | dimethylaminoethyl |
| 1-151 | 2-ethoxypyridin-3-yl | 4-chloro-2-(trifluoromethyl)phenyl | N | pyrrolidin-3-yl |
| 1-152 | 2-ethoxypyridin-3-yl | 4-chloro-2-(trifluoromethyl)phenyl | N | 1-methylpyrrolidin-3-yl |
| 1-153 | 2-ethoxypyridin-3-yl | 4-chloro-2-cyanophenyl | CF | methylaminoethyl |
| 1-154 | 2-ethoxypyridin-3-yl | 4-cyano-2-(trifluoromethyl)phenyl | CF | methylaminoethyl |
| 1-155 | 2-ethoxypyridin-3-yl | 4-methoxy-2-(trifluoromethyl)phenyl | CF | methylaminoethyl |
| 1-156 | 2-ethoxypyridin-3-yl | 2,4-dichlorophenyl | CF | methylaminoethyl |
| 1-157 | 2-ethoxypyridin-3-yl | 4-(trifluoromethyl)-2-cyanophenyl | CF | methylaminoethyl |

TABLE 1-continued

| Compound No. | R^A | R^B | X^1 | R^4 |
|---|---|---|---|---|
| 1-158 | 2-ethoxypyridin-3-yl | 5-chloro-2-cyanophenyl | N | -CH₂CH₂CH₂N(CH₃)₂ |
| 1-159 | 2-ethoxypyridin-3-yl | 2-methoxy-6-(trifluoromethyl)pyridin-3-yl | CH | —CH₂CH₂NH₂ |
| 1-160 | 2-ethoxypyridin-3-yl | 2-(dimethylamino)-6-methylpyridin-3-yl | CH | —CH₂CH₂NH₂ |
| 1-161 | 2-ethoxypyridin-3-yl | 2-(azetidin-1-yl)-4-fluorophenyl | CH | -CH₂CH₂CH₂N(CH₃)₂ |
| 1-162 | 2-ethoxypyridin-3-yl | 4-fluoro-2-(pyrrolidin-1-yl)phenyl | CH | -CH₂CH₂CH₂N(CH₃)₂ |
| 1-163 | 2-ethoxypyridin-3-yl | 6-(methylamino)-2-(trifluoromethyl)pyridin-3-yl | CF | -CH₂CH₂CH₂NHCH₃ |
| 1-164 | 2-ethoxypyridin-3-yl | 6-methoxy-2-(trifluoromethyl)pyridin-3-yl | CF | -CH₂CH₂CH₂NHCH₃ |

TABLE 1-continued

| Compound No. | R^A | R^B | X^1 | R^4 |
|---|---|---|---|---|
| 1-165 | 2-ethoxypyridin-3-yl | 6-ethoxy-2-(trifluoromethyl)pyridin-3-yl | CF | methylaminopropyl (NHMe) |
| 1-166 | 2-ethoxypyridin-3-yl | 6-(trifluoromethyl)-2-methoxypyridin-3-yl | CF | methylaminopropyl (NHMe) |
| 1-167 | 2-ethoxypyridin-3-yl | 4-methoxy-2-(trifluoromethyl)phenyl | N | methylaminopropyl (NHMe) |
| 1-168 | 2-ethoxypyridin-3-yl | 4-methoxy-2-(trifluoromethyl)phenyl | CF | dimethylaminopropyl (NMe2) |
| 1-169 | 2-ethoxypyridin-3-yl | 4-methoxy-2-(trifluoromethyl)phenyl | N | dimethylaminopropyl (NMe2) |
| 1-170 | 2-ethoxypyridin-3-yl | 4-methoxy-2-(trifluoromethyl)phenyl | CF | 4,5-dihydro-1H-imidazol-2-yl |
| 1-171 | 2-ethoxypyridin-3-yl | 4-chloro-2-cyanophenyl | N | methylaminopropyl (NHMe) |

TABLE 1-continued
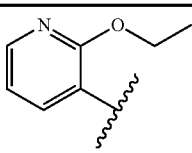
| Compound No. | $R^A$ | $R^B$ | $X^1$ | $R^4$ |
|---|---|---|---|---|
| 1-172 | 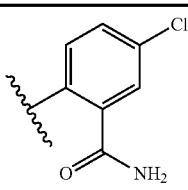 | 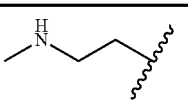 | N | 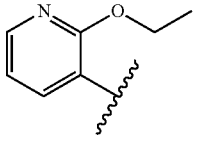 [SMILES: *c1cccnc1OCC] |
| 1-173 | 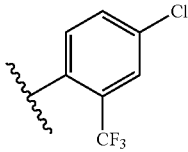 | 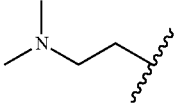 [SMILES: *CCN(C)C] | CF | 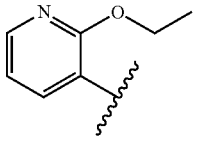 [SMILES: *c1cccnc1OCC] |
| 1-174 | 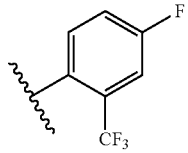 | 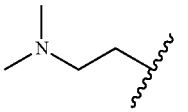 [SMILES: *CCN(C)C] | CF | 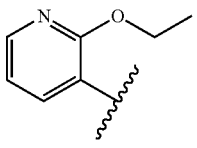 [SMILES: *c1cccnc1OCC] |
| 1-175 | 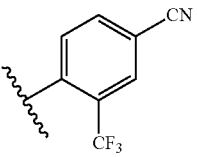 [SMILES: *c1ccc(C#N)cc1C(F)(F)F] | 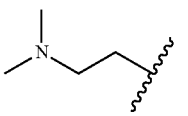 [SMILES: *CCN(C)C] | CF | 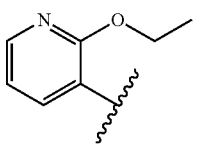 [SMILES: *c1cccnc1OCC] |
| 1-176 | 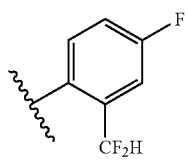 | 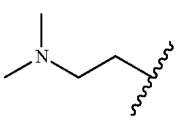 [SMILES: *CCN(C)C] | CF | 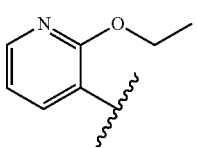 [SMILES: *c1cccnc1OCC] |
| 1-177 | 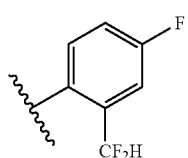 | 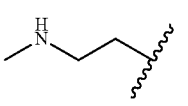 | CF | 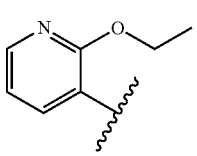 [SMILES: *c1cccnc1OCC] |
| 1-178 | 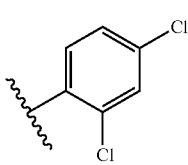 | 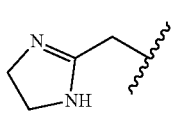 | CF | 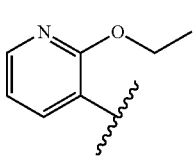 [SMILES: *c1cccnc1OCC] |
| 1-179 | 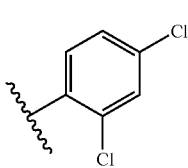 [SMILES: *c1ccc(Cl)cc1Cl] | 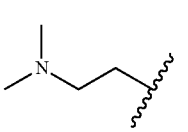 [SMILES: *CCN(C)C] | CF | |

TABLE 1-continued

| Compound No. | $R^A$ | $R^B$ | $X^1$ | $R^4$ |
|---|---|---|---|---|
| 1-180 | 2-ethoxypyridin-3-yl | 5-chloro-2-[(3R)-3-(dimethylamino)pyrrolidin-1-yl]phenyl | CF | dimethylaminoethyl |
| 1-181 | 2-ethoxypyridin-3-yl | 6-ethoxy-2-(trifluoromethyl)pyridin-3-yl | N | methylaminoethyl |
| 1-182 | 2-ethoxypyridin-3-yl | 4-fluoro-2-(trifluoromethyl)phenyl | CF | 4,5-dihydro-1H-imidazol-2-ylmethyl |
| 1-183 | 2-ethoxypyridin-3-yl | 4-chloro-2-(difluoromethyl)phenyl | CF | methylaminoethyl |
| 1-184 | 2-ethoxypyridin-3-yl | 4-chloro-2-(difluoromethyl)phenyl | CF | dimethylaminoethyl |
| 1-185 | 2-ethoxypyridin-3-yl | 6-methyl-2-(trifluoromethyl)pyridin-3-yl | N | methylaminoethyl |
| 1-186 | 2-ethoxypyridin-3-yl | 4-chloro-2-cyanophenyl | CF | dimethylaminoethyl |

TABLE 1-continued
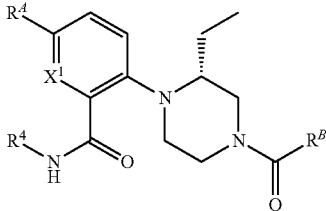
| Compound No. | $R^A$ | $R^B$ | $X^1$ | $R^4$ |
|---|---|---|---|---|
| 1-187 | 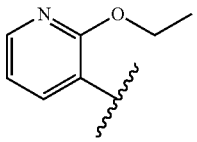 [SMILES: *c1cccnc1OCC] | 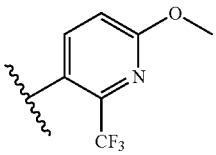 [SMILES: *c1ccc(OC)nc1C(F)(F)F] | N | 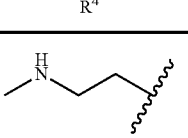 |
| 1-188 | 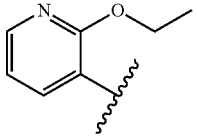 [SMILES: *c1cccnc1OCC] | 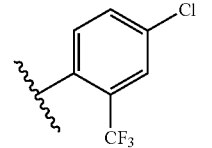 [SMILES: *c1ccc(Cl)cc1C(F)(F)F] | CF | 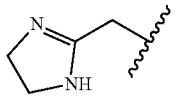 |
| 1-189 | 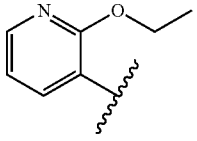 [SMILES: *c1cccnc1OCC] | 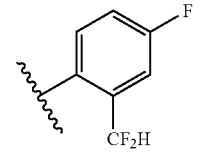 | CF | 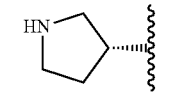 |
| 1-190 | 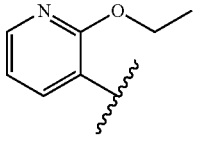 [SMILES: *c1cccnc1OCC] | 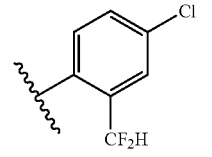 | CF | 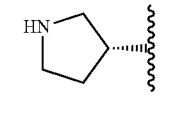 |
| 1-191 | 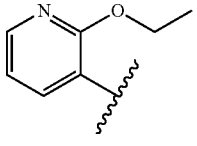 [SMILES: *c1cccnc1OCC] | 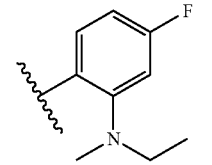 [SMILES: *c1ccc(F)cc1N(C)CC] | CH | 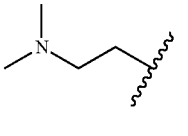 [SMILES: *CCN(C)C] |
| 1-192 | 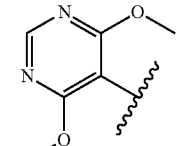 | 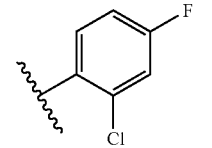 | CH | 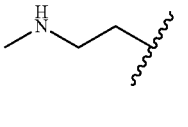 [SMILES: *CCNC] |
| 1-193 | 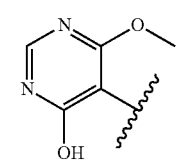 [SMILES: *c1c(O)ncnc1OC] | 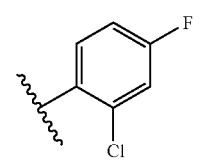 | CH | 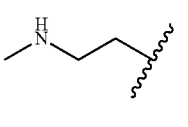 [SMILES: *CCNC] |

TABLE 1-continued

| Compound No. | R^A | R^B | X^1 | R^4 |
|---|---|---|---|---|
| 1-194 | 2-ethyl-pyridin-3-yl | 4-chloro-2-(trifluoromethyl)phenyl | N | NHMe-ethyl |
| 1-195 | 2-ethoxy-pyridin-3-yl | 2-chloro-4-ethoxyphenyl | N | NHMe-ethyl |
| 1-196 | 2-ethoxy-pyridin-3-yl | 2-chloro-4-ethoxyphenyl | N | NMe2-ethyl |
| 1-197 | 2-ethoxy-pyridin-3-yl | 4-chloro-2-((3-(dimethylamino)pyrrolidin-1-yl))phenyl | CF | NHMe-ethyl |
| 1-198 | 2-ethoxy-pyridin-3-yl | 4-chloro-2-(trifluoromethyl)phenyl | CF | azetidin-3-yl |
| 1-199 | 2-ethoxy-pyridin-3-yl | 4-chloro-2-(trifluoromethyl)phenyl | CF | 1-methylpyrrolidin-3-yl |
| 1-200 | 2-ethoxy-pyridin-3-yl | 4-chloro-2-(trifluoromethyl)phenyl | CF | pyrrolidin-3-yl |

TABLE 1-continued

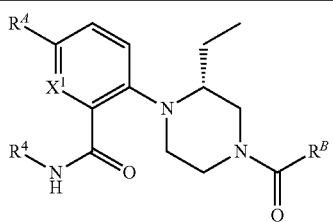

| Compound No. | R^A | R^B | X^1 | R^4 |
|---|---|---|---|---|
| 1-201 | 2-ethoxypyridin-3-yl | 4-chloro-2-(trifluoromethyl)phenyl | CF | (R)-1-methylpyrrolidin-3-yl |
| 1-202 | 2-ethoxypyridin-3-yl | 4-methoxy-2-(trifluoromethyl)phenyl | CF | azetidin-3-yl |
| 1-203 | 2-ethoxypyridin-3-yl | 4-methoxy-2-(trifluoromethyl)phenyl | CF | 1-methylazetidin-3-yl |
| 1-204 | 2-ethoxypyridin-3-yl | 4-chloro-2-(trifluoromethyl)phenyl | CF | 1-methylazetidin-3-yl |
| 1-205 | 2-ethylpyridin-3-yl | 4-chloro-2-(trifluoromethyl)phenyl | N | 2-(dimethylamino)ethyl |
| 1-206 | 2-ethoxyphenyl | 4-chloro-2-(trifluoromethyl)phenyl | N | (R)-1-methylpyrrolidin-3-yl |
| 1-207 | 2-ethoxypyridin-3-yl | 6-ethoxy-2-(trifluoromethyl)pyridin-3-yl | N | 2-(dimethylamino)ethyl |
| 1-208 | 2-ethoxyphenyl | 4-chloro-2-(trifluoromethyl)phenyl | N | 2-(methylamino)ethyl |

TABLE 1-continued
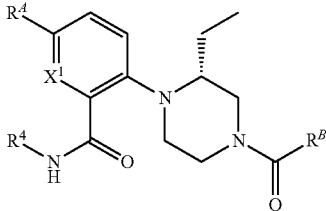
| Compound No. | R^A | R^B | X^1 | R^4 |
|---|---|---|---|---|
| 1-209 | 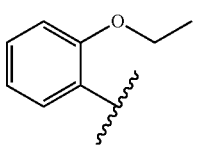 [SMILES: *c1ccccc1OCC] | 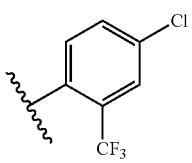 [SMILES: *c1ccc(Cl)cc1C(F)(F)F] | N | 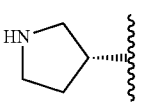 |
| 1-210 | 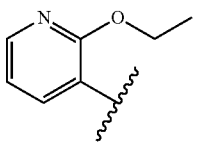 [SMILES: *c1cccnc1OCC] | 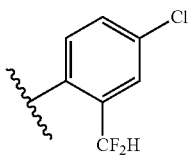 | N | 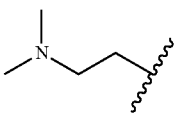 [SMILES: *CCN(C)C] |
| 1-211 | 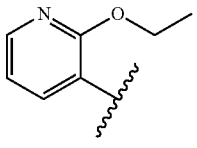 [SMILES: *c1cccnc1OCC] | 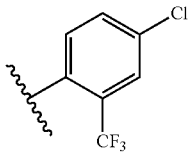 | N | 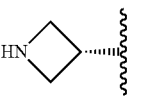 |
| 1-212 | 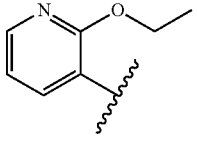 [SMILES: *c1cccnc1OCC] | 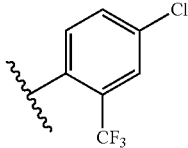 [SMILES: *c1ccc(Cl)cc1C(F)(F)F] | N | 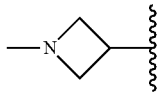 |
| 1-213 | 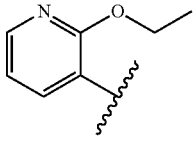 [SMILES: *c1cccnc1OCC] | 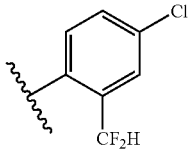 | N | 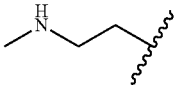 [SMILES: *CCNC] |
| 1-214 | 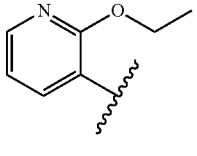 [SMILES: *c1cccnc1OCC] | 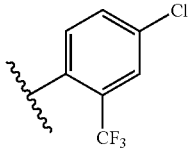 [SMILES: *c1ccc(Cl)cc1C(F)(F)F] | N | 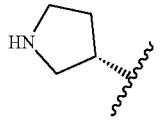 |
| 1-215 | 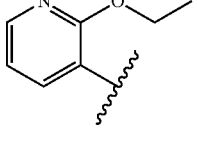 | 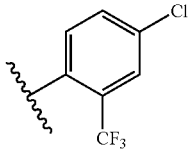 [SMILES: *c1ccc(Cl)cc1C(F)(F)F] | N | 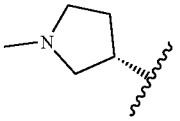 [SMILES: *[C@H]1CCN(C)C1] |

TABLE 1-continued
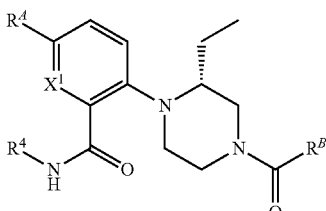
| Compound No. | R^A | R^B | X^1 | R^4 |
|---|---|---|---|---|
| 1-216 | 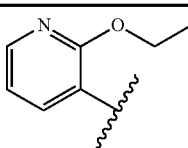 | 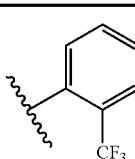 | CH | 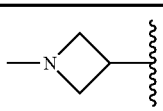 |
| 1-217 | 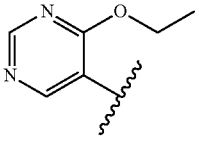 [SMILES: *c1cncnc1OCC] | 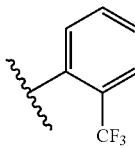 | CF | 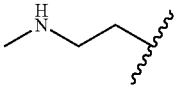 |
| 1-218 | 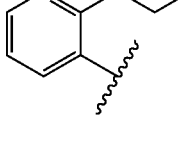 | 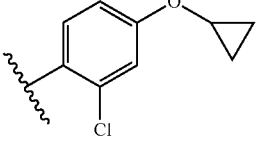 | N | 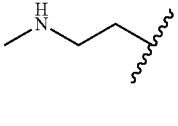 [SMILES: *CCNC] |
| 1-219 | 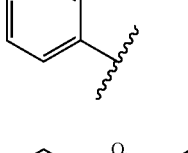 | 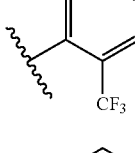 | CF | 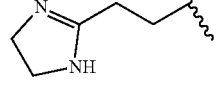 |
| 1-220 | 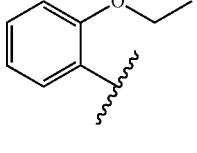 | 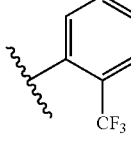 | N | 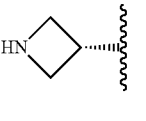 |
| 1-221 | 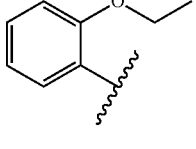 | 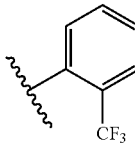 | N | 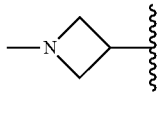 |
| 1-222 | 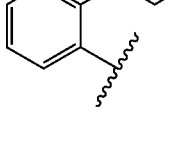 | 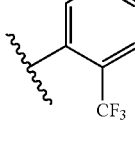 | N | 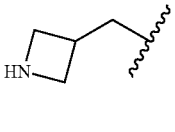 |
| 1-223 | 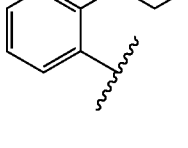 | 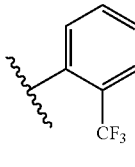 | N | 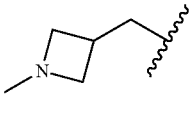 [SMILES: *CC1CN(C)C1] |

TABLE 1-continued
| Compound No. | R^A | R^B | X^1 | R^4 |
|---|---|---|---|---|
| 1-224 | 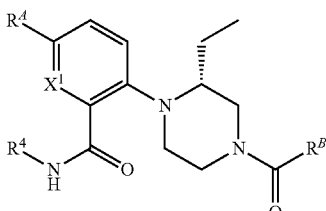 | 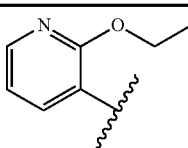 | N | 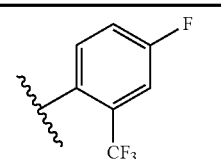 |
| 1-225 | 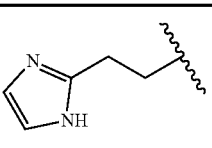 | 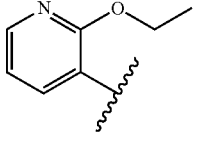 [SMILES: *c1cccnc1OCC] | N | 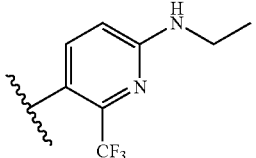 |
| 1-226 | 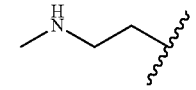 [SMILES: *CCNC] | 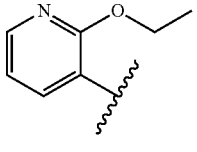 [SMILES: *c1cccnc1OCC] | N | 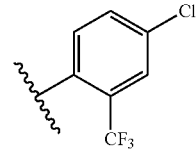 |
| 1-227 | 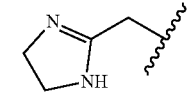 | 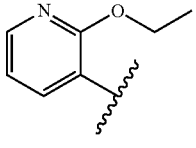 [SMILES: *c1cccnc1OCC] | N | 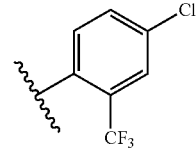 [SMILES: *c1ccc(Cl)cc1C(F)(F)F] |
| 1-228 | 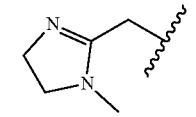 | 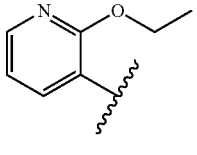 [SMILES: *c1cccnc1OCC] | CH | 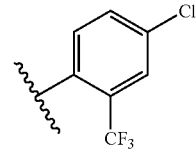 |
| 1-229 | 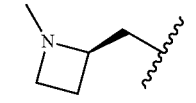 [SMILES: *C[C@H]1CCN1C] | 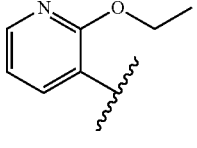 [SMILES: *c1cccnc1OCC] | CF | 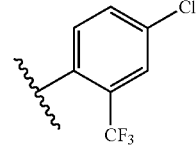 |
| 1-230 | 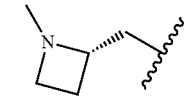 | 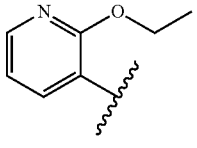 [SMILES: *c1cccnc1OCC] | N | 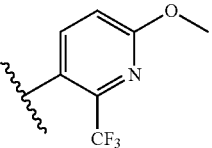 [SMILES: *c1ccc(OC)nc1C(F)(F)F] |
| 1-231 | 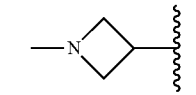 | 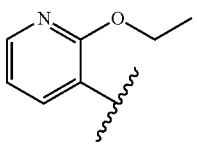 [SMILES: *c1cccnc1OCC] | N | 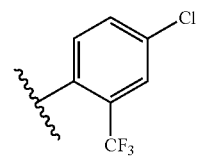 [SMILES: *c1ccc(Cl)cc1C(F)(F)F] |

TABLE 1-continued

| Compound No. | $R^A$ | $R^B$ | $X^1$ | $R^4$ |
|---|---|---|---|---|
| 1-232 | 2-ethoxypyridin-3-yl | 4-chloro-2-(trifluoromethyl)phenyl | N | (2S)-1-methylazetidin-2-ylmethyl |
| 1-233 | 2-ethoxypyridin-3-yl | 6-ethoxy-2-(trifluoromethyl)pyridin-3-yl | N | 1-methylazetidin-3-yl |
| 1-234 | 2-ethoxypyridin-3-yl | 4-chloro-2-(trifluoromethyl)phenyl | N | 3-(1-methyl-1H-imidazol-2-yl)propyl |
| 1-235 | 2-ethoxypyridin-3-yl | 1-(trifluoromethyl)cyclopropyl | N | 1-methylazetidin-3-yl |
| 1-236 | 2-ethoxyphenyl | 6-methoxy-2-(trifluoromethyl)pyridin-3-yl | N | 1-methylazetidin-3-yl |
| 1-237 | 2-ethoxyphenyl | 6-ethoxy-2-(trifluoromethyl)pyridin-3-yl | N | 1-methylazetidin-3-yl |
| 1-238 | 2-ethoxypyridin-3-yl | adamantan-2-yl | N | 1-methylazetidin-3-yl |
| 1-239 | 2-ethoxypyridin-3-yl | 6-methoxy-2-(trifluoromethyl)pyridin-3-yl | N | (3R)-1-methylpyrrolidin-3-yl |

TABLE 1-continued
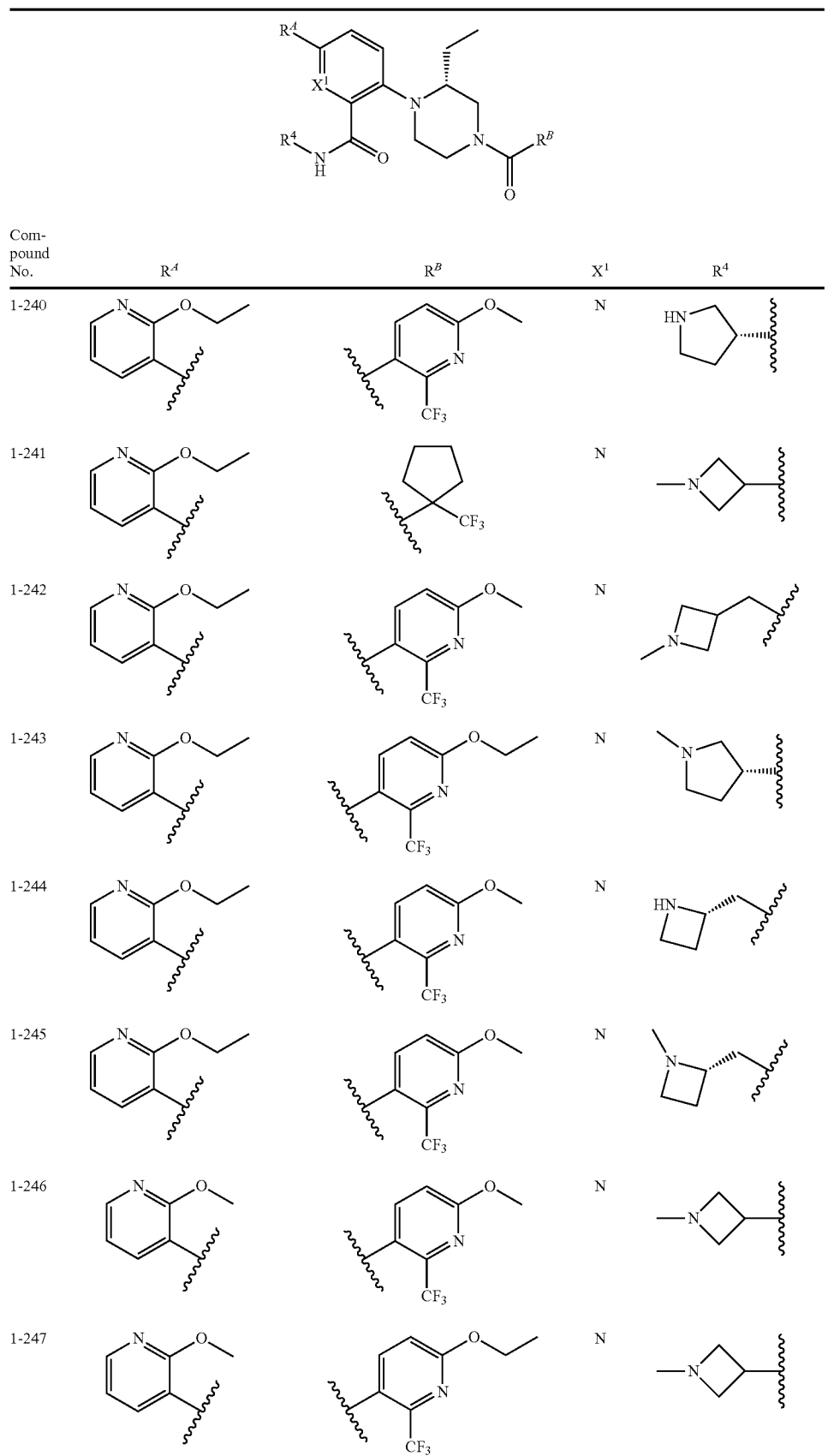

TABLE 1-continued

| Compound No. | $R^A$ | $R^B$ | $X^1$ | $R^4$ |
|---|---|---|---|---|
| 1-248 | 2-ethoxypyridin-3-yl | 1-(2,2-difluoroethyl)cyclobutyl | N | 1-methylazetidin-3-yl |
| 1-249 | 2-ethoxypyridin-3-yl | 6-ethoxy-2-(trifluoromethyl)pyridin-3-yl | N | (1-methylazetidin-3-yl)methyl |
| 1-250 | 2-ethoxypyridin-3-yl | 1-ethylcyclobutyl | N | methylamino (N-methyl) |
| 1-251 | 2-ethoxypyridin-3-yl | cis-4-(trifluoromethyl)cyclohexyl | CF | methylamino (N-methyl) |
| 1-252 | 2-ethoxypyridin-3-yl | trans-4-(trifluoromethyl)cyclohexyl | CF | methylamino (N-methyl) |
| 1-253 | 2-ethoxyphenyl | 6-methoxy-2-(trifluoromethyl)pyridin-4-yl | N | (3S)-1-methylpyrrolidin-3-yl |
| 1-254 | 2-ethoxyphenyl | 5-methoxy-2-(trifluoromethyl)pyridin-3-yl | N | (3S)-pyrrolidin-3-yl |
| 1-255 | 2-ethoxypyridin-3-yl | 1-(trifluoromethyl)cyclopentyl | N | (3S)-1-methylpyrrolidin-3-yl |

TABLE 1-continued

| Compound No. | $R^A$ | $R^B$ | $X^1$ | $R^4$ |
|---|---|---|---|---|
| 1-256 | 2-ethoxypyridin-3-yl | 6-ethoxy-2-(trifluoromethyl)pyridin-3-yl | N | (S)-azetidin-2-ylmethyl (NH) |
| 1-257 | 2-ethoxypyridin-3-yl | 6-ethoxy-2-(trifluoromethyl)pyridin-3-yl | N | (S)-1-methylazetidin-2-ylmethyl |
| 1-258 | 2-ethoxypyridin-3-yl | 4-fluoro-2-(trifluoromethyl)phenyl | N | 1-methylpyrrolidin-3-yl |
| 1-259 | 2-ethoxypyridin-3-yl | 2,4-dichlorophenyl | N | 1-methylpyrrolidin-3-yl |
| 1-260 | 2-ethoxypyridin-3-yl | 4-chloro-2-cyanophenyl | N | 1-methylpyrrolidin-3-yl |
| 1-261 | 2-ethoxypyridin-3-yl | 2-chloro-4-fluorophenyl | N | 1-methylpyrrolidin-3-yl |
| 1-262 | 2-ethoxypyridin-3-yl | 4-chloro-2-(difluoromethyl)phenyl | N | 1-methylpyrrolidin-3-yl |
| 1-263 | 2-ethoxypyridin-3-yl | 1-(trifluoromethyl)cyclopentyl | N | pyrrolidin-3-yl (NH) |

TABLE 1-continued

| Compound No. | R^A | R^B | X^1 | R^4 |
|---|---|---|---|---|
| 1-264 | 2-ethoxypyridin-3-yl | 1-ethylcyclopentyl | N | methylaminoethyl |
| 1-265 | 2-ethoxypyridin-3-yl | 4-chloro-2-(difluoromethyl)phenyl | N | pyrrolidin-3-yl |
| 1-266 | 2-ethoxypyridin-3-yl | 4-fluoro-2-(trifluoromethyl)phenyl | N | pyrrolidin-3-yl |
| 1-267 | 2-ethoxypyridin-3-yl | 2,4-dichlorophenyl | N | pyrrolidin-3-yl |
| 1-268 | 3-ethoxypyrazin-2-yl | 4-chloro-2-(trifluoromethyl)phenyl | N | 1-methylpyrrolidin-3-yl |
| 1-269 | 3-ethoxypyrazin-2-yl | 4-chloro-2-(trifluoromethyl)phenyl | N | 1-methylazetidin-3-yl |
| 1-270 | 2-ethoxypyridin-3-yl | 6-methoxy-2-(trifluoromethyl)pyridin-3-yl | CF | 1-methylpyrrolidin-3-yl |

TABLE 1-continued

| Compound No. | R^A | R^B | X^1 | R^4 |
|---|---|---|---|---|
| 1-271 | 2-ethoxypyridin-3-yl | 6-methoxy-2-(trifluoromethyl)pyridin-3-yl | CF | pyrrolidin-3-yl (HN) |
| 1-272 | 3-ethoxypyrazin-2-yl | 4-chloro-2-(trifluoromethyl)phenyl | N | pyrrolidin-3-yl (HN) |
| 1-273 | 2-ethoxypyridin-3-yl | 1-(trifluoromethyl)cyclohexyl | N | pyrrolidin-3-yl (HN) |
| 1-274 | 2-ethoxypyridin-3-yl | 4-(trifluoromethyl)bicyclo[2.2.2]octan-1-yl | N | pyrrolidin-3-yl (HN) |
| 1-275 | 2-ethoxypyridin-3-yl | 4-chloro-2-(trifluoromethyl)phenyl | N | trans-4-fluoropyrrolidin-3-yl |
| 1-276 | 2-ethoxypyridin-3-yl | 4-chloro-3-(trifluoromethyl)pyridin-2-yl | N | trans-4-fluoropyrrolidin-3-yl |
| 1-277 | 2-ethoxypyridin-3-yl | 4-chloro-2-cyanophenyl | N | pyrrolidin-3-yl (HN) |
| 1-278 | 2-ethoxypyridin-3-yl | 2-(difluoromethyl)-4-fluorophenyl | N | pyrrolidin-3-yl (HN) |

TABLE 1-continued

| Compound No. | R^A | R^B | X^1 | R^4 |
|---|---|---|---|---|
| 1-279 | 2-ethoxypyridin-3-yl | 4-fluoro-2-(difluoromethyl)phenyl | N | (S)-1-methylpyrrolidin-3-yl |
| 1-280 | 2-ethoxypyridin-3-yl | 1-(trifluoromethyl)cyclobutyl | N | pyrrolidin-3-yl |
| 1-281 | 2-ethoxypyridin-3-yl | 4-(trifluoromethyl)bicyclo[2.2.2]octan-1-yl | N | 1-methylazetidin-3-yl |
| 1-282 | 2-ethoxypyridin-3-yl | 4-(trifluoromethyl)bicyclo[2.2.2]octan-1-yl | N | 1-methylpyrrolidin-3-yl |
| 1-283 | 2-ethoxypyridin-3-yl | 1-(trifluoromethyl)cyclobutyl | N | 1-methylpyrrolidin-3-yl |
| 1-284 | 2-ethoxypyridin-3-yl | 3,5,7-trifluoroadamantan-1-yl | N | 1-methylpyrrolidin-3-yl |
| 1-285 | 2-ethoxypyridin-3-yl | 3,5,7-trifluoroadamantan-1-yl | N | pyrrolidin-3-yl |

TABLE 1-continued

| Compound No. | R^A | R^B | X^1 | R^4 |
|---|---|---|---|---|
| 1-286 | 2-ethoxypyridin-3-yl | 4-(trifluoromethyl)cyclohexyl, cis | N | 1-methylpyrrolidin-3-yl |
| 1-287 | 2-ethoxyphenyl | 4-chloro-2-(difluoromethyl)phenyl | N | 1-methylpyrrolidin-3-yl |
| 1-288 | 2-ethoxyphenyl | 4-chloro-2-(difluoromethyl)phenyl | N | pyrrolidin-3-yl |
| 1-289 | 2-ethoxypyridin-3-yl | 6-methoxy-2-(trifluoromethyl)pyridin-3-yl | N | (3,4)-4-fluoropyrrolidin-3-yl |
| 1-290 | 2-ethoxypyridin-3-yl | 6-methoxy-2-(trifluoromethyl)pyridin-3-yl | N | (3,4)-4-fluoro-1-methylpyrrolidin-3-yl |
| 1-291 | 2-ethoxypyridin-3-yl | 6-methoxy-2-(trifluoromethyl)pyridin-3-yl | N | (3,4)-4-fluoropyrrolidin-3-yl |
| 1-292 | 2-ethoxyphenyl | 4-fluoro-2-(difluoromethyl)phenyl | N | pyrrolidin-3-yl |

TABLE 1-continued
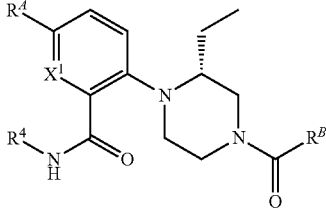
| Compound No. | R^A | R^B | X^1 | R^4 |
|---|---|---|---|---|
| 1-293 | 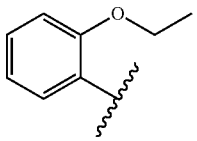 [SMILES: *c1ccccc1OCC] | 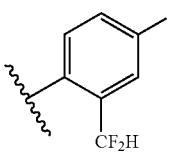 | N | 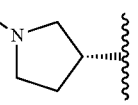 |
| 1-294 | 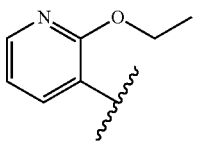 [SMILES: *c1cccnc1OCC] | 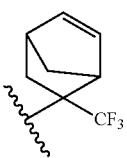 | N | 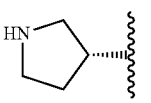 |
| 1-295 | 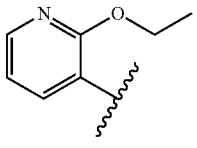 [SMILES: *c1cccnc1OCC] | 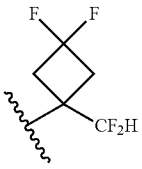 [SMILES: *C1(C(F)F)CC(F)(F)C1] | N | 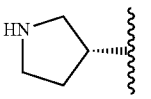 |
| 1-296 | 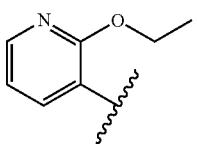 [SMILES: *c1cccnc1OCC] | 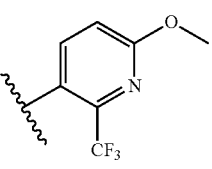 [SMILES: *c1ccc(OC)nc1C(F)(F)F] | N | 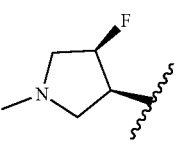 [SMILES: *[C@H]1CN(C)C[C@H]1F] |
| 1-297 | 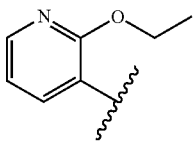 [SMILES: *c1cccnc1OCC] | 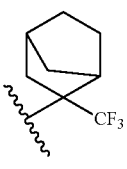 | N | 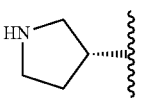 |
| 1-298 | 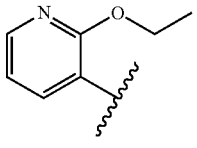 [SMILES: *c1cccnc1OCC] | 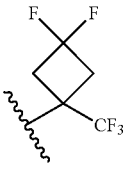 [SMILES: *C1(C(F)(F)F)CC(F)(F)C1] | N | 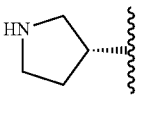 |
| 1-299 | 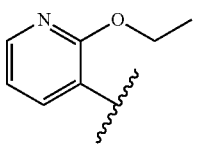 [SMILES: *c1cccnc1OCC] | 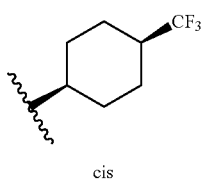 [SMILES: *[C@H]1CC[C@@H](C(F)(F)F)CC1]
cis | N | 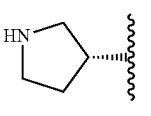 |

TABLE 1-continued
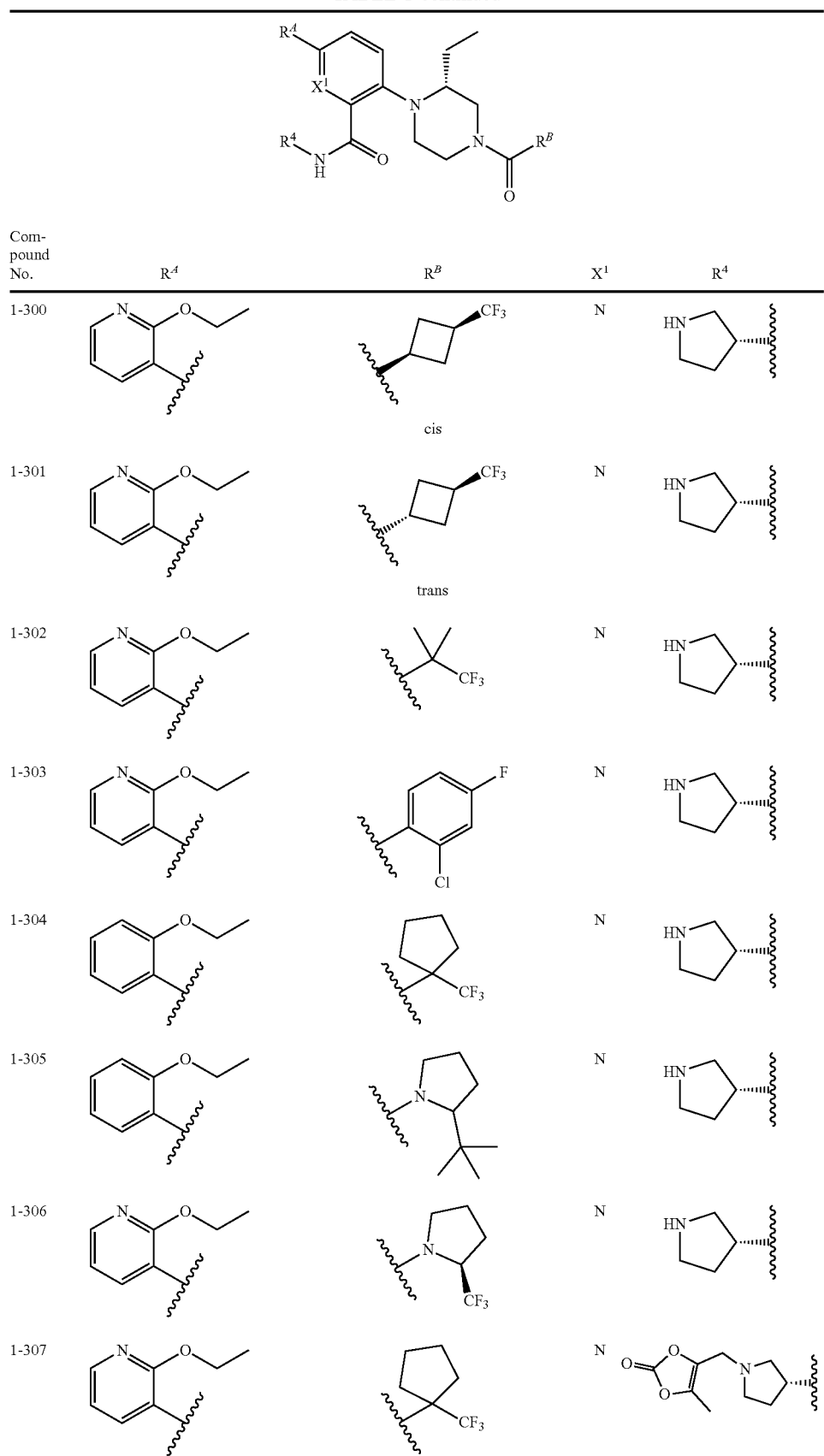

TABLE 1-continued

| Compound No. | R^A | R^B | X^1 | R^4 |
|---|---|---|---|---|
| 1-308 | 2-ethoxypyridin-3-yl | 1,2,2,3-tetramethylcyclopentyl (racemic) | N | (R)-pyrrolidin-3-yl |
| 1-309 | 2-ethoxypyridin-3-yl | O-C(CH3)2CF3 | N | (R)-pyrrolidin-3-yl |
| 1-310 | 2-ethoxypyridin-3-yl | 2-(trifluoromethyl)pyrrolidin-1-yl | N | (R)-pyrrolidin-3-yl |
| 1-311 | 2-ethoxypyridin-3-yl | 2-cyclopropylpyrrolidin-1-yl | N | (R)-pyrrolidin-3-yl |
| 1-312 | 2-ethoxypyridin-3-yl | O-CH(C(CH3)3)CF3 | N | (R)-pyrrolidin-3-yl |
| 1-313 | 2-ethoxypyridin-3-yl | 1-(trifluoromethyl)cyclopentyl | N | (1-methylazetidin-3-yl)methyl |
| 1-314 | 2-ethoxypyridin-3-yl | bornyl | N | (R)-pyrrolidin-3-yl |
| 1-315 | 2-ethoxyphenyl | 2-tert-butylpyrrolidin-1-yl | N | (R)-pyrrolidin-3-yl |

TABLE 1-continued

| Compound No. | R^A | R^B | X^1 | R^4 |
|---|---|---|---|---|
| 1-316 | 2-ethoxyphenyl | (S)-2-tert-butylpyrrolidin-1-yl | N | (R)-pyrrolidin-3-yl (NH) |
| 1-317 | 2-ethoxypyridin-3-yl | indolin-1-yl | N | (R)-pyrrolidin-3-yl (NH) |
| 1-318 | 2-ethoxypyridin-3-yl | 1-(trifluoromethyl)cyclopentyl | N | 3-fluoroazetidin-3-yl-methyl |
| 1-319 | 2-ethoxypyridin-3-yl | 1-(trifluoromethyl)cyclopentyl | N | 3-fluoroazetidin-3-yl-methyl |
| 1-320 | 2-ethoxypyridin-3-yl | (S)-2-(2-fluoropropan-2-yl)pyrrolidin-1-yl | N | (R)-pyrrolidin-3-yl (NH) |
| 1-321 | 2-ethoxypyridin-3-yl | (R)-1-(trifluoromethyl)cyclopentyl | N | (S)-pyrrolidin-3-yl (NH) |
| 1-322 | 2-ethoxypyridin-3-yl | cis-4-(trifluoromethyl)cyclohexyl | N | (1-methylazetidin-3-yl)methyl |
| 1-323 | 2-ethoxypyridin-3-yl | 2,2-diethylpyrrolidin-1-yl | N | (R)-pyrrolidin-3-yl (NH) |

TABLE 1-continued
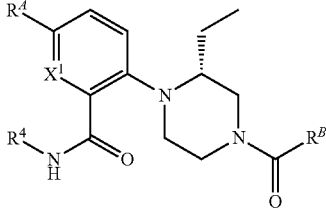
| Compound No. | R^A | R^B | X^1 | R^4 |
|---|---|---|---|---|
| 1-324 | 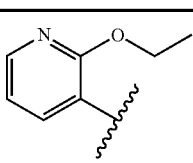 | 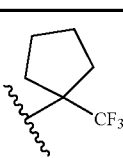 | N | 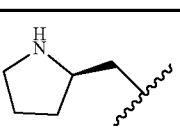 |
| 1-325 | 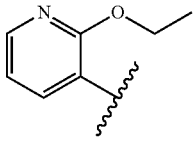 [SMILES: *c1cccnc1OCC] | 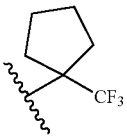 [SMILES: *C1(C(F)(F)F)CCCC1] | N | 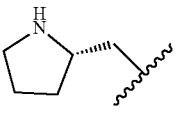 [SMILES: *C[C@@H]1CCCN1] |
| 1-326 | 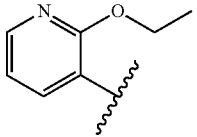 [SMILES: *c1cccnc1OCC] | 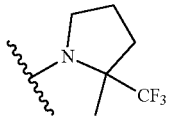 [SMILES: *N1CCCC1(C)C(F)(F)F] | N | 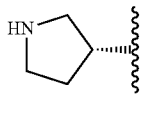 |
| 1-327 | 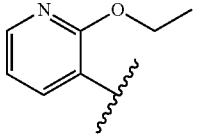 [SMILES: *c1cccnc1OCC] | 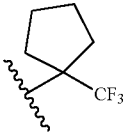 [SMILES: *C1(C(F)(F)F)CCCC1] | N | 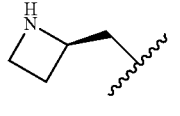 |
| 1-328 | 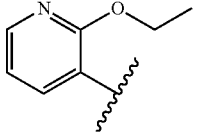 [SMILES: *c1cccnc1OCC] | 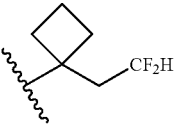 [SMILES: *C1(CC(F)F)CCC1] | N | 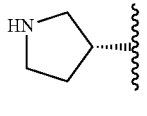 |
| 1-329 | 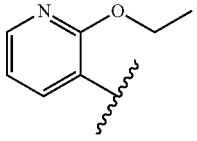 [SMILES: *c1cccnc1OCC] | 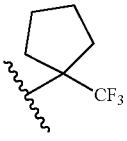 [SMILES: *C1(C(F)(F)F)CCCC1] | N | 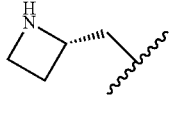 |
| 1-330 | 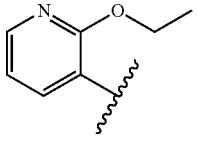 [SMILES: *c1cccnc1OCC] | 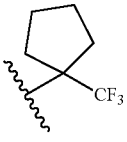 [SMILES: *C1(C(F)(F)F)CCCC1] | N | 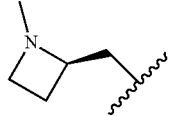 [SMILES: *C[C@H]1CCN1C] |
| 1-331 | 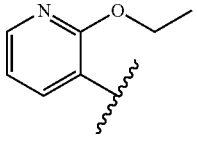 [SMILES: *c1cccnc1OCC] | 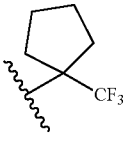 [SMILES: *C1(C(F)(F)F)CCCC1] | N | 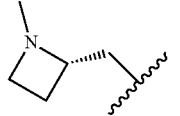 [SMILES: *C[C@@H]1CCN1C] |

TABLE 1-continued

| Compound No. | R^A | R^B | X^1 | R^4 |
|---|---|---|---|---|
| 1-332 | 2-ethoxypyridin-3-yl | 1-(trifluoromethyl)cyclopentyl | N | (1-methylpyrrolidin-2-yl)methyl |
| 1-333 | 2-ethoxypyridin-3-yl | 1-(trifluoromethyl)cyclopentyl | N | (1-methylpyrrolidin-2-yl)methyl |
| 1-334 | 2-ethoxypyridin-3-yl | 1-(trifluoromethyl)cyclopentyl | N | (3-methoxy-1-methylazetidin-3-yl)methyl |
| 1-335 | 2-ethoxyphenyl | cis-4-(trifluoromethyl)cyclohexyl | N | pyrrolidin-3-yl |
| 1-336 | 2-ethoxyphenyl | cis-4-(trifluoromethyl)cyclohexyl | N | 1-methylpyrrolidin-3-yl |
| 1-337 | 2-ethoxypyridin-3-yl | 1-(trifluoromethyl)cyclopentyl | N | 3-(azetidin-1-yl)propyl |
| 1-338 | 2-ethoxyphenyl | 3-(trifluoromethyl)oxetan-3-yl | N | pyrrolidin-3-yl |
| 1-339 | 2-ethoxypyridin-3-yl | 1-(trifluoromethyl)bicyclo[2.2.1]heptyl | N | (1-methylazetidin-3-yl)methyl |

TABLE 1-continued
| Compound No. | R$^A$ | R$^B$ | X$^1$ | R$^4$ |
|---|---|---|---|---|
| 1-340 | 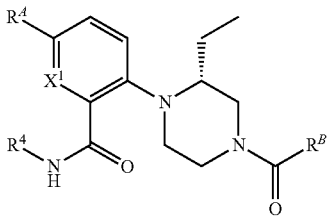 | 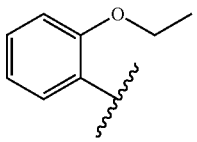 [SMILES: *c1ccccc1OCC] | N | 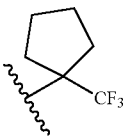 [SMILES: *C1(C(F)(F)F)CCCC1] |
| 1-341 | 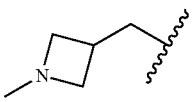 [SMILES: *CC1CN(C)C1] | 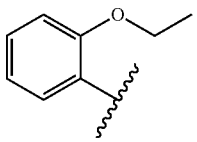 [SMILES: *c1ccccc1OCC] | N | 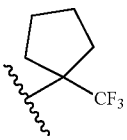 [SMILES: *C1(C(F)(F)F)CCCC1] |
| 1-342 | 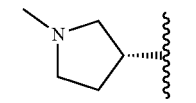 [SMILES: *[C@@H]1CCN(C)C1] | 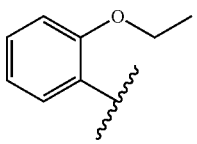 [SMILES: *c1ccccc1OCC] | N | 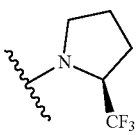 |
| 1-343 | 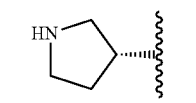 | 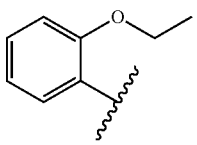 [SMILES: *c1ccccc1OCC] | N | 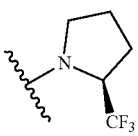 |
| 1-344 | 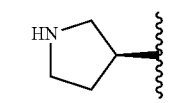 | 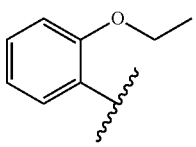 [SMILES: *c1ccccc1OCC] | N | 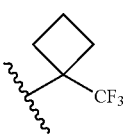 [SMILES: *C1(C(F)(F)F)CCC1] |
| 1-345 | 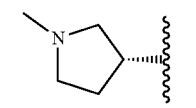 [SMILES: *[C@@H]1CCN(C)C1] | 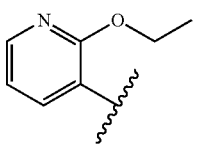 [SMILES: *c1cccnc1OCC] | N | 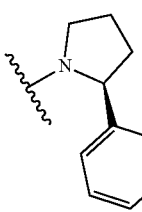 |
| 1-346 | 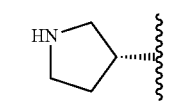 | 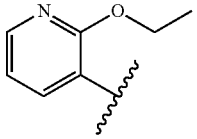 [SMILES: *c1cccnc1OCC] | N | 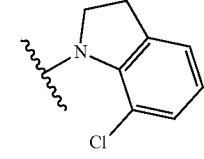 [SMILES: *N1CCc2cccc(Cl)c21] |
| 1-347 | 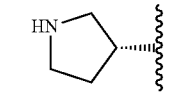 | 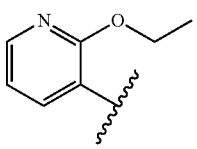 [SMILES: *c1cccnc1OCC] | N | 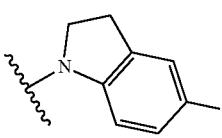 |

TABLE 1-continued

| Compound No. | R^A | R^B | X^1 | R^4 |
|---|---|---|---|---|
| 1-348 | 2-ethoxyphenyl | -OCH(CF₃)C(CH₃)₃ | N | (3R)-pyrrolidin-3-yl (HN) |
| 1-349 | 2-ethoxyphenyl | 1-(2,2,2-trifluoroethyl)cyclobutyl | N | 1-methylpyrrolidin-3-yl |
| 1-350 | 2-ethoxypyridin-3-yl | 7-fluoroindolin-1-yl | N | (3R)-pyrrolidin-3-yl (HN) |
| 1-351 | 2-ethoxypyridin-3-yl | -OCH(CF₃)(phenyl) | N | (3R)-pyrrolidin-3-yl (HN) |
| 1-352 | 2-ethoxypyridin-3-yl | 1-phenylcyclopentyl | N | (3R)-pyrrolidin-3-yl (HN) |
| 1-353 | 2-ethoxypyridin-3-yl | 1-phenylcyclobutyl | N | (3R)-pyrrolidin-3-yl (HN) |
| 1-354 | 2-ethoxypyridin-3-yl | gem-difluoro bornyl | N | (3R)-pyrrolidin-3-yl (HN) |

TABLE 1-continued
| Compound No. | R^A | R^B | X^1 | R^4 |
|---|---|---|---|---|
| 1-355 | 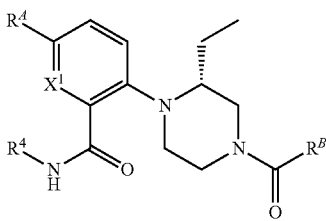 | 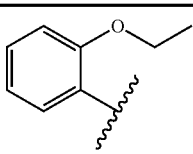 | N | 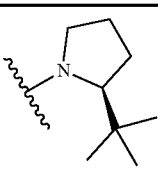 |
| 1-356 | 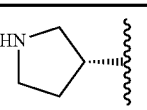 | 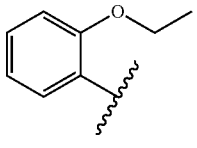 [SMILES: *c1ccccc1OCC] | N | 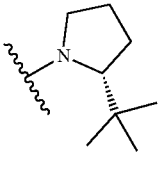 [SMILES: *N1CCC[C@@H]1C(C)(C)C] |
| 1-357 | 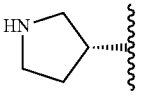 | 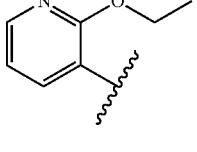 | N | 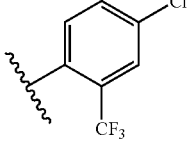 |
| 1-358 | 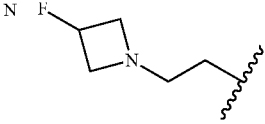 | 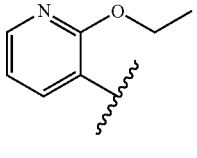 [SMILES: *c1cccnc1OCC] | N | 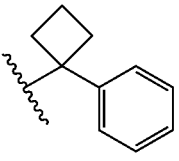 [SMILES: *C1(c2ccccc2)CCC1] |
| 1-359 | 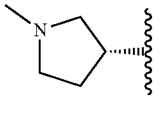 [SMILES: *[C@@H]1CCN(C)C1] | 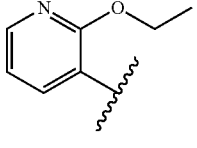 [SMILES: *c1cccnc1OCC] | N | 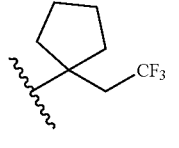 [SMILES: *C1(CC(F)(F)F)CCCC1] |
| 1-360 | 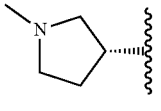 [SMILES: *[C@@H]1CCN(C)C1] | 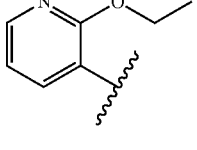 | N | 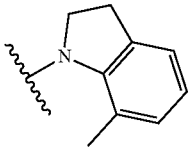 [SMILES: *N1CCc2cccc(C)c21] |
| 1-361 | 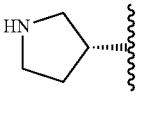 | 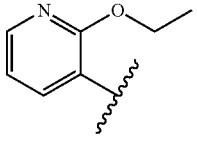 [SMILES: *c1cccnc1OCC] | N | 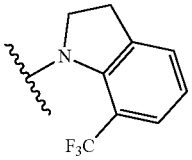 [SMILES: *N1CCc2cccc(C(F)(F)F)c21] |
| 1-362 | 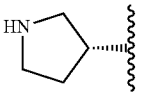 | 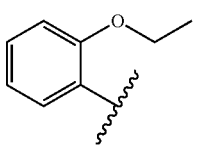 | N | 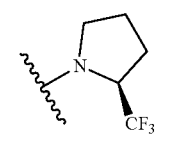 [SMILES: *N1CCC[C@H]1C(F)(F)F] |

TABLE 1-continued
| Compound No. | R^A | R^B | X^1 | R^4 |
|---|---|---|---|---|
| 1-363 | 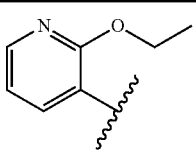 | 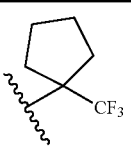 | N | 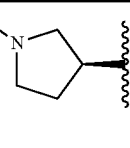 |
| 1-364 | 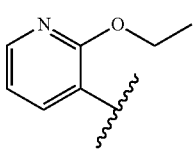 [SMILES: *c1cccnc1OCC] | 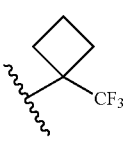 [SMILES: *C1(C(F)(F)F)CCC1] | N | 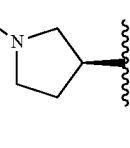 |
| 1-365 | 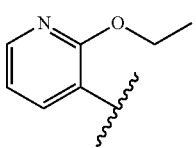 [SMILES: *c1cccnc1OCC] | 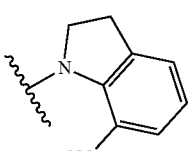 | N | 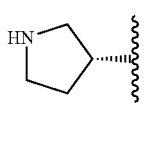 |
| 1-366 | 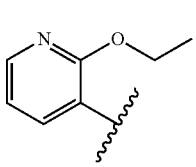 [SMILES: *c1cccnc1OCC] | 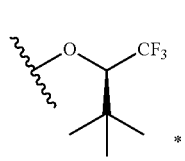 | N | 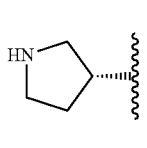 |
| 1-367 | 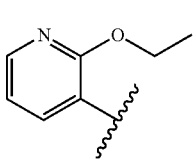 [SMILES: *c1cccnc1OCC] | 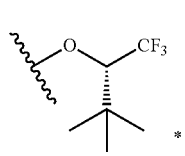 [SMILES: *O[C@@H](C(C)(C)C)C(F)(F)F] | N | 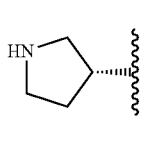 |
| 1-368 | 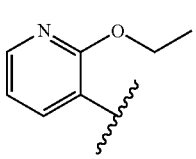 [SMILES: *c1cccnc1OCC] | 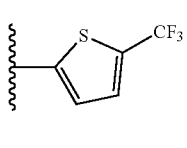 | N | 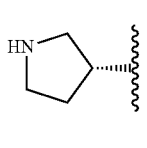 |
| 1-369 | 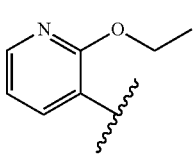 [SMILES: *c1cccnc1OCC] | 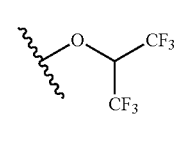 | N | 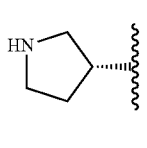 |
| 1-370 | 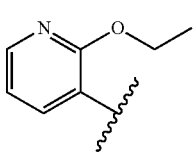 [SMILES: *c1cccnc1OCC] | 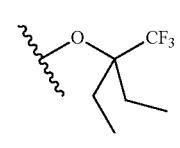 [SMILES: *OC(CC)(CC)C(F)(F)F] | N | 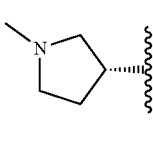 |

TABLE 1-continued
| Compound No. | R<sup>A</sup> | R<sup>B</sup> | X<sup>1</sup> | R<sup>4</sup> |
|---|---|---|---|---|
| 1-371 | 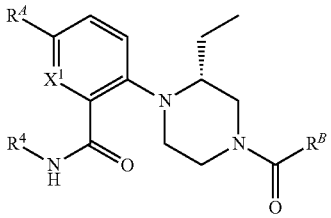 | 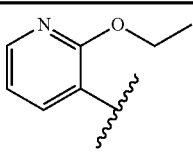 | N | 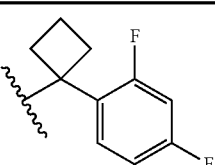 |
| 1-372 | 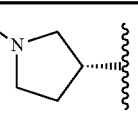 | 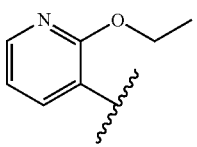 [SMILES: *c1cccnc1OCC] | N | 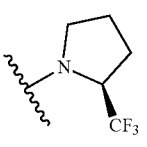 |
| 1-373 | 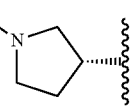 | 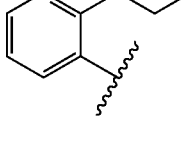 | N | 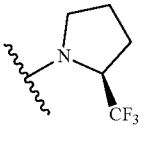 [SMILES: *N1CCC[C@H]1C(F)(F)F] |
| 1-374 | 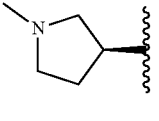 [SMILES: *[C@H]1CCN(C)C1] | 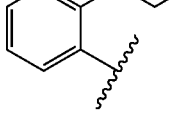 | N | 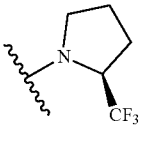 |
| 1-375 | 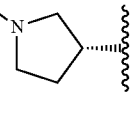 | 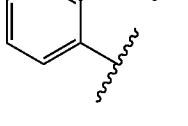 | N | 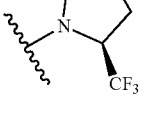 |
| 1-376 | 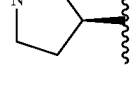 | 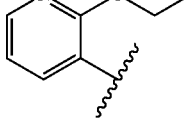 | N | 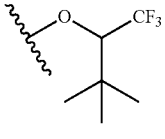 [SMILES: *OC(C(C)(C)C)C(F)(F)F] |
| 1-377 | 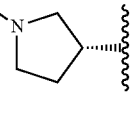 | 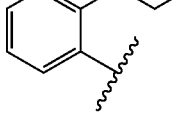 | N | 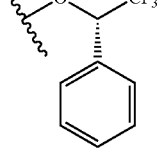 |
| 1-378 | 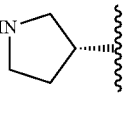 | 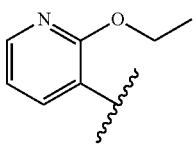 [SMILES: *c1cccnc1OCC] | N | 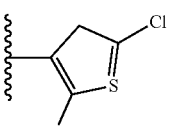 |

TABLE 1-continued
| Compound No. | R^A | R^B | X^1 | R^4 |
|---|---|---|---|---|
| 1-379 | 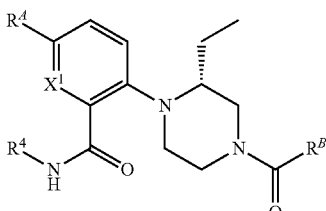 | 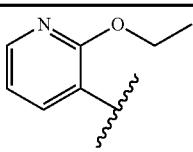 | N | 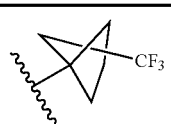 |
| 1-380 | 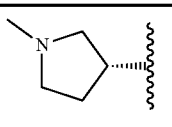 | 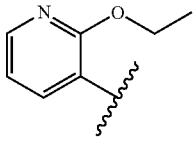 | N | 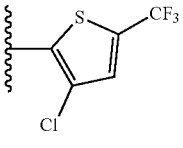 [SMILES: *c1sc(C(F)(F)F)cc1Cl] |
| 1-381 | 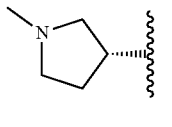 [SMILES: *[C@@H]1CCN(C)C1] | 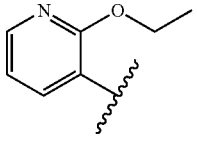 [SMILES: *c1cccnc1OCC] | N | 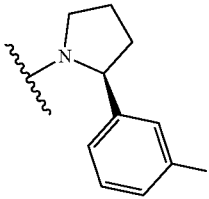 |
| 1-382 | 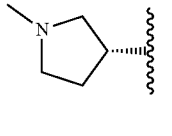 [SMILES: *[C@@H]1CCN(C)C1] | 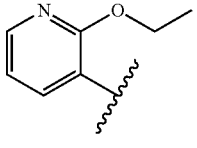 [SMILES: *c1cccnc1OCC] | N | 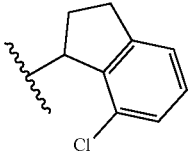 [SMILES: *C1CCc2cccc(Cl)c21] |
| 1-383 | 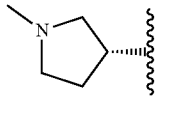 [SMILES: *[C@@H]1CCN(C)C1] | 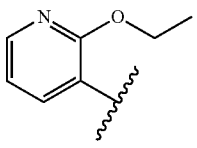 [SMILES: *c1cccnc1OCC] | N | 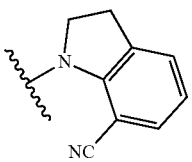 [SMILES: *N1CCc2cccc(C#N)c21] |
| 1-384 | 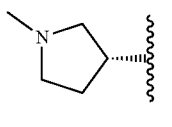 [SMILES: *[C@@H]1CCN(C)C1] | 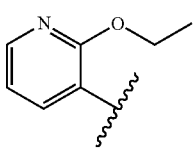 | N | 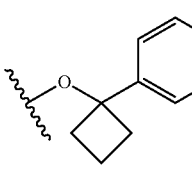 |
| 1-385 | 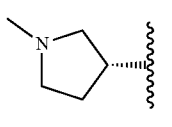 [SMILES: *[C@@H]1CCN(C)C1] | 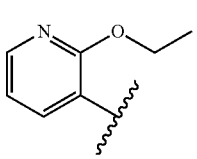 [SMILES: *c1cccnc1OCC] | N | 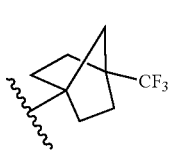 [SMILES: *C12CCC(C(F)(F)F)(CC1)C2] |
| 1-386 | 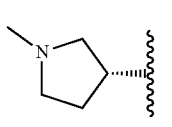 [SMILES: *[C@@H]1CCN(C)C1] | 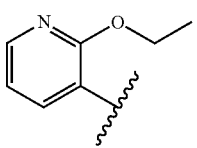 [SMILES: *c1cccnc1OCC] | N | 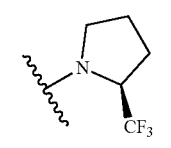 [SMILES: *N1CCC[C@H]1C(F)(F)F] |

TABLE 1-continued
| Compound No. | $R^A$ | $R^B$ | $X^1$ | $R^4$ |
|---|---|---|---|---|
| 1-387 | 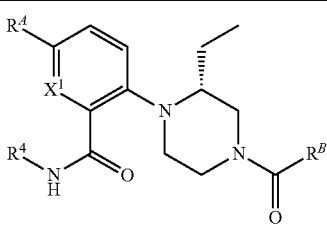 | 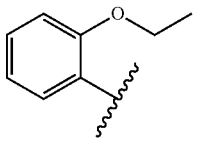 [SMILES: *c1ccccc1OCC] | N | 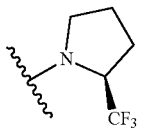 |
| 1-388 | 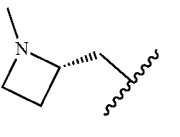 | 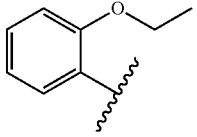 [SMILES: *c1ccccc1OCC] | N | 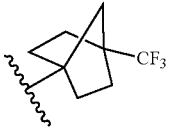 [SMILES: *C12CCC(C(F)(F)F)(CC1)C2] |
| 1-389 | 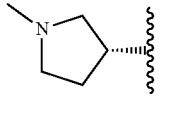 [SMILES: *[C@@H]1CCN(C)C1] | 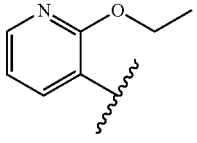 [SMILES: *c1cccnc1OCC] | N | 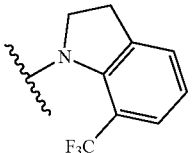 |
| 1-390 | 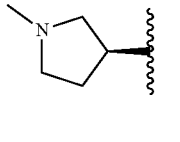 [SMILES: *[C@H]1CCN(C)C1] | 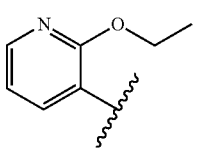 [SMILES: *c1cccnc1OCC] | N | 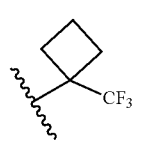 |
| 1-391 | 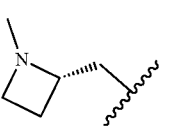 [SMILES: *C[C@@H]1CCN1C] | 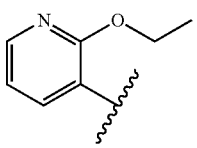 [SMILES: *c1cccnc1OCC] | N | 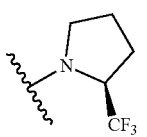 |
| 1-392 | 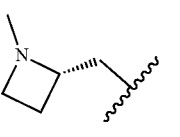 [SMILES: *C[C@@H]1CCN1C] | 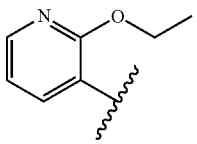 [SMILES: *c1cccnc1OCC] | N | 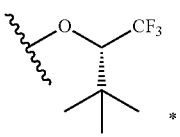 [SMILES: *O[C@@H](C(C)(C)C)C(F)(F)F] |
| 1-393 | 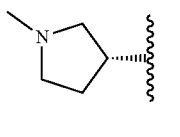 [SMILES: *[C@@H]1CCN(C)C1] | 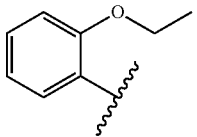 [SMILES: *c1ccccc1OCC] | N | 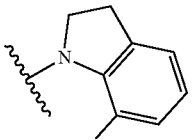 |
| 1-394 | 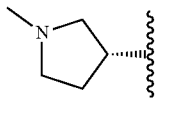 [SMILES: *[C@@H]1CCN(C)C1] | 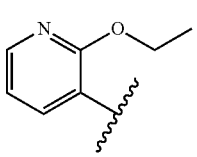 [SMILES: *c1cccnc1OCC] | N | 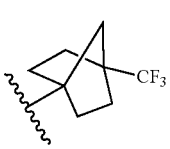 [SMILES: *C12CCC(C(F)(F)F)(CC1)C2] |

TABLE 1-continued

| Compound No. | $R^A$ | $R^B$ | $X^1$ | $R^4$ |
|---|---|---|---|---|
| 1-395 | 2-ethoxypyridin-3-yl | 1-(trifluoromethyl)bicyclo[2.2.1]heptan-4-yl | N | 1-methylazetidin-3-ylmethyl |
| 1-396 | 2-ethoxypyridin-3-yl | (S)-1,1,1-trifluoro-3,3-dimethylbutan-2-yloxy | N | 1-methylazetidin-3-ylmethyl |
| 1-397 | 2-ethoxypyridin-3-yl | 1-ethylcyclopentyloxy | N | (R)-1-methylpyrrolidin-3-yl |
| 1-398 | 2-ethoxypyridin-3-yl | 4-chloro-2-(trifluoromethyl)phenyl | N | quinuclidin-3-yl |
| 1-399 | 2-ethoxyphenyl | 1-(trifluoromethyl)cyclopentyl | N | (S)-1-methylazetidin-3-yl |
| 1-400 | 2-ethoxypyridin-3-yl | 1-(trifluoromethyl)cyclopentyl | N | quinuclidin-3-yl |
| 1-401 | 2-ethoxyphenyl | 1-(trifluoromethyl)cyclopentyl | N | (R)-1-methylpyrrolidin-3-yl |
| 1-402 | 2-ethoxyphenyl | 7-(trifluoromethyl)indolin-1-yl | N | (R)-1-methylpyrrolidin-3-yl |

TABLE 1-continued

| Compound No. | $R^A$ | $R^B$ | $X^1$ | $R^4$ |
|---|---|---|---|---|
| 1-403 | 2-ethoxypyridin-3-yl | (S)-1-(trifluoromethyl)-2,2-dimethylpropoxy * | N | 1-azabicyclo[2.2.1]heptan-4-yl |
| 1-404 | 2-ethoxypyridin-3-yl | 7-cyanoindolin-1-yl | N | 1-methylpyrrolidin-3-yl |
| 1-405 | 2-ethoxypyridin-3-yl | 1-(trifluoromethyl)cyclopentyl | N | 1-azabicyclo[2.2.1]heptan-4-yl |
| 1-406 | 2-ethoxypyridin-3-yl | (S)-1-(trifluoromethyl)-2,2-dimethylpropoxy * | N | 1-methylpyrrolidin-3-yl |
| 1-407 | 2-ethoxyphenyl | (S)-1-(trifluoromethyl)-2,2-dimethylpropoxy * | N | pyrrolidin-3-yl |
| 1-408 | 2-ethoxypyridin-3-yl | 1-phenyl-2,2-dimethylpropoxy | N | 1-methylpyrrolidin-3-yl |
| 1-409 | 2-ethoxypyridin-3-yl | 7-cyanoindolin-1-yl | N | 1-methylazetidin-3-yl |
| 1-410 | 2-ethoxyphenyl | 1-(trifluoromethyl)cyclobutyl | N | 1-azabicyclo[2.2.1]heptan-4-yl |

TABLE 1-continued

| Compound No. | $R^A$ | $R^B$ | $X^1$ | $R^4$ |
|---|---|---|---|---|
| 1-411 | 2-ethoxypyridin-3-yl | 1-(trifluoromethyl)cyclobutyl | N | quinuclidin-3-yl |
| 1-412 | 2-ethoxyphenyl | 2-(2-fluoropropan-2-yl)pyrrolidin-1-yl | N | 1-methylpyrrolidin-3-yl |
| 1-413 | 2-ethoxypyridin-3-yl | 2-(2-fluoropropan-2-yl)pyrrolidin-1-yl | N | 1-methylpyrrolidin-3-yl |
| 1-414 | 2-ethoxyphenyl | 7-cyano-2,3-dihydro-1H-indol-1-yl | N | 1-methylazetidin-3-yl |
| 1-415 | 2-ethoxypyridin-3-yl | 1-(trifluoromethyl)cyclopentyl | N | 1-methyl-4,5-dihydro-1H-imidazol-2-ylmethyl |
| 1-416 | 2-ethoxypyridin-3-yl | 1-(difluoromethyl)cyclopentyl | N | 1-methylpyrrolidin-3-yl |
| 1-417 | 2-ethoxyphenyl | 1-(difluoromethyl)cyclopentyl | N | 1-methylpyrrolidin-3-yl |
| 1-418 | 2-ethoxypyridin-3-yl | 7-(trifluoromethyl)-2,3-dihydro-1H-indol-1-yl | N | 1-methylazetidin-3-yl |

TABLE 1-continued

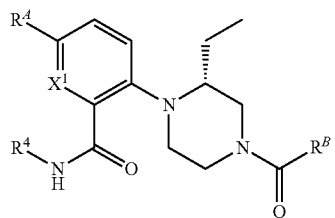

| Compound No. | R^A | R^B | X^1 | R^4 |
|---|---|---|---|---|
| 1-419 | 2-ethoxypyridin-3-yl | 7-chloro-5-fluoroindolin-1-yl | N | (R or S)-1-methylpyrrolidin-3-yl |
| 1-420 | 2-ethoxypyridin-3-yl | 7-chloro-5-fluoroindolin-1-yl | N | 1-methylazetidin-3-yl |
| 1-421 | 2-ethoxyphenyl | 7-chloro-5-fluoroindolin-1-yl | N | 1-methylpyrrolidin-3-yl |
| 1-422 | 2-ethoxypyridin-3-yl | 7-cyano-5-fluoroindolin-1-yl | N | 1-methylazetidin-3-yl |
| 1-423 | 2-ethoxypyridin-3-yl | 7-cyano-5-fluoroindolin-1-yl | N | 1-methylpyrrolidin-3-yl |
| 1-424 | 2-ethoxyphenyl | 7-cyano-5-fluoroindolin-1-yl | N | 1-methylazetidin-3-yl |
| 1-425 | 2-ethoxypyridin-3-yl | 7-chloro-5-fluoroindol-1-yl | N | 1-methylpyrrolidin-3-yl |

TABLE 1-continued
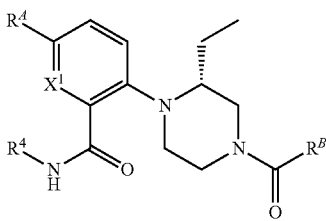
| Compound No. | R^A | R^B | X^1 | R^4 |
|---|---|---|---|---|
| 1-426 | 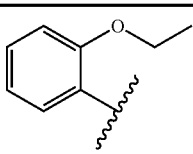 | 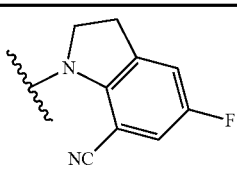 | N | 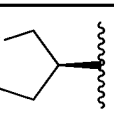 |
| 1-427 | 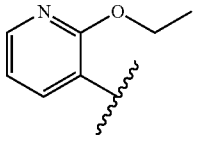 [SMILES: *c1cccnc1OCC] | 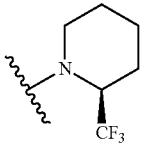 [SMILES: *N1CCCC[C@H]1C(F)(F)F] | N | 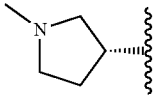 |
| 1-428 | 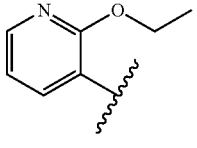 [SMILES: *c1cccnc1OCC] | 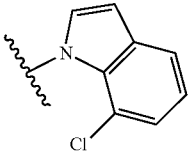 [SMILES: *n1ccc2cccc(Cl)c21] | N | 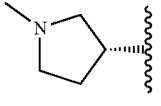 [SMILES: *[C@@H]1CCN(C)C1] |
| 1-429 | 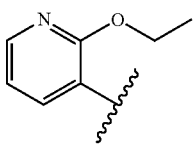 [SMILES: *c1cccnc1OCC] | 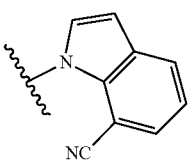 [SMILES: *n1ccc2cccc(C#N)c21] | N | 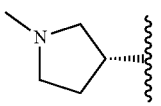 [SMILES: *[C@@H]1CCN(C)C1] |
| 1-430 | 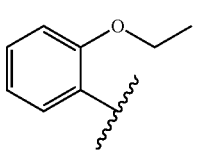 [SMILES: *c1ccccc1OCC] | 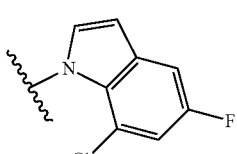 | N | 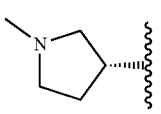 [SMILES: *[C@@H]1CCN(C)C1] |
| 1-431 | 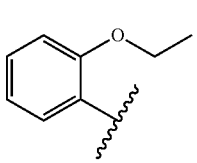 | 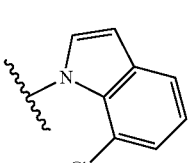 | N | 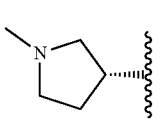 [SMILES: *[C@@H]1CCN(C)C1] |
| 1-432 | 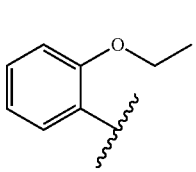 [SMILES: *c1ccccc1OCC] | 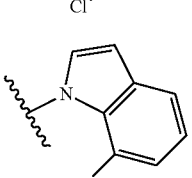 | N | 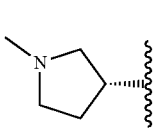 |
| 1-433 | 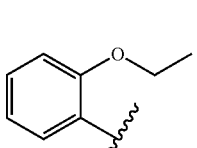 | 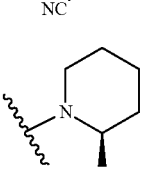 | N | 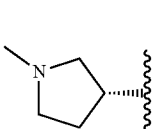 |

TABLE 1-continued

| Compound No. | R^A | R^B | X^1 | R^4 |
|---|---|---|---|---|
| 1-434 | 2-ethoxypyridin-3-yl | (2R)-2-(trifluoromethyl)piperidin-1-yl | N | 1-methylpyrrolidin-3-yl |
| 1-435 | 2-ethoxyphenyl | (2R)-2-(trifluoromethyl)piperidin-1-yl | N | 1-methylpyrrolidin-3-yl |
| 1-436 | 2-ethoxypyridin-3-yl | 7-(trifluoromethyl)-1H-indol-1-yl | N | 1-methylpyrrolidin-3-yl |
| 1-437 | 2-ethoxyphenyl | 7-(trifluoromethyl)-1H-indol-1-yl | N | 1-methylpyrrolidin-3-yl |
| 1-438 | 2-ethoxypyridin-3-yl | 7-cyano-5-fluoro-1H-indol-1-yl | N | 1-methylpyrrolidin-3-yl |
| 1-439 | 2-ethoxyphenyl | 7-cyano-5-fluoro-1H-indol-1-yl | N | 1-methylpyrrolidin-3-yl |

\* absolute stereochemistry not determined

Compounds in Table 1 are named:
1-1: N-(2-aminoethyl)-4-[(2R)-4-[2-chloro-4-(trifluoromethyl)benzoyl]-2-ethylpiperazin-1-yl]-2',3 difluoro-[1,1'-biphenyl]-3-carboxamide;
1-2: N-(2-aminoethyl)-4-[(2R)-4-[2-chloro-4-(trifluoromethyl)benzoyl]-2-ethylpiperazin-1-yl]-2'-methoxy-[1,1'-biphenyl]-3-carboxamide;
1-3: N-(2-aminoethyl)-4-[(2R)-4-[2-chloro-4-(trifluoromethyl)benzoyl]-2-ethylpiperazin-1-yl]-2'-ethoxy-[1,1'-biphenyl]-3-carboxamide;
1-4: N-(2-aminoethyl)-4-[(2R)-4-[2-chloro-4-(trifluoromethyl)benzoyl]-2-ethylpiperazin-1-yl]-2'-fluoro-[1,1'-biphenyl]-3-carboxamide;
1-5: N-(2-aminoethyl)-4-[(2R)-4-[2-chloro-4-(trifluoromethyl)benzoyl]-2-ethylpiperazin-1-yl]-2'-ethyl-[1,1'-biphenyl]-3-carboxamide;
1-6: N-(2-aminoethyl)-2'-chloro-4-[(2R)-4-[2-chloro-4-(trifluoromethyl)benzoyl]-2-ethylpiperazin-1-yl]-[1,1'-biphenyl]-3-carboxamide;

1-7: N-(2-aminoethyl)-4-[(2R)-4-[2-chloro-4-(trifluoromethyl)benzoyl]-2-ethylpiperazin-1-yl]-2'-cyano-[1,1'-biphenyl]-3-carboxamide;
1-8: N-(2-aminoethyl)-4-[(2R)-4-[2-chloro-4-(trifluoromethyl)benzoyl]-2-ethylpiperazin-1-yl]-2'-methyl-[1,1'-biphenyl]-3-carboxamide;
1-9: N-(2-aminoethyl)-2'-chloro-4-[(2R)-4-[2-chloro-4-(trifluoromethyl)benzoyl]-2-ethylpiperazin-1-yl]-3'-fluoro-[1,1'-biphenyl]-3-carboxamide;
1-10: N-(2-aminoethyl)-4-[(2R)-4-[2-chloro-4-(trifluoromethyl)benzoyl]-2-ethylpiperazin-1-yl]-3'-ethoxy-[1,1'-biphenyl]-3-carboxamide;
1-11: N-(2-aminoethyl)-4-[(2R)-4-[2-chloro-4-(trifluoromethyl)benzoyl]-2-ethylpiperazin-1-yl]-2'-propoxy-[1,1'-biphenyl]-3-carboxamide;
1-12: N-(2-aminoethyl)-4-[(2R)-4-[2-chloro-4-(trifluoromethyl)benzoyl]-2-ethylpiperazin-1-yl]-2'-(propan-2-yloxy)-[1,1'-biphenyl]-3-carboxamide;
1-13: N-(2-aminoethyl)-4-[(2R)-4-[2-chloro-4-(trifluoromethyl)benzoyl]-2-ethylpiperazin-1-yl]-2'-hydroxy-[1,1'-biphenyl]-3-carboxamide;
1-14: N-(2-aminoethyl)-4-[(2R)-4-[2-chloro-4-(trifluoromethyl)benzoyl]-2-ethylpiperazin-1-yl]-2'-cyclopropoxy-[1,1'-biphenyl]-3-carboxamide;
1-15: (R)—N-(2-aminoethyl)-4-(4-(2,4-dichlorobenzoyl)-2-ethylpiperazin-1-yl)-2'-ethoxy-[1,1'-biphenyl]-3-carboxamide;
1-16: (R)—N-(2-aminoethyl)-4-(4-(2-chloro-4-(trifluoromethyl)benzoyl)-2-ethylpiperazin-1-yl)-2'-(methoxymethyl)-[1,1'-biphenyl]-3-carboxamide;
1-17: (R)—N-(2-aminoethyl)-4-(4-(4'-(aminomethyl)-5-fluoro-[1,1'-biphenyl]-2-carbonyl)-2-ethylpiperazin-1-yl)-2'-ethoxy-[1,1'-biphenyl]-3-carboxamide;
1-18: (R)—N-(2-aminoethyl)-4-(4-(4'-(aminomethyl)-5-methyl-[1,1'-biphenyl]-2-carbonyl)-2-ethylpiperazin-1-yl)-2'-ethoxy-[1,1'-biphenyl]-3-carboxamide;
1-19: methyl (R)-3'-((2-aminoethyl)carbamoyl)-4'-(4-(2-chloro-4-(trifluoromethyl)benzoyl)-2-ethylpiperazin-1-yl)-[1,1'-biphenyl]-2-carboxylate;
1-20: (R)—N3'-(2-aminoethyl)-4'-(4-(2-chloro-4-(trifluoromethyl)benzoyl)-2-ethylpiperazin-1-yl)-N2-methyl-[1,1'-biphenyl]-2,3'-dicarboxamide;
1-21: (R)—N3'-(2-aminoethyl)-4'-(4-(2-chloro-4-(trifluoromethyl)benzoyl)-2-ethylpiperazin-1-yl)-N2,N2-dimethyl-[1,1'-biphenyl]-2,3'-dicarboxamide;
1-22: N-(2-aminoethyl)-2'-(aminomethyl)-4-[(2R)-4-[2-chloro-4-(trifluoromethyl)benzoyl]-2-ethylpiperazin-1-yl]-[1,1'-biphenyl]-3-carboxamide;
1-23: N-(3-aminopropyl)-4-[(2R)-4-[2-chloro-4-(trifluoromethyl)benzoyl]-2-ethylpiperazin-1-yl]-2'-ethoxy-[1,1'-biphenyl]-3-carboxamide;
1-24: N-(2-aminoethyl)-4-[(2R)-4-[4'-(aminomethyl)-[1,1'-biphenyl]-2-carbonyl]-2-ethylpiperazin-1-yl]-2'-ethoxy-[1,1'-biphenyl]-3-carboxamide;
1-25: N-(2-aminoethyl)-4-[(2R)-4-[4-chloro-2-(trifluoromethyl)benzoyl]-2-ethylpiperazin-1-yl]-2'-ethoxy-[1,1'-biphenyl]-3-carboxamide;
1-26: N-(2-aminoethyl)-4-[(2R)-4-[4'-(aminomethyl)-3'-fluoro-[1,1'-biphenyl]-2-carbonyl]-2-ethylpiperazin-1-yl]-2'-ethoxy-[1,1'-biphenyl]-3-carboxamide;
1-27: N-(2-aminoethyl)-4-[(2R)-4-[4'-(aminomethyl)-3-fluoro-5-methyl-[1,1'-biphenyl]-2-carbonyl]-2-ethylpiperazin-1-yl]-2'-ethoxy-[1,1'-biphenyl]-3-carboxamide;
1-28: N-(2-aminoethyl)-4-[(2R)-4-[2-chloro-4-(trifluoromethyl)benzoyl]-2-ethylpiperazin-1-yl]-2'-propyl-[1,1'-biphenyl]-3-carboxamide;
1-29: N-(2-aminoethyl)-4-[(2R)-4-[2-chloro-4-(trifluoromethyl)benzoyl]-2-ethylpiperazin-1-yl]-4'-propyl-[1,1'-biphenyl]-3-carboxamide;
1-30: N-(2-aminoethyl)-2-[(2R)-4-[2-chloro-4-(trifluoromethyl)benzoyl]-2-ethylpiperazin-1-yl]-5-(pyridin-2-yl)benzamide;
1-31: N-(2-aminoethyl)-2-[(2R)-4-[2-chloro-4-(trifluoromethyl)benzoyl]-2-ethylpiperazin-1-yl]-5-(pyridin-3-yl)benzamide;
1-32: N-(2-aminoethyl)-2-[(2R)-4-[2-chloro-4-(trifluoromethyl)benzoyl]-2-ethylpiperazin-1-yl]-5-(3-ethoxypyridin-2-yl)benzamide;
1-33: N-(2-aminoethyl)-2-[(2R)-4-[2-chloro-4-(trifluoromethyl)benzoyl]-2-ethylpiperazin-1-yl]-5-(3-ethoxypyridin-4-yl)benzamide;
1-34: N-(2-aminoethyl)-2-[(2R)-4-[2-chloro-4-(trifluoromethyl)benzoyl]-2-ethylpiperazin-1-yl]-5-(2-ethoxypyridin-3-yl)benzamide;
1-35: N-(2-aminoethyl)-2-[(2R)-4-[2-chloro-4-(trifluoromethyl)benzoyl]-2-ethylpiperazin-1-yl]-5-(4-ethoxypyridin-3-yl)benzamide;
1-36: N-(2-aminoethyl)-2-[(2R)-4-[4'-(aminomethyl)-5-fluoro-[1,1'-biphenyl]-2-carbonyl]-2-ethylpiperazin-1-yl]-5-(2-ethoxypyridin-3-yl)benzamide;
1-37: N-(2-aminoethyl)-2-[(2R)-4-[4-chloro-2-(trifluoromethyl)benzoyl]-2-ethylpiperazin-1-yl]-5-(2-ethoxypyridin-3-yl)benzamide;
1-38: N-(2-aminoethyl)-2-[(2R)-4-(2-chloro-4-fluorobenzoyl)-2-ethylpiperazin-1-yl]-5-(2-ethoxypyridin-3-yl)benzamide;
1-39: N-(2-aminoethyl)-5-(2-ethoxypyridin-3-yl)-2-[(2R)-2-ethyl-4-[4-fluoro-2-(pyridin-4-yl)benzoyl]piperazin-1-yl]benzamide;
1-40: N-(2-aminoethyl)-2-[(2R)-4-{2-[(3R)-3-(aminoethyl)pyrrolidin-1-yl]-4-chlorobenzoyl}-2-ethylpiperazin-1-yl]-5-(2-ethoxypyridin-3-yl)benzamide;
1-41: N-(2-aminoethyl)-2-[(2R)-4-{2-[(3S)-3-(aminoethyl)pyrrolidin-1-yl]-4-chlorobenzoyl}-2-ethylpiperazin-1-yl]-5-(2-ethoxypyridin-3-yl)benzamide;
1-42: N-(2-aminoethyl)-2-[(2R)-4-(2,4-dichlorobenzoyl)-2-ethylpiperazin-1-yl]-5-(2-ethoxypyridin-3-yl)benzamide;
1-43: N-(2-aminoethyl)-2-[(2R)-4-(2-chloro-4-methylbenzoyl)-2-ethylpiperazin-1-yl]-5-(2-ethoxypyridin-3-yl)benzamide;
1-44: N-(2-aminoethyl)-2-[(2R)-4-[4'-(aminomethyl)-3-fluoro-5-methyl-[1,1'-biphenyl]-2-carbonyl]-2-ethylpiperazin-1-yl]-5-(2-ethoxypyridin-3-yl)benzamide;
1-45: 2-[(2R)-4-[4-chloro-2-(trifluoromethyl)benzoyl]-2-ethylpiperazin-1-yl]-5-(2-ethoxypyridin-3-yl)-N-[(3R)-pyrrolidin-3-yl]benzamide;
1-46: 2-[(2R)-4-[4-chloro-2-(trifluoromethyl)benzoyl]-2-ethylpiperazin-1-yl]-5-(2-ethoxypyridin-3-yl)-N-[2-(methylamino)ethyl]benzamide;
1-47: 2-[(2R)-4-[4-chloro-2-(trifluoromethyl)benzoyl]-2-ethylpiperazin-1-yl]-N-[2-(dimethylamino)ethyl]-5-(2-ethoxypyridin-3-yl)benzamide;
1-48: 2-[(2R)-4-[4-chloro-2-(trifluoromethyl)benzoyl]-2-ethylpiperazin-1-yl]-5-(2-ethoxypyridin-3-yl)-N-[(3R)-1-methylpyrrolidin-3-yl]benzamide;
1-49: 2-[(2R)-4-[4-chloro-2-(trifluoromethyl)benzoyl]-2-ethylpiperazin-1-yl]-5-(2-ethoxypyridin-3-yl)-N-[2-(pyrrolidin-1-yl)ethyl]benzamide;
1-50: N-(2-aminoethyl)-2-[(2R)-4-{2-[3-(aminomethyl)pyrrolidin-1-yl]-4-(trifluoromethyl)benzoyl}-2-ethylpiperazin-1-yl]-5-(2-ethoxypyridin-3-yl)benzamide;

1-51: N-(2-aminoethyl)-2-[(2R)-4-{2-[3-(aminomethyl)pyrrolidin-1-yl]-4-fluorobenzoyl}-2-ethylpiperazin-1-yl]-5-(2-ethoxypyridin-3-yl)benzamide;

1-52: N-(2-aminoethyl)-2-[(2R)-4-[2-(4-aminopiperidin-1-yl)-4-chlorobenzoyl]-2-ethylpiperazin-1-yl]-5-(2-ethoxypyridin-3-yl)benzamide;

1-53: N-(2-aminoethyl)-2-[(2R)-4-(3,5-dichloropyridine-2-carbonyl)-2-ethylpiperazin-1-yl]-5-(2-ethoxypyridin-3-yl)benzamide;

1-54: N-(2-aminoethyl)-2-[(2R)-4-(4-chloro-2-methoxybenzoyl)-2-ethylpiperazin-1-yl]-5-(2-ethoxypyridin-3-yl)benzamide;

1-55: N-(2-aminoethyl)-2-[(2R)-4-(2-chloro-4-cyanobenzoyl)-2-ethylpiperazin-1-yl]-5-(2-ethoxypyridin-3-yl)benzamide;

1-56: N-(2-aminoethyl)-2-[(2R)-4-{4-[3-(aminomethyl)pyrrolidin-1-yl]-2-fluorobenzoyl}-2-ethylpiperazin-1-yl]-5-(2-ethoxypyridin-3-yl)benzamide;

1-57: N-(2-aminoethyl)-2-[(2R)-4-{2-[(3S)-3-aminopyrrolidin-1-yl]-4-chlorobenzoyl}-2-ethylpiperazin-1-yl]-5-(2-ethoxypyridin-3-yl)benzamide;

1-58: N-(2-aminoethyl)-5-(2-ethoxypyridin-3-yl)-2-[(2R)-2-ethyl-4-[4-fluoro-2-(trifluoromethyl)benzoyl]piperazin-1-yl]benzamide;

1-59: N-(2-aminoethyl)-5-(2-ethoxypyridin-3-yl)-2-[(2R)-2-ethyl-4-[4-methyl-2-(trifluoromethyl)benzoyl]piperazin-1-yl]benzamide;

1-60: N-(2-aminoethyl)-2-[(2R)-4-(2,4-dimethylbenzoyl)-2-ethylpiperazin-1-yl]-5-(2-ethoxypyridin-3-yl)benzamide;

1-61: N-(2-aminoethyl)-2-[(2R)-4-[4-chloro-2-(pyrrolidin-1-yl)benzoyl]-2-ethylpiperazin-1-yl]-5-(2-ethoxypyridin-3-yl)benzamide;

1-62: N-(2-aminoethyl)-5-(2-ethoxypyridin-3-yl)-2-[(2R)-2-ethyl-4-[2-(trifluoromethyl)benzoyl]piperazin-1-yl]benzamide;

1-63: N-(2-aminoethyl)-2-[(2R)-4-(2-cyclopropylbenzoyl)-2-ethylpiperazin-1-yl]-5-(2-ethoxypyridin-3-yl)benzamide;

1-64: 2-[(2R)-4-[4-chloro-2-(trifluoromethyl)benzoyl]-2-ethylpiperazin-1-yl]-5-(2-ethoxypyridin-3-yl)-N-[(pyridin-2-yl)methyl]benzamide;

1-65: 2-[(2R)-4-[4-chloro-2-(trifluoromethyl)benzoyl]-2-ethylpiperazin-1-yl]-5-(2-ethoxypyridin-3-yl)-N-[(pyridin-3-yl)methyl]benzamide;

1-66: 2-[(2R)-4-[4-chloro-2-(trifluoromethyl)benzoyl]-2-ethylpiperazin-1-yl]-5-(2-ethoxypyridin-3-yl)-N-[(pyridin-4-yl)methyl]benzamide;

1-67: N-(2-aminoethyl)-5-(2-ethoxypyridin-3-yl)-2-[(2R)-2-ethyl-4-{4-methyl-2-[(3S)-3-(methylamino)pyrrolidin-1-yl]benzoyl}piperazin-1-yl]benzamide;

1-68: N-(2-aminoethyl)-2-[(2R)-4-{2-[(3S)-3-(dimethylamino)pyrrolidin-1-yl]-4-methylbenzoyl}-2-ethylpiperazin-1-yl]-5-(2-ethoxypyridin-3-yl)benzamide;

1-69: N-(2-aminoethyl)-6-[(2R)-4-[4-chloro-2-(trifluoromethyl)benzoyl]-2-ethylpiperazin-1-yl]-3-(2-ethoxypyridin-3-yl)-2-fluorobenzamide;

1-70: 2-[(2R)-4-[4-chloro-2-(trifluoromethyl)benzoyl]-2-ethylpiperazin-1-yl]-5-(2-ethoxypyridin-3-yl)-N-(pyridin-4-yl)benzamide;

1-71: N-(2-aminoethyl)-2-[(2R)-4-[4-chloro-2-(trifluoromethyl)benzoyl]-2-ethylpiperazin-1-yl]-5-(2-methoxypyridin-3-yl)benzamide;

1-72: 6-[(2R)-4-[4-chloro-2-(trifluoromethyl)benzoyl]-2-ethylpiperazin-1-yl]-3-(2-ethoxypyridin-3-yl)-2-fluoro-N-[(3R)-pyrrolidin-3-yl]benzamide;

1-73: 6-[(2R)-4-(2-chloro-4-fluorobenzoyl)-2-ethylpiperazin-1-yl]-3-(2-ethoxypyridin-3-yl)-2-fluoro-N-[(3R)-pyrrolidin-3-yl]benzamide;

1-74: N-(2-aminoethyl)-5-(2-ethoxypyridin-3-yl)-2-[(2R)-2-ethyl-4-[4-fluoro-2-(piperidin-4-yl)benzoyl]piperazin-1-yl]benzamide;

1-75: N-(2-aminoethyl)-2-[(2R)-4-[2-(6-aminopyridin-3-yl)-4-fluorobenzoyl]-2-ethylpiperazin-1-yl]-5-(2-ethoxypyridin-3-yl)benzamide;

1-76: N-(2-aminoethyl)-2-[(2R)-4-[2-(dimethylamino)-6-(trifluoromethyl)pyridine-3-carbonyl]-2-ethylpiperazin-1-yl]-5-(2-ethoxypyridin-3-yl)benzamide;

1-77: N-(2-aminoethyl)-2-[(2R)-4-(2,6-dimethylpyridine-3-carbonyl)-2-ethylpiperazin-1-yl]-5-(2-ethoxypyridin-3-yl)benzamide;

1-78: N-(2-aminoethyl)-5-(2-ethoxypyridin-3-yl)-2-[(2R)-2-ethyl-4-(4-fluoro-2-methylbenzoyl)piperazin-1-yl]benzamide;

1-79: N-(2-aminoethyl)-5-(2-ethoxypyridin-3-yl)-2-[(2R)-2-ethyl-4-(4-fluoro-2-methoxybenzoyl)piperazin-1-yl]benzamide;

1-80: N-(2-aminoethyl)-5-(2-ethoxypyridin-3-yl)-2-[(2R)-2-ethyl-4-(2-methoxy-4-methylbenzoyl)piperazin-1-yl]benzamide;

1-81: N-(2-aminoethyl)-2-[(2R)-4-(4-tert-butylbenzoyl)-2-ethylpiperazin-1-yl]-5-(2-ethoxypyridin-3-yl)benzamide;

1-82: 2-[(2R)-4-(2-chloro-4-fluorobenzoyl)-2-ethylpiperazin-1-yl]-5-(2-ethoxypyridin-3-yl)-N-[(3R)-pyrrolidin-3-yl]benzamide;

1-83: 2-[(2R)-4-[4-chloro-2-(trifluoromethyl)benzoyl]-2-ethylpiperazin-1-yl]-5-(2-ethoxypyridin-3-yl)-N-[(1H-imidazol-5-yl)methyl]benzamide;

1-84: 2-[(2R)-4-[4-chloro-2-(trifluoromethyl)benzoyl]-2-ethylpiperazin-1-yl]-5-(2-ethoxypyridin-3-yl)-N-[2-(1H-imidazol-5-yl)ethyl]benzamide;

1-85: N-(2-aminoethyl)-2-[(2R)-4-[2-(2-aminopyridin-4-yl)-4-fluorobenzoyl]-2-ethylpiperazin-1-yl]-5-(2-ethoxypyridin-3-yl)benzamide;

1-86: N-(2-aminoethyl)-2-[(2R)-4-(4,6-dimethylpyridine-3-carbonyl)-2-ethylpiperazin-1-yl]-5-(2-ethoxypyridin-3-yl)benzamide;

1-87: N-(2-aminoethyl)-2-[(2R)-4-(4-chloro-2-methylbenzoyl)-2-ethylpiperazin-1-yl]-5-(2-ethoxypyridin-3-yl)benzamide;

1-88: N-(2-aminoethyl)-2-[(2R)-4-(4-cyclopropyl-2-methylbenzoyl)-2-ethylpiperazin-1-yl]-5-(2-ethoxypyridin-3-yl)benzamide;

1-89: N-(2-aminoethyl)-2-[(2R)-4-(3-chloro-5-fluoropyridine-2-carbonyl)-2-ethylpiperazin-1-yl]-5-(2-ethoxypyridin-3-yl)benzamide;

1-90: 2-[(2R)-4-[4-chloro-2-(piperazin-1-yl)benzoyl]-2-ethylpiperazin-1-yl]-5-(2-ethoxypyridin-3-yl)-N-[(3R)-pyrrolidin-3-yl]benzamide;

1-91: 2-[(2R)-4-[4-chloro-2-(dimethyl amino)benzoyl]-2-ethylpiperazin-1-yl]-5-(2-ethoxypyridin-3-yl)-N-[(3R)-pyrrolidin-3-yl]benzamide;

1-92: 2-[(2R)-4-[4-chloro-2-(trifluoromethyl)benzoyl]-2-ethylpiperazin-1-yl]-5-(2-ethoxypyridin-3-yl)-N-[(3S)-pyrrolidin-3-yl]benzamide;

1-93: 2-[(2R)-4-[4-chloro-2-(trifluoromethyl)benzoyl]-2-ethylpiperazin-1-yl]-5-(2-ethoxypyridin-3-yl)-N-[2-(1H-imidazol-2-yl)ethyl]benzamide;

1-94: 5-(2-ethoxypyridin-3-yl)-2-[(2R)-2-ethyl-4-{4-methyl-2-[(3S)-3-(methylamino)pyrrolidin-1-yl]benzoyl}piperazin-1-yl]-N-[(3R)-pyrrolidin-3-yl]benzamide;

1-95: 6-[(2R)-4-[4-chloro-2-(trifluoromethyl)benzoyl]-2-ethylpiperazin-1-yl]-3-(2-ethoxypyridin-3-yl)-2-fluoro-N-[2-(methylamino)ethyl]benzamide;

1-96: 6-[(2R)-4-(2-chloro-4-fluorobenzoyl)-2-ethylpiperazin-1-yl]-3-(2-ethoxypyridin-3-yl)-2-fluoro-N-[2-(methylamino)ethyl]benzamide;

1-97: N-{[(2S)-azetidin-2-yl]methyl}-2-[(2R)-4-[4-chloro-2-(trifluoromethyl)benzoyl]-2-ethylpiperazin-1-yl]-5-(2-ethoxypyridin-3-yl)benzamide;

1-98: 2-[(2R)-4-[4-chloro-2-(trifluoromethyl)benzoyl]-2-ethylpiperazin-1-yl]-5-(2-ethoxypyridin-3-yl)-N-{[(2S)-pyrrolidin-2-yl]methyl}benzamide;

1-99: 2-[(2R)-4-[4-chloro-2-(trifluoromethyl)benzoyl]-2-ethylpiperazin-1-yl]-5-(2-ethoxypyridin-3-yl)-N-[(3R)-piperidin-3-yl]benzamide;

1-100: 2-[(2R)-4-[4-chloro-2-(trifluoromethyl)benzoyl]-2-ethylpiperazin-1-yl]-5-(2-ethoxypyridin-3-yl)-N-[(3S)-piperidin-3-yl]benzamide;

1-101: 5-(2-ethoxypyridin-3-yl)-2-[(2R)-2-ethyl-4-{4-fluoro-2-[(3S)-3-(methyl amino)pyrrolidin-1-yl]benzoyl}piperazin-1-yl]-N-[(3R)-pyrrolidin-3-yl]benzamide;

1-102: N-{[(2R)-azetidin-2-yl]methyl}-2-[(2R)-4-[4-chloro-2-(trifluoromethyl)benzoyl]-2-ethylpiperazin-1-yl]-5-(2-ethoxypyridin-3-yl)benzamide;

1-103: 5-(2-ethoxypyridin-3-yl)-2-[(2R)-2-ethyl-4-{2-fluoro-4-[(3S)-3-(methyl amino)pyrrolidin-1-yl]benzoyl}piperazin-1-yl]-N-[(3R)-pyrrolidin-3-yl]benzamide;

1-104: N-(2-aminoethyl)-2-[(2R)-4-{2-[3-(aminomethyl)pyrrolidin-1-yl]-4-methylbenzoyl}-2-ethylpiperazin-1-yl]-5-(2-ethoxypyridin-3-yl)benzamide;

1-105: N-(2-aminoethyl)-5-(2-ethoxypyridin-3-yl)-2-[(2R)-2-ethyl-4-[2-(morpholin-4-yl)-6-(trifluoromethyl)pyridine-3-carbonyl]piperazin-1-yl]benzamide;

1-106: N-(2-aminoethyl)-2-[(2R)-4-[3-(dimethylamino)-5-(trifluoromethyl)pyridine-2-carbonyl]-2-ethylpiperazin-1-yl]-5-(2-ethoxypyridin-3-yl)benzamide;

1-107: N-(2-aminoethyl)-2-[(2R)-4-[2-(dimethylamino)-4-(trifluoromethyl)benzoyl]-2-ethylpiperazin-1-yl]-5-(2-ethoxypyridin-3-yl)benzamide;

1-108: 2-[(2R)-4-[4-chloro-2-(trifluoromethyl)benzoyl]-2-ethylpiperazin-1-yl]-5-(2-ethoxypyridin-3-yl)-N-{[(2R)-pyrrolidin-2-yl]methyl}benzamide;

1-109: 2-[(2R)-4-[4-chloro-2-(trifluoromethyl)benzoyl]-2-ethylpiperazin-1-yl]-5-(2-ethoxypyridin-3-yl)-N-{[(2S)-morpholin-2-yl]methyl}benzamide;

1-110: 6-[(2R)-4-(2-chloro-4-methylbenzoyl)-2-ethylpiperazin-1-yl]-3-(2-ethoxypyridin-3-yl)-2-fluoro-N-[(3R)-pyrrolidin-3-yl]benzamide;

1-111: 3-(2-ethoxypyridin-3-yl)-6-[(2R)-2-ethyl-4-[4-fluoro-2-(trifluoromethyl)benzoyl]piperazin-1-yl]-2-fluoro-N-[(3R)-pyrrolidin-3-yl]benzamide;

1-112: N-{[(2S)-azetidin-2-yl]methyl}-6-[(2R)-4-[4-chloro-2-(trifluoromethyl)benzoyl]-2-ethylpiperazin-1-yl]-3-(2-ethoxypyridin-3-yl)-2-fluorobenzamide;

1-113: 6-[(2R)-4-(2-chloro-4-methylbenzoyl)-2-ethylpiperazin-1-yl]-3-(2-ethoxypyridin-3-yl)-2-fluoro-N-[2-(methylamino)ethyl]benzamide;

1-114: 3-(2-ethoxypyridin-3-yl)-6-[(2R)-2-ethyl-4-[4-fluoro-2-(trifluoromethyl)benzoyl]piperazin-1-yl]-2-fluoro-N-[2-(methylamino)ethyl]benzamide;

1-115: 2-[(2R)-4-{4-chloro-2-[(3S)-3-(dimethylamino)pyrrolidin-1-yl]benzoyl}-2-ethylpiperazin-1-yl]-5-(2-ethoxypyridin-3-yl)-N-[(3R)-pyrrolidin-3-yl]benzamide;

1-116: 6-[(2R)-4-[4-chloro-2-(trifluoromethyl)benzoyl]-2-ethylpiperazin-1-yl]-3-(2-ethoxypyridin-3-yl)-2-fluoro-N-[2-(1H-imidazol-2-yl)ethyl]benzamide;

1-117: N-(2-aminoethyl)-2-[(2R)-4-(4-chloro-2-cyanobenzoyl)-2-ethylpiperazin-1-yl]-5-(2-ethoxypyridin-3-yl)benzamide;

1-118: N-(2-aminoethyl)-5-(2-ethoxypyridin-3-yl)-2-[(2R)-2-ethyl-4-[5-fluoro-3-(trifluoromethyl)pyridine-2-carbonyl]piperazin-1-yl]benzamide;

1-119: N-(2-aminoethyl)-5-(2-ethoxypyridin-3-yl)-2-[(2R)-2-ethyl-4-[2-(methylamino)-6-(trifluoromethyl)pyridine-3-carbonyl]piperazin-1-yl]benzamide;

1-120: N-(2-aminoethyl)-5-(2-ethoxypyridin-3-yl)-2-[(2R)-2-ethyl-4-[2-(pyrrolidin-1-yl)-6-(trifluoromethyl)pyridine-3-carbonyl]piperazin-1-yl]benzamide;

1-121: 3-(2-ethoxypyridin-3-yl)-6-[(2R)-2-ethyl-4-[2-(trifluoromethyl)benzoyl]piperazin-1-yl]-2-fluoro-N-[2-(methylamino)ethyl]benzamide;

1-122: 3-(2-ethoxypyridin-3-yl)-6-[(2R)-2-ethyl-4-[2-(trifluoromethyl)benzoyl]piperazin-1-yl]-2-fluoro-N-[(3R)-pyrrolidin-3-yl]benzamide;

1-123: N-{[(2R)-azetidin-2-yl]methyl}-6-[(2R)-4-[4-chloro-2-(trifluoromethyl)benzoyl]-2-ethylpiperazin-1-yl]-3-(2-ethoxypyridin-3-yl)-2-fluorobenzamide;

1-124: 6-[(2R)-4-[4-chloro-2-(trifluoromethyl)benzoyl]-2-ethylpiperazin-1-yl]-3-(2-ethoxypyridin-3-yl)-2-fluoro-N-{[(2R)-pyrrolidin-2-yl]methyl}benzamide;

1-125: 2-[(2R)-4-[4-chloro-2-(trifluoromethyl)benzoyl]-2-ethylpiperazin-1-yl]-N-[(4,5-dihydro-1H-imidazol-2-yl)methyl]-5-(2-ethoxypyridin-3-yl)benzamide;

1-126: 2-[(2R)-4-[2-amino-6-(trifluoromethyl)pyridine-3-carbonyl]-2-ethylpiperazin-1-yl]-N-(2-aminoethyl)-5-(2-ethoxypyridin-3-yl)benzamide;

1-127: N-(2-aminoethyl)-2-[(2R)-4-[6-(dimethylamino)-2-(trifluoromethyl)pyridine-3-carbonyl]-2-ethylpiperazin-1-yl]-5-(2-ethoxypyridin-3-yl)benzamide;

1-128: 2-[(2R)-4-[4-chloro-2-(difluoromethyl)benzoyl]-2-ethylpiperazin-1-yl]-5-(2-ethoxypyridin-3-yl)-N-[2-(methylamino)ethyl]benzamide;

1-129: N-[2-(dimethylamino)ethyl]-5-(2-ethoxypyridin-3-yl)-2-[(2R)-2-ethyl-4-[4-fluoro-2-(1H-imidazol-1-yl)benzoyl]piperazin-1-yl]benzamide;

1-130: N-[2-(dimethylamino)ethyl]-5-(2-ethoxypyridin-3-yl)-2-[(2R)-2-ethyl-4-[4-fluoro-2-(1H-pyrrol-1-yl)benzoyl]piperazin-1-yl]benzamide;

1-131: N-[2-(dimethylamino)ethyl]-5-(2-ethoxypyridin-3-yl)-2-[(2R)-2-ethyl-4-[4-fluoro-2-(1H-pyrazol-1-yl)benzoyl]piperazin-1-yl]benzamide;

1-132: 2-[(2R)-4-[4-chloro-2-(trifluoromethyl)benzoyl]-2-ethylpiperazin-1-yl]-5-(2-ethoxypyridin-3-yl)-N-[(1H-imidazol-2-yl)methyl]benzamide;

1-133: 5-(2-ethoxypyridin-3-yl)-2-[(2R)-2-ethyl-4-[5-(trifluoromethyl)pyridine-2-carbonyl]piperazin-1-yl]-N-[(3R)-pyrrolidin-3-yl]benzamide;

1-134: 2-[(2R)-4-[3-chloro-5-(trifluoromethyl)pyridine-2-carbonyl]-2-ethylpiperazin-1-yl]-5-(2-ethoxypyridin-3-yl)-N-[(3R)-pyrrolidin-3-yl]benzamide;

1-135: 5-[(2R)-4-[4-chloro-2-(trifluoromethyl)benzoyl]-2-ethylpiperazin-1-yl]-2'-ethoxy-N-[2-(methylamino)ethyl]-[2,3'-bipyridine]-6-carboxamide;

1-136: 2'-ethoxy-5-[(2R)-2-ethyl-4-[4-fluoro-2-(trifluoromethyl)benzoyl]piperazin-1-yl]-N-[2-(methylamino)ethyl]-[2,3'-bipyridine]-6-carboxamide;

1-137: 2'-ethoxy-5-[(2R)-4-[4-ethoxy-2-(trifluoromethyl)benzoyl]-2-ethylpiperazin-1-yl]-N-[2-(methylamino)ethyl]-[2,3'-bipyridine]-6-carboxamide;

1-138: 2-[(2R)-4-[4-chloro-2-(trifluoromethyl)benzoyl]-2-ethylpiperazin-1-yl]-5-(2-ethoxypyridin-3-yl)-N-{[(3S)-morpholin-3-yl]methyl}benzamide;
1-139: 2-[(2R)-4-[4-chloro-2-(trifluoromethyl)benzoyl]-2-ethylpiperazin-1-yl]-5-(2-ethoxypyridin-3-yl)-N-[2-(1H-1,2,4-triazol-1-yl)ethyl]benzamide;
1-140: 6-[(2R)-4-(4-chloro-2-cyanobenzoyl)-2-ethylpiperazin-1-yl]-3-(2-ethoxypyridin-3-yl)-2-fluoro-N-[2-(1H-imidazol-2-yl)ethyl]benzamide;
1-141: 6-[(2R)-4-(4-chloro-2-ethoxybenzoyl)-2-ethylpiperazin-1-yl]-3-(2-ethoxypyridin-3-yl)-2-fluoro-N-[2-(1H-imidazol-2-yl)ethyl]benzamide;
1-142: 2-[(2R)-4-(4-chloro-2-cyanobenzoyl)-2-ethylpiperazin-1-yl]-5-(2-ethoxypyridin-3-yl)-N-[(3R)-pyrrolidin-3-yl]benzamide;
1-143: 5-(2-ethoxypyridin-3-yl)-2-[(2R)-2-ethyl-4-[4-methoxy-2-(trifluoromethyl)benzoyl]piperazin-1-yl]-N-[(3R)-pyrrolidin-3-yl]benzamide;
1-144: 2-[(2R)-4-[4-cyano-2-(trifluoromethyl)benzoyl]-2-ethylpiperazin-1-yl]-5-(2-ethoxypyridin-3-yl)-N-[(3R)-pyrrolidin-3-yl]benzamide;
1-145: 2-[(2R)-4-[6-amino-2-(trifluoromethyl)pyridine-3-carbonyl]-2-ethylpiperazin-1-yl]-N-(2-aminoethyl)-5-(2-ethoxypyridin-3-yl)benzamide;
1-146: N-(2-aminoethyl)-2-[(2R)-4-[4-(dimethylamino)-6-(trifluoromethyl)pyridine-3-carbonyl]-2-ethylpiperazin-1-yl]-5-(2-ethoxypyridin-3-yl)benzamide;
1-147: 2-[(2R)-4-[2-(dimethylamino)-4-fluorobenzoyl]-2-ethylpiperazin-1-yl]-N-[2-(dimethylamino)ethyl]-5-(2-ethoxypyridin-3-yl)benzamide;
1-148: 2-[(2R)-4-[2-(3-aminoazetidin-1-yl)-4-fluorobenzoyl]-2-ethylpiperazin-1-yl]-N-[2-(dimethylamino)ethyl]-5-(2-ethoxypyridin-3-yl)benzamide;
1-149: 3-[(2R)-4-[4-chloro-2-(trifluoromethyl)benzoyl]-2-ethylpiperazin-1-yl]-N-[2-(dimethylamino)ethyl]-6-(2-ethoxyphenyl)pyridine-2-carboxamide;
1-150: 5-[(2R)-4-[4-chloro-2-(trifluoromethyl)benzoyl]-2-ethylpiperazin-1-yl]-N-[2-(dimethylamino)ethyl]-2'-ethoxy-[2,3'-bipyridine]-6-carboxamide;
1-151: 5-[(2R)-4-[4-chloro-2-(trifluoromethyl)benzoyl]-2-ethylpiperazin-1-yl]-2'-ethoxy-N-[(3R)-pyrrolidin-3-yl]-[2,3'-bipyridine]-6-carboxamide;
1-152: 5-[(2R)-4-[4-chloro-2-(trifluoromethyl)benzoyl]-2-ethylpiperazin-1-yl]-2'-ethoxy-N-[(3R)-1-methylpyrrolidin-3-yl]-[2,3'-bipyridine]-6-carboxamide;
1-153: 6-[(2R)-4-(4-chloro-2-cyanobenzoyl)-2-ethylpiperazin-1-yl]-3-(2-ethoxypyridin-3-yl)-2-fluoro-N-[2-(methylamino)ethyl]benzamide;
1-154: 6-[(2R)-4-[4-cyano-2-(trifluoromethyl)benzoyl]-2-ethylpiperazin-1-yl]-3-(2-ethoxypyridin-3-yl)-2-fluoro-N-[2-(methylamino)ethyl]benzamide;
1-155: 3-(2-ethoxypyridin-3-yl)-6-[(2R)-2-ethyl-4-[4-methoxy-2-(trifluoromethyl)benzoyl]piperazin-1-yl]-2-fluoro-N-[2-(methylamino)ethyl]benzamide;
1-156: 6-[(2R)-4-(2,4-dichlorobenzoyl)-2-ethylpiperazin-1-yl]-3-(2-ethoxypyridin-3-yl)-2-fluoro-N-[2-(methylamino)ethyl]benzamide;
1-157: 6-[(2R)-4-[2-cyano-4-(trifluoromethyl)benzoyl]-2-ethylpiperazin-1-yl]-3-(2-ethoxypyridin-3-yl)-2-fluoro-N-[2-(methylamino)ethyl]benzamide;
1-158: 5-[(2R)-4-(4-chloro-2-cyanobenzoyl)-2-ethylpiperazin-1-yl]-N-[2-(dimethylamino)ethyl]-2'-ethoxy-[2,3'-bipyridine]-6-carboxamide;
1-159: N-(2-aminoethyl)-5-(2-ethoxypyridin-3-yl)-2-[(2R)-2-ethyl-4-[2-methoxy-6-(trifluoromethyl)pyridine-3-carbonyl]piperazin-1-yl]benzamide;
1-160: N-(2-aminoethyl)-2-[(2R)-4-[2-(dimethylamino)-6-methylpyridine-3-carbonyl]-2-ethylpiperazin-1-yl]-5-(2-ethoxypyridin-3-yl)benzamide;
1-161: 2-[(2R)-4-[2-(azetidin-1-yl)-4-fluorobenzoyl]-2-ethylpiperazin-1-yl]-N-[2-(dimethylamino)ethyl]-5-(2-ethoxypyridin-3-yl)benzamide;
1-162: N-[2-(dimethylamino)ethyl]-5-(2-ethoxypyridin-3-yl)-2-[(2R)-2-ethyl-4-[4-fluoro-2-(pyrrolidin-1-yl)benzoyl]piperazin-1-yl]benzamide;
1-163: 3-(2-ethoxypyridin-3-yl)-6-[(2R)-2-ethyl-4-[6-(methyl amino)-2-(trifluoromethyl)pyridine-3-carbonyl]piperazin-1-yl]-2-fluoro-N-[2-(methylamino)ethyl]benzamide;
1-164: 3-(2-ethoxypyridin-3-yl)-6-[(2R)-2-ethyl-4-[6-methoxy-2-(trifluoromethyl)pyridine-3-carbonyl]piperazin-1-yl]-2-fluoro-N-[2-(methylamino)ethyl]benzamide;
1-165: 6-[(2R)-4-[6-ethoxy-2-(trifluoromethyl)pyridine-3-carbonyl]-2-ethylpiperazin-1-yl]-3-(2-ethoxypyridin-3-yl)-2-fluoro-N-[2-(methylamino)ethyl]benzamide;
1-166: 3-(2-ethoxypyridin-3-yl)-6-[(2R)-2-ethyl-4-[2-methoxy-6-(trifluoromethyl)pyridine-3-carbonyl]piperazin-1-yl]-2-fluoro-N-[2-(methylamino)ethyl]benzamide;
1-167: 2'-ethoxy-5-[(2R)-2-ethyl-4-[4-methoxy-2-(trifluoromethyl)benzoyl]piperazin-1-yl]-N-[2-(methylamino)ethyl]-[2,3'-bipyridine]-6-carboxamide;
1-168: N-[2-(dimethylamino)ethyl]-3-(2-ethoxypyridin-3-yl)-6-[(2R)-2-ethyl-4-[4-methoxy-2-(trifluoromethyl)benzoyl]piperazin-1-yl]-2-fluorobenzamide;
1-169: N-[2-(dimethylamino)ethyl]-2'-ethoxy-5-[(2R)-2-ethyl-4-[4-methoxy-2-(trifluoromethyl)benzoyl]piperazin-1-yl]-[2,3'-bipyridine]-6-carboxamide;
1-170: N-[(4,5-dihydro-1H-imidazol-2-yl)methyl]-3-(2-ethoxypyridin-3-yl)-6-[(2R)-2-ethyl-4-[4-methoxy-2-(trifluoromethyl)benzoyl]piperazin-1-yl]-2-fluorobenzamide;
1-171: 5-[(2R)-4-(4-chloro-2-cyanobenzoyl)-2-ethylpiperazin-1-yl]-2'-ethoxy-N-[2-(methylamino)ethyl]-[2,3'-bipyridine]-6-carboxamide;
1-172: 5-[(2R)-4-(2-carbamoyl-4-chlorobenzoyl)-2-ethylpiperazin-1-yl]-2'-ethoxy-N-[2-(methylamino)ethyl]-[2,3'-bipyridine]-6-carboxamide;
1-173: 6-[(2R)-4-[4-chloro-2-(trifluoromethyl)benzoyl]-2-ethylpiperazin-1-yl]-N-[2-(dimethylamino)ethyl]-3-(2-ethoxypyridin-3-yl)-2-fluorobenzamide;
1-174: N-[2-(dimethylamino)ethyl]-3-(2-ethoxypyridin-3-yl)-6-[(2R)-2-ethyl-4-[4-fluoro-2-(trifluoromethyl)benzoyl]piperazin-1-yl]-2-fluorobenzamide;
1-175: 6-[(2R)-4-[4-cyano-2-(trifluoromethyl)benzoyl]-2-ethylpiperazin-1-yl]-N-[2-(dimethylamino)ethyl]-3-(2-ethoxypyridin-3-yl)-2-fluorobenzamide;
1-176: 6-[(2R)-4-[2-(difluoromethyl)-4-fluorobenzoyl]-2-ethylpiperazin-1-yl]-N-[2-(dimethylamino)ethyl]-3-(2-ethoxypyridin-3-yl)-2-fluorobenzamide;
1-177: 6-[(2R)-4-[2-(difluoromethyl)-4-fluorobenzoyl]-2-ethylpiperazin-1-yl]-3-(2-ethoxypyridin-3-yl)-2-fluoro-N-[2-(methylamino)ethyl]benzamide;
1-178: 6-[(2R)-4-(2,4-dichlorobenzoyl)-2-ethylpiperazin-1-yl]-N-[(4,5-dihydro-1H-imidazol-2-yl)methyl]-3-(2-ethoxypyridin-3-yl)-2-fluorobenzamide;
1-179: 6-[(2R)-4-(2,4-dichlorobenzoyl)-2-ethylpiperazin-1-yl]-N-[2-(dimethylamino)ethyl]-3-(2-ethoxypyridin-3-yl)-2-fluorobenzamide;
1-180: 6-[(2R)-4-{4-chloro-2-[(3S)-3-(dimethylamino)pyrrolidin-1-yl]benzoyl}-2-ethylpiperazin-1-yl]-N-[2-(dimethylamino)ethyl]-3-(2-ethoxypyridin-3-yl)-2-fluorobenzamide;

1-181: 2'-ethoxy-5-[(2R)-4-[6-ethoxy-2-(trifluoromethyl)pyridine-3-carbonyl]-2-ethylpiperazin-1-yl]-N-[2-(methylamino)ethyl]-[2,3'-bipyridine]-6-carboxamide;

1-182: N-[(4,5-dihydro-1H-imidazol-2-yl)methyl]-3-(2-ethoxypyridin-3-yl)-6-[(2R)-2-ethyl-4-[4-fluoro-2-(trifluoromethyl)benzoyl]piperazin-1-yl]-2-fluorobenzamide;

1-183: 6-[(2R)-4-[4-chloro-2-(difluoromethyl)benzoyl]-2-ethylpiperazin-1-yl]-3-(2-ethoxypyridin-3-yl)-2-fluoro-N-[2-(methylamino)ethyl]benzamide;

1-184: 6-[(2R)-4-[4-chloro-2-(difluoromethyl)benzoyl]-2-ethylpiperazin-1-yl]-N-[2-(dimethylamino)ethyl]-3-(2-ethoxypyridin-3-yl)-2-fluorobenzamide;

1-185: 2'-ethoxy-5-[(2R)-2-ethyl-4-[6-methyl-2-(trifluoromethyl)pyridine-3-carbonyl]piperazin-1-yl]-N-[2-(methylamino)ethyl]-[2,3'-bipyridine]-6-carboxamide;

1-186: 6-[(2R)-4-(4-chloro-2-cyanobenzoyl)-2-ethylpiperazin-1-yl]-N-[2-(dimethyl amino)ethyl]-3-(2-ethoxypyridin-3-yl)-2-fluorobenzamide;

1-187: 2'-ethoxy-5-[(2R)-2-ethyl-4-[6-methoxy-2-(trifluoromethyl)pyridine-3-carbonyl]piperazin-1-yl]-N-[2-(methylamino)ethyl]-[2,3'-bipyridine]-6-carboxamide;

1-188: 6-[(2R)-4-[4-chloro-2-(trifluoromethyl)benzoyl]-2-ethylpiperazin-1-yl]-N-[(4,5-dihydro-1H-imidazol-2-yl)methyl]-3-(2-ethoxypyridin-3-yl)-2-fluorobenzamide;

1-189: 6-[(2R)-4-[2-(difluoromethyl)-4-fluorobenzoyl]-2-ethylpiperazin-1-yl]-3-(2-ethoxypyridin-3-yl)-2-fluoro-N-[(3R)-pyrrolidin-3-yl]benzamide;

1-190: 6-[(2R)-4-[4-chloro-2-(difluoromethyl)benzoyl]-2-ethylpiperazin-1-yl]-3-(2-ethoxypyridin-3-yl)-2-fluoro-N-[(3R)-pyrrolidin-3-yl]benzamide;

1-191: N-[2-(dimethylamino)ethyl]-5-(2-ethoxypyridin-3-yl)-2-[(2R)-2-ethyl-4-{2-[ethyl(methyl)amino]-4-fluorobenzoyl}piperazin-1-yl]benzamide;

1-192: 2-[(2R)-4-(2-chloro-4-fluorobenzoyl)-2-ethylpiperazin-1-yl]-5-(4,6-dimethoxypyrimidin-5-yl)-N-[2-(methylamino)ethyl]benzamide;

1-193: 2-[(2R)-4-(2-chloro-4-fluorobenzoyl)-2-ethylpiperazin-1-yl]-5-(6-methoxy-4-oxo-1,4-dihydropyrimidin-5-yl)-N-[2-(methylamino)ethyl]benzamide;

1-194: 5-[(2R)-4-[4-chloro-2-(trifluoromethyl)benzoyl]-2-ethylpiperazin-1-yl]-2'-ethyl-N-[2-(methylamino)ethyl]-[2,3'-bipyridine]-6-carboxamide;

1-195: 5-[(2R)-4-(2-chloro-4-ethoxybenzoyl)-2-ethylpiperazin-1-yl]-2'-ethoxy-N-[2-(methylamino)ethyl]-[2,3'-bipyridine]-6-carboxamide;

1-196: 5-[(2R)-4-(2-chloro-4-ethoxybenzoyl)-2-ethylpiperazin-1-yl]-N-[2-(dimethyl amino)ethyl]-2'-ethoxy-[2,3'-bipyridine]-6-carboxamide;

1-197: 6-[(2R)-4-{4-chloro-2-[(3S)-3-(dimethylamino)pyrrolidin-1-yl]benzoyl}-2-ethylpiperazin-1-yl]-3-(2-ethoxypyridin-3-yl)-2-fluoro-N-[2-(methylamino)ethyl]benzamide;

1-198: N-(azetidin-3-yl)-6-[(2R)-4-[4-chloro-2-(trifluoromethyl)benzoyl]-2-ethylpiperazin-1-yl]-3-(2-ethoxypyridin-3-yl)-2-fluorobenzamide;

1-199: 6-[(2R)-4-[4-chloro-2-(trifluoromethyl)benzoyl]-2-ethylpiperazin-1-yl]-3-(2-ethoxypyridin-3-yl)-2-fluoro-N-[(3R)-1-methylpyrrolidin-3-yl]benzamide;

1-200: 6-[(2R)-4-[4-chloro-2-(trifluoromethyl)benzoyl]-2-ethylpiperazin-1-yl]-3-(2-ethoxypyridin-3-yl)-2-fluoro-N-[(3S)-pyrrolidin-3-yl]benzamide;

1-201: 6-[(2R)-4-[4-chloro-2-(trifluoromethyl)benzoyl]-2-ethylpiperazin-1-yl]-3-(2-ethoxypyridin-3-yl)-2-fluoro-N-[(3S)-1-methylpyrrolidin-3-yl]benzamide;

1-202: N-(azetidin-3-yl)-3-(2-ethoxypyridin-3-yl)-6-[(2R)-2-ethyl-4-[4-methoxy-2-(trifluoromethyl)benzoyl]piperazin-1-yl]-2-fluorobenzamide;

1-203: 3-(2-ethoxypyridin-3-yl)-6-[(2R)-2-ethyl-4-[4-methoxy-2-(trifluoromethyl)benzoyl]piperazin-1-yl]-2-fluoro-N-(1-methylazetidin-3-yl)benzamide;

1-204: 6-[(2R)-4-[4-chloro-2-(trifluoromethyl)benzoyl]-2-ethylpiperazin-1-yl]-3-(2-ethoxypyridin-3-yl)-2-fluoro-N-(1-methylazetidin-3-yl)benzamide;

1-205: 5-[(2R)-4-[4-chloro-2-(trifluoromethyl)benzoyl]-2-ethylpiperazin-1-yl]-N-[2-(dimethylamino)ethyl]-2'-ethyl-[2,3'-bipyridine]-6-carboxamide;

1-206: 3-[(2R)-4-[4-chloro-2-(trifluoromethyl)benzoyl]-2-ethylpiperazin-1-yl]-6-(2-ethoxyphenyl)-N-[(3R)-1-methylpyrrolidin-3-yl]pyridine-2-carboxamide;

1-207: N-[2-(dimethylamino)ethyl]-2'-ethoxy-5-[(2R)-4-[6-ethoxy-2-(trifluoromethyl)pyridine-3-carbonyl]-2-ethylpiperazin-1-yl]-[2,3'-bipyridine]-6-carboxamide;

1-208: 3-[(2R)-4-[4-chloro-2-(trifluoromethyl)benzoyl]-2-ethylpiperazin-1-yl]-6-(2-ethoxyphenyl)-N-[2-(methylamino)ethyl]pyridine-2-carboxamide;

1-209: 3-[(2R)-4-[4-chloro-2-(trifluoromethyl)benzoyl]-2-ethylpiperazin-1-yl]-6-(2-ethoxyphenyl)-N-[(3R)-pyrrolidin-3-yl]pyridine-2-carboxamide;

1-210: 5-[(2R)-4-[4-chloro-2-(difluoromethyl)benzoyl]-2-ethylpiperazin-1-yl]-N-[2-(dimethylamino)ethyl]-2'-ethoxy-[2,3'-bipyridine]-6-carboxamide;

1-211: N-(azetidin-3-yl)-5-[(2R)-4-[4-chloro-2-(trifluoromethyl)benzoyl]-2-ethylpiperazin-1-yl]-2'-ethoxy-[2,3'-bipyridine]-6-carboxamide;

1-212: 5-[(2R)-4-[4-chloro-2-(trifluoromethyl)benzoyl]-2-ethylpiperazin-1-yl]-2'-ethoxy-N-(1-methylazetidin-3-yl)-[2,3'-bipyridine]-6-carboxamide;

1-213: 5-[(2R)-4-[4-chloro-2-(difluoromethyl)benzoyl]-2-ethylpiperazin-1-yl]-2'-ethoxy-N-[2-(methylamino)ethyl]-[2,3'-bipyridine]-6-carboxamide;

1-214: 5-[(2R)-4-[4-chloro-2-(trifluoromethyl)benzoyl]-2-ethylpiperazin-1-yl]-2'-ethoxy-N-[(3S)-pyrrolidin-3-yl]-[2,3'-bipyridine]-6-carboxamide;

1-215: 5-[(2R)-4-[4-chloro-2-(trifluoromethyl)benzoyl]-2-ethylpiperazin-1-yl]-2'-ethoxy-N-[(3S)-1-methylpyrrolidin-3-yl]-[2,3'-bipyridine]-6-carboxamide.

1-216: 2-[(2R)-4-[4-chloro-2-(trifluoromethyl)benzoyl]-2-ethylpiperazin-1-yl]-5-(2-ethoxypyridin-3-yl)-N-(1-methylazetidin-3-yl)benzamide;

1-217: 6-[(2R)-4-[4-chloro-2-(trifluoromethyl)benzoyl]-2-ethylpiperazin-1-yl]-3-(4-ethoxypyrimidin-5-yl)-2-fluoro-N-[2-(methylamino)ethyl]benzamide;

1-218: 5-[(2R)-4-(2-chloro-4-cyclopropoxybenzoyl)-2-ethylpiperazin-1-yl]-2'-ethoxy-N-[2-(methylamino)ethyl]-[2,3'-bipyridine]-6-carboxamide;

1-219: 6-[(2R)-4-[4-chloro-2-(trifluoromethyl)benzoyl]-2-ethylpiperazin-1-yl]-N-[2-(4,5-dihydro-1H-imidazol-2-yl)ethyl]-3-(2-ethoxypyridin-3-yl)-2-fluorobenzamide;

1-220: N-(azetidin-3-yl)-3-[(2R)-4-[4-chloro-2-(trifluoromethyl)benzoyl]-2-ethylpiperazin-1-yl]-6-(2-ethoxyphenyl)pyridine-2-carboxamide;

1-221: 3-[(2R)-4-[4-chloro-2-(trifluoromethyl)benzoyl]-2-ethylpiperazin-1-yl]-6-(2-ethoxyphenyl)-N-(1-methylazetidin-3-yl)pyridine-2-carboxamide.

1-222: N-[(azetidin-3-yl)methyl]-5-[(2R)-4-[4-chloro-2-(trifluoromethyl)benzoyl]-2-ethylpiperazin-1-yl]-2'-ethoxy-[2,3'-bipyridine]-6-carboxamide;

1-223: 5-[(2R)-4-[4-chloro-2-(trifluoromethyl)benzoyl]-2-ethylpiperazin-1-yl]-2'-ethoxy-N-[(1-methylazetidin-3-yl)methyl]-[2,3'-bipyridine]-6-carboxamide;

1-224: 2'-ethoxy-5-[(2R)-2-ethyl-4-[4-fluoro-2-(trifluoromethyl)benzoyl]piperazin-1-yl]-N-[2-(1H-imidazol-2-yl)ethyl]-[2,3'-bipyridine]-6-carboxamide;

1-225: 2'-ethoxy-5-[(2R)-2-ethyl-4-[6-(ethyl amino)-2-(trifluoromethyl)pyridine-3-carbonyl]piperazin-1-yl]-N-[2-(methylamino)ethyl]-[2,3'-bipyridine]-6-carboxamide;

1-226: 5-[(2R)-4-[4-chloro-2-(trifluoromethyl)benzoyl]-2-ethylpiperazin-1-yl]-N-[(4,5-dihydro-1H-imidazol-2-yl)methyl]-2'-ethoxy-[2,3'-bipyridine]-6-carboxamide;

1-227: 5-[(2R)-4-[4-chloro-2-(trifluoromethyl)benzoyl]-2-ethylpiperazin-1-yl]-2'-ethoxy-N-[(1-methyl-4,5-dihydro-1H-imidazol-2-yl)methyl]-[2,3'-bipyridine]-6-carboxamide;

1-228: 2-[(2R)-4-[4-chloro-2-(trifluoromethyl)benzoyl]-2-ethylpiperazin-1-yl]-5-(2-ethoxypyridin-3-yl)-N-{[(2R)-1-methylazetidin-2-yl]methyl}benzamide;

1-229: 6-[(2R)-4-[4-chloro-2-(trifluoromethyl)benzoyl]-2-ethylpiperazin-1-yl]-3-(2-ethoxypyridin-3-yl)-2-fluoro-N-{[(2S)-1-methylazetidin-2-yl]methyl}benzamide.

1-230: 2'-ethoxy-5-[(2R)-2-ethyl-4-[6-methoxy-2-(trifluoromethyl)pyridine-3-carbonyl]piperazin-1-yl]-N-(1-methylazetidin-3-yl)-[2,3'-bipyridine]-6-carboxamide;

1-231: 5-[(2R)-4-[4-chloro-2-(trifluoromethyl)benzoyl]-2-ethylpiperazin-1-yl]-2'-ethoxy-N-{[(2R)-1-methylazetidin-2-yl]methyl}-[2,3'-bipyridine]-6-carboxamide;

1-232: 5-[(2R)-4-[4-chloro-2-(trifluoromethyl)benzoyl]-2-ethylpiperazin-1-yl]-2'-ethoxy-N-{[(2S)-1-methylazetidin-2-yl]methyl}-[2,3'-bipyridine]-6-carboxamide;

1-233: 2'-ethoxy-5-[(2R)-4-[6-ethoxy-2-(trifluoromethyl)pyridine-3-carbonyl]-2-ethylpiperazin-1-yl]-N-(1-methylazetidin-3-yl)-[2,3'-bipyridine]-6-carboxamide;

1-234: 5-[(2R)-4-[4-chloro-2-(trifluoromethyl)benzoyl]-2-ethylpiperazin-1-yl]-2'-ethoxy-N-[2-(1-methyl-1H-imidazol-2-yl)ethyl]-[2,3'-bipyridine]-6-carboxamide;

1-235: 2'-ethoxy-5-[(2R)-2-ethyl-4-[1-(trifluoromethyl)cyclopropanecarbonyl]piperazin-1-yl]-N-(1-methylazetidin-3-yl)-[2,3'-bipyridine]-6-carboxamide;

1-236: 6-(2-ethoxyphenyl)-3-[(2R)-2-ethyl-4-[6-methoxy-2-(trifluoromethyl)pyridine-3-carbonyl]piperazin-1-yl]-N-(1-methylazetidin-3-yl)pyridine-2-carboxamide;

1-237: 3-[(2R)-4-[6-ethoxy-2-(trifluoromethyl)pyridine-3-carbonyl]-2-ethylpiperazin-1-yl]-6-(2-ethoxyphenyl)-N-(1-methylazetidin-3-yl)pyridine-2-carboxamide;

1-238: 5-[(2R)-4-(adamantane-2-carbonyl)-2-ethylpiperazin-1-yl]-2'-ethoxy-N-(1-methyl azetidin-3-yl)-[2,3'-bipyridine]-6-carboxamide;

1-239: 2'-ethoxy-5-[(2R)-2-ethyl-4-[6-methoxy-2-(trifluoromethyl)pyridine-3-carbonyl]piperazin-1-yl]-N-[(3R)-1-methylpyrrolidin-3-yl]-[2,3'-bipyridine]-6-carboxamide;

1-240: 2'-ethoxy-5-[(2R)-2-ethyl-4-[6-methoxy-2-(trifluoromethyl)pyridine-3-carbonyl]piperazin-1-yl]-N-[(3R)-pyrrolidin-3-yl]-[2,3'-bipyridine]-6-carboxamide;

1-241: 2'-ethoxy-5-[(2R)-2-ethyl-4-[1-(trifluoromethyl)cyclopentanecarbonyl]piperazin-1-yl]-N-(1-methylazetidin-3-yl)-[2,3'-bipyridine]-6-carboxamide;

1-242: 2'-ethoxy-5-[(2R)-2-ethyl-4-[6-methoxy-2-(trifluoromethyl)pyridine-3-carbonyl]piperazin-1-yl]-N-[(1-methylazetidin-3-yl)methyl]-[2,3'-bipyridine]-6-carboxamide;

1-243: 2'-ethoxy-5-[(2R)-4-[6-ethoxy-2-(trifluoromethyl)pyridine-3-carbonyl]-2-ethylpiperazin-1-yl]-N-[(3R)-1-methylpyrrolidin-3-yl]-[2,3'-bipyridine]-6-carboxamide;

1-244: N-{[(2S)-azetidin-2-yl]methyl}-2'-ethoxy-5-[(2R)-2-ethyl-4-[6-methoxy-2-(trifluoromethyl)pyridine-3-carbonyl]piperazin-1-yl]-[2,3'-bipyridine]-6-carboxamide;

1-245: 2'-ethoxy-5-[(2R)-2-ethyl-4-[6-methoxy-2-(trifluoromethyl)pyridine-3-carbonyl]piperazin-1-yl]-N-{[(2S)-1-methylazetidin-2-yl]methyl}-[2,3'-bipyridine]-6-carboxamide;

1-246: 5-[(2R)-2-ethyl-4-[6-methoxy-2-(trifluoromethyl)pyridine-3-carbonyl]piperazin-1-yl]-2'-methoxy-N-(1-methylazetidin-3-yl)-[2,3'-bipyridine]-6-carboxamide;

1-247: 5-[(2R)-4-[6-ethoxy-2-(trifluoromethyl)pyridine-3-carbonyl]-2-ethylpiperazin-1-yl]-2'-methoxy-N-(1-methylazetidin-3-yl)-[2,3'-bipyridine]-6-carboxamide;

1-248: 5-[(2R)-4-[1-(2,2-difluoroethyl)cyclobutanecarbonyl]-2-ethylpiperazin-1-yl]-2'-ethoxy-N-(1-methylazetidin-3-yl)-[2,3'-bipyridine]-6-carboxamide;

1-249: 2'-ethoxy-5-[(2R)-4-[6-ethoxy-2-(trifluoromethyl)pyridine-3-carbonyl]-2-ethylpiperazin-1-yl]-N-[(1-methylazetidin-3-yl)methyl]-[2,3'-bipyridine]-6-carboxamide;

1-250: 2'-ethoxy-5-[(2R)-2-ethyl-4-(1-ethylcyclobutanecarbonyl)piperazin-1-yl]-N-[2-(methylamino)ethyl]-[2,3'-bipyridine]-6-carboxamide;

1-251: 3-(2-ethoxypyridin-3-yl)-6-[(2R)-2-ethyl-4-[cis-4-(trifluoromethyl)cyclohexanecarbonyl]piperazin-1-yl]-2-fluoro-N-[2-(methylamino)ethyl]benzamide;

1-252: 3-(2-ethoxypyridin-3-yl)-6-[(2R)-2-ethyl-4-[trans-4-(trifluoromethyl)cyclohexanecarbonyl]piperazin-1-yl]-2-fluoro-N-[2-(methylamino)ethyl]benzamide;

1-253: 6-(2-ethoxyphenyl)-3-[(2R)-2-ethyl-4-[6-methoxy-2-(trifluoromethyl)pyridine-3-carbonyl]piperazin-1-yl]-N-[(3R)-1-methylpyrrolidin-3-yl]pyridine-2-carboxamide;

1-254: 6-(2-ethoxyphenyl)-3-[(2R)-2-ethyl-4-[6-methoxy-2-(trifluoromethyl)pyridine-3-carbonyl]piperazin-1-yl]-N-[(3R)-pyrrolidin-3-yl]pyridine-2-carboxamide;

1-255: 2'-ethoxy-5-[(2R)-2-ethyl-4-[1-(trifluoromethyl)cyclopentanecarbonyl]piperazin-1-yl]-N-[(3R)-1-methylpyrrolidin-3-yl]-[2,3'-bipyridine]-6-carboxamide;

1-256: N-{[(2S)-azetidin-2-yl]methyl}-2'-ethoxy-5-[(2R)-4-[6-ethoxy-2-(trifluoromethyl)pyridine-3-carbonyl]-2-ethylpiperazin-1-yl]-[2,3'-bipyridine]-6-carboxamide;

1-257: 2'-ethoxy-5-[(2R)-4-[6-ethoxy-2-(trifluoromethyl)pyridine-3-carbonyl]-2-ethylpiperazin-1-yl]-N-{[(2S)-1-methylazetidin-2-yl]methyl}-[2,3'-bipyridine]-6-carboxamide;

1-258: 2'-ethoxy-5-[(2R)-2-ethyl-4-[4-fluoro-2-(trifluoromethyl)benzoyl]piperazin-1-yl]-N-[(3R)-1-methylpyrrolidin-3-yl]-[2,3'-bipyridine]-6-carboxamide;

1-259: 5-[(2R)-4-(2,4-dichlorobenzoyl)-2-ethylpiperazin-1-yl]-2'-ethoxy-N-[(3R)-1-methylpyrrolidin-3-yl]-[2,3'-bipyridine]-6-carboxamide;

1-260: 5-[(2R)-4-(4-chloro-2-cyanobenzoyl)-2-ethylpiperazin-1-yl]-2'-ethoxy-N-[(3R)-1-methylpyrrolidin-3-yl]-[2,3'-bipyridine]-6-carboxamide;

1-261: 5-[(2R)-4-(2-chloro-4-fluorobenzoyl)-2-ethylpiperazin-1-yl]-2'-ethoxy-N-[(3R)-1-methylpyrrolidin-3-yl]-[2,3'-bipyridine]-6-carboxamide;

1-262: 5-[(2R)-4-[4-chloro-2-(difluoromethyl)benzoyl]-2-ethylpiperazin-1-yl]-2'-ethoxy-N-[(3R)-1-methylpyrrolidin-3-yl]-[2,3'-bipyridine]-6-carboxamide;

1-263: 2'-ethoxy-5-[(2R)-2-ethyl-4-[1-(trifluoromethyl)cyclopentanecarbonyl]piperazin-1-yl]-N-[(3R)-pyrrolidin-3-yl]-[2,3'-bipyridine]-6-carboxamide;

1-264: 2'-ethoxy-5-[(2R)-2-ethyl-4-(1-ethylcyclopentanecarbonyl)piperazin-1-yl]-N-[2-(methylamino)ethyl]-[2,3'-bipyridine]-6-carboxamide;

1-265: 5-[(2R)-4-[4-chloro-2-(difluoromethyl)benzoyl]-2-ethylpiperazin-1-yl]-2'-ethoxy-N-[(3R)-pyrrolidin-3-yl]-[2,3'-bipyridine]-6-carboxamide;

1-266: 2'-ethoxy-5-[(2R)-2-ethyl-4-[4-fluoro-2-(trifluoromethyl)benzoyl]piperazin-1-yl]-N-[(3R)-pyrrolidin-3-yl]-[2,3'-bipyridine]-6-carboxamide;

1-267: 5-[(2R)-4-(2,4-dichlorobenzoyl)-2-ethylpiperazin-1-yl]-2'-ethoxy-N-[(3R)-pyrrolidin-3-yl]-[2,3'-bipyridine]-6-carboxamide;

1-268: 3-[(2R)-4-[4-chloro-2-(trifluoromethyl)benzoyl]-2-ethylpiperazin-1-yl]-6-(3-ethoxypyrazin-2-yl)-N-[(3R)-1-methylpyrrolidin-3-yl]pyridine-2-carboxamide;

1-269: 3-[(2R)-4-[4-chloro-2-(trifluoromethyl)benzoyl]-2-ethylpiperazin-1-yl]-6-(3-ethoxypyrazin-2-yl)-N-(1-methylazetidin-3-yl)pyridine-2-carboxamide;

1-270: 3-(2-ethoxypyridin-3-yl)-6-[(2R)-2-ethyl-4-[6-methoxy-2-(trifluoromethyl)pyridine-3-carbonyl]piperazin-1-yl]-2-fluoro-N-[(3R)-1-methylpyrrolidin-3-yl]benzamide;

1-271: 3-(2-ethoxypyridin-3-yl)-6-[(2R)-2-ethyl-4-[6-methoxy-2-(trifluoromethyl)pyridine-3-carbonyl]piperazin-1-yl]-2-fluoro-N-[(3R)-pyrrolidin-3-yl]benzamide;

1-272: 3-[(2R)-4-[4-chloro-2-(trifluoromethyl)benzoyl]-2-ethylpiperazin-1-yl]-6-(3-ethoxypyrazin-2-yl)-N-[(3R)-pyrrolidin-3-yl]pyridine-2-carboxamide;

1-273: 2'-ethoxy-5-[(2R)-2-ethyl-4-[1-(trifluoromethyl)cyclohexanecarbonyl]piperazin-1-yl]-N-[(3R)-pyrrolidin-3-yl]-[2,3'-bipyridine]-6-carboxamide;

1-274: 2'-ethoxy-5-[(2R)-2-ethyl-4-[4-(trifluoromethyl)bicyclo[2.2.2]octane-1-carbonyl]piperazin-1-yl]-N-[(3R)-pyrrolidin-3-yl]-[2,3'-bipyridine]-6-carboxamide;

1-275: 5-[(2R)-4-[4-chloro-2-(trifluoromethyl)benzoyl]-2-ethylpiperazin-1-yl]-2'-ethoxy-N-[(3 S,4R)-4-fluoropyrrolidin-3-yl]-[2,3'-bipyridine]-6-carboxamide;

1-276: 5-[(2R)-4-[4-chloro-2-(trifluoromethyl)benzoyl]-2-ethylpiperazin-1-yl]-2'-ethoxy-N-[(3R,4R)-4-fluoropyrrolidin-3-yl]-[2,3'-bipyridine]-6-carboxamide;

1-277: 5-[(2R)-4-(4-chloro-2-cyanobenzoyl)-2-ethylpiperazin-1-yl]-2'-ethoxy-N-[(3R)-pyrrolidin-3-yl]-[2,3'-bipyridine]-6-carboxamide;

1-278: 5-[(2R)-4-[2-(difluoromethyl)-4-fluorobenzoyl]-2-ethylpiperazin-1-yl]-2'-ethoxy-N-[(3R)-pyrrolidin-3-yl]-[2,3'-bipyridine]-6-carboxamide;

1-279: 5-[(2R)-4-[2-(difluoromethyl)-4-fluorobenzoyl]-2-ethylpiperazin-1-yl]-2'-ethoxy-N-[(3R)-1-methylpyrrolidin-3-yl]-[2,3'-bipyridine]-6-carboxamide;

1-280: 2'-ethoxy-5-[(2R)-2-ethyl-4-[1-(trifluoromethyl)cyclobutanecarbonyl]piperazin-1-yl]-N-[(3R)-pyrrolidin-3-yl]-[2,3'-bipyridine]-6-carboxamide;

1-281: 2'-ethoxy-5-[(2R)-2-ethyl-4-[4-(trifluoromethyl)bicyclo[2.2.2]octane-1-carbonyl]piperazin-1-yl]-N-(1-methylazetidin-3-yl)-[2,3'-bipyridine]-6-carboxamide;

1-282: 2'-ethoxy-5-[(2R)-2-ethyl-4-[4-(trifluoromethyl)bicyclo[2.2.2]octane-1-carbonyl]piperazin-1-yl]-N-[(3R)-1-methylpyrrolidin-3-yl]-[2,3'-bipyridine]-6-carboxamide;

1-283: 2'-ethoxy-5-[(2R)-2-ethyl-4-[1-(trifluoromethyl)cyclobutanecarbonyl]piperazin-1-yl]-N-[(3R)-1-methylpyrrolidin-3-yl]-[2,3'-bipyridine]-6-carboxamide;

1-284: 2'-ethoxy-5-[(2R)-2-ethyl-4-(3,5,7-trifluoroadamantane-1-carbonyl)piperazin-1-yl]-N-[(3R)-1-methylpyrrolidin-3-yl]-[2,3'-bipyridine]-6-carboxamide;

1-285: 2'-ethoxy-5-[(2R)-2-ethyl-4-(3,5,7-trifluoroadamantane-1-carbonyl)piperazin-1-yl]-N-[(3R)-pyrrolidin-3-yl]-[2,3'-bipyridine]-6-carboxamide;

1-286: 2'-ethoxy-5-[(2R)-2-ethyl-4-[cis-4-(trifluoromethyl)cyclohexanecarbonyl]piperazin-1-yl]-N-[(3R)-1-methylpyrrolidin-3-yl]-[2,3'-bipyridine]-6-carboxamide;

1-287: 3-[(2R)-4-[4-chloro-2-(difluoromethyl)benzoyl]-2-ethylpiperazin-1-yl]-6-(2-ethoxyphenyl)-N-[(3R)-1-methylpyrrolidin-3-yl]pyridine-2-carboxamide;

1-288: 3-[(2R)-4-[4-chloro-2-(difluoromethyl)benzoyl]-2-ethylpiperazin-1-yl]-6-(2-ethoxyphenyl)-N-[(3R)-pyrrolidin-3-yl]pyridine-2-carboxamide;

1-289: 2'-ethoxy-5-[(2R)-2-ethyl-4-[6-methoxy-2-(trifluoromethyl)pyridine-3-carbonyl]piperazin-1-yl]-N-[(3R,4R)-4-fluoropyrrolidin-3-yl]-[2,3'-bipyridine]-6-carboxamide;

1-290: 2'-ethoxy-5-[(2R)-2-ethyl-4-[6-methoxy-2-(trifluoromethyl)pyridine-3-carbonyl]piperazin-1-yl]-N-[(3R,4R)-4-fluoro-1-methylpyrrolidin-3-yl]-[2,3'-bipyridine]-6-carboxamide;

1-291: 2'-ethoxy-5-[(2R)-2-ethyl-4-[6-methoxy-2-(trifluoromethyl)pyridine-3-carbonyl]piperazin-1-yl]-N-[(3 S,4R)-4-fluoropyrrolidin-3-yl]-[2,3'-bipyridine]-6-carboxamide;

1-292: 3-[(2R)-4-[2-(difluoromethyl)-4-fluorobenzoyl]-2-ethylpiperazin-1-yl]-6-(2-ethoxyphenyl)-N-[(3R)-pyrrolidin-3-yl]pyridine-2-carboxamide;

1-293: 3-[(2R)-4-[2-(difluoromethyl)-4-fluorobenzoyl]-2-ethylpiperazin-1-yl]-6-(2-ethoxyphenyl)-N-[(3R)-1-methylpyrrolidin-3-yl]pyridine-2-carboxamide;

1-294: 2'-ethoxy-5-[(2R)-2-ethyl-4-[2-(trifluoromethyl)bicyclo[2.2.1]hept-5-ene-2-carbonyl]piperazin-1-yl]-N-[(3R)-pyrrolidin-3-yl]-[2,3'-bipyridine]-6-carboxamide;

1-295: 5-[(2R)-4-[1-(difluoromethyl)-3,3-difluorocyclobutanecarbonyl]-2-ethylpiperazin-1-yl]-2'-ethoxy-N-[(3R)-pyrrolidin-3-yl]-[2,3'-bipyridine]-6-carboxamide;

1-296: 2'-ethoxy-5-[(2R)-2-ethyl-4-[6-methoxy-2-(trifluoromethyl)pyridine-3-carbonyl]piperazin-1-yl]-N-[(3 S,4R)-4-fluoro-1-methylpyrrolidin-3-yl]-[2,3'-bipyridine]-6-carboxamide;

1-297: 2'-ethoxy-5-[(2R)-2-ethyl-4-[2-(trifluoromethyl)bicyclo[2.2.1]heptane-2-carbonyl]piperazin-1-yl]-N-[(3R)-pyrrolidin-3-yl]-[2,3'-bipyridine]-6-carboxamide;

1-298: 5-[(2R)-4-[3,3-difluoro-1-(trifluoromethyl)cyclobutanecarbonyl]-2-ethylpiperazin-1-yl]-2'-ethoxy-N-[(3R)-pyrrolidin-3-yl]-[2,3'-bipyridine]-6-carboxamide;

1-299: 2'-ethoxy-5-[(2R)-2-ethyl-4-[cis-4-(trifluoromethyl)cyclohexanecarbonyl]piperazin-1-yl]-N-[(3R)-pyrrolidin-3-yl]-[2,3'-bipyridine]-6-carboxamide;

1-300: 2'-ethoxy-5-[(2R)-2-ethyl-4-[cis-3-(trifluoromethyl)cyclobutanecarbonyl]piperazin-1-yl]-N-[(3R)-pyrrolidin-3-yl]-[2,3'-bipyridine]-6-carboxamide;

1-301: 2'-ethoxy-5-[(2R)-2-ethyl-4-[trans-3-(trifluoromethyl)cyclobutanecarbonyl]piperazin-1-yl]-N-[(3R)-pyrrolidin-3-yl]-[2,3'-bipyridine]-6-carboxamide;

1-302: 2'-ethoxy-5-[(2R)-2-ethyl-4-(3,3,3-trifluoro-2,2-dimethylpropanoyl)piperazin-1-yl]-N-[(3R)-pyrrolidin-3-yl]-[2,3'-bipyridine]-6-carboxamide;

1-303: 5-[(2R)-4-(2-chloro-4-fluorobenzoyl)-2-ethylpiperazin-1-yl]-2'-ethoxy-N-[(3R)-pyrrolidin-3-yl]-[2,3'-bipyridine]-6-carboxamide;

1-304: 6-(2-ethoxyphenyl)-3-[(2R)-2-ethyl-4-[1-(trifluoromethyl)cyclopentanecarbonyl]piperazin-1-yl]-N-[(3R)-pyrrolidin-3-yl]pyridine-2-carboxamide;

1-305: 3-[(2R)-4-(2-tert-butylpyrrolidine-1-carbonyl)-2-ethylpiperazin-1-yl]-6-(2-ethoxyphenyl)-N-[(3R)-pyrrolidin-3-yl]pyridine-2-carboxamide;

1-306: 2'-ethoxy-5-[(2R)-2-ethyl-4-[(2S)-2-(trifluoromethyl)pyrrolidine-1-carbonyl]piperazin-1-yl]-N-[(3R)-pyrrolidin-3-yl]-[2,3'-bipyridine]-6-carboxamide;

1-307: 2'-ethoxy-5-[(2R)-2-ethyl-4-[1-(trifluoromethyl)cyclopentanecarbonyl]piperazin-1-yl]-N-[(3R)-1-[(5-methyl-2-oxo-2H-1,3-dioxol-4-yl)methyl]pyrrolidin-3-yl]-[2,3'-bipyridine]-6-carboxamide;

1-308: 2'-ethoxy-5-[(2R)-2-ethyl-4-[1,2,2,3-tetramethylcyclopentanecarbonyl]piperazin-1-yl]-N-[(3R)-pyrrolidin-3-yl]-[2,3'-bipyridine]-6-carboxamide;

1-309: 1,1,1-trifluoro-2-methylpropan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate;

1-310: 2'-ethoxy-5-[(2R)-2-ethyl-4-[(2R)-2-(trifluoromethyl)pyrrolidine-1-carbonyl]piperazin-1-yl]-N-[(3R)-pyrrolidin-3-yl]-[2,3'-bipyridine]-6-carboxamide;

1-311: 5-[(2R)-4-(2-cyclopropylpyrrolidine-1-carbonyl)-2-ethylpiperazin-1-yl]-2'-ethoxy-N-[(3R)-pyrrolidin-3-yl]-[2,3'-bipyridine]-6-carboxamide;

1-312: 1,1,1-trifluoro-3,3-dimethylbutan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate;

1-313: 2'-ethoxy-5-[(2R)-2-ethyl-4-[1-(trifluoromethyl)cyclopentanecarbonyl]piperazin-1-yl]-N-[(1-methylazetidin-3-yl)methyl]-[2,3'-bipyridine]-6-carboxamide;

1-314: 5-[(2R)-4-{7,7-dimethylbicyclo[2.2.1]heptane-1-carbonyl}-2-ethylpiperazin-1-yl]-2'-ethoxy-N-[(3R)-pyrrolidin-3-yl]-[2,3'-bipyridine]-6-carboxamide;

1-315: 3-[(2R)-4-[(2S)-2-tert-butylpyrrolidine-1-carbonyl]-2-ethylpiperazin-1-yl]-6-(2-methoxyphenyl)-N-[(3R)-pyrrolidin-3-yl]pyridine-2-carboxamide;

1-316: 3-[(2R)-4-[(2R)-2-tert-butylpyrrolidine-1-carbonyl]-2-ethylpiperazin-1-yl]-6-(2-methoxyphenyl)-N-[(3R)-pyrrolidin-3-yl]pyridine-2-carboxamide;

1-317: 5-[(2R)-4-(2,3-dihydro-1H-indole-1-carbonyl)-2-ethylpiperazin-1-yl]-2'-ethoxy-N-[(3R)-pyrrolidin-3-yl]-[2,3'-bipyridine]-6-carboxamide;

1-318: 2'-ethoxy-5-[(2R)-2-ethyl-4-[1-(trifluoromethyl)cyclopentanecarbonyl]piperazin-1-yl]-N-[(3-fluoroazetidin-3-yl)methyl]-[2,3'-bipyridine]-6-carboxamide;

1-319: 2'-ethoxy-5-[(2R)-2-ethyl-4-[1-(trifluoromethyl)cyclopentanecarbonyl]piperazin-1-yl]-N-[(3-fluoro-1-methylazetidin-3-yl)methyl]-[2,3'-bipyridine]-6-carboxamide;

1-320: 2'-ethoxy-5-[(2R)-2-ethyl-4-[(2S)-2-(2-fluoropropan-2-yl)pyrrolidine-1-carbonyl]piperazin-1-yl]-N-[(3R)-pyrrolidin-3-yl]-[2,3'-bipyridine]-6-carboxamide;

1-321: 2'-ethoxy-5-[(2R)-2-ethyl-4-[1-(trifluoromethyl)cyclopentanecarbonyl]piperazin-1-yl]-N-[(3S)-pyrrolidin-3-yl]-[2,3'-bipyridine]-6-carboxamide;

1-322: 2'-ethoxy-5-[(2R)-2-ethyl-4-[cis-4-(trifluoromethyl)cyclohexanecarbonyl]piperazin-1-yl]-N-[(1-methylazetidin-3-yl)methyl]-[2,3'-bipyridine]-6-carboxamide;

1-323: 5-[(2R)-4-(2,2-di ethylpyrrolidine-1-carbonyl)-2-ethylpiperazin-1-yl]-2'-ethoxy-N-[(3R)-pyrrolidin-3-yl]-[2,3'-bipyridine]-6-carboxamide;

1-324: 2'-ethoxy-5-[(2R)-2-ethyl-4-[1-(trifluoromethyl)cyclopentanecarbonyl]piperazin-1-yl]-N-{[(2R)-pyrrolidin-2-yl]methyl}-[2,3'-bipyridine]-6-carboxamide;

1-325: 2'-ethoxy-5-[(2R)-2-ethyl-4-[1-(trifluoromethyl)cyclopentanecarbonyl]piperazin-1-yl]-N-{[(2S)-pyrrolidin-2-yl]methyl}-[2,3'-bipyridine]-6-carboxamide;

1-326: 2'-ethoxy-5-[(2R)-2-ethyl-4-[2-methyl-2-(trifluoromethyl)pyrrolidine-1-carbonyl]piperazin-1-yl]-N-[(3R)-pyrrolidin-3-yl]-[2,3'-bipyridine]-6-carboxamide;

1-327: N-{[(2R)-azetidin-2-yl]methyl}-2'-ethoxy-5-[(2R)-2-ethyl-4-[1-(trifluoromethyl)cyclopentanecarbonyl]piperazin-1-yl]-[2,3'-bipyridine]-6-carboxamide;

1-328: 5-[(2R)-4-[1-(2,2-difluoroethyl)cyclobutanecarbonyl]-2-ethylpiperazin-1-yl]-2'-ethoxy-N-[(3R)-pyrrolidin-3-yl]-[2,3'-bipyridine]-6-carboxamide;

1-329: N-{[(2S)-azetidin-2-yl]methyl}-2'-ethoxy-5-[(2R)-2-ethyl-4-[1-(trifluoromethyl)cyclopentanecarbonyl]piperazin-1-yl]-[2,3'-bipyridine]-6-carboxamide;

1-330: 2'-ethoxy-5-[(2R)-2-ethyl-4-[1-(trifluoromethyl)cyclopentanecarbonyl]piperazin-1-yl]-N-{[(2R)-1-methylazetidin-2-yl]methyl}-[2,3'-bipyridine]-6-carboxamide;

1-331: 2'-ethoxy-5-[(2R)-2-ethyl-4-[1-(trifluoromethyl)cyclopentanecarbonyl]piperazin-1-yl]-N-{[(2S)-1-methylazetidin-2-yl]methyl}-[2,3'-bipyridine]-6-carboxamide;

1-332: 2'-ethoxy-5-[(2R)-2-ethyl-4-[1-(trifluoromethyl)cyclopentanecarbonyl]piperazin-1-yl]-N-{[(2S)-1-methylpyrrolidin-2-yl]methyl}-[2,3'-bipyridine]-6-carboxamide;

1-333: 2'-ethoxy-5-[(2R)-2-ethyl-4-[1-(trifluoromethyl)cyclopentanecarbonyl]piperazin-1-yl]-N-{[(2R)-1-methylpyrrolidin-2-yl]methyl}-[2,3'-bipyridine]-6-carboxamide;

1-334: 2'-ethoxy-5-[(2R)-2-ethyl-4-[1-(trifluoromethyl)cyclopentanecarbonyl]piperazin-1-yl]-N-[(3-methoxy-1-methylazetidin-3-yl)methyl]-[2,3'-bipyridine]-6-carboxamide;

1-335: 6-(2-ethoxyphenyl)-3-[(2R)-2-ethyl-4-[cis-4-(trifluoromethyl)cyclohexanecarbonyl]piperazin-1-yl]-N-[(3R)-pyrrolidin-3-yl]pyridine-2-carboxamide;

1-336: 6-(2-ethoxyphenyl)-3-[(2R)-2-ethyl-4-[cis-4-(trifluoromethyl)cyclohexanecarbonyl]piperazin-1-yl]-N-[(3R)-1-methylpyrrolidin-3-yl]pyridine-2-carboxamide;

1-337: N-[2-(azetidin-1-yl)ethyl]-2'-ethoxy-5-[(2R)-2-ethyl-4-[1-(trifluoromethyl)cyclopentanecarbonyl]piperazin-1-yl]-[2,3'-bipyridine]-6-carboxamide;

1-338: 1-(trifluoromethyl)cyclobutyl (3R)-4-[6-(2-ethoxyphenyl)-2-{[(3R)-pyrrolidin-3-yl]carbamoyl}pyridin-3-yl]-3-ethylpiperazine-1-carboxylate;

1-339: 2'-ethoxy-5-[(2R)-2-ethyl-4-[2-(trifluoromethyl)bicyclo[2.2.1]heptane-2-carbonyl]piperazin-1-yl]-N-[(1-methylazetidin-3-yl)methyl]-[2,3'-bipyridine]-6-carboxamide;

1-340: 6-(2-ethoxyphenyl)-3-[(2R)-2-ethyl-4-[1-(trifluoromethyl)cyclopentanecarbonyl]piperazin-1-yl]-N-[(1-methylazetidin-3-yl)methyl]pyridine-2-carboxamide;

1-341: 6-(2-ethoxyphenyl)-3-[(2R)-2-ethyl-4-[1-(trifluoromethyl)cyclopentanecarbonyl]piperazin-1-yl]-N-[(3R)-1-methylpyrrolidin-3-yl]pyridine-2-carboxamide;

1-342: 6-(2-ethoxyphenyl)-3-[(2R)-2-ethyl-4-[(2S)-2-(trifluoromethyl)pyrrolidine-1-carbonyl]piperazin-1-yl]-N-[(3R)-pyrrolidin-3-yl]pyridine-2-carboxamide;

1-343: 6-(2-ethoxyphenyl)-3-[(2R)-2-ethyl-4-[(2S)-2-(trifluoromethyl)pyrrolidine-1-carbonyl]piperazin-1-yl]-N-[(3S)-pyrrolidin-3-yl]pyridine-2-carboxamide;

1-344: 6-(2-ethoxyphenyl)-3-[(2R)-2-ethyl-4-[1-(trifluoromethyl)cyclobutanecarbonyl]piperazin-1-yl]-N-[(3R)-1-methylpyrrolidin-3-yl]pyridine-2-carboxamide;

1-345: 2'-ethoxy-5-[(2R)-2-ethyl-4-[(2S)-2-phenylpyrrolidine-1-carbonyl]piperazin-1-yl]-N-[(3R)-pyrrolidin-3-yl]-[2,3'-bipyridine]-6-carboxamide;

1-346: 5-[(2R)-4-(7-chloro-2,3-dihydro-1H-indole-1-carbonyl)-2-ethylpiperazin-1-yl]-2'-ethoxy-N-[(3R)-pyrrolidin-3-yl]-[2,3'-bipyridine]-6-carboxamide;

1-347: 5-[(2R)-4-(5-chloro-2,3-dihydro-1H-indole-1-carbonyl)-2-ethylpiperazin-1-yl]-2'-ethoxy-N-[(3R)-pyrrolidin-3-yl]-[2,3'-bipyridine]-6-carboxamide;

1-348: 1,1,1-trifluoro-3,3-dimethylbutan-2-yl (3R)-4-[6-(2-ethoxyphenyl)-2-{[(3R)-pyrrolidin-3-yl]carbamoyl}pyridin-3-yl]-3-ethylpiperazine-1-carboxylate;

1-349: 6-(2-ethoxyphenyl)-3-[(2R)-2-ethyl-4-[1-(2,2,2-trifluoroethyl)cyclobutanecarbonyl]piperazin-1-yl]-N-[(3R)-1-methylpyrrolidin-3-yl]pyridine-2-carboxamide;

1-350: 2'-ethoxy-5-[(2R)-2-ethyl-4-(7-fluoro-2,3-dihydro-1H-indole-1-carbonyl)piperazin-1-yl]-N-[(3R)-pyrrolidin-3-yl]-[2,3'-bipyridine]-6-carboxamide;
1-351: (1R)-2,2,2-trifluoro-1-phenylethyl (3R)-4-(2'-ethoxy-6-{[(3R)-pyrrolidin-3-yl]carbamoyl}-[2,3'-bipyridin]-5-yl)-3-ethylpiperazine-1-carboxylate;
1-352: T-ethoxy-5-[(2R)-2-ethyl-4-(1-phenylcyclopentanecarbonyl)piperazin-1-yl]-N-[(3R)-pyrrolidin-3-yl]-[2,3'-bipyridine]-6-carboxamide;
1-353: 2'-ethoxy-5-[(2R)-2-ethyl-4-(1-phenylcyclobutanecarbonyl)piperazin-1-yl]-N-[(3R)-pyrrolidin-3-yl]-[2,3'-bipyridine]-6-carboxamide;
1-354: 5-[(2R)-4-[2,2-difluoro-7,7-dimethylbicyclo[2.2.1]heptane-1-carbonyl]-2-ethylpiperazin-1-yl]-2'-ethoxy-N-[(3R)-pyrrolidin-3-yl]-[2,3'-bipyridine]-6-carboxamide;
1-355: 3-[(2R)-4-[(2S)-2-tert-butylpyrrolidine-1-carbonyl]-2-ethylpiperazin-1-yl]-6-(2-ethoxyphenyl)-N-[(3R)-pyrrolidin-3-yl]pyridine-2-carboxamide;
1-356: 3-[(2R)-4-[(2R)-2-tert-butylpyrrolidine-1-carbonyl]-2-ethylpiperazin-1-yl]-6-(2-ethoxyphenyl)-N-[(3R)-pyrrolidin-3-yl]pyridine-2-carboxamide;
1-357: 5-[(2R)-4-[4-chloro-2-(trifluoromethyl)benzoyl]-2-ethylpiperazin-1-yl]-2'-ethoxy-N-[2-(3-fluoroazetidin-1-yl)ethyl]-[2,3'-bipyridine]-6-carboxamide;
1-358: 2'-ethoxy-5-[(2R)-2-ethyl-4-(1-phenylcyclobutanecarbonyl)piperazin-1-yl]-N-[(3R)-1-methylpyrrolidin-3-yl]-[2,3'-bipyridine]-6-carboxamide;
1-359: 2'-ethoxy-5-[(2R)-2-ethyl-4-[1-(2,2,2-trifluoroethyl)cyclopentanecarbonyl]piperazin-1-yl]-N-[(3R)-1-methylpyrrolidin-3-yl]-[2,3'-bipyridine]-6-carboxamide;
1-360: 2'-ethoxy-5-[(2R)-2-ethyl-4-(7-methyl-2,3-dihydro-1H-indole-1-carbonyl)piperazin-1-yl]-N-[(3R)-pyrrolidin-3-yl]-[2,3'-bipyridine]-6-carboxamide;
1-361: 2'-ethoxy-5-[(2R)-2-ethyl-4-[7-(trifluoromethyl)-2,3-dihydro-1H-indole-1-carbonyl]piperazin-1-yl]-N-[(3R)-pyrrolidin-3-yl]-[2,3'-bipyridine]-6-carboxamide;
1-362: 6-(2-ethoxyphenyl)-3-[(2R)-2-ethyl-4-[(2S)-2-(trifluoromethyl)pyrrolidine-1-carbonyl]piperazin-1-yl]-N-[(1-methylazetidin-3-yl)methyl]pyridine-2-carboxamide;
1-363: 2'-ethoxy-5-[(2R)-2-ethyl-4-[1-(trifluoromethyl)cyclopentanecarbonyl]piperazin-1-yl]-N-[(3S)-1-methylpyrrolidin-3-yl]-[2,3'-bipyridine]-6-carboxamide;
1-364: 2'-ethoxy-5-[(2R)-2-ethyl-4-[1-(trifluoromethyl)cyclobutanecarbonyl]piperazin-1-yl]-N-[(3S)-1-methylpyrrolidin-3-yl]-[2,3'-bipyridine]-6-carboxamide;
1-365: 5-[(2R)-4-(7-cyano-2,3-dihydro-1H-indole-1-carbonyl)-2-ethylpiperazin-1-yl]-2'-ethoxy-N-[(3R)-pyrrolidin-3-yl]-[2,3'-bipyridine]-6-carboxamide;
1-366: (2R)-1,1,1-trifluoro-3,3-dimethylbutan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate;
1-367: (2S)-1,1,1-trifluoro-3,3-dimethylbutan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate;
1-368: 2'-ethoxy-5-[(2R)-2-ethyl-4-[5-(trifluoromethyl)thiophene-2-carbonyl]piperazin-1-yl]-N-[(3R)-pyrrolidin-3-yl]-[2,3'-bipyridine]-6-carboxamide;
1-369: 1,1,1,3,3,3-hexafluoropropan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate;
1-370: 3-(trifluoromethyl)pentan-3-yl (3R)-4-(2'-ethoxy-6-{[(3R)-1-methylpyrrolidin-3-yl]carbamoyl}-[2,3'-bipyridin]-5-yl)-3-ethylpiperazine-1-carboxylate;
1-371: 5-[(2R)-4-[1-(2,4-difluorophenyl)cyclobutanecarbonyl]-2-ethylpiperazin-1-yl]-2'-ethoxy-N-[(3R)-1-methylpyrrolidin-3-yl]-[2,3'-bipyridine]-6-carboxamide;
1-372: 2'-ethoxy-5-[(2R)-2-ethyl-4-[(2S)-2-(trifluoromethyl)pyrrolidine-1-carbonyl]piperazin-1-yl]-N-[(3R)-1-methylpyrrolidin-3-yl]-[2,3'-bipyridine]-6-carboxamide;
1-373: 2'-ethoxy-5-[(2R)-2-ethyl-4-[(2S)-2-(trifluoromethyl)pyrrolidine-1-carbonyl]piperazin-1-yl]-N-[(3S)-1-methylpyrrolidin-3-yl]-[2,3'-bipyridine]-6-carboxamide;
1-374: 6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide;
1-375: 6-(2-ethoxyphenyl)-3-[(2R)-2-ethyl-4-[(2S)-2-(trifluoromethyl)pyrrolidine-1-carbonyl]piperazin-1-yl]-N-[(3S)-1-methylpyrrolidin-3-yl]pyridine-2-carboxamide;
1-376: 1,1,1-trifluoro-3,3-dimethylbutan-2-yl (3R)-4-(2'-ethoxy-6-{[(3R)-1-methylpyrrolidin-3-yl]carbamoyl}-[2,3'-bipyridin]-5-yl)-3-ethylpiperazine-1-carboxylate;
1-377: (1S)-2,2,2-trifluoro-1-phenylethyl (3R)-4-(2'-ethoxy-6-{[(3R)-pyrrolidin-3-yl]carbamoyl}-[2,3'-bipyridin]-5-yl)-3-ethylpiperazine-1-carboxylate;
1-378: 5-[(2R)-4-(2,5-di chlorothiophene-3-carbonyl)-2-ethylpiperazin-1-yl]-2'-ethoxy-N-[(3R)-1-methylpyrrolidin-3-yl]-[2,3'-bipyridine]-6-carboxamide;
1-379: 2'-ethoxy-5-[(2R)-2-ethyl-4-[3-(trifluoromethyl)bicyclo[1.1.1]pentane-1-carbonyl]piperazin-1-yl]-N-[(3R)-1-methylpyrrolidin-3-yl]-[2,3'-bipyridine]-6-carboxamide;
1-380: 5-[(2R)-4-(3,5-di chlorothiophene-2-carbonyl)-2-ethylpiperazin-1-yl]-2'-ethoxy-N-[(3R)-1-methylpyrrolidin-3-yl]-[2,3'-bipyridine]-6-carboxamide;
1-381: 2'-ethoxy-5-[(2R)-2-ethyl-4-[(2S)-2-(3-fluorophenyl)pyrrolidine-1-carbonyl]piperazin-1-yl]-N-[(3R)-1-methylpyrrolidin-3-yl]-[2,3'-bipyridine]-6-carboxamide;
1-382: 5-[(2R)-4-(7-chloro-2,3-dihydro-1H-indene-1-carbonyl)-2-ethylpiperazin-1-yl]-2'-ethoxy-N-[(3R)-1-methylpyrrolidin-3-yl]-[2,3'-bipyridine]-6-carboxamide;
1-383: 5-[(2R)-4-(7-cyano-2,3-dihydro-1H-indole-1-carbonyl)-2-ethylpiperazin-1-yl]-2'-ethoxy-N-[(3R)-1-methylpyrrolidin-3-yl]-[2,3'-bipyridine]-6-carboxamide;
1-384: 1-phenylcyclobutyl (3R)-4-(2'-ethoxy-6-{[(3R)-1-methylpyrrolidin-3-yl]carbamoyl}-[2,3'-bipyridin]-5-yl)-3-ethylpiperazine-1-carboxylate;
1-385: 2'-ethoxy-5-[(2R)-2-ethyl-4-[4-(trifluoromethyl)bicyclo[2.2.1]heptane-1-carbonyl]piperazin-1-yl]-N-[(3R)-1-methylpyrrolidin-3-yl]-[2,3'-bipyridine]-6-carboxamide;
1-386: 2'-ethoxy-5-[(2R)-2-ethyl-4-[(2S)-2-(trifluoromethyl)pyrrolidine-1-carbonyl]piperazin-1-yl]-N-{[(2R)-1-methylazetidin-2-yl]methyl}-[2,3'-bipyridine]-6-carboxamide;
1-387: 6-(2-ethoxyphenyl)-3-[(2R)-2-ethyl-4-[(2S)-2-(trifluoromethyl)pyrrolidine-1-carbonyl]piperazin-1-yl]-N-{[(2S)-1-methylazetidin-2-yl]methyl}pyridine-2-carboxamide;
1-388: 6-(2-ethoxyphenyl)-3-[(2R)-2-ethyl-4-[4-(trifluoromethyl)bicyclo[2.2.1]heptane-1-carbonyl]piperazin-1-yl]-N-[(3R)-1-methylpyrrolidin-3-yl]pyridine-2-carboxamide;
1-389: 2'-ethoxy-5-[(2R)-2-ethyl-4-[7-(trifluoromethyl)-2,3-dihydro-1H-indole-1-carbonyl]piperazin-1-yl]-N-[(3S)-1-methylpyrrolidin-3-yl]-[2,3'-bipyridine]-6-carboxamide;
1-390: 2'-ethoxy-5-[(2R)-2-ethyl-4-[1-(trifluoromethyl)cyclobutanecarbonyl]piperazin-1-yl]-N-{[(2S)-1-methylazetidin-2-yl]methyl}-[2,3'-bipyridine]-6-carboxamide;
1-391: 2'-ethoxy-5-[(2R)-2-ethyl-4-[(2S)-2-(trifluoromethyl)pyrrolidine-1-carbonyl]piperazin-1-yl]-N-{[(2S)-1-methylazetidin-2-yl]methyl}-[2,3'-bipyridine]-6-carboxamide;

1-392: (2S)-1,1,1-trifluoro-3,3-dimethylbutan-2-yl (3R)-4-(2'-ethoxy-6-{[(3R)-1-methylpyrrolidin-3-yl]carbamoyl}-[2,3'-bipyridin]-5-yl)-3-ethylpiperazine-1-carboxylate; or (2R)-1,1,1-trifluoro-3,3-dimethylbutan-2-yl (3R)-4-(2'-ethoxy-6-{[(3R)-1-methylpyrrolidin-3-yl] carbamoyl}-[2,3'-bipyridin]-5-yl)-3-ethylpiperazine-1-carboxylate;

1-393: 3-[(2R)-4-(7-cyano-2,3-dihydro-1H-indole-1-carbonyl)-2-ethylpiperazin-1-yl]-6-(2-ethoxyphenyl)-N-[(3R)-1-methylpyrrolidin-3-yl]pyridine-2-carboxamide;

1-394: 2'-ethoxy-5-[(2R)-2-ethyl-4-[4-(trifluoromethyl)bicyclo[2.2.1]heptane-1-carbonyl]piperazin-1-yl]-N-(1-methylazetidin-3-yl)-[2,3'-bipyridine]-6-carboxamide;

1-395: 2'-ethoxy-5-[(2R)-2-ethyl-4-[4-(trifluoromethyl)bicyclo[2.2.1]heptane-1-carbonyl]piperazin-1-yl]-N-[(1-methylazetidin-3-yl)methyl]-[2,3'-bipyridine]-6-carboxamide;

1-396: (2S)-1,1,1-trifluoro-3,3-dimethylbutan-2-yl (3R)-4-(2'-ethoxy-6-{[(1-methyl azetidin-3-yl)methyl]carbamoyl}-[2,3'-bipyridin]-5-yl)-3-ethylpiperazine-1-carboxylate; or (2R)-1,1,1-trifluoro-3,3-dimethylbutan-2-yl (3R)-4-(2'-ethoxy-6-{[(1-methyl azetidin-3-yl)methyl] carbamoyl}-[2,3'-bipyridin]-5-yl)-3-ethylpiperazine-1-carboxylate;

1-397: 1-ethylcyclopentyl (3R)-4-(2'-ethoxy-6-{[(3R)-1-methylpyrrolidin-3-yl]carbamoyl}-[2,3'-bipyridin]-5-yl)-3-ethylpiperazine-1-carboxylate;

1-398: N-[(3S)-1-azabicyclo[2.2.2]octan-3-yl]-5-[(2R)-4-[4-chloro-2-(trifluoromethyl)benzoyl]-2-ethylpiperazin-1-yl]-2'-ethoxy-[2,3'-bipyridine]-6-carboxamide;

1-399: 6-(2-ethoxyphenyl)-3-[(2R)-2-ethyl-4-[1-(trifluoromethyl)cyclopentanecarbonyl]piperazin-1-yl]-N-(1-methylazetidin-3-yl)pyridine-2-carboxamide;

1-400: N-[(3S)-1-azabicyclo[2.2.2]octan-3-yl]-2'-ethoxy-5-[(2R)-2-ethyl-4-[1-(trifluoromethyl)cyclopentanecarbonyl]piperazin-1-yl]-[2,3'-bipyridine]-6-carboxamide;

1-401: 6-(2-ethoxyphenyl)-3-[(2R)-2-ethyl-4-[1-(trifluoromethyl)cyclopentanecarbonyl]piperazin-1-yl]-N-[(3S)-1-methylpyrrolidin-3-yl]pyridine-2-carboxamide;

1-402: 6-(2-ethoxyphenyl)-3-[(2R)-2-ethyl-4-[7-(trifluoromethyl)-2,3-dihydro-1H-indol e-1-carbonyl]piperazin-1-yl]-N-[(3S)-1-methylpyrrolidin-3-yl]pyridine-2-carboxamide;

1-403: (2S)-1,1,1-trifluoro-3,3-dimethylbutan-2-yl (3R)-4-(6-{[(3S)-1-azabicyclo[2.2.2]octan-3-yl]carbamoyl}-2'-ethoxy-[2,3'-bipyridin]-5-yl)-3-ethylpiperazine-1-carboxylate; or (2R)-1,1,1-trifluoro-3,3-dimethylbutan-2-yl (3R)-4-(6-{[(3S)-1-azabicyclo[2.2.2]octan-3-yl]carbamoyl}-2'-ethoxy-[2,3'-bipyridin]-5-yl)-3-ethylpiperazine-1-carboxylate;

1-404: 5-[(2R)-4-(7-cyano-2,3-dihydro-1H-indole-1-carbonyl)-2-ethylpiperazin-1-yl]-2'-ethoxy-N-[(3S)-1-methylpyrrolidin-3-yl]-[2,3'-bipyridine]-6-carboxamide;

1-405: N-{1-azabicyclo[2.2.1]heptan-4-yl}-2'-ethoxy-5-[(2R)-2-ethyl-4-[1-(trifluoromethyl)cyclopentanecarbonyl]piperazin-1-yl]-[2,3'-bipyridine]-6-carboxamide;

1-406: (2R)-1,1,1-trifluoro-3,3-dimethylbutan-2-yl(3R)-4-(2'-ethoxy-6-{[(3R)-1-methylpyrrolidin-3-yl]carbamoyl}-[2,3'-bipyridin]-5-yl)-3-ethylpiperazine-1-carboxylate;

1-407: (2S)-1,1,1-trifluoro-3,3-dimethylbutan-2-yl(3R)-4-(2'-ethoxy-6-{[(3R)-1-methylpyrrolidin-3-yl]carbamoyl}-[2,3'-bipyridin]-5-yl)-3-ethylpiperazine-1-carboxylate;

1-408: 2,2-dimethyl-1-phenylpropyl (3R)-4-(2'-ethoxy-6-{[(3R)-1-methylpyrrolidin-3-yl]carbamoyl}-[2,3'-bipyridin]-5-yl)-3-ethylpiperazine-1-carboxylate;

1-409: 5-[(2R)-4-(7-cyano-2,3-dihydro-1H-indole-1-carbonyl)-2-ethylpiperazin-1-yl]-2'-ethoxy-N-(1-methylazetidin-3-yl)-[2,3'-bipyridine]-6-carboxamide;

1-410: N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide;

1-411: N-[(3S)-1-azabicyclo[2.2.2]octan-3-yl]-2'-ethoxy-5-[(2R)-2-ethyl-4-[1-(trifluoromethyl)cyclobutanecarbonyl]piperazin-1-yl]-[2,3'-bipyridine]-6-carboxamide;

1-412: 6-(2-ethoxyphenyl)-3-[(2R)-2-ethyl-4-[(2S)-2-(2-fluoropropan-2-yl)pyrrolidine-1-carbonyl]piperazin-1-yl]-N-[(3R)-1-methylpyrrolidin-3-yl]pyridine-2-carboxamide;

1-413: 2'-ethoxy-5-[(2R)-2-ethyl-4-[(2S)-2-(2-fluoropropan-2-yl)pyrrolidine-1-carbonyl]piperazin-1-yl]-N-[(3R)-1-methylpyrrolidin-3-yl]-[2,3'-bipyridine]-6-carboxamide;

1-414: 3-[(2R)-4-(7-cyano-2,3-dihydro-1H-indole-1-carbonyl)-2-ethylpiperazin-1-yl]-6-(2-ethoxyphenyl)-N-(1-methylazetidin-3-yl)pyridine-2-carboxamide;

1-415: 2'-ethoxy-5-[(2R)-2-ethyl-4-[1-(trifluoromethyl)cyclopentanecarbonyl]piperazin-1-yl]-N-[(1-methyl-4,5-dihydro-1H-imidazol-2-yl)methyl]-[2,3'-bipyridine]-6-carboxamide;

1-416: 5-[(2R)-4-[1-(difluoromethyl)cyclopentanecarbonyl]-2-ethylpiperazin-1-yl]-2'-ethoxy-N-[(3R)-1-methylpyrrolidin-3-yl]-[2,3'-bipyridine]-6-carboxamide;

1-417: 3-[(2R)-4-[1-(difluoromethyl)cyclopentanecarbonyl]-2-ethylpiperazin-1-yl]-6-(2-ethoxyphenyl)-N-[(3R)-1-methylpyrrolidin-3-yl]pyridine-2-carboxamide;

1-418: 2'-ethoxy-5-[(2R)-2-ethyl-4-[7-(trifluoromethyl)-2,3-dihydro-1H-indole-1-carbonyl]piperazin-1-yl]-N-(1-methylazetidin-3-yl)-[2,3'-bipyridine]-6-carboxamide;

1-419: 5-[(2R)-4-(7-chloro-5-fluoro-2,3-dihydro-1H-indole-1-carbonyl)-2-ethylpiperazin-1-yl]-2'-ethoxy-N-[(3S)-1-methylpyrrolidin-3-yl]-[2,3'-bipyridine]-6-carboxamide;

1-420: 5-[(2R)-4-(7-chloro-5-fluoro-2,3-dihydro-1H-indole-1-carbonyl)-2-ethylpiperazin-1-yl]-2'-ethoxy-N-(1-methylazetidin-3-yl)-[2,3'-bipyridine]-6-carboxamide;

1-421: 3-[(2R)-4-(7-chloro-5-fluoro-2,3-dihydro-1H-indole-1-carbonyl)-2-ethylpiperazin-1-yl]-6-(2-ethoxyphenyl)-N-[(3S)-1-methylpyrrolidin-3-yl]pyridine-2-carboxamide;

1-422: 5-[(2R)-4-(7-cyano-5-fluoro-2,3-dihydro-1H-indole-1-carbonyl)-2-ethylpiperazin-1-yl]-2'-ethoxy-N-(1-methylazetidin-3-yl)-[2,3'-bipyridine]-6-carboxamide;

1-423: 5-[(2R)-4-(7-cyano-5-fluoro-2,3-dihydro-1H-indole-1-carbonyl)-2-ethylpiperazin-1-yl]-2'-ethoxy-N-[(3S)-1-methylpyrrolidin-3-yl]-[2,3'-bipyridine]-6-carboxamide;

1-424: 3-[(2R)-4-(7-cyano-5-fluoro-2,3-dihydro-1H-indole-1-carbonyl)-2-ethylpiperazin-1-yl]-6-(2-ethoxyphenyl)-N-(1-methylazetidin-3-yl)pyridine-2-carboxamide;

1-425: 5-[(2R)-4-(7-chloro-5-fluoro-1H-indole-1-carbonyl)-2-ethylpiperazin-1-yl]-2'-ethoxy-N-[(3R)-1-methylpyrrolidin-3-yl]-[2,3'-bipyridine]-6-carboxamide;

1-426: 3-[(2R)-4-(7-cyano-5-fluoro-2,3-dihydro-1H-indole-1-carbonyl)-2-ethylpiperazin-1-yl]-6-(2-ethoxyphenyl)-N-[(3S)-1-methylpyrrolidin-3-yl]pyridine-2-carboxamide;

1-427: 2'-ethoxy-5-[(2R)-2-ethyl-4-[(2S)-2-(trifluoromethyl)piperidine-1-carbonyl]piperazin-1-yl]-N-[(3R)-1-methylpyrrolidin-3-yl]-[2,3'-bipyridine]-6-carboxamide;

1-428: 5-[(2R)-4-(7-chloro-1H-indole-1-carbonyl)-2-ethylpiperazin-1-yl]-2'-ethoxy-N-[(3R)-1-methylpyrrolidin-3-yl]-[2,3'-bipyridine]-6-carboxamide;

1-429: 5-[(2R)-4-(7-cyano-1H-indole-1-carbonyl)-2-ethylpiperazin-1-yl]-2'-ethoxy-N-[(3R)-1-methylpyrrolidin-3-yl]-[2,3'-bipyridine]-6-carboxamide;

1-430: 3-[(2R)-4-(7-chloro-5-fluoro-1H-indole-1-carbonyl)-2-ethylpiperazin-1-yl]-6-(2-ethoxyphenyl)-N-[(3R)-1-methylpyrrolidin-3-yl]pyridine-2-carboxamide;

1-431: 3-[(2R)-4-(7-chloro-1H-indole-1-carbonyl)-2-ethylpiperazin-1-yl]-6-(2-ethoxyphenyl)-N-[(3R)-1-methylpyrrolidin-3-yl]pyridine-2-carboxamide;

1-432: 3-[(2R)-4-(7-cyano-1H-indole-1-carbonyl)-2-ethylpiperazin-1-yl]-6-(2-ethoxyphenyl)-N-[(3R)-1-methylpyrrolidin-3-yl]pyridine-2-carboxamide;

1-433: 6-(2-ethoxyphenyl)-3-[(2R)-2-ethyl-4-[(2S)-2-(trifluoromethyl)piperidine-1-carbonyl]piperazin-1-yl]-N-[(3R)-1-methylpyrrolidin-3-yl]pyridine-2-carboxamide;

1-434: 2'-ethoxy-5-[(2R)-2-ethyl-4-[(2S)-2-(trifluoromethyl)piperidine-1-carbonyl]piperazin-1-yl]-N-[(3S)-1-methylpyrrolidin-3-yl]-[2,3'-bipyridine]-6-carboxamide;

1-435: 6-(2-ethoxyphenyl)-3-[(2R)-2-ethyl-4-[(2S)-2-(trifluoromethyl)piperidine-1-carbonyl]piperazin-1-yl]-N-[(3S)-1-methylpyrrolidin-3-yl]pyridine-2-carboxamide;

1-436: 2'-ethoxy-5-[(2R)-2-ethyl-4-[7-(trifluoromethyl)-1H-indole-1-carbonyl]piperazin-1-yl]-N-[(3R)-1-methylpyrrolidin-3-yl]-[2,3'-bipyridine]-6-carboxamide;

1-437: 6-(2-ethoxyphenyl)-3-[(2R)-2-ethyl-4-[7-(trifluoromethyl)-1H-indole-1-carbonyl]piperazin-1-yl]-N-[(3R)-1-methylpyrrolidin-3-yl]pyridine-2-carboxamide;

1-438: 5-[(2R)-4-(7-cyano-5-fluoro-1H-indole-1-carbonyl)-2-ethylpiperazin-1-yl]-2'-ethoxy-N-[(3R)-1-methylpyrrolidin-3-yl]-[2,3'-bipyridine]-6-carboxamide; and 1-439: 3-[(2R)-4-(7-cyano-5-fluoro-1H-indole-1-carbonyl)-2-ethylpiperazin-1-yl]-6-(2-ethoxyphenyl)-N-[(3R)-1-methylpyrrolidin-3-yl]pyridine-2-carboxamide.

TABLE 2

| Compound No. | $R^A$ | $R^B$ | $X^1$ | $R^4$ |
|---|---|---|---|---|
| 2-1 | 2-ethoxyphenyl | 2-chloro-4-(trifluoromethyl)phenyl | CH | HO-propyl |
| 2-2 | 2-ethoxyphenyl | 2-chloro-4-(trifluoromethyl)phenyl | CH | (S)-HO-propyl |
| 2-3 | 2-methoxyphenyl | 4-chloro-2-(trifluoromethyl)phenyl | CH | H |
| 2-4 | 2-(2-methoxyethoxy)phenyl | 4-chloro-2-(trifluoromethyl)phenyl | CH | H |
| 2-5 | 2-propoxyphenyl | 4-chloro-2-(trifluoromethyl)phenyl | CH | H |

TABLE 2-continued

| Compound No. | R^A | R^B | X^1 | R^4 |
|---|---|---|---|---|
| 2-6 | 2-(2-hydroxyethoxy)phenyl | 4-chloro-2-(trifluoromethyl)phenyl | CH | H |
| 2-7 | 2-(2-hydroxyethoxy)phenyl | 2-(trifluoromethyl)phenyl | CH | H |
| 2-8 | 2-(hydroxymethyl)phenyl | 4-chloro-2-(trifluoromethyl)phenyl | CH | H |
| 2-9 | 2-ethoxypyridin-3-yl | 4-chloro-2-(trifluoromethyl)phenyl | CH | H |
| 2-10 | 2-ethoxypyridin-3-yl | 4'-(aminomethyl)-5-fluoro-[1,1'-biphenyl]-2-yl | CH | H |
| 2-11 | 2-ethoxypyridin-3-yl | 2-chloro-4-fluorophenyl | CF | H |
| 2-12 | 2-ethoxyphenyl | 4-chloro-2-(trifluoromethyl)phenyl | N | H |
| 2-13 | 2-ethoxypyridin-3-yl | 4-chloro-2-(trifluoromethyl)phenyl | N | H |

TABLE 2-continued
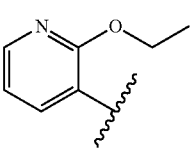
| Compound No. | R^A | R^B | X^1 | R^4 |
|---|---|---|---|---|
| 2-14 | 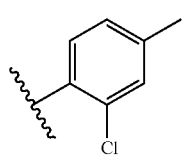 | 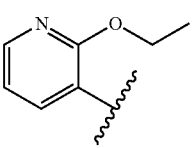 [SMILES: *c1cccnc1OCC] | N | H |
| 2-15 | 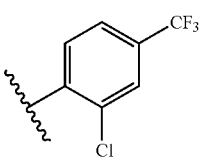 | 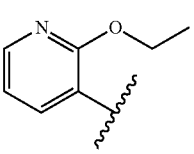 [SMILES: *c1cccnc1OCC] | N | H |
| 2-16 | 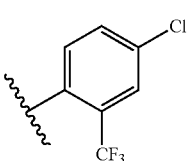 | 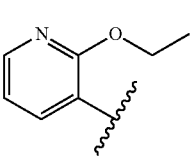 [SMILES: *c1cccnc1OCC] | N | —CH$_3$ |
| 2-17 | 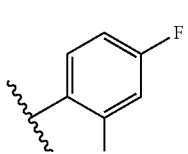 | 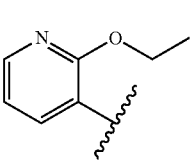 [SMILES: *c1cccnc1OCC] | N | H |
| 2-18 | 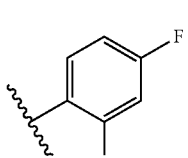 | 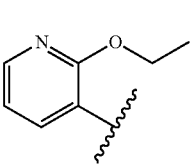 [SMILES: *c1cccnc1OCC] | CF | H |
| 2-19 | 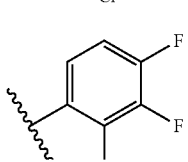 | 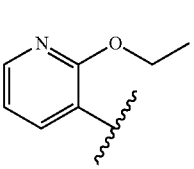 [SMILES: *c1cccnc1OCC] | N | H |
| 2-20 | 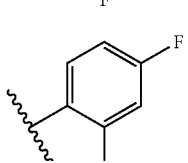 | 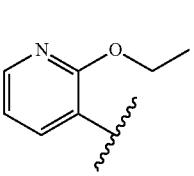 [SMILES: *c1cccnc1OCC] | N | H |
| 2-21 | 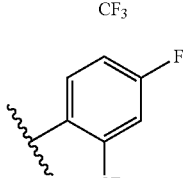 | 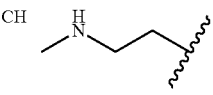 | CH | 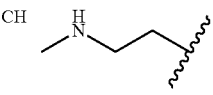 |

TABLE 2-continued

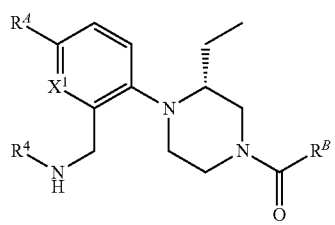

| Compound No. | R^A | R^B | X^1 | R^4 |
|---|---|---|---|---|
| 2-22 | 3-(methylamino)pyridin-2-yl | 4-chloro-2-(trifluoromethyl)phenyl | CH | H |
| 2-23 | 3-(dimethylamino)pyridin-2-yl | 4-chloro-2-(trifluoromethyl)phenyl | CH | H |
| 2-24 | 2-(pyrrolidin-1-yl)pyridin-3-yl | 4-chloro-2-(trifluoromethyl)phenyl | CH | H |
| 2-25 | 2-ethoxypyridin-3-yl | 4-ethoxy-2-(trifluoromethyl)phenyl | N | H |
| 2-26 | 3-fluoro-2-ethoxyphenyl | 4-methyl-2-(trifluoromethyl)phenyl | CH | H |
| 2-27 | 2-ethoxyphenyl | 4-methyl-2-(trifluoromethyl)phenyl | CH | H |
| 2-28 | 5-fluoro-2-ethoxyphenyl | 4-methyl-2-(trifluoromethyl)phenyl | CH | H |

TABLE 2-continued

| Compound No. | R^A | R^B | X^1 | R^4 |
|---|---|---|---|---|
| 2-29 | 4-fluoro-2-ethoxyphenyl | 2-trifluoromethyl-4-methylphenyl | CH | H |
| 2-30 | 2-ethoxypyridin-3-yl | 6-ethoxy-2-(trifluoromethyl)pyridin-3-yl | N | H |
| 2-31 | 2-ethoxypyridin-3-yl | 6-methoxy-2-(trifluoromethyl)pyridin-3-yl | N | H |

Compounds in Table 2 are named:

2-1: 2-[({4-[(2R)-4-[2-chloro-4-(trifluoromethyl)benzoyl]-2-ethylpiperazin-1-yl]-2'-ethoxy-[1,1'-biphenyl]-3-yl}methyl)amino]ethan-1-ol;

2-2: (2S)-1-[({4-[(2R)-4-[2-chloro-4-(trifluoromethyl)benzoyl]-2-ethylpiperazin-1-yl]-2'-ethoxy-[1,1'-biphenyl]-3-yl}methyl)amino]propan-2-ol;

2-3: 1-{4-[(2R)-4-[4-chloro-2-(trifluoromethyl)benzoyl]-2-ethylpiperazin-1-yl]-2'-methoxy-[1,1'-biphenyl]-3-yl}methanamine;

2-4: 1-{4-[(2R)-4-[4-chloro-2-(trifluoromethyl)benzoyl]-2-ethylpiperazin-1-yl]-2'-(2-methoxyethoxy)-[1,1'-biphenyl]-3-yl}methanamine;

2-5: 1-{4-[(2R)-4-[4-chloro-2-(trifluoromethyl)benzoyl]-2-ethylpiperazin-1-yl]-2'-propoxy-[1,1'-biphenyl]-3-yl}methanamine;

2-6: 2-{[3'-(aminomethyl)-4'-[(2R)-4-[4-chloro-2-(trifluoromethyl)benzoyl]-2-ethylpiperazin-1-yl]-[1,1'-biphenyl]-2-yl]oxy}ethan-1-ol;

2-7: 2-{[3'-(aminomethyl)-4'-[(2R)-2-ethyl-4-[2-(trifluoromethyl)benzoyl]piperazin-1-yl]-[1,1'-biphenyl]-2-yl]oxy}ethan-1-ol;

2-8: [3'-(aminomethyl)-4'-[(2R)-4-[4-chloro-2-(trifluoromethyl)benzoyl]-2-ethylpiperazin-1-yl]-[1,1'-biphenyl]-2-yl]methanol;

2-9: 1-{2-[(2R)-4-[4-chloro-2-(trifluoromethyl)benzoyl]-2-ethylpiperazin-1-yl]-5-(2-ethoxypyridin-3-yl)phenyl}methanamine;

2-10: 1-{2-[(2R)-4-[4'-(aminomethyl)-5-fluoro-[1,1'-biphenyl]-2-carbonyl]-2-ethylpiperazin-1-yl]-5-(2-ethoxypyridin-3-yl)phenyl}methanamine;

2-11: 1-{6-[(2R)-4-[2-chloro-4-fluorobenzoyl]-2-ethylpiperazin-1-yl]-3-(2-ethoxypyridin-3-yl)-2-fluorophenyl}methanamine;

2-12: 1-{3-[(2R)-4-[4-chloro-2-(trifluoromethyl)benzoyl]-2-ethylpiperazin-1-yl]-6-(2-ethoxyphenyl)pyridin-2-yl}methanamine;

2-13: 1-{5-[(2R)-4-[4-chloro-2-(trifluoromethyl)benzoyl]-2-ethylpiperazin-1-yl]-2'-ethoxy-[2,3'-bipyridin]-6-yl}methanamine;

2-14: 1-{5-[(2R)-4-(2-chloro-4-methylbenzoyl)-2-ethylpiperazin-1-yl]-2'-ethoxy-[2,3'-bipyridin]-6-yl}methanamine;

2-15: 1-{5-[(2R)-4-[2-chloro-4-(trifluoromethyl)benzoyl]-2-ethylpiperazin-1-yl]-2'-ethoxy-[2,3'-bipyridin]-6-yl}methanamine;

2-16: ({5-[(2R)-4-[4-chloro-2-(trifluoromethyl)benzoyl]-2-ethylpiperazin-1-yl]-2'-ethoxy-[2,3'-bipyridin]-6-yl}methyl)(methyl)amine;

2-17: 1-{5-[(2R)-4-(2-chloro-4-fluorobenzoyl)-2-ethylpiperazin-1-yl]-2'-ethoxy-[2,3'-bipyridin]-6-yl}methanamine;

2-18: 1-{6-[(2R)-4-(2-chloro-4-fluorobenzoyl)-2-ethylpiperazin-1-yl]-3-(2-ethoxypyridin-3-yl)-2-fluorophenyl}methanamine;

2-19: 1-{2'-ethoxy-5-[(2R)-2-ethyl-4-(2,3,4-trifluorobenzoyl)piperazin-1-yl]-[2,3'-bipyridin]-6-yl}methanamine;

2-20: 1-{2'-ethoxy-5-[(2R)-2-ethyl-4-[4-fluoro-2-(trifluoromethyl)benzoyl]piperazin-1-yl]-[2,3'-bipyridin]-6-yl}methanamine;

2-21: {[5-(2-ethoxypyridin-3-yl)-2-[(2R)-2-ethyl-4-[4-fluoro-2-(trifluoromethyl)benzoyl]piperazin-1-yl]phenyl]methyl}[2-(methylamino)ethyl]amine;

2-22: 13-[3-(aminomethyl)-4-[(2R)-4-[4-chloro-2-(trifluoromethyl)benzoyl]-2-ethylpiperazin-1-yl]phenyl]-N-methylpyridin-2-amine;

2-23: 3-[3-(aminomethyl)-4-[(2R)-4-[4-chloro-2-(trifluoromethyl)benzoyl]-2-ethylpiperazin-1-yl]phenyl]-N,N-dimethylpyridin-2-amine;

2-24: 1-{2-[(2R)-4-[4-chloro-2-(trifluoromethyl)benzoyl]-2-ethylpiperazin-1-yl]-5-[2-(pyrrolidin-1-yl)pyridin-3-yl]phenyl}methanamine;

2-25: 1-{2'-ethoxy-5-[(2R)-4-[4-ethoxy-2-(trifluoromethyl)benzoyl]-2-ethylpiperazin-1-yl]-[2,3'-bipyridin]-6-yl}methanamine;

2-26: 1-{2'-ethoxy-4-[(2R)-2-ethyl-4-[4-methyl-2-(trifluoromethyl)benzoyl]piperazin-1-yl]-3'-fluoro-[1,1'-biphenyl]-3-yl}methanamine;

2-27: 1-{2'-ethoxy-4-[(2R)-2-ethyl-4-[4-methyl-2-(trifluoromethyl)benzoyl]piperazin-1-yl]-[1,1'-biphenyl]-3-yl}methanamine;

2-28: 1-{2'-ethoxy-4-[(2R)-2-ethyl-4-[4-methyl-2-(trifluoromethyl)benzoyl]piperazin-1-yl]-4'-fluoro-[1,1'-biphenyl]-3-yl}methanamine;

2-29: 1-{2'-ethoxy-4-[(2R)-2-ethyl-4-[4-methyl-2-(trifluoromethyl)benzoyl]piperazin-1-yl]-5'-fluoro-[1,1'-biphenyl]-3-yl}methanamine;

2-30: 1-{2'-ethoxy-5-[(2R)-4-[6-ethoxy-2-(trifluoromethyl)pyridine-3-carbonyl]-2-ethylpiperazin-1-yl]-[2,3'-bipyridin]-6-yl}methanamine; and 2-31: 1-{2'-ethoxy-5-[(2R)-2-ethyl-4-[6-methoxy-2-(trifluoromethyl)pyridine-3-carbonyl]piperazin-1-yl]-[2,3'-bipyridin]-6-yl}methanamine.

TABLE 3

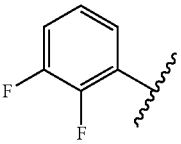

| Compound No. | $R^A$ | —L—$R^B$ | $X^1$ | $X^2$ | $X^3$ | $R^1$ | $R^4$ |
|---|---|---|---|---|---|---|---|
| 3-1 | 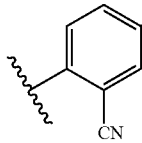 | 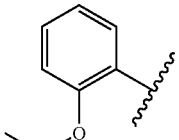 | CH | CH | CH | H | 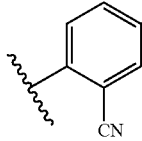 |
| 3-2 | 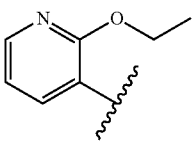 [SMILES: *c1cccnc1OCC] | 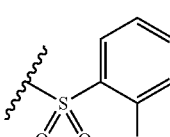 | CH | CH | CH | H | 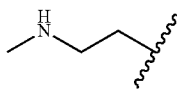 |
| 3-3 | 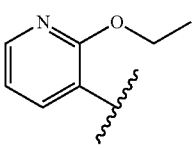 | 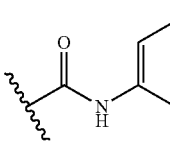 | CF | CH | CH | (2R)-CH$_2$CH$_3$ | 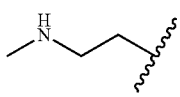 |
| 3-4 | 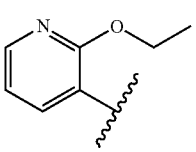 | 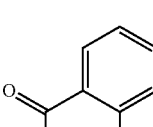 | CF | CH | CH | (2R)-CH$_2$CH$_3$ | 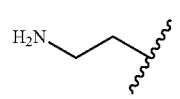 |
| 3-5 | 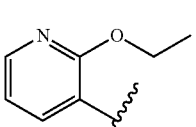 | 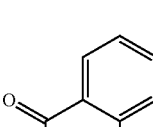 | CH | CH | CH | (3R)-CH$_2$CH$_3$ | H$_2$N~ |
| 3-6 | 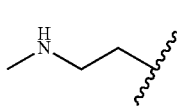 [SMILES: *CCNC] | | CH | CH | CH | (3R)-CH$_3$ | |

TABLE 3-continued

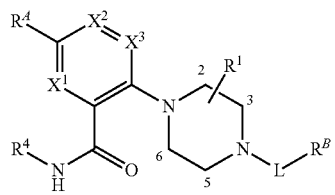

| Compound No. | $R^A$ | —L—$R^B$ | $X^1$ | $X^2$ | $X^3$ | $R^1$ | $R^4$ |
|---|---|---|---|---|---|---|---|
| 3-7 | pyridine with OEt | 4-Cl, 2-CF₃ benzoyl | N | CH | N | (2R)-CH₂CH₃ | N,N-dimethylaminoethyl |
| 3-8 | pyridine with OEt | 4-Cl, 2-CF₃ benzoyl | N | CH | N | (2R)-CH₂CH₃ | N-methylaminoethyl |
| 3-9 | 2-ethoxyphenyl | 2-Cl, 4-CF₃ benzoyl | CH | N | CH | (2R)-CH₂CH₃ | H₂N-ethyl |

Compounds in Table 3 are named:
3-1: N-(3-aminopropyl)-4-{4-[2-cyano-4-(trifluoromethyl)phenyl]piperazin-1-yl}-2',3'-difluoro-[1,1'-biphenyl]-3-carboxamide;
3-2: N-(3-aminopropyl)-4-{4-[2-cyano-4-(trifluoromethyl)phenyl]piperazin-1-yl}-2'-ethoxy-[1,1'-biphenyl]-3-carboxamide;
3-3: 6-[(2R)-4-(2,4-dichlorobenzenesulfonyl)-2-ethylpiperazin-1-yl]-3-(2-ethoxypyridin-3-yl)-2-fluoro-N-[2-(methylamino)ethyl]benzamide;
3-4: (3R)—N-(2,4-di chlorophenyl)-4-[4-(2-ethoxypyridin-3-yl)-3-fluoro-2-{[2-(methylamino)ethyl]carbamoyl}phenyl]-3-ethylpiperazine-1-carb oxamide;
3-5: N-(2-aminoethyl)-2-[(3R)-4-[4-chloro-2-(trifluoromethyl)benzoyl]-3-ethylpiperazin-1-yl]-5-(2-ethoxypyridin-3-yl)benzamide;
3-6: 2-[(3R)-4-[4-chloro-2-(trifluoromethyl)benzoyl]-3-methylpiperazin-1-yl]-5-(2-ethoxypyridin-3-yl)-N-[2-(methylamino)ethyl]benzamide;
3-7: 3-[(2R)-4-[4-chloro-2-(trifluoromethyl)benzoyl]-2-ethylpiperazin-1-yl]-N-[2-(dimethylamino)ethyl]-6-(2-ethoxypyridin-3-yl)pyrazine-2-carboxamide;
3-8: 3-[(2R)-4-[4-chloro-2-(trifluoromethyl)benzoyl]-2-ethylpiperazin-1-yl]-6-(2-ethoxypyridin-3-yl)-N-[2-(methylamino)ethyl]pyrazine-2-carboxamide; and
3-9: N-(2-aminoethyl)-5-[(2R)-4-[2-chloro-4-(trifluoromethyl)benzoyl]-2-ethylpiperazin-1-yl]-2-(2-ethoxyphenyl)pyridine-4-carb oxamide.

In one aspect, compounds described herein are in the form of pharmaceutically acceptable salts. As well, active metabolites of these compounds having the same type of activity are included in the scope of the present disclosure.

In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

Scheme A

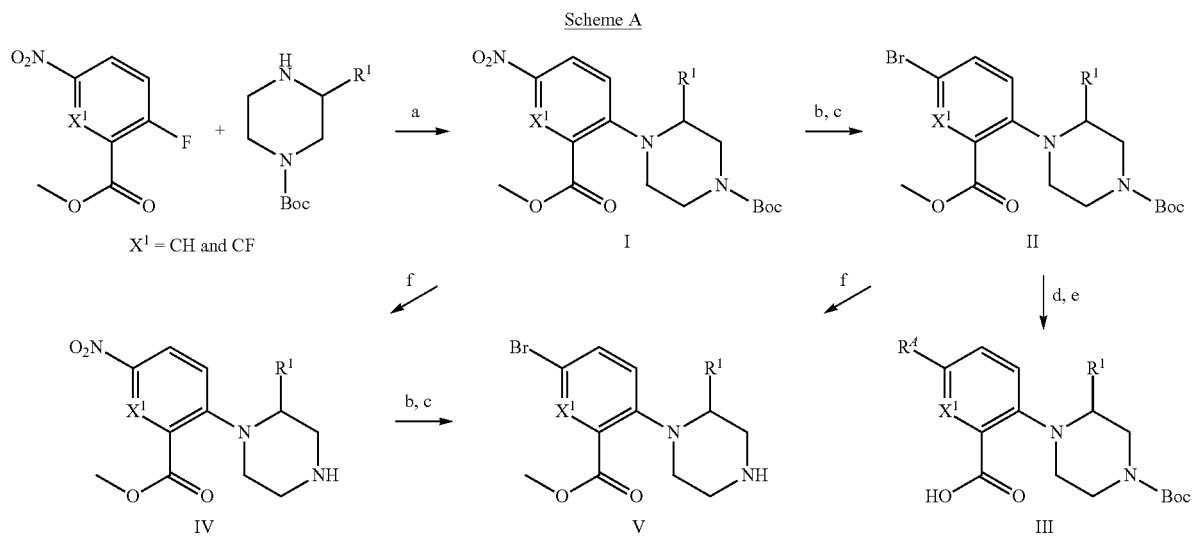

a) DMSO, Et$_3$N, 100° C.; b) Fe, NH$_4$Cl, EtOH/H$_2$O, 70° C.; c) n-Butylnitrite, CuBr$_2$, ACN, 70° C.; d) R$^A$B(OH)$_2$, Pd$_2$(dba)$_3$HCl$_3$, P(t-Bu)$_3$HBF$_4$, K$_3$PO$_4$, toluene, 70° C.; e) LiOH·H$_2$O H$_2$O/MeOH/THF; f) TFA, DCM.

Compound I is obtained by heating methyl 2-fluoro-5-nitrobenzoate or methyl 2,6-difluoro-3-nitrobenzoate with a mono-protected substituted piperazine in the presence of organic base such as N,N-diisopropylethylamine. An iron-catalyzed reduction of nitro group yields an aryl amine, which is subsequently transformed to an aryl bromide (II) via preparation of diazonim salt and subsequent displacement with Br anion under copper (I) catalysis. Compound II is subjected to organometallic coupling reaction such as Suzuki-Miyaura reaction with R$^A$B(OH)$_2$ or its corresponding ester and is followed by a standard hydrolysis to generate compound III. Compound IV is converted to the intermediate V via an iron-catalyzed nitro reduction and a subsequent Sandmeyer reaction of the aniline. Alternatively, Compound V can be also obtained from a standard deprotection of II.

In some embodiments, compounds described herein are prepared as described in Scheme B.

Scheme B

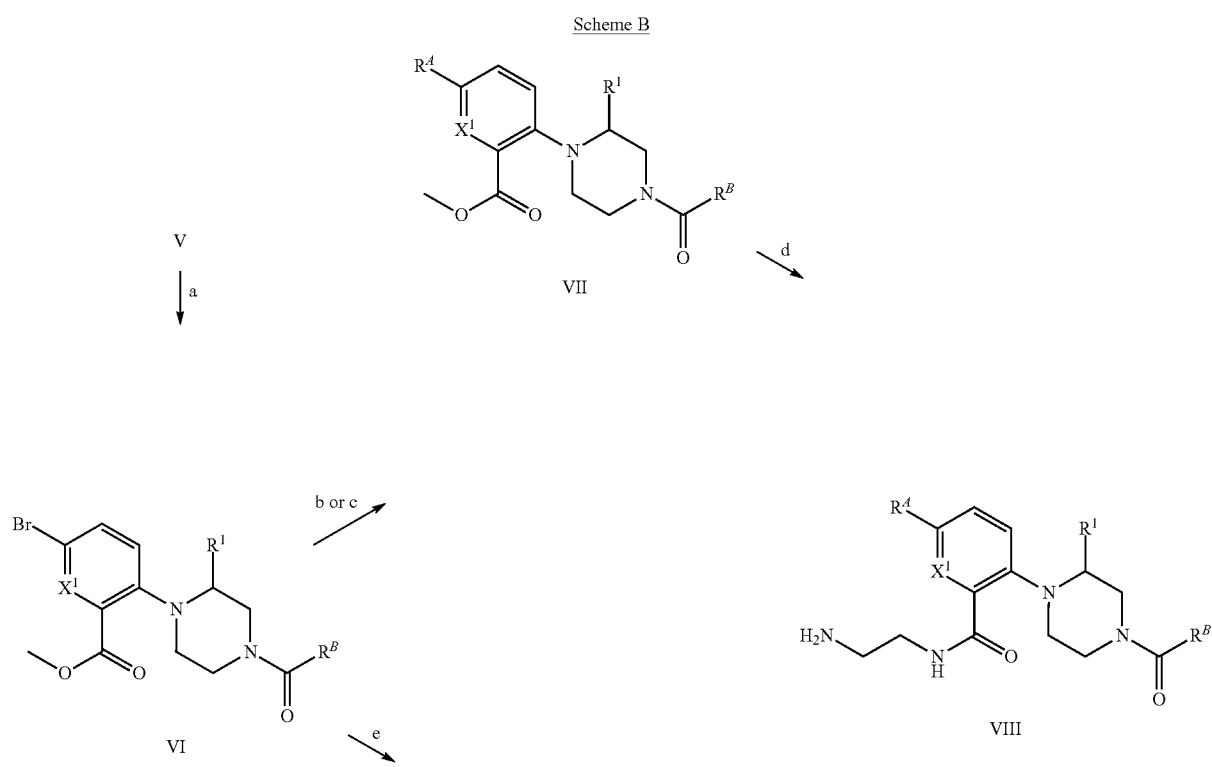

-continued

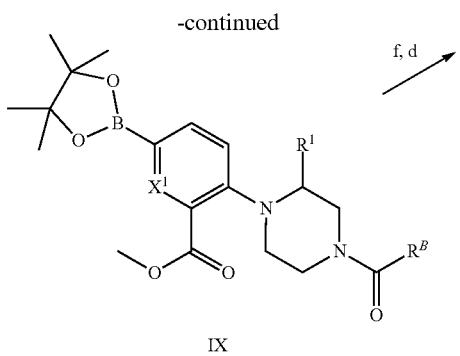

IX a) $R^B$—$CO_2H$ HATU, $Et_3N$, or $R^BCOCl$, $Et_3N$; b) $R^4B(OH)_2$, $Pd_2(dba)_3HCl_3$, $P(t-Bu)_3HBF_4$, $K_3PO_4$, toluene, 70° C.; c) Aryl tributyltin, $Pd(dppf)Cl_2$, CuO, DMF, 100° C.; d) IPA, $NH_2CH_2CH_2NH_2$, 70° C., e) Bis(pinacolato)diboron, $Pd(DTBPF)Cl_2$, KOAc, dioxane, $H_2O$, 90° C.; f) $R^4$—Br, $Pd(DTBPF)Cl_2$, $K_2CO_3$, dioxzane, $H_2O$, 80° C.

Compound V is converted to the intermediate VI by treating with an activated carboxylic acid using HATU and triethylamine or an acyl chloride in the presence of triethylamine or other bases. Compound VII is prepared from the aryl bromide (VI) by organometallic coupling reactions such as Suzuki-Miyaura reaction with boronic acid $R^4B(OH)_2$ or its ester or Stifle coupling with $R^4SnBu_3$. The direct conversion of the carboxylic ester (VII) to the amide (VIII) is achieved by heating it with a diamine in a polar protic solvent. Alternatively, compound VI is converted into the corresponding boronic ester intermediate (LX) which is subsequently subject to coupling reaction such as Suzuki-Miyaura reaction with an aryl halide such as $R^4$—Br and is followed by the conversion of the ester to the amide to yield VIII.

In some embodiments, compounds described herein are prepared as described in Scheme C.

Compound III is reacted with an amine ($R^4R^5NH$) in the presence of HATU and triethylamine yielding intermediate X. Compound X is subjected to removal of Boc group with TFA or other acid and then formation of the amide with $R^ACO_2H$, or $R^ACOCl$ to give XI. If $R^4$ or $R^5$ contains a protecting group, then an additional deprotection step takes place to produce XI. Alternatively, intermediate XII is obtained from deprotection of III by TFA is converted to XIII by treating with pre-activated $R^BCO_2H$. Compound XIII is utilized to produce the corresponding amides (XI) similarly.

In some embodiments, compounds described herein are prepared as described in Scheme D.

Scheme C

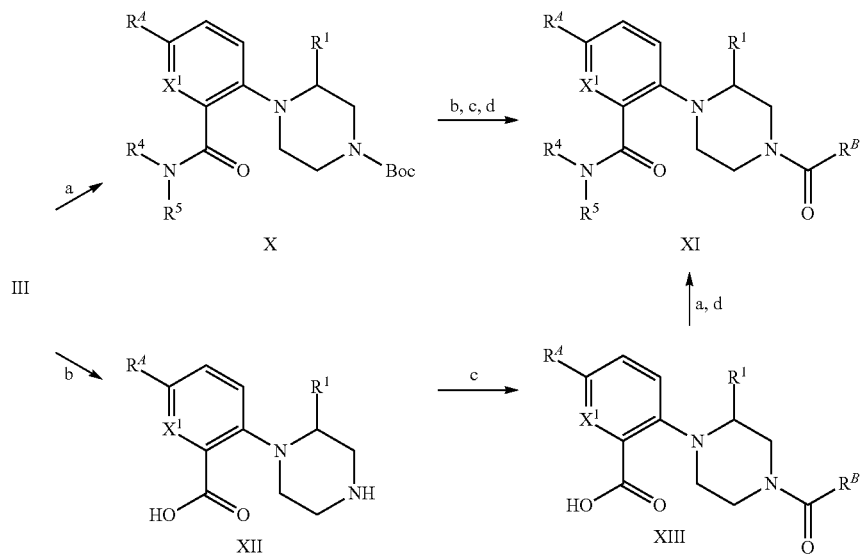

a) $R^4R^5NH$, HATU, $Et_3N$; b) TFA, DCM; c) $R^BCO_2H$, HATU, $Et_3N$, or $R^BCOCl$, $Et_3N$; d) deprotection (optically).

Scheme D

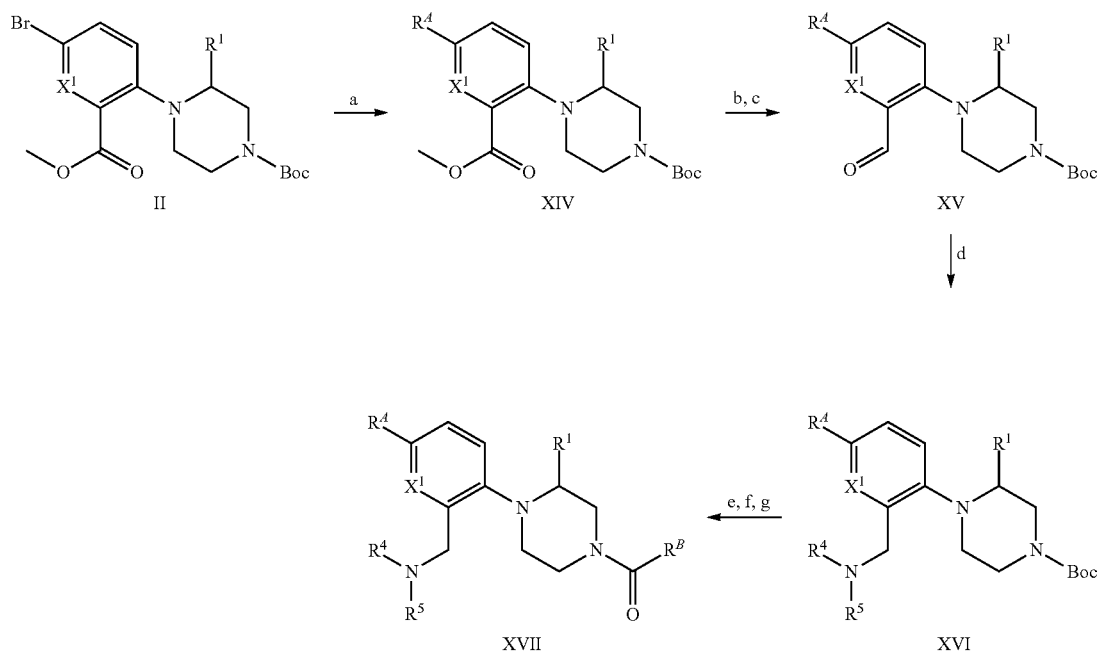

a) $R^4B(OH)_2$, $Pd_2(dba)_3HCl_3$, $P(t\text{-}Bu)_3HBF_4$, $K_3PO_4$, toluene, 70° C.; b) $NaBH_4$, MeOH, 50° C.; c) IBX; d) $R^4R^5NH$, $NaBH(OAc)_3$; e) TFA, DCM; f) $R^BCO_2H$, HATU, $Et_3N$; g) deprotection (if needed)

Compound II is subjected to a Suzuki coupling with boronic acid $R^BB(OH)_2$ in the presence of a transition metal catalyst, yielding the intermediate (XIV). The carboxylic ester on XIV is reduced to an alcohol using $NaBH_4$ followed by oxidation with 2-iodoxybenzoic acid to afford the benzaldehyde XV, which is subjected to reductive amination reaction with an appropriate amine ($R^4R^5NH$) and a reducing agent such as $NaBH(OAc)_3$ to afford XVI. A subsequent Boc deprotection and then amide formation with $R^BCO_2H$ yields compound XVII. If $R^4$ contains a protecting group, then an additional deprotection step takes place to produce XVII.

In some embodiments, compounds described herein are prepared as described in Scheme E.

Scheme E

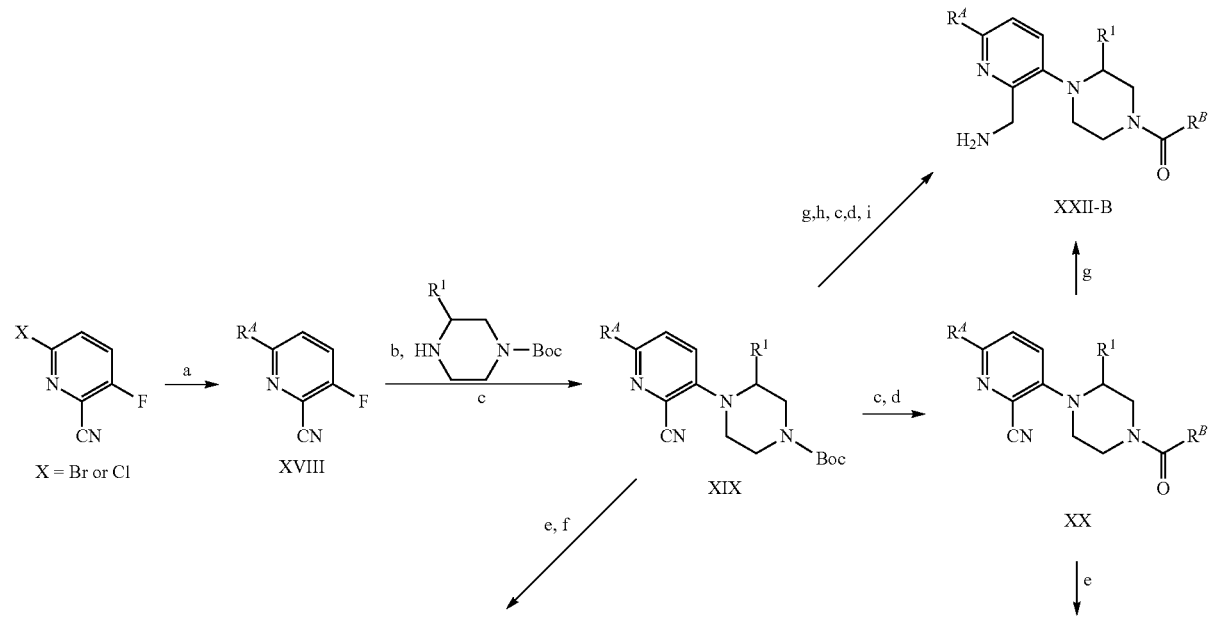

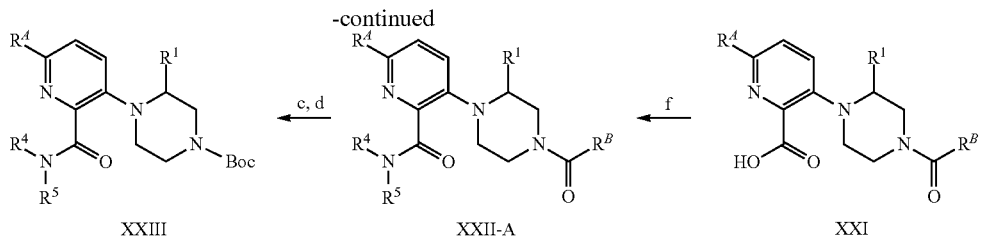

a) R⁴B(OH)₂, PdCl₂(t-Bu₂PPhNME₂)₂, K₂CO₃, dioxane/H₂O; b) DMSO, DIEA, 140° C.; c) TFA or HCl d) R^B CO₂H, HATU, Et₃N, or R^B COCl, Et₃N; e) KOH, EtOH/H₂O, 100° C.; f) R⁴R⁵NH, HATU, Et₃N; g) NiCl₂, NaBH₄; h) Cbz—Cl, DIPEA, DCM or CbzOSu, DCM; i) TFA, 70° C.

Compound XVIII is prepared by Suzuki-Miyaura coupling reaction with a boronic acid R⁴B(OH)₂ or Stifle coupling with R⁴SnBu₃, which reacts with a mono-protected substituted piperazine in the presence of an organic base such as DIEA to afford XIX. Subsequently, Boc group is removed by an acid and the corresponding amide is formed via standard amide formation reaction with R^B CO₂H to afford XX. Nickel (II) catalyzed reduction of the carbonitrile produces benzyl amine analogues (XXII-B). Hydrolysis of CN on XX with a strong inorganic base such as KOH affords the carboxylic acid intermediate (XXI), which is converted to compound XXII-A by coupling reaction with R⁴R⁵NH. If R⁴ contains a protecting group, then an additional deprotection step takes place to produce XXII. Alternatively, XXII-A is prepared via 4-step synthesis starting from XIX by first hydrolysis of cyano group to the carboxylic acid, followed by amide formation with R⁴R⁵NH to form XXIII, then Boc group is removed and R^B CO₂H or R^B COCl is used to obtain XXII-A. If R⁴ contains a protecting group, then appropriate deprotection step to remove the protecting group is conducted to produce XXII In some embodiments, compound XXII-B is prepared via an alternative pathway from XIX as follows: cyano group is reduced by NaBH₄ in the presence of NiCl₂. The newly formed amine is then protected by a Cbz group. Subsequently Boc group is removed, followed by amide formation with R^B CO₂H. Finally, Cbz group is removed by stirring in hot TFA to afford XXXII-B.

In some embodiments, compounds described herein are prepared as described in Scheme F.

Scheme F

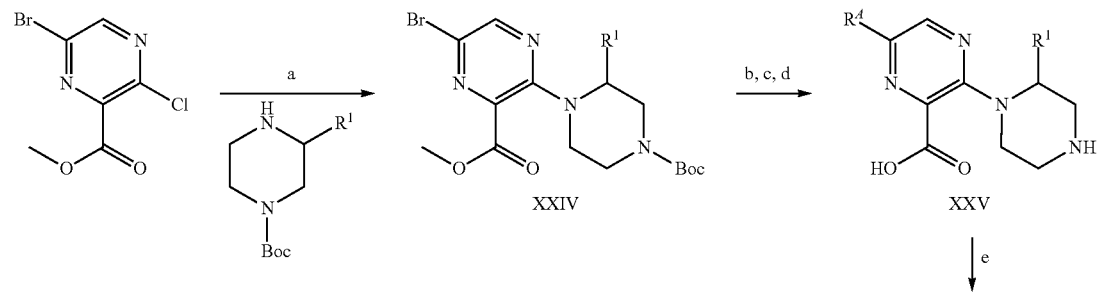

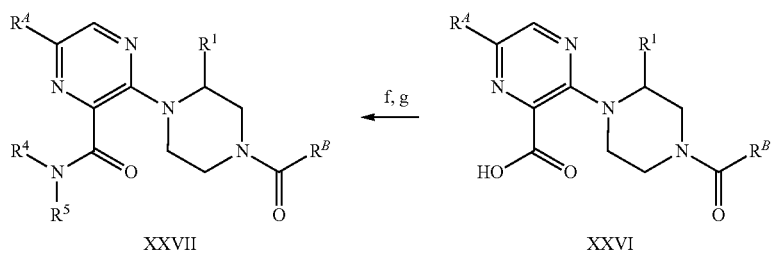

a) DMSO, DIEA, 120° C.; b) R⁴B(OH)₂, PdCl₂(t-Bu₂PPhNMe₂)₂, K₂CO₃, dioxane/H₂O, 100° C.; c) LiOH·H₂O, MeOH/H₂O/THF; d) TFA, DCM, e) R^B CO2H, HATU, Et₃N; f) HATU, R⁴R⁵NH; g) deprotection (if necessary)

Heating of methyl 6-bromo-3-chloropyrazine-2-carboxylate with a mono-protected substituted piperazine yields compound XXIV, which is subsequently subjected to Suzuki-Miyaura coupling reaction with R⁴B(OH)₂ and is followed by hydrolysis of ester to acid and a standard de-Boc procedure to yield XXV. XXVI is obtained from a coupling reaction with a pre-activated R^B CO₂H and further reaction with R⁴R⁵NH in the presence of HATU affords XXVII. If R⁴ or R⁵ contains a protecting group, then an additional deprotection step takes place to produce XXII.

In some embodiments, compounds described herein are prepared as described in Scheme G.

Scheme G

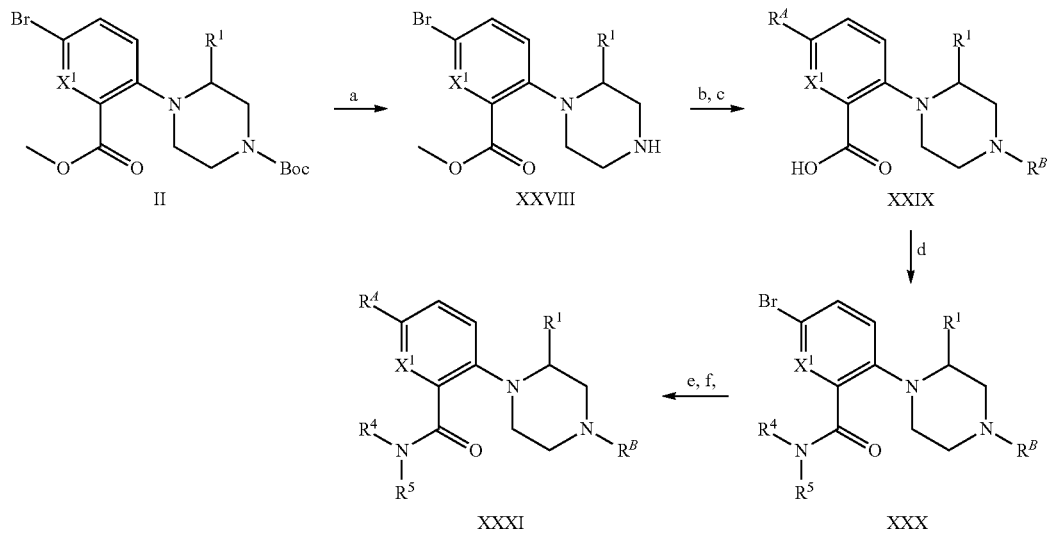

a) TFA, DCM; b) R$^B$—Cl (or F), DIEA, DMSO; c) LiOH·H$_2$O, H$_2$O/MeOH/THF; d) R$^4$R$^5$NH, HATU, Et$_3$N; e) R$^A$B(OH)$_2$, Pd (II), K$_2$CO$_3$, dioxane/H$_2$O/; f) deprotection The Boc group on II is removed to yield XXVIII, which is treated with R$^B$-Cl or R$^B$—F and is followed by saponification of ester to form XXIX. Coupling reaction of XXIX with R$^4$R$^5$NH yields XXX, which undergoes Suzuki-Miyaura reaction with the boronic acid R$^A$B(OH)$_2$ to afford XXXI. An additional removal of protecting group takes place if R$^4$ or R$^5$ contains a protecting group on XXXI.

In some embodiments, compounds described herein are prepared as described in Scheme H.

Scheme H

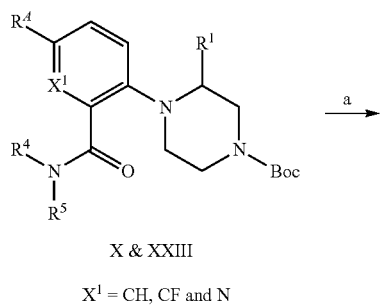

X & XXIII

X$^1$ = CH, CF and N

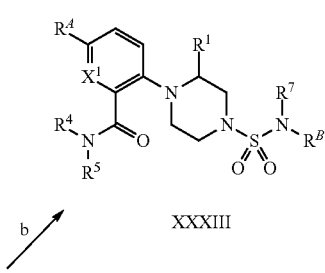

XXXIII

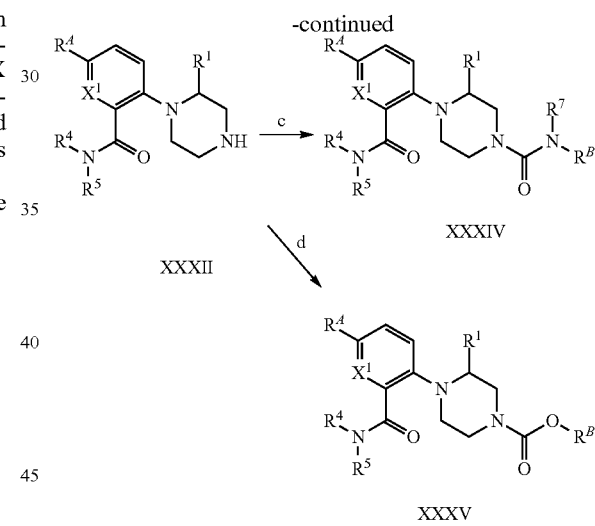

a) TFA; b) R$^B$SO$^2$Cl, Et$_3$N;
c) R$^B$NCO or R$^B$R$^7$NCO$_2$Ph, Et$_3$N or triphosgene, Et$_3$N, then R$^B$R$^7$NH·Et$_3$N.
d) CDI, R$^B$OH, DIEA, Δ

The Boc group of on X is removed to form XXXII, which is reacted with aryl sulfonyl chloride in the presence of an organic base to afford XXXIII In a similar manner, urea analogues (XXXIV) are prepared by either reaction with an isocyanates (R$^B$NCO) or reaction R$^B$R$^7$CO$_2$Ph or reacting XXXII with triphosgene and then R$^B$R$^7$NH. In addition, an efficient synthesis of carbamate derivatives (XXXV) was achieved by reacting XXXII with the CDI activated alcohols. If R$^4$ contains a protecting group, then it is removed subquently with an appropriate condition on XXXIII, XXXIV, or XXXV.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$-, —$CH_2CH_2$-, —$CH_2CH_2CH_2$-, —$CH_2CH_2CH_2CH_2$-, and the like. In some embodiments, an alkylene is —$CH_2$-.

An "alkoxy" group refers to a (alkyl)O— group, where alkyl is as defined herein.

The term "alkylamine" refers to the N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "alkenyl" refers to a type of alkyl group in which at least one carbon-carbon double bond is present. In one embodiment, an alkenyl group has the formula C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C(CH$_3$)=$CH_2$, —CH=CHCH$_3$, —C(CH$_3$)=CHCH$_3$, and CH$_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, a carbocycle is a monocyclic carbocycle or a bicyclic carbocycle. In some embodiments, a carbocycle is a monocyclic carbocycle. Carbocycles are non-aromatic or aromatic. Non-aromatice carbocyles are saturated or partially unsaturated. In some embodiments, a carbocycle is a bicyclic carbocycle. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic, bicyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl, norbornenyl, bicycle[1.1.1]pentyl, adamantyl, norbornyl, norbornenyl, decalinyl, or 7,7-dimethyl-bicyclo[2.2.1]heptanyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent 0 or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicycicic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH ($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2$$C_1$-$C_4$alkyl. In some other embodiments, optional substituents are independently selected from halogen, —CN, —NH$_2$, —NH(CH$_3$), —N(CH$_3$)$_2$, —OH, —CO$_2$H, —CO$_2$($C_1$-$C_4$alkyl), —C(=O)NH$_2$, —C(=O)NH($C_1$-$C_4$alkyl), —C(=O)N($C_1$-$C_4$alkyl)$_2$, —S(=O)$_2$NH$_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_2$-$C_6$heterocycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2$$C_1$-$C_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of melanocortin receptor activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

Abbreviations:
DIEA: N,N-diisopropylethylamine;
DMSO: dimethyl sulfoxide;
Pd(PPh$_3$)$_4$: tetrakis(triphenylphosphine)palladium(0)
Pd(dppf)Cl$_2$: [1,1'-bis(diphenylphosphino)ferrocene]palladium(II) dichloride;
CuI: copper(I) iodide;
TBAF: tetra-n-butylammonium fluoride;
P(t-Bu)$_3$: tri-tert-buytlphosphine;
HBF$_4$: tetrafluoroboric acid;
DBU: 1,8-diazabicyclo[5.4.0]undec-7-ene;
Prep-HPLC: preparative high performance liquid chromatography;
TFA: trifluoroacetic acid;
CH$_3$CN, MeCN, or ACN: acetonitrile;
MeOD: deuterated methanol;
CDCl$_3$: deuterated chloroform
DME: 1,2-dimethoxyethane;
DMF: N,N-dimethylformamide
DCM: dichloromethane
H$_2$O: water;
KOAc: potassium acetate;
NaOAc: sodium acetate;
Cs$_2$CO$_3$: cesium carbonate
P-TsOH: p-toluenesulfonic acid;
NaNO$_2$: sodium nitrite;
THF: tetrahydrofuran;
NBS: N-bromosuccinimide;
Br$_2$: bromine;
AgF: silver fluoride;
LiAlH$_4$: lithium aluminium hydride;
IBX: 2-iodoxybenzoic acid;
TEA: trimethylamine;
DMAP: N,N-dimethylpyridine-4-amine
HOBT: hydroxybenzotriazole;
EDCI: 1-ethyl-3-(3-dimethylaminopropyl)carbodiimide;
Pd(PPh$_3$)$_2$Cl$_2$: bis(triphenylphosphine)palladium(II) dichloride;
PdAMphos or Pd (amphos)Cl$_2$ or: bis(di-tert-butyl(4-dimethylaminophenyl)phosphine)dichloropalladium(II);
Pd(DTBPF)Cl$_2$: [1,1'-bis(di-tert-butylphosphino)ferrocene]dichloropalladium(II);
cc: column chromatography
rt: room temperature;
h: hour or hours.

EXAMPLES

The following examples are provided for illustrative purposes only and not to limit the scope of the claims provided herein.

Synthesis of Compounds

Example 1: N-(2-aminoethyl)-4-[(2R)-4-[2-chloro-4-(trifluoromethyl)benzoyl]-2-ethylpiperazin-1-yl]-2',3'-difluoro-[1,1'-biphenyl]-3-carboxamide (Compound 1-1)

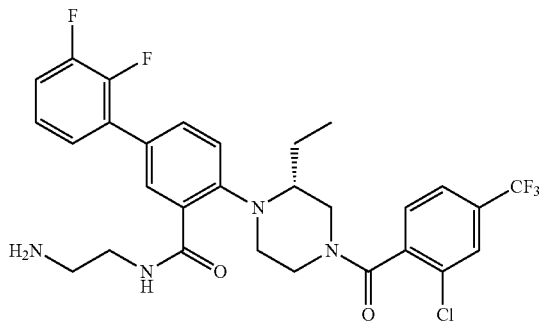 [SMILES: CC[C@@H]1CN(C(=O)c2ccc(C(F)(F)F)cc2Cl)CCN1c1ccc(-c2cccc(F)c2F)cc1C(=O)NCCN]

Step 1-1, preparation of tert-butyl (3R)-3-ethyl-4-[2-(methoxycarbonyl)-4-nitrophenyl]piperazine-1-carboxylate: into a 40-mL round bottom flask, was placed methyl 2-fluoro-5-nitrobenzoate (2.2 g, 0.01 mmol, 1.2 eq.), tert-butyl (3R)-3-ethylpiperazine-1-carboxylate (2.0 g, 9.33 mmol), TEA (2.8 g, 0.03 mmol, 3.0 eq.) and DMSO (20 mL). The resulting solution was stirred at 100° C. for 2 h and cooled to rt. The reaction was diluted with water (50 mL) and extracted with ethyl acetate (3×50 mL). The combined organic layers were washed with brine (2×50 mL), dried over anhydrous sodium sulfate, and concentrated under vacuum. The residue was purified by a silica gel column eluting with ethyl acetate/petroleum ether (1:3). 3.3 g (90%) of the title compound as a brown oil. LCMS (M+H)$^+$: 394.2.

Step 1-2, preparation of methyl 2-[(2R)-2-ethylpiperazin-1-yl]-5-nitrobenzoate: a solution of tert-butyl (3R)-3-ethyl-4-[2-(methoxycarbonyl)-4-nitrophenyl]piperazine-1-carboxylate (3.3 g, 8.39 mmol) in TFA (3 mL)/DCM (6 mL) was stirred at 30° C. for 2 hrs. The resulting mixture was concentrated under vacuum. This resulted in 3.3 g (97%) of the title compound as a brown oil. LCMS (M+H)$^+$: 294.1.

Step 1-3, preparation of tert-butyl (3R)-4-[4-bromo-2-(methoxycarbonyl)phenyl]-3-ethylpiperazine-1-carboxylate: 2-chloro-4-(trifluoromethyl)benzoic acid (860 mg, 3.83 mmol, 1.2 eq.) and HATU (1.46 g, 3.83 mmol, 1.2 eq.) were dissolved in DMF (20 mL). After stirring for 5 min at rt, the resulting solution was treated with methyl 2-[(2R)-2-ethylpiperazin-1-yl]-5-nitrobenzoate trifluoroacetate (1.3 g, 3.19 mmol) and DIEA (1.23 g, 9.57 mmol, 3.0 eq.). The reaction was stirred for 1 h at room temperature, diluted with water (50 mL), and extracted with ethyl acetate (3×50 mL). The combined organic layers were washed with brine (2×50 mL), dried over anhydrous sodium sulfate and concentrated under vacuum. The residue was purified by a silica gel column eluting with ethyl acetate/petroleum ether (1:1). 1.8 g (83%) of the title compound was obtained as a yellow oil. LCMS (M+H)$^+$: 500.1.

Step 1-4, preparation of 5-amino-2-[(2R)-4-[2-chloro-4-(trifluoromethyl)benzoyl]-2-ethylpiperazin-1-yl]benzoate: into a 40-mL round-bottom flask, was placed methyl 2-[(2R)-4-[2-chloro-4-(trifluoromethyl)benzoyl]-2-ethylpiperazin-1-yl]-5-nitrobenzoate (1.8 g, 3.60 mmol), Fe (1 g, 18.00 mmol, 5.0 eq.), NH$_4$C$_1$ (963 mg, 18.00 mmol, 5.0 eq.), and EtOH (20 mL)/H$_2$O (4 mL). The resulting solution was stirred at 70° C. for 1 h and cooled to rt. The reaction was diluted with water (50 mL) and extracted with ethyl acetate (3×60 mL). The combined organic layers were dried and concentrated under vacuum. The residue was purified by a silica gel column eluting with ethyl acetate/petroleum ether (1:1). 1.1 g (65%) of the title compound was isolated as a yellow oil. LCMS (M+H)$^+$: 470.1.

Step 1-5, preparation of methyl 5-bromo-2-[(2R)-4-[2-chloro-4-(trifluoromethyl)benzoyl]-2-ethylpiperazin-1-yl]benzoate: into a 40-mL round-bottom flask, was placed CuBr$_2$ (1.31 g, 5.85 mmol, 2.5 eq.), n-butyl nitrite (482 mg, 4.68 mmol, 2.0 eq.), and ACN (20 mL). The resulting solution was stirred for 5 min at 0° C. and treated with a solution of methyl 5-amino-2-[(2R)-4-[2-chloro-4-(trifluoromethyl)benzoyl]-2-ethylpiperazin-1-yl]benzoate (1.1 g, 2.34 mmol) in ACN (5 mL) dropwise at 0° C. The resulting solution was stirred at 50° C. for 1 h. The reaction mixture was cooled to rt and diluted with water (50 mL). The resulting solution was extracted with ethyl acetate (3×50 mL). The combined organic layers were dried and concentrated under vacuum. The residue was purified by a silica gel column eluting with ethyl acetate/petroleum ether (1:1). 520 mg (42%) of the title compound was isolated as a light yellow oil. LCMS (M+H)$^+$: 533.0.

Step 1-6, preparation of methyl 4-[(2R)-4-[2-chloro-4-(trifluoromethyl)benzoyl]-2-ethylpiperazin-1-yl]-2',3'-difluoro-[1,1'-biphenyl]-3-carboxylate: Into a 8-mL pressure tube vessel, was placed methyl 5-bromo-2-[(2R)-4-[2-chloro-4-(trifluoromethyl)benzoyl]-2-ethylpiperazin-1-yl]benzoate (30 mg, 0.06 mmol), 2,3-difluorophenylboronic acid (13.3 mg, 0.08 mmol), Pd$_2$(dba)$_3$CHCl$_3$ (5.8 mg, 0.01 mmol), P(t-Bu)$_3$.HBF$_4$ (1.6 mg, 0.01 mmol), K$_3$PO$_4$ (35.8 mg, 0.17 mmol), and toluene/H$_2$O (1 mL/0.1 mL). The resulting solution was degassed for 5 min with N2, sealed, and stirred at 70° C. for 2 hrs in an oil bath. The resulting mixture was cooled to rt and concentrated under vacuum. The residue was applied onto a silica gel column eluting with ethyl acetate/petroleum ether (1:3), resulting in 20 mg (63%) of the title compound. LCMS (M+H)$^+$: 567.1.

Step 1-7, preparation of N-(2-aminoethyl)-4-[(2R)-4-[2-chloro-4-(trifluoromethyl)benzoyl]-2-ethylpiperazin-1-yl]-2',3'-difluoro-[1,1'-biphenyl]-3-carboxamide: a 8-mL pressure tube vessel, was placed methyl 4-[(2R)-4-[2-chloro-4-(trifluoromethyl)benzoyl]-2-ethylpiperazin-1-yl]-2',3'-difluoro-[1,1'-biphenyl]-3-carboxylate (20 mg, 0.04 mmol), ethane-1,2-diamine (0.5 mL), and IPA (0.5 mL). The resulting solution was sealed and stirred at 70° C. for 16 hrs. The resulting mixture was cooled to rt and concentrated under vacuum. The residue was purified by Prep-HPLC with the following conditions: SunFire Prep C18 OBD column; mobile phase, phase A: water (0.05% TFA); phase B: ACN (30% up to 45% in 6 min); flow rate: 20 mL/min; detector, 220 & 254 nm, resulting in 7.4 mg (30%) of the title compound. LCMS (M+H)$^+$: 595.2.

The following compounds were prepared similarly to Example 1 with appropriate substituting reagents and substrates at different steps. Some examples may require additional functional group transformations to introduce an appropriate substituent on aryl rings.

| Compound no. | MS (M + H)$^+$ |
|---|---|
| 1-2 | 589.1 |
| 1-3 | 603.1 |
| 1-4 | 577.2 |

-continued

| Compound no. | MS (M + H)+ |
|---|---|
| 1-5 | 593.2 |
| 1-6 | 593.2 |
| 1-7 | 584.2 |
| 1-8 | 573.2 |
| 1-9 | 611.1 |
| 1-10 | 603.2 |
| 1-11 | 617.2 |
| 1-12 | 617.3 |
| 1-13 | 575.2 |
| 1-16 | 603.2 |
| 1-22 | 588.2 |
| 1-23 | 617.3 |
| 1-28 | 601.2 |
| 1-29 | 601.2 |
| 1-30 | 560.2 |
| 1-31 | 560.2 |
| 1-34 | 604.3 |

Example 2: N-(2-aminoethyl)-4-[(2R)-4-[2-chloro-4-(trifluoromethyl)benzoyl]-2-ethylpiperazin-1-yl]-2'-cyclopropoxy-[1,1'-biphenyl]-3-carboxamide (Compound 1-14)

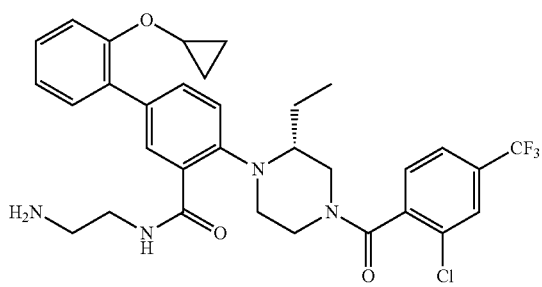 [SMILES: CC[C@@H]1CN(C(=O)c2ccc(C(F)(F)F)cc2Cl)CCN1c1ccc(-c2ccccc2OC2CC2)cc1C(=O)NCCN]

Step 2-1, preparation of methyl 2-[(2R)-4-[2-chloro-4-(trifluoromethyl)benzoyl]-2-ethylpiperazin-1-yl]-5-(4,4,5,5-tetramethyl-1,3,2-dioxaborolan-2-yl)benzoate: Into a 8-mL pressure tube vessel purged and maintained with an inert atmosphere of nitrogen, was placed methyl 5-bromo-2-[(2R)-4-[2-chloro-4-(trifluoromethyl)benzoyl]-2-ethylpiperazin-1-yl]benzoate from Example 1, Step 1-5 (250 mg, 0.47 mmol), 4,4,5,5-tetramethyl-2-(4,4,5,5-tetramethyl-1,3,2-dioxaborolan-2-yl)-1,3,2-dioxaborolane (178 mg, 0.70 mmol), Pd(DTBPF)Cl₂ (25 mg, 0.04 mmol), KOAc (138 mg, 1.4 mmol), and dioxane (5 mL). The resulting solution was degassed for 10 min with N2, sealed, and stirred at 90° C. for 3 h in an oil bath. The resulting mixture was cooled to rt and concentrated under vacuum. The residue was applied onto a silica gel column eluting with ethyl acetate/petroleum ether (1:3). This resulted in 120 mg (44%) of the title compound. LCMS (M+H)+: 581.2.

Step 2-2, preparation of methyl 4-[(2R)-4-[2-chloro-4-(trifluoromethyl)benzoyl]-2-ethylpiperazin-1-yl]-2'-cyclopropoxy-[1,1'-biphenyl]-3-carboxylate: to a 8-mL pressure tube vessel, was placed 2-[(2R)-4-[2-chloro-4-(trifluoromethyl)benzoyl]-2-ethylpiperazin-1-yl]-5-(4,4,5,5-tetramethyl-1,3,2-dioxaborolan-2-yl)benzoate (43 mg, 0.07 mmol), 1-bromo-2-cyclopropoxybenzene (28 mg, 0.13 mmol), Pd(DTBPF)C₁₂ (2 mg, 0.003 mmol), K₂CO₃ (20 mg, 0.14 mmol), and dioxane/H₂O (2 mL/0.2 mL). The resulting solution was degassed for 10 min with N₂, sealed, and stirred at 90° C. for 2 h in an oil bath. The reaction mixture was cooled to rt and concentrated under vacuum. The residue was purified by a prep-TLC with ethyl acetate/petroleum ether (1:3), resulting in 25 mg (57%) of the title compound. LCMS (M+H)+: 587.0.

Step 2-3, preparation of N-(2-aminoethyl)-4-[(2R)-4-[2-chloro-4-(trifluoromethyl)benzoyl]-2-ethylpiperazin-1-yl]-2'-cyclopropoxy-[1,1'-biphenyl]-3-carboxamide: to a 8-mL pressure tube vessel, was placed methyl 4-[(2R)-4-[2-chloro-4-(trifluoromethyl)benzoyl]-2-ethylpiperazin-1-yl]-2'-cyclopropoxy-[1,1'-biphenyl]-3-carboxylate (25 mg, 0.04 mmol), ethane-1,2-diamine (2 mL), and IPA (2 mL). The resulting solution was sealed and stirred at 70° C. for 16 h. The resulting mixture was cooled to rt and concentrated under vacuum. The residue was purified by Prep-HPLC with the following conditions: SunFire Prep C18 OBD column; mobile phase, phase A: water (0.05% TFA); phase B: ACN (21% up to 38% in 6 min); flow rate: 20 mL/min; detector, 220 & 254 nm, yielding 10.7 mg (34%) of the title compound. LCMS (M+H)+: 615.2.

The following compounds were prepared similarly to Example 2 with appropriate substituting reagents and substrates at different steps:

| Compound no. | MS (M + H)+ |
|---|---|
| 1-32 | 604.2 |
| 1-33 | 604.2 |
| 1-35 | 604.2 |

Example 3: 6-[(2R)-4-[4-chloro-2-(trifluoromethyl)benzoyl]-2-ethylpiperazin-1-yl]-3-(2-ethoxypyridin-3-yl)-2-fluoro-N-[2-(methylamino)ethyl]benzamide (Compound 1-95)

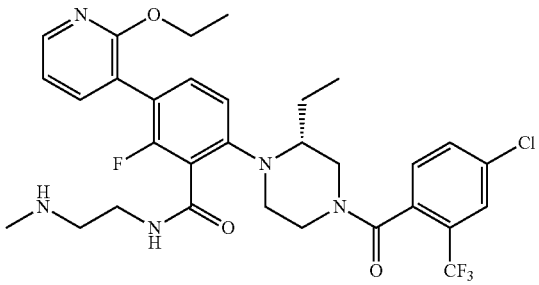 [SMILES: CCOc1ncccc1-c1ccc(N2CCN(C(=O)c3ccc(Cl)cc3C(F)(F)F)C[C@H]2CC)c(C(=O)NCCNC)c1F]

Step 3-1, preparation of tert-butyl (3R)-3-ethyl-4-[3-fluoro-2-(methoxycarbonyl)-4-nitrophenyl]piperazine-1-carboxylate: to a solution of tert-butyl-(3R)-3-ethylpiperazine-1-carboxylate (555 mg, 2.59 mmol) and methyl 2,6-difluoro-3-nitrobenzoate (843 mg, 3.89 mmol) in DMSO (2 mL) was added DIEA (0.90 mL, 5.2 mmol). The mixture was heated at 130° C. for 1 h. The mixture was purified by C18 reversed phase column chromatography to give the title compound (813 mg, 76% yield) as a brownish yellow gum. LCMS (M+H)+: 412.3.

Step 3-2, preparation of tert-butyl (3R)-4-[4-amino-3-fluoro-2-(methoxycarbonyl)phenyl]-3-ethylpiperazine-1-carboxylate: to a solution of tert-butyl (3R)-3-ethyl-4-[3-fluoro-2-(methoxycarbonyl)-4-nitrophenyl]piperazine-1-carboxylate (813 mg, 1.98 mmol) in MeOH (30 mL) was added 10% Pd/C (213 mg, 0.0941 mmol) and NH₄C₁ (1.188 g, 18.83 mmol). The mixture was heated at 80° C. for 20 min. The mixture was filtered through Celite and the filtrate was concentrated and purified by C18 reversed phase column chromatography to give the title compound (612 mg, 81% yield) as a reddish brown gum. LCMS (M+H)$^+$: 382.3.

Step 3-3, preparation of tert-butyl (3R)-4-[4-bromo-3-fluoro-2-(methoxycarbonyl)phenyl]-3-ethylpiperazine-1-carboxylate: to a solution of tert-butyl (3R)-4-[4-amino-3-fluoro-2-(methoxycarbonyl)phenyl]-3-ethylpiperazine-1-carboxylate (612 mg, 1.60 mmol) in MeCN (10 mL) under nitrogen was added CuBr$_2$ (197 mg, 0.882 mmol) and 90% tert-butyl nitrite (0.24 mL, 1.8 mmol). The mixture was heated at 70° C. for 30 min. The mixture was quenched with ice water and extracted with DCM (3×). The combined organic layers were washed with saturated NaHCO$_3$ (aq), concentrated, and purified by C18 reversed phase column chromatography to give the title compound (267 mg, 0.600 mmol, 38% yield) as a brown gum. LCMS (M+H)$^+$: 445.2.

Step 3-4, preparation of tert-butyl (3R)-4-[4-(2-ethoxypyridin-3-yl)-3-fluoro-2-(methoxycarbonyl)phenyl]-3-ethylpiperazine-1-carboxylate: to a mixture of tert-butyl (3R)-4-[4-bromo-3-fluoro-2-(methoxycarbonyl)phenyl]-3-ethylpiperazine-1-carboxylate (267 mg, 0.600 mmol), (2-ethoxypyridin-3-yl)boronic acid (150 mg, 0.900 mmol), Pd[t-Bu$_2$P(4-NMe$_2$C$_6$H$_4$)]$_2$Cl$_2$) (42.5 mg, 0.0600 mmol), and K$_2$CO$_3$ (249 mg, 1.80 mmol) in a sealed tube was added dioxane (4 mL) and H$_2$O (0.4 mL). The resulting solution was degassed with N2 (g) for 10 min, sealed, and stirred at 100° C. for 30 min. The reaction was treated with additional (2-ethoxypyridin-3-yl)boronic acid (37.8 mg, 0.226 mmol), Pd[t-Bu$_2$P(4-NMe$_2$C$_6$H$_4$)]$_2$Cl$_2$) (13.4 mg, 0.0189 mmol), and K$_2$CO$_3$ (78.3 mg, 0.567 mmol) and stirred at 100° C. for additional 30 min. The mixture was concentrated and purified by C18 reversed phase column chromatography to give the title compound (255 mg, 87% yield) as a brown gum. LCMS (M+H)$^+$: 488.4.

Step 3-5, preparation of 6-[(2R)-4-[(tert-butoxy)carbonyl]-2-ethylpiperazin-1-yl]-3-(2-ethoxypyridin-3-yl)-2-fluorobenzoic acid: to a solution of tert-butyl (3R)-4-[4-(2-ethoxypyridin-3-yl)-3-fluoro-2-(methoxycarbonyl)phenyl]-3-ethylpiperazine-1-carboxylate (255 mg, 0.523 mmol) in THF/MeOH/H$_2$O (4.5/1.5/1.5 mL) was added LiOH.H$_2$O (220 mg, 5.24 mmol). The mixture was heated at 60° C. overnight. About 50% of the reaction was completed. After addition of additional LiOH.H$_2$O (220 mg, 5.24 mmol), the mixture was continued to heat at 70° C. for 2 days. After removal of volatile solvent, the aqueous residue was diluted with ice water and acidified with 1N HCl (aq) to pH 4. The solid was collected by vacuum filtration and dried to give the title compound (239 mg, 97% yield) as a brown solid. LCMS (M+H)$^+$: 474.2.

Step 3-6, preparation of 3-(2-ethoxypyridin-3-yl)-6-[(2R)-2-ethylpiperazin-1-yl]-2-fluorobenzoic acid dihydrochloride: to a solution of 6-[(2R)-4-[(tert-butoxy)carbonyl]-2-ethylpiperazin-1-yl]-3-(2-ethoxypyridin-3-yl)-2-fluorobenzoic acid (100 mg, 0.211 mmol) in DCM (0.3 mL) was added 4N HCl in dioxane (0.30 mL, 1.2 mmol). The mixture was stirred at rt for 1 hr. The solution was decanted and the residue was rinsed with DCM (3×) and dried under vacuum to give the title compound as a medium brown solid. LCMS (M+H)$^+$: 374.3.

Step 3-7, preparation of 6-[(2R)-4-[4-chloro-2-(trifluoromethyl)benzoyl]-2-ethylpiperazin-1-yl]-3-(2-ethoxypyridin-3-yl)-2-fluorobenzoic acid: to a solution of 4-chloro-2-(trifluoromethyl)benzoic acid (94.9 mg, 0.423 mmol) and HATU (145 mg, 0.381 mmol) in DMF (0.5 mL) was added DIEA (0.073 mL, 0.42 mmol). After stirring at rt for 5 min, the resulting solution was added to a solution of 3-(2-ethoxypyridin-3-yl)-6-[(2R)-2-ethylpiperazin-1-yl]-2-fluorobenzoic acid dihydrochloride (0.211 mmol) and DIEA (0.11 mL, 0.42 mmol) in DMF (0.2 mL). The mixture was stirred at RT for 10 min. The reaction was directly purified by C18 reversed phase column chromatography to give the title compound (69.8 mg, 57% yield) as a white solid. LCMS (M+H)$^+$: 580.3.

Step 3-8, preparation of tert-butyl N-[2-({6-[(2R)-4-[4-chloro-2-(trifluoromethyl)benzoyl]-2-ethylpiperazin-1-yl]-3-(2-ethoxypyridin-3-yl)-2-fluorophenyl}formamido)ethyl]-N-methylcarbamate: to a solution of 6-[(2R)-4-[4-chloro-2-(trifluoromethyl)benzoyl]-2-ethylpiperazin-1-yl]-3-(2-ethoxypyridin-3-yl)-2-fluorobenzoic acid (35.0 mg, 0.06 mmol) and HATU (34.4 mg, 0.091 mmol) in DMF (0.2 mL) was added DIEA (0.021 mL, 0.12 mmol). After stirring at rt for 5 min, the reaction was treated with tert-butyl N-(2-aminoethyl)-N-methylcarbamate (21.0 mg, 0.121 mmol) and stirred at rt for 5 min. The mixture was purified by C18 reversed phase column chromatography to give the title compound (35.6 mg, 80% yield) as an off-white solid. LCMS (M+H)$^+$: 736.4.

Step 3-9, preparation of 6-[(2R)-4-[4-chloro-2-(trifluoromethyl)benzoyl]-2-ethylpiperazin-1-yl]-3-(2-ethoxypyridin-3-yl)-2-fluoro-N-[2-(methylamino)ethyl]benzamide: To a solution of tert-butyl N-[2-({6-[(2R)-4-[4-chloro-2-(trifluoromethyl)benzoyl]-2-ethylpiperazin-1-yl]-3-(2-ethoxypyridin-3-yl)-2-fluorophenyl}formamido)ethyl]-N-methylcarbamate (35.6 mg, 0.0484 mmol) in DCM (0.1 mL) was added 4N HCl in dioxane (0.10 mL, 0.40 mmol). The mixture was stirred at rt for 10 min. The solution was decanted and the residue was rinsed with DCM (3×) and dried under vacuum. The HCl salt of product was triturated with saturated NaHCO$_3$ (aq) and dried to give the title compound (24.6 mg, 80% yield) as an off-white solid. LCMS (M+H)$^+$: 636.3.

The following compounds were prepared similarly to Example 3 with appropriate substituting reagents and substrates at different steps. Some examples may require additional functional group transformations to introduce an appropriate substituent on aryl rings. In some examples, the final deprotecting step may not be required:

| Compound no. | MS (M + H)$^+$ |
|---|---|
| 1-15 | 569.2 |
| 1-19 | 617.2 |
| 1-20 | 616.2 |
| 1-21 | 630.2 |
| 1-25 | 603.3 |
| 1-45 | 630.4 |
| 1-46 | 618.3 |
| 1-48 | 644.5 |
| 1-49 | 658.5 |
| 1-69 | 622.3 |
| 1-92 | 630.5 |
| 1-97 | 630.5 |
| 1-98 | 644.5 |
| 1-99 | 644.5 |
| 1-100 | 644.4 |
| 1-102 | 630.6 |
| 1-108 | 644.4 |
| 1-109 | 660.2 |
| 1-112 | 648.3 |
| 1-123 | 648.4 |
| 1-124 | 662.5 |
| 1-138 | 660.3 |
| 1-198 | 634.3 |
| 1-199 | 662.3 |

-continued

| Compound no. | MS (M + H)+ |
|---|---|
| 1-200 | 648.4 |
| 1-201 | 662.3 |
| 1-202 | 630.4 |
| 1-203 | 644.5 |
| 1-204 | 648.5 |
| 3-5 | 604.2 |
| 3-6 | 590.3 |
| 1-216 | 630.5 |
| 1-217 | 659.2 |

Example 4: 6-[(2R)-4-[4-chloro-2-(trifluoromethyl)benzoyl]-2-ethylpiperazin-1-yl]-N-[2-(dimethylamino)ethyl]-3-(2-ethoxypyridin-3-yl)-2-fluorobenzamide (Compound 1-173)

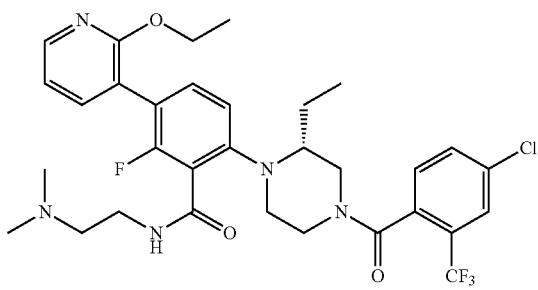 [SMILES: CCOc1ncccc1-c1ccc(N2CCN(C(=O)c3ccc(Cl)cc3C(F)(F)F)C[C@H]2CC)c(C(=O)NCCN(C)C)c1F]

Step 4-1, preparation of tert-butyl (3R)-4-(2-{[2-(dimethylamino)ethyl]carbamoyl}-4-(2-ethoxypyridin-3-yl)-3-fluorophenyl)-3-ethylpiperazine-1-carboxylate: to a solution of 6-[(2R)-4-[(tert-butoxy)carbonyl]-2-ethylpiperazin-1-yl]-3-(2-ethoxypyridin-3-yl)-2-fluorobenzoic acid from Example 3, step 3-5 (1.000 g, 2.111 mmol) and HATU (963 mg, 2.53 mmol) in DMF (1 mL) was added DIEA (0.92 mL, 5.3 mmol). After stirring at RT for 5 min, the resulting solution was treated with (2-aminoethyl)dimethylamine (0.35 mL, 3.1 mmol) and stirred at rt for 10 min. The reaction was purified by C18 reversed phase column chromatography to give the title compound (973.7 mg, 85% yield) as a light yellow solid. LCMS (M+H)+: 544.4.

Step 4-2, preparation of N-[2-(dimethylamino)ethyl]-3-(2-ethoxypyridin-3-yl)-6-[(2R)-2-ethylpiperazin-1-yl]-2-fluorobenzamide trihydrochloride: to a solution of tert-butyl (3R)-4-(2-{[2-(dimethylamino)ethyl]carbamoyl}-4-(2-ethoxypyridin-3-yl)-3-fluorophenyl)-3-ethylpiperazine-1-carboxylate (973.7 mg, 1.791 mmol) in DCM (2 mL) was added 4N HCl in dioxane (2.3 mL, 9.2 mmol). The mixture was stirred at rt for 2 hrs. The reaction was treated with additional 4N HCl in dioxane (2.0 mL, 8.0 mmol) and continued to stir for 2 hrs. The solution was decanted and the residue was rinsed with DCM (3×) and dried under vacuum to give the title compound as a light yellow solid. LCMS (M+H)+: 444.3.

Step 4-3, preparation of 6-[(2R)-4-[4-chloro-2-(trifluoromethyl)benzoyl]-2-ethylpiperazin-1-yl]-N-[2-(dimethylamino)ethyl]-3-(2-ethoxypyridin-3-yl)-2-fluorobenzamide: to a solution of 4-chloro-2-(trifluoromethyl)benzoic acid (40.6 mg, 0.181 mmol) and HATU (61.9 mg, 0.163 mmol) in DMF (0.2 mL) was added DIEA (0.047 mL, 0.27 mmol). After stirring at rt for 5 min, the resulting solution was added to a solution of N-[2-(dimethylamino)ethyl]-3-(2-ethoxypyridin-3-yl)-6-[(2R)-2-ethylpiperazin-1-yl]-2-fluorobenzamide trihydrochloride (40.0 mg, 0.0723 mmol) and DIEA (0.110 mL, 0.631 mmol) in DMF (0.2 mL). After stirring at rt for 10 min, the reaction was purified by C18 reversed phase column chromatography to give the title compound (35.3 mg, 75% yield) as an off-white solid. LCMS (M+H)+: 650.3.

The following compounds were prepared similarly to Example 4 with appropriate substituting reagents and substrates at different steps. Some examples may require additional functional group transformations to introduce an appropriate substituent on aryl rings. In some examples, an additional deprotection is required in the final step:

| Compound no. | MS (M + H)+ |
|---|---|
| 1-37 | 604.4 |
| 1-38 | 554.2 |
| 1-39 | 597.3 |
| 1-42 | 570.2 |
| 1-43 | 550.2 |
| 1-47 | 632.4 |
| 1-53 | 571.2 |
| 1-54 | 566.3 |
| 1-55 | 561.2 |
| 1-58 | 588.3 |
| 1-59 | 584.0 |
| 1-60 | 530.3 |
| 1-61 | 605.3 |
| 1-62 | 570.4 |
| 1-63 | 542.4 |
| 1-71 | 590.3 |
| 1-72 | 648.3 |
| 1-73 | 598.2 |
| 1-74 | 603.4 |
| 1-76 | 614.4 |
| 1-77 | 531.5 |
| 1-78 | 534.3 |
| 1-79 | 550.3 |
| 1-80 | 546.3 |
| 1-81 | 558.4 |
| 1-82 | 580.3 |
| 1-86 | 531.4 |
| 1-87 | 550.3 |
| 1-88 | 556.4 |
| 1-89 | 555.5 |
| 1-91 | 605.4 |
| 1-96 | 586.2 |
| 1-105 | 656.4 |
| 1-106 | 614.4 |
| 1-107 | 613.4 |
| 1-110 | 594.3 |
| 1-111 | 632.3 |
| 1-113 | 582.2 |
| 1-114 | 620.4 |
| 1-117 | 561.3 |
| 1-118 | 589.4 |
| 1-119 | 600.2 |
| 1-120 | 640.4 |
| 1-121 | 602.5 |
| 1-122 | 614.4 |
| 1-126 | 586.3 |
| 1-127 | 614.3 |
| 1-129 | 614.3 |
| 1-130 | 613.3 |
| 1-131 | 614.3 |
| 1-133 | 597.4 |
| 1-134 | 631.5 |
| 1-142 | 587.3 |
| 1-143 | 626.5 |
| 1-144 | 621.5 |
| 1-145 | 586.3 |
| 1-146 | 614.3 |
| 1-147 | 591.4 |
| 1-153 | 593.2 |
| 1-154 | 627.2 |

-continued

| Compound no. | MS (M + H)+ |
|---|---|
| 1-155 | 632.4 |
| 1-156 | 602.4 |
| 1-157 | 627.4 |
| 1-159 | 601.3 |
| 1-160 | 560.4 |
| 1-161 | 603.3 |
| 1-162 | 617.4 |
| 1-163 | 632.3 |
| 1-164 | 633.3 |
| 1-165 | 647.3 |
| 1-166 | 633.3 |
| 1-168 | 646.4 |
| 1-174 | 634.4 |
| 1-175 | 641.4 |
| 1-179 | 616.3 |
| 1-186 | 607.1 |
| 1-191 | 605.3 |
| 1-192 | 585.2 |
| 1-193 | 571.2 |
| 1-228 | 644.5 |
| 1-229 | 662.2 |
| 1-270 | 659.4 |
| 1-271 | 645.5 |

Example 5: 6-[(2R)-4-[4-chloro-2-(difluoromethyl)benzoyl]-2-ethylpiperazin-1-yl]-N-[2-(dimethylamino)ethyl]-3-(2-ethoxypyridin-3-yl)-2-fluorobenzamide (Compound 1-184)

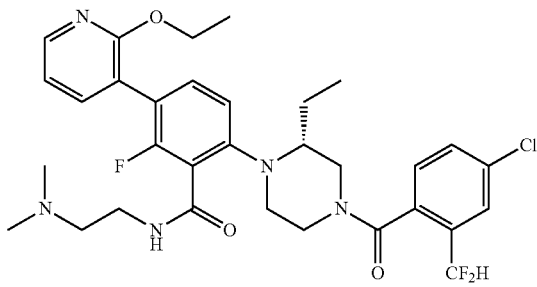 [SMILES: CCOc1ncccc1-c1ccc(N2CCN(C(=O)c3ccc(Cl)cc3C(F)F)C[C@H]2CC)c(C(=O)NCCN(C)C)c1F]

Step 5-1, preparation of 4-chloro-2-(difluoromethyl)benzoic acid: to a mixture of 4-chloro-2-methylbenzoic acid (0.460 g, 2.70 mmol), Selectfluor (2.697 g, 7.612 mmol) and $Na_2S_2O_8$ (0.365 g, 1.53 mmol) in a sealed tube was added MeCN (2 mL) and water (2 mL). N2 (g) was bubbled and then the mixture was cooled to −78° C. under nitrogen and $AgNO_3$ (51.8 mg, 0.305 mmmol) was added. After addition, the mixture was warmed to rt under nitrogen and then heated at 80° C. for 3 hrs, filtered through Celite and rinsed with EtOAc. The filtrate was washed with saturated $NaHCO_3$ (aq) (3×25 mL). The combined basic aqueous solution was acidified with 1N HCl (aq) to pH 2-3 and extracted with EtOAc (2×). The combined organic layers were concentrated and purified by C18 reversed phase column chromatography to give the title compound (128.8 mg, 23% yield) as an off-white solid.

Step 5-2, preparation of 6-[(2R)-4-[4-chloro-2-(difluoromethyl)benzoyl]-2-ethylpiperazin-1-yl]-N-[2-(dimethylamino)ethyl]-3-(2-ethoxypyridin-3-yl)-2-fluorobenzamide: to a solution of 4-chloro-2-(difluoromethyl)benzoic acid (37.3 mg, 0.181 mmol) and HATU (61.9 mg, 0.163 mmol) in DMF (0.2 mL) was added DIEA (0.047 mL, 0.27 mmol). After stirring at rt for 5 min, the resulting solution was added to a solution of N-[2-(dimethylamino)ethyl]-3-(2-ethoxypyridin-3-yl)-6-[(2R)-2-ethylpiperazin-1-yl]-2-fluorobenzamide trihydrochloride from Example 4, step 4-2 (43.0 mg, 0.0778 mmol) and DIEA (0.110 mL, 0.631 mmol) in DMF (0.2 mL). The mixture was stirred at rt for 10 min. The mixture was purified by C18 reversed phase column chromatography to give the title compound (20.6 mg, 0.0326 mmol, 41.9% yield) as an off-white solid. LCMS (M+H)+: 632.3.

The following compounds were prepared similarly to Example 5 with appropriate substituting reagents and substrates at different steps. In some examples, an additional deprotection is required in the final step:

| Compound no. | MS (M + H)+ |
|---|---|
| 1-128 | 600.4 |
| 1-176 | 616.5 |
| 1-177 | 602.5 |
| 1-183 | 618.6 |
| 1-189 | 614.4 |
| 1-190 | 630.6 |
| 1-210 | 615.4 |
| 1-213 | 601.4 |

Example 6: 6-[(2R)-4-[4-chloro-2-(trifluoromethyl)benzoyl]-2-ethylpiperazin-1-yl]-N-[(4,5-dihydro-1H-imidazol-2-yl)methyl]-3-(2-ethoxypyridin-3-yl)-2-fluorobenzamide (Compound 1-188)

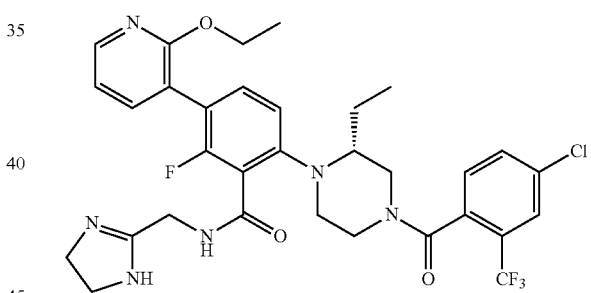

Step 6-1, preparation of 6-[(2R)-4-[4-chloro-2-(trifluoromethyl)benzoyl]-2-ethylpiperazin-1-yl]-N-[(4,5-dihydro-1H-imidazol-2-yl)methyl]-3-(2-ethoxypyridin-3-yl)-2-fluorobenzamide: to a solution of 6-[(2R)-4-[4-chloro-2-(trifluoromethyl)benzoyl]-2-ethylpiperazin-1-yl]-3-(2-ethoxypyridin-3-yl)-2-fluorobenzoic acid from Example 3, step 3-7 (48 mg, 0.082 mmol) in ACN (1 mL) was added HATU (31 mg, 0.082 mmol) and $Et_3N$ (17 µL, 0.12 mmol). After stirring for 5 min at rt, the resulting solution was treated with (4,5-dihydro-1H-imidazol-2-yl)methylamine dihydrochloride (14 mg, 0.081 mmol) which was pre-neutralized with $Et_3N$ (34 µL, 0.24 mmol) in ACN (1 mL). The reaction was stirred at rt for 20 min, diluted with DCM, and washed with $H_2O$ and brine. The organic layer was dried with anhydrous $Na_2SO_4$ and concentrated. The residue was purified from a silica gel column chromatography eluting with DCM/MeOH (100/0 to 85/15) to afford the title compound (21 mg, 39%). LCMS (M+H)+: 661.2.

The following compounds were prepared similarly to Example 6 with appropriate substituting reagents and substrates at different steps:

| Compound no. | MS (M + H)+ |
|---|---|
| 1-64 | 652.4 |
| 1-65 | 652.4 |
| 1-66 | 652.4 |
| 1-70 | 638.2 |
| 1-83 | 641.4 |
| 1-84 | 655.6 |
| 1-93 | 655.1 |
| 1-116 | 673.4 |
| 1-125 | 643.4 |
| 1-132 | 641.3 |
| 1-139 | 656.6 |
| 1-140 | 630.6 |
| 1-141 | 649.5 |
| 1-170 | 657.5 |
| 1-178 | 627.3 |
| 1-182 | 645.4 |
| 1-219 | 675.2 |
| 1-224 | 640.3 |
| 1-226 | 644.5 |
| 1-227 | 658.4 |
| 1-234 | 670.4 |

Example 7: N-(2-aminoethyl)-2-[(2R)-4-{2-[(3S)-3-aminopyrrolidin-1-yl]-4-chlorobenzoyl}-2-ethylpiperazin-1-yl]-5-(2-ethoxypyridin-3-yl)benzamide (Compound 1-57)

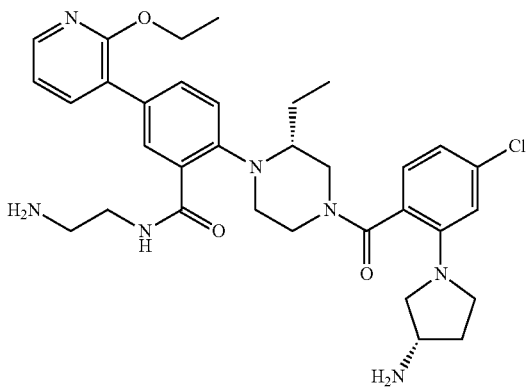 [SMILES: CCOc1ncccc1-c1ccc(N2CCN(C(=O)c3ccc(Cl)cc3N3CC[C@H](N)C3)C[C@H]2CC)c(C(=O)NCCN)c1]

Step 7-1, preparation of 2-[(3S)-3-{[(tert-butoxy)carbonyl]amino}pyrrolidin-1-yl]-4-chlorobenzoic acid: to a 15-mL pressure tube vessel, was placed a solution of 4-chloro-2-fluorobenzoic acid methyl ester (80 mg, 0.42 mmol), pyrrolidin-3-yl-carbamic acid tert-butyl ester (118 mg, 0.63 mmol), and DIEA (0.11 mL, 0.63 mmol) in DMSO (2 mL). The resulting solution was stirred at 140° C. for 2.5 hrs in an oil bath. The reaction progress was monitored by LCMS. The resulting mixture was cooled to rt and purified from C18 reversed phase column chromatography with 0.1% TFA-ACN/0.1% TFA-H₂O to afford 2-[(3S)-3-{[(tert-butoxy)carbonyl]amino}pyrrolidin-1-yl]-4-chlorobenzoic acid methyl ester (150 mg, 100%). LCMS (M+H)+: 355.3. To a 25-mL round-bottom flask, was placed a solution of 2-[(3S)-3-{[(tert-butoxy)carbonyl]amino}pyrrolidin-1-yl]-4-chlorobenzoic acid methyl ester (150 mg, 0.42 mmol) in H₂O/MeOH/THF (0.6/0.6/1.8 mL). The resulting solution was treated with LiOH monohydrate (170 mg, 4.2 mmol) and stirred overnight at 70° C. The reaction was cooled to rt, concentrated, and then diluted with H₂O (~2 mL). The resulting solution was acidified with 1N-HCl, and then extracted with EtOAc (2×). The combined organic layers were washed with brine, dried, and concentrated to afford 2-[(3S)-3-{[(tert-butoxy)carbonyl]amino}pyrrolidin-1-yl]-4-chlorobenzoic acid (110 mg, 82%). LCMS (M+H)+: 341.1.

Step 7-2, preparation of benzyl N-[2-({2-[(2R)-4-{2-[(3S)-3-{[(tert-butoxy)carbonyl]amino}pyrrolidin-1-yl]-4-chlorobenzoyl}-2-ethylpiperazin-1-yl]-5-(2-ethoxypyridin-3-yl)phenyl}formamido)ethyl]carbamate: to a 10-mL round-bottom flask, was placed a solution of 2-[(3S)-3-{[(tert-butoxy)carbonyl]amino}pyrrolidin-1-yl]-4-chlorobenzoic acid (25 mg, 0.073 mmol) in ACN (1.0 mL). The solution was treated with HATU (30 mg, 0.079 mmol) and Et₃N (11 µL, 0.079 mmol). After stirring for 5 min, the resulting solution was treated with benzyl N-(2-{[5-(2-ethoxypyridin-3-yl)-2-[(2R)-2-ethylpiperazin-1-yl]phenyl]formamido}ethyl) carbamate (40 mg, 0.073 mmol) and stirred at rt for 20 min. The resulting mixture was directly purified from C18 reversed phase column chromatography with 0.1% TFA-ACN/0.1% TFA-H₂O to afford benzyl N-[2-({2-[(2R)-4-{2-[(3S)-3-{[(tert-butoxy)carbonyl]amino}pyrrolidin-1-yl]-4-chlorobenzoyl}-2-ethylpiperazin-1-yl]-5-(2-ethoxypyridin-3-yl)phenyl}formamido)ethyl] carbamate (30 mg, 48%). LCMS (M+H)+: 854.5.

Step 7-3, preparation of N-(2-aminoethyl)-2-[(2R)-4-{2-[(3S)-3-aminopyrrolidin-1-yl]-4-chlorobenzoyl}-2-ethylpiperazin-1-yl]-5-(2-ethoxypyridin-3-yl)benzamide: A solution of benzyl N-[2-({2-[(2R)-4-{2-[(3S)-3-{[(tert-butoxy)carbonyl]amino}pyrrolidin-1-yl]-4-chlorobenzoyl}-2-ethylpiperazin-1-yl]-5-(2-ethoxypyridin-3-yl)phenyl}formamido)ethyl]carbamate (28 mg, 0.032 mmol) and catalytic amount of thioanisole (1-2 drops) in TFA (0.5 mL) was stirred at 60° C. for 30 min. The reaction was cooled to rt and concentrated. The residue was purified from C18 reversed phase column chromatography with 0.1% TFA-ACN/0.1% TFA-H₂O to afford N-(2-aminoethyl)-2-[(2R)-4-{2-[(3S)-3-aminopyrrolidin-1-yl]-4-chlorobenzoyl}-2-ethylpiperazin-1-yl]-5-(2-ethoxypyridin-3-yl)benzamide (13 mg, 65%). LCMS (M+H)+: 620.5.

The following compounds were prepared similarly to Example 7 with appropriate substituting reagents and substrates at different steps. Some examples may require additional functional group transformations to introduce an appropriate substituent on aryl rings. In some examples, the acid-catalyzed deprotection is not required in the final step:

| Compound no. | MS (M + H)+ |
|---|---|
| 1-40 | 634.3 |
| 1-41 | 634.2 |
| 1-50 | 668.3 |
| 1-51 | 618.3 |
| 1-52 | 634.3 |
| 1-56 | 618.4 |
| 1-67 | 614.4 |
| 1-68 | 628.6 |
| 1-90 | 646.5 |
| 1-94 | 640.3 |
| 1-101 | 644.6 |
| 1-103 | 644.7 |
| 1-104 | 614.4 |
| 1-115 | 674.4 |
| 1-148 | 618.6 |
| 1-180 | 694.5 |
| 1-197 | 680.4 |

Example 8: N-(2-aminoethyl)-4-[(2R)-4-[4'-(aminomethyl)-5-fluoro-[1,1'-biphenyl]-2-carbonyl]-2-ethylpiperazin-1-yl]-2'-ethoxy-[1,1'-biphenyl]-3-carboxamide (Compound 1-17)

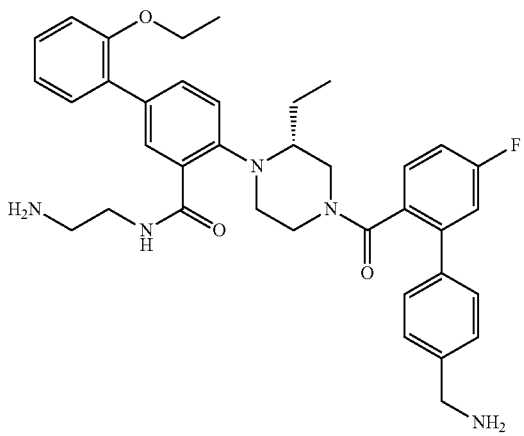 [SMILES: CCOc1ccccc1-c1ccc(N2CCN(C(=O)c3ccc(F)cc3-c3ccc(CN)cc3)C[C@H]2CC)c(C(=O)NCCN)c1]

Step 8-1, preparation of benzyl N-[2-({4-[(2R)-4-(2-bromo-4-fluorobenzoyl)-2-ethylpiperazin-1-yl]-2'-ethoxy-[1,1'-biphenyl]-3-yl}formamido)ethyl]carbamate: to a 10-mL round-bottom flask, was placed a solution of 2-bromo-4-fluorobenzoic acid (40 mg, 0.18 mmol) in ACN (2.0 mL). The solution was treated with HATU (76 mg, 0.2 mmol) and Et$_3$N (36 µL, 0.27 mmol). After stirring for 5 min, the resulting solution was treated with benzyl N-[2-({2'-ethoxy-4-[(2R)-2-ethylpiperazin-1-yl]-[1,1'-biphenyl]-3-yl}formamido)ethyl]carbamate trifluoroacetate (120 mg, 0.18 mmol) and stirred at rt for 20 min. The resulting mixture was directly purified from C18 reversed phase column chromatography eluting with 0.1% TFA-ACN/0.1% TFA-H$_2$O to afford benzyl N-[2-({4-[(2R)-4-(2-bromo-4-fluorobenzoyl)-2-ethylpiperazin-1-yl]-2'-ethoxy-[1,1'-biphenyl]-3-yl}formamido)ethyl]carbamate (54 mg, 41%). LCMS (M+H)$^+$: 731.5.

Step 8-2, preparation of benzyl N-[2-({4-[(2R)-4-[4'-({[(tert-butoxy)carbonyl]amino}methyl)-5-fluoro-[1,1'-biphenyl]-2-carbonyl]-2-ethylpiperazin-1-yl]-2'-ethoxy-[1,1'-biphenyl]-3-yl}formamido)ethyl]carbamate: to a 15-mL pressure tube vessel, was placed benzyl N-[2-({4-[(2R)-4-(2-bromo-4-fluorobenzoyl)-2-ethylpiperazin-1-yl]-2'-ethoxy-[1,1'-biphenyl]-3-yl}formamido)ethyl]carbamate (50 mg, 0.068 mmol), [4-({[(tert-butoxy)carbonyl]amino}methyl) phenyl]boronic acid (35 mg, 0.14 mmol), PdCl$_2$(t-Bu$_2$PPhNMe$_2$)$_2$ (5 mg, 0.007 mmol), K$_2$CO$_3$ (19 mg, 0.14 mmol), and dioxane/H$_2$O (2 mL/0.2 mL). The resulting solution was degassed with N2 for 5 min and then sealed with a cap. The reaction was stirred at 85° C. for 2 hrs in an oil bath. The resulting mixture was cooled to rt, diluted with EtOAc, and washed with 1N-HCl and brine. The organic layer was dried with anhydrous MgSO$_4$ and concentrated. The residue was purified from C18 reversed phase column chromatography eluting with 0.1% TFA-ACN/0.1% TFA-H$_2$O to afford benzyl N-[2-({4-[(2R)-4-[4'-({[(tert-butoxy)carbonyl]amino}methyl)-5-fluoro-[1,1'-biphenyl]-2-carbonyl]-2-ethylpiperazin-1-yl]-2'-ethoxy-[1,1'-biphenyl]-3-yl}formamido)ethyl]carbamate (43 mg, 74%). LCMS (M+H)$^+$: 858.8.

Step 8-3, preparation of N-(2-aminoethyl)-4-[(2R)-4-[4'-(aminomethyl)-5-fluoro-[1,1'-biphenyl]-2-carbonyl]-2-ethylpiperazin-1-yl]-2'-ethoxy-[1,1'-biphenyl]-3-carboxamide: a solution of benzyl N-[2-({4-[(2R)-4-[4'-({[(tert-butoxy)carbonyl]amino}methyl)-5-fluoro-[1,1'-biphenyl]-2-carbonyl]-2-ethylpiperazin-1-yl]-2'-ethoxy-[1,1'-biphenyl]-3-yl}formamido)ethyl]carbamate (43 mg, 0.050 mmol) and catalytic amount of thioanisole (1-2 drops) in TFA (0.5 mL) was stirred at 60° C. for 30 min. The reaction was cooled to rt and concentrated. The residue was purified from C18 reversed phase column chromatography eluting with 0.1% TFA-ACN/0.1% TFA-H$_2$O to afford N-(2-aminoethyl)-4-[(2R)-4-[4'-(aminomethyl)-5-fluoro-[1,1'-biphenyl]-2-carbonyl]-2-ethylpiperazin-1-yl]-2'-ethoxy-[1,1'-biphenyl]-3-carboxamide (22 mg, 71%). LCMS (M+H)$^+$: 624.4.

The following compounds were prepared similarly to Example 8 with appropriate substituting reagents and substrates at different steps. Some examples may require CN reduction to introduce the benzyl amine in the final step:

| Compound no. | MS (M + H)$^+$ |
|---|---|
| 1-18 | 620.5 |
| 1-24 | 606.3 |
| 1-26 | 624.4 |
| 1-27 | 638.5 |
| 1-36 | 625.6 |
| 1-44 | 639.4 |
| 1-75 | 612.3 |
| 1-85 | 612.4 |

Example 9. 5-[(2R)-4-[4-chloro-2-(trifluoromethyl)benzoyl]-2-ethylpiperazin-1-yl]-2'-ethoxy-N-[2-(methylamino)ethyl]-[2,3'-bipyridine]-6-carboxamide (Compound 1-135)

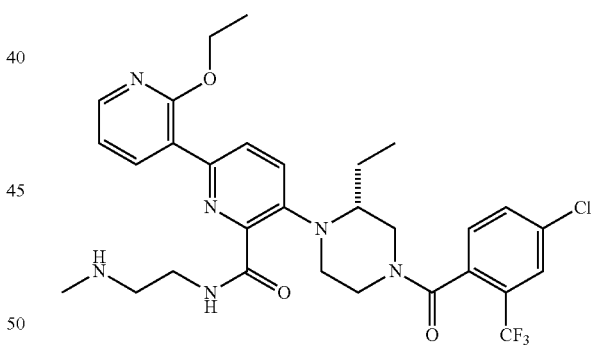

Step 9-1, preparation of 2'-ethoxy-5-fluoro-[2,3'-bipyridine]-6-carbonitrile: to a solution of the mixture of 6-bromo-3-fluoropyridine-2-carbonitrile and 6-chloro-3-fluoropyridine-2-carbonitrile (4:1 ratio, 1.0 equiv, 1.0 mmol, 200 mg) in dioxane (4 mL) was added Pd(Amphos)Cl$_2$ (0.025 equiv, 0.025 mmol, 18 mg), 2-ethoxypyridin-3-ylboronic acid (2.0 equiv, 2.0 mmol, 334 mg), K$_2$CO$_3$ (2.2 equiv, 2.2 mmol, 304 mg) and water (0.4 mL). The resulting solution was purged with nitrogen and heated at 100° C. for 1 h. LCMS showed complete consumption of starting material and formation of desired product. This reaction was repeated on 5.0 mmol scale under similar conditions. These two batches of reaction mixture were combined, diluted with ethyl acetate (50 mL), washed with water and brined, dried with anhydrous Na$_2$SO$_4$, filtered and concentrated. The remaining residue was purified by silica gel chromatography eluting with EtOAc/hexane (0-50%) to afford 1.7 g (>100%) of the desired product containing unidentified impurities. LCMS (M+H)⁺=244.1.

Step 9-2, preparation of tert-butyl (3R)-4-{6-cyano-2'-ethoxy-[2,3'-bipyridin]-5-yl}-3-ethylpiperazine-1-carboxylate: to a solution of 2'-ethoxy-5-fluoro-[2,3'-bipyridine]-6-carbonitrile (1.0 equiv, 6.0 mmol, 1.7 g) in DMSO (10 mL) was added tert-butyl (3R)-3-ethylpiperazine-1-carboxylate (1.5 equiv, 9.0 mmol, 1.9 g) and DIEA (2.0 equiv, 12 mmol, 2.0 mL). The resulting solution was purged with nitrogen and heated at 140° C. for 2 days. LCMS showed the desired product formed but Boc protecting group was partially lost. Thus, the reaction was cooled to rt and followed by addition of DIPEA (2.0 equiv, 12 mmol, 2.0 mL) and di-tert-butyl dicarbonate (2.0 equiv, 12 mmol, 2.75 mmol) and stirred for 1 h. Then reaction solution was diluted with ethyl acetate (50 mL), washed with water and brine, dried with anhydrous Na₂SO₄, filtered and concentrated. The residue was purified by C18 reversed phase column chromatography eluting with MeCN/water (5-100%). Pure fractions were combined, neutralized with saturated NaHCO₃, and extracted with ethyl acetate. The combined organic layers were dried with MgSO₄, concentrated, and dried under high vacuum to give 1.20 g (46%) of the desired product. LCMS (M+H)⁺=438.3.

Step 9-3, preparation of 2'-ethoxy-5-[(2R)-2-ethylpiperazin-1-yl]-[2,3'-bipyridine]-6-carbonitrile trifluoroacetate: to a solution of tert-butyl (3R)-4-{6-cyano-2'-ethoxy-[2,3'-bipyridin]-5-yl}-3-ethylpiperazine-1-carboxylate (1.0 equiv, 0.73 mmol, 320 mg) in DCM (3.0 mL) was added TFA (1.0 mL). The resulting mixture was stirred at ambient temperature for 1 h. The reaction was concentrated under vacuum to afford crude product (560 mg) as TFA salt. This material was used for next step without further purification. LCMS (M+H)⁺=338.4.

Step 9-4, preparation of 5-[(2R)-4-[4-chloro-2-(trifluoromethyl)benzoyl]-2-ethylpiperazin-1-yl]-2'-ethoxy-[2,3'-bipyridine]-6-carbonitrile: to a solution of 2'-ethoxy-5-[(2R)-2-ethylpiperazin-1-yl]-[2,3'-bipyridine]-6-carbonitrile trifluoroacetate (560 mg crude, 0.73 mmol,) in DMF (3.0 mL) was added DIEA (1.06 mL, 4.38 mmol, 6.0 eq.), HATU (570 mg, 1.5 mmol, 2.0 eq.) and 2-trifluoromethyl-4-chlorobenzoic acid (224 mg, 1.0 mmol, 1.35 eq.). The resulting mixture was stirred at rt for 10 min and LCMS showed complete consumption of starting material. The reaction solution was diluted with ethyl acetate (50 mL), washed with water and brine, with anhydrous Na₂SO₄, filtered and concentrated. The residue was purified by silica gel chromatography eluting with EtOAc/hexane (0-50%) to afford 230 mg (58%) of the desired product. LCMS (M+H)⁺=544.3.

Step 9-5, preparation of 5-[(2R)-4-[4-chloro-2-(trifluoromethyl)benzoyl]-2-ethylpiperazin-1-yl]-2'-ethoxy-[2,3'-bipyridine]-6-carboxylic acid: to a solution of 5-[(2R)-4-[4-chloro-2-(trifluoromethyl)benzoyl]-2-ethylpiperazin-1-yl]-2'-ethoxy-[2,3'-bipyridine]-6-carbonitrile (27 mg, 0.05 mmol,) in EtOH (0.25 mL) was added KOH (85%, 28 mg, 0.50 mmol, 10 eq.) and water (0.25 mL). The resulting mixture was heated at 100° C. for overnight. The reaction mixture was cooled to rt, diluted with ethyl acetate (10 mL), washed with saturated NaHSO₄ (5.0 mL) and brine, dried and concentrated to afford 26 mg of crude title compound. This material was used for next step without further purification. LCMS (M+H)⁺=563.3.

Step 9-6, preparation of tert-butyl N-[2-({5-[(2R)-4-[4-chloro-2-(trifluoromethyl)benzoyl]-2-ethylpiperazin-1-yl]-2'-ethoxy-[2,3'-bipyridin]-6-yl}formamido)ethyl]-N-methylcarbamate: to a solution of 5-[(2R)-4-[4-chloro-2-(trifluoromethyl)benzoyl]-2-ethylpiperazin-1-yl]-2'-ethoxy-[2,3'-bipyridine]-6-carboxylic acid (26 mg, 0.05 mmol) in DMF (0.5 mL) was added DIEA (0.10 mL, 0.55 mmol, 11 eq.), HATU (38 mg, 0.10 mmol, 2.0 eq.) and 1-boc-1-methylethylenediamine (19 mg, 0.10 mmol, 2.0 eq.). The resulting mixture was stirred at ambient temperature for 0.5 h. The crude reaction solution was purified by a C18 reversed phase column chromatography eluting with MeCN/water (5-100%). Pure fractions were combined, neutralized with saturated NaHCO₃ and NaCl, extracted with ethyl acetate and dried with MgSO₄. The organic layer was concentrated and dried under high vacuum to give 15 mg (47%) of the desired product. LCMS (M+H)⁺=719.3.

Step 9-7, preparation of 5-[(2R)-4-[4-chloro-2-(trifluoromethyl)benzoyl]-2-ethylpiperazin-1-yl]-2'-ethoxy-N-[2-(methylamino)ethyl]-[2,3'-bipyridine]-6-carboxamide: to a solution of tert-butyl N-[2-({5-[(2R)-4-[4-chloro-2-(trifluoromethyl)benzoyl]-2-ethylpiperazin-1-yl]-2'-ethoxy-[2,3'-bipyridin]-6-yl}formamido)ethyl]-N-methylcarbamate (15 mg, 0.021 mmol) in DCM (0.5 mL) was added TFA (0.2 mL). The resulting mixture was stirred at ambient temperature for 0.5 h. The reaction was concentrated and purified by a C18 reversed phase column chromatography eluting with MeCN/water (5-60%). Pure fractions were combined, neutralized with saturated NaHCO₃ and NaCl, extracted with ethyl acetate and dried with MgSO₄. The organic layer was concentrated and dried under high vacuum to give 9 mg (70%) of the desired product. LCMS (M+H)⁺=619.4.

The following compounds were prepared similarly to Example 9 with appropriate substituting reagents and substrates at different steps. Some examples may require additional functional group transformations to introduce an appropriate substituent on aryl rings. In some examples, an additional deprotection is not required in the final step.

| Compound no. | MS (M + H)⁺ |
| --- | --- |
| 1-136 | 602.6 |
| 1-137 | 629.6 |
| 1-149 | 632.3 |
| 1-151 | 631.4 |
| 1-167 | 615.4 |
| 1-171 | 576.4 |
| 1-172 | 594.5 |
| 1-181 | 630.6 |
| 1-185 | 600.4 |
| 1-187 | 616.6 |
| 1-194 | 603.4 |
| 1-195 | 595.3 |
| 1-205 | 617.4 |
| 1-206 | 644.4 |
| 1-208 | 618.6 |
| 1-209 | 630.5 |
| 1-211 | 617.5 |
| 1-214 | 631.4 |
| 1-215 | 645.5 |
| 1-218 | 607.3 |
| 1-220 | 616.3 |
| 1-221 | 630.5 |
| 1-222 | 631.3 |
| 1-223 | 645.4 |
| 1-230 | 628.4 |
| 1-231 | 645.3 |
| 1-232 | 645.5 |
| 1-233 | 642.4 |
| 1-236 | 627.4 |
| 1-237 | 641.4 |
| 1-239 | 642.5 |
| 1-240 | 628.5 |
| 1-242 | 642.5 |
| 1-243 | 656.5 |

| Compound no. | MS (M + H)+ |
|---|---|
| 1-244 | 628.4 |
| 1-245 | 642.4 |
| 1-246 | 614.3 |
| 1-247 | 628.4 |
| 1-249 | 656.6 |
| 1-256 | 642.4 |
| 1-257 | 656.6 |
| 1-268 | 646.3 |
| 1-269 | 632.3 |
| 1-272 | 632.1 |
| 1-275 | 649.3 |
| 1-276 | 649.5 |
| 1-289 | 646.4 |
| 1-290 | 660.5 |
| 1-291 | 646.5 |
| 1-296 | 660.3 |
| 1-303 | 581.2 |

Example 10. 5-[(2R)-4-[4-chloro-2-(trifluoromethyl)benzoyl]-2-ethylpiperazin-1-yl]-N-[2-(dimethylamino)ethyl]-2'-ethoxy-[2,3'-bipyridine]-6-carboxamide Acetate (Compound 1-150)

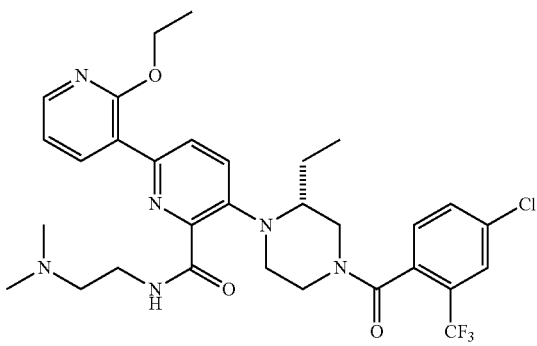 [SMILES: CCOc1ncccc1-c1ccc(N2CCN(C(=O)c3ccc(Cl)cc3C(F)(F)F)C[C@H]2CC)c(C(=O)NCCN(C)C)n1]

Step 10-1, preparation of 5-[(2R)-4-[(tert-butoxy)carbonyl]-2-ethylpiperazin-1-yl]-2'-ethoxy-[2,3'-bipyridine]-6-carboxylic acid: to a solution of tert-butyl (3R)-4-{6-cyano-2'-ethoxy-[2,3'-bipyridin]-5-yl}-3-ethylpiperazine-1-carboxylate from Example 9, step 9-2 (271 mg, 0.62 mmol) in EtOH (3 mL) was added KOH (85%, 409 mg, 6.2 mmol, 10 eq.) and water (3.0 mL). The resulting mixture was heated at 100° C. for overnight. The reaction mixture was cooled to rt, diluted with ethyl acetate (10 mL), washed with saturated NaHSO$_4$ (10 mL) and brine, dried and concentrated to afford 283 mg of crude title compound. This material was used for next step without further purification. LCMS (M+H)+=457.3.

Step 10-2, preparation of tert-butyl (3R)-4-(6-{[2-(dimethylamino)ethyl]carbamoyl}-2'-ethoxy-[2,3'-bipyridin]-5-yl)-3-ethylpiperazine-1-carboxylate: to a solution of 5-[(2R)-4-[(tert-butoxy)carbonyl]-2-ethylpiperazin-1-yl]-2'-ethoxy-[2,3'-bipyridine]-6-carboxylic acid (283 mg, 0.619 mmol) in DMF (5.0 mL) was added HATU (353 mg, 0.93 mmol, 1.5 eq.), DIEA (0.31 mL, 1.86 mmol, 3.0 eq.) and N,N-dimethylethylenediamine (84 mg, 0.93 mmol, 1.5 eq.). The resulting mixture was stirred at 50° C. for 0.5 h. The reaction mixture was diluted with ethyl acetate, washed with water and brine, dried with Na$_2$SO$_4$, filtered and concentrated. The residue was purified by silica gel chromatography eluting with MeOH/DCM (0-15%) to afford 396 mg of the desired product as brown oil. LCMS (M+H)+=527.4.

Step 10-3, preparation of N-[2-(dimethylamino)ethyl]-2'-ethoxy-5-[(2R)-2-ethylpiperazin-1-yl]-[2,3'-bipyridine]-6-carboxamide: to a solution of tert-butyl (3R)-4-(6-{[2-(dimethylamino)ethyl]carbamoyl}-2'-ethoxy-[2,3'-bipyridin]-5-yl)-3-ethylpiperazine-1-carboxylate (396 mg, 0.75 mmol) in DCM (4.0 mL) was added TFA (2.0 mL). The resulting mixture was stirred at ambient temperature for 0.5 h and concentrated under vacuum. The residue was neutralized with saturated NaHCO$_3$, extracted with ethyl acetate, dried with Na$_2$SO$_4$, filtered and concentrated. The residue was purified by silica gel chromatography eluting with MeOH/DCM (0-20%) to afford 201 mg (64%) of the desired product as brown oil. LCMS (M+H)+=427.4.

Step 10-4, preparation of 5-[(2R)-4-[4-chloro-2-(trifluoromethyl)benzoyl]-2-ethylpiperazin-1-yl]-N-[2-(dimethylamino)ethyl]-2'-ethoxy-[2,3'-bipyridine]-6-carboxamide acetate: to a solution of N-[2-(dimethylamino)ethyl]-2'-ethoxy-5-[(2R)-2-ethylpiperazin-1-yl]-[2,3'-bipyridine]-6-carboxamide (89 mg, 0.20 mmol) in DMF (2 mL) was added HATU (91 mg, 0.24 mmol, 1.2 eq.), DIEA (0.092 mL, 0.50 mmol, 2.5 eq) and 2-trifluoromethyl-4-chlorobenzoic acid (45 mg, 0.20 mmol, 1.0 eq.). The resulting mixture was heated at 50° C. for 0.5 h. The reaction mixture was diluted with ethyl acetate, washed with water and brine, dried with Na$_2$SO$_4$, filtered and concentrated. The residue was purified by silica gel chromatography eluting with MeOH/DCM (0-9%). Pure fraction were combined and concentrated with HOAc (0.1 mL) to afford 90 mg (64%) of the desired product. LCMS (M+H)+=633.4.

The following compounds were prepared similarly to Example 10 with appropriate substituting reagents and substrates at different steps. In some examples, an additional deprotection is required in the final step.

| Compound no. | MS (M + H)+ |
|---|---|
| 1-158 | 590.1 |
| 1-169 | 629.5 |
| 1-196 | 609.3 |
| 1-207 | 644.5 |
| 1-225 | 629.3 |
| 1-253 | 641.1 |
| 1-254 | 627.4 |
| 1-258 | 629.4 |
| 1-259 | 611.2 |
| 1-260 | 602.4 |
| 1-266 | 615.2 |
| 1-267 | 597.2 |
| 1-277 | 588.2 |

Example 11: 3-[(2R)-4-[4-chloro-2-(trifluoromethyl)benzoyl]-2-ethylpiperazin-1-yl]-6-(2-ethoxypyridin-3-yl)-N-[2-(methylamino)ethyl]pyrazine-2-carboxamide (Compound 3-8)

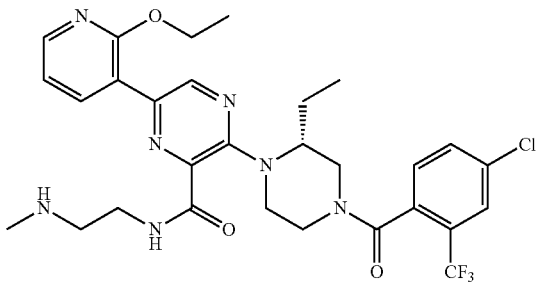

Step 11-1, preparation of methyl 6-bromo-3-[(2R)-4-[(tert-butoxy)carbonyl]-2-ethylpiperazin-1-yl]pyrazine-2-carboxylate: to a 15-mL pressure tube vessel, was placed 6-bromo-3-chloropyrazine-2-carboxylic acid methyl ester (300 mg, 1.19 mmol), tert-butyl (3R)-3-ethylpiperazine-1-carboxylate (370 mg, 1.72 mmol, 1.4 equiv), DIEA (0.3 mL, 1.78 mmol, 1.5 equiv), and DMSO (6 mL). The resulting solution was stirred at 140° C. for 1 h, cooled to rt, and diluted with EtOAc (~15 mL). The organic layer was washed with 1N HCl (2×) and brine (1×), dried with anhydrous Na$_2$SO$_4$, and concentrated. The residue was purified from C18 reversed phase column chromatography eluting with 0.1% TFA-ACN/0.1% TFA-H$_2$O. 140 mg (27%) of methyl 6-bromo-3-[(2R)-4-[(tert-butoxy)carbonyl]-2-ethylpiperazin-1-yl]pyrazine-2-carboxylate was isolated. LCMS (M+H)$^+$: 429.3.

Step 11-2, preparation of methyl 3-[(2R)-4-[(tert-butoxy)carbonyl]-2-ethylpiperazin-1-yl]-6-(2-ethoxypyridin-3-yl)pyrazine-2-carboxylate: to a 15-mL pressure tube vessel, was placed 66-bromo-3-[(2R)-4-[(tert-butoxy)carbonyl]-2-ethylpiperazin-1-yl]pyrazine-2-carboxylate (100 mg, 0.23 mmol), 2-ethoxypyridine-3-boronic acid (78 mg, 0.46 mmol), PdCl$_2$(t-Bu$_2$PPhNMe$_2$)$_2$ (24 mg, 0.033 mmol), K$_2$CO$_3$ (64 mg, 0.46 mmol), and dioxane/H$_2$O (2.5 mL/0.25 mL). The resulting solution was degassed with N2 for 5 min and then sealed with a cap. The reaction was stirred at 100° C. for 1 h in an oil bath. The resulting mixture was cooled to rt, diluted with EtOAc, and washed with 1N-HCl and brine. The organic layer was dried with anhydrous Na$_2$SO$_4$ and concentrated. The residue was purified from C18 reversed phase column chromatography eluting with 0.1% TFA-ACN/0.1% TFA-H$_2$O to afford methyl 3-[(2R)-4-[(tert-butoxy)carbonyl]-2-ethylpiperazin-1-yl]-6-(2-ethoxypyridin-3-yl)pyrazine-2-carboxylate (85 mg, 77%). LCMS (M+H)$^+$: 472.3.

Step 11-3, preparation of 3-[(2R)-4-[(tert-butoxy)carbonyl]-2-ethylpiperazin-1-yl]-6-(2-ethoxypyridin-3-yl)pyrazine-2-carboxylic acid: to a solution of methyl 3-[(2R)-4-[(tert-butoxy)carbonyl]-2-ethylpiperazin-1-yl]-6-(2-ethoxypyridin-3-yl)pyrazine-2-carboxylate (85 mg, 0.18 mmol) in MeOH/H$_2$O/THF (1/1/3 mL) was added lithium hydroxide hydrate (108 mg, 15 eq.). The resulting solution was stirred at rt for 3 hrs. After removal of the volatile sovent, the aqueous residue was diluted with H$_2$O (~3 mL), and then acidified with 1N HCl. The resulting aqueous layer was extracted with DCM (3×). The combined organic layers were washed with brine, dried with with anhydrous Na$_2$SO$_4$, and concentrated under vacuum to afford 3-[(2R)-4-[(tert-butoxy)carbonyl]-2-ethylpiperazin-1-yl]-6-(2-ethoxypyridin-3-yl)pyrazine-2-carboxylic acid (75 mg, 91%). LCMS (M+H)$^+$: 458.3.

Step 11-4, preparation of 6-(2-ethoxypyridin-3-yl)-3-[(2R)-2-ethylpiperazin-1-yl]pyrazine-2-carboxylic acid: a solution of 3-[(2R)-4-[(tert-butoxy)carbonyl]-2-ethylpiperazin-1-yl]-6-(2-ethoxypyridin-3-yl)pyrazine-2-carboxylic acid (75 mg, 0.16 mmol) in TFA (0.2 mL)/DCM (0.6 mL) was stirred at rt for 1.5 h. The resulting mixture was concentrated under vacuum. The residue (~100%) was diluted with ACN (1 mL) and neutralized with Et$_3$N, which was used in the next step without further purification. LCMS (M+H)$^+$: 358.2.

Step 11-5, preparation of 3-[(2R)-4-[4-chloro-2-(trifluoromethyl)benzoyl]-2-ethylpiperazin-1-yl]-6-(2-ethoxypyridin-3-yl)pyrazine-2-carboxylic acid: to a solution of 4-chloro-2-(trifluoromethyl)benzoic acid (45 mg, 0.2 mmol, 1.33 eq.) in ACN (1 mL) was added HATU (75 mg, 0.2 mmol) and followed by Et$_3$N (40 µL, 0.35 mmol). The resulting solution was stirred for 5 min at rt and treated with 6-(2-ethoxypyridin-3-yl)-3-[(2R)-2-ethylpiperazin-1-yl]pyrazine-2-carboxylic acid (~55 mg, 0.15 mmol, 1 eq.) prepared from the previous step. The resulting solution was stirred for 20 min at room temperature and concentrated under vacuum. The residue was purified from C18 reversed phase column chromatography eluting with 0.1% TFA-ACN/0.1% TFA-H$_2$O to afford 3-[(2R)-4-[4-chloro-2-(trifluoromethyl)benzoyl]-2-ethylpiperazin-1-yl]-6-(2-ethoxypyridin-3-yl)pyrazine-2-carboxylic acid (55 mg, 64%). LCMS (M+H)$^+$: 564.5.

Step 11-6, preparation of tert-butyl N-[2-({3-[(2R)-4-[4-chloro-2-(trifluoromethyl)benzoyl]-2-ethylpiperazin-1-yl]-6-(2-ethoxypyridin-3-yl)pyrazin-2-yl}formamido)ethyl]-N-methylcarbamate: to a 10-mL vial, was placed 3-[(2R)-4-[4-chloro-2-(trifluoromethyl)benzoyl]-2-ethylpiperazin-1-yl]-6-(2-ethoxypyridin-3-yl)pyrazine-2-carboxylic acid (30 mg, 0.053 mmol, 1.00 eq.), HATU (21 mg, 0.056 mmol), Et3N (11 µL, 0.08 mmol) and ACN (1 mL). The resulting solution was stirred for 5 min at rt and treated with tert-butyl N-(2-aminoethyl)-N-methylcarbamate (11 mg, 0.063 mmol, 1.2 eq.). The reaction was stirred for 20 min at room temperature and concentrated under vacuum. The residue was purified from C18 reversed phase column chromatography eluting with 0.1% TFA-ACN/0.1% TFA-H$_2$O to afford tert-butyl N-[2-({3-[(2R)-4-[4-chloro-2-(trifluoromethyl)benzoyl]-2-ethylpiperazin-1-yl]-6-(2-ethoxypyridin-3-yl)pyrazin-2-yl}formamido)ethyl]-N-methylcarbamate (18 mg, 47%). LCMS (M+H)$^+$: 720.3.

Step 11-7, preparation of 3-[(2R)-4-[4-chloro-2-(trifluoromethyl)benzoyl]-2-ethylpiperazin-1-yl]-6-(2-ethoxypyridin-3-yl)-N-[2-(methylamino)ethyl]pyrazine-2-carboxamide: a solution of tert-butyl N-[2-({3-[(2R)-4-[4-chloro-2-(trifluoromethyl)benzoyl]-2-ethylpiperazin-1-yl]-6-(2-ethoxypyridin-3-yl)pyrazin-2-yl}formamido)ethyl]-N-methylcarbamate (18 mg, 0.025 mmol) in TFA (0.2 mL)/DCM (0.6 mL) was stirred at rt for 1.5 h. The resulting mixture was concentrated under vacuum. The residue was purified from C18 reversed phase column chromatography eluting with 0.1% TFA-ACN/0.1% TFA-H$_2$O to afford 3-[(2R)-4-[4-chloro-2-(trifluoromethyl)benzoyl]-2-ethylpiperazin-1-yl]-6-(2-ethoxypyridin-3-yl)-N-[2-(methylamino)ethyl]pyrazine-2-carboxamide (10 mg, 67%). LCMS (M+H)$^+$: 620.4.

The following compounds were prepared similarly to Example 11 with appropriate substituting reagents and substrates at different steps. In some examples, an additional deprotection is not required in the final step.

| Compound no. | MS (M + H)+ |
|---|---|
| 3-7 | 634.2 |

Example 12: 1-{5-[(2R)-4-[4-chloro-2-(trifluoromethyl)benzoyl]-2-ethylpiperazin-1-yl]-2'-ethoxy-[2,3'-bipyridin]-6-yl}methanamine (Compound 2-13)

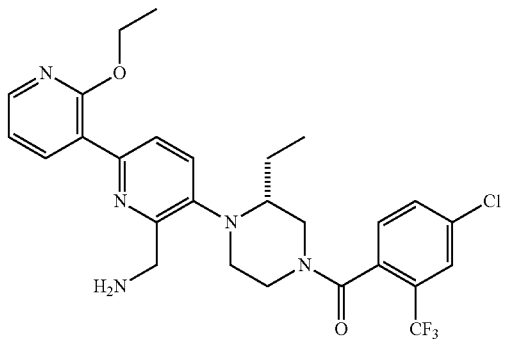 [SMILES: CCOc1ncccc1-c1ccc(N2CCN(C(=O)c3ccc(Cl)cc3C(F)(F)F)C[C@H]2CC)c(CN)n1]

Step 12-1, preparation of 1-{5-[(2R)-4-[4-chloro-2-(trifluoromethyl)benzoyl]-2-ethylpiperazin-1-yl]-2'-ethoxy-[2,3'-bipyridin]-6-yl}methanamine: to a solution of 5-[(2R)-4-[4-chloro-2-(trifluoromethyl)benzoyl]-2-ethylpiperazin-1-yl]-2'-ethoxy-[2,3'-bipyridine]-6-carbonitrile from Example 9, step 9-4 (65 mg, 0.12 mmol) in MeOH (1.0 mL) was added $NiCl_2$ (8.0 mg, 0.06 mmol, 0.5 eq.) and $NaBH_4$ (36 mg, 0.96 mmol, 8.0 eq.) at 0° C. The resulting mixture was stirred at the same temperature for 15 min and LCMS analysis showed about 40% conversion to the desired product. At 0° C., an additional $NiCl_2$ (0.5 equiv, 0.06 mmol, 8.0 mg) and $NaBH_4$ (8.0 equiv, 0.96 mmol, 36 mg) were added and the resulting mixture was stirred for another 15 min. The reaction mixture was diluted with ethyl acetate and washed with saturated $NH_4Cl$. The organic layer was dried and concentrated. The residue was purified by a C18 reversed-phase column chromatography eluting with MeCN/water (5-60%). Pure fractions were combined, neutralized with saturated $NaHCO_3$ and NaCl, extracted with ethyl acetate and dried with $MgSO_4$. The organic layer was concentrated and dried under high vacuum to give 8 mg (12%) of the desired product. LCMS (M+H)+=548.3.

The following compounds were prepared similarly to Example 12 with appropriate substituting reagents and substrates at different steps. Some examples may require additional functional group transformations to introduce an appropriate substituent on aryl rings.

| Compound no. | MS (M + H)+ |
|---|---|
| 2-3 | 532.2 |
| 2-4 | 576.4 |
| 2-5 | 560.2 |
| 2-6 | 562.4 |
| 2-7 | 528.2 |
| 2-8 | 532.2 |
| 2-9 | 547.3 |
| 2-10 | 568.5 |
| 2-11 | 515.3 |
| 2-12 | 547.3 |
| 2-14 | 494.3 |
| 2-15 | 548.2 |
| 2-16 | 562.3 |
| 2-17 | 498.2 |
| 2-18 | 515.3 |
| 2-19 | 500.3 |
| 2-20 | 531.9 |
| 2-22 | 532.1 |
| 2-23 | 546.3 |
| 2-24 | 572.3 |
| 2-25 | 558.1 |
| 2-26 | 544.3 |
| 2-27 | 526.3 |
| 2-28 | 544.3 |
| 2-29 | 544.4 |

Example 13: 2-[({4-[(2R)-4-[2-chloro-4-(trifluoromethyl)benzoyl]-2-ethylpiperazin-1-yl]-2'-ethoxy-[1,1'-biphenyl]-3-yl}methyl)amino]ethan-1-ol (Compound 2-1)

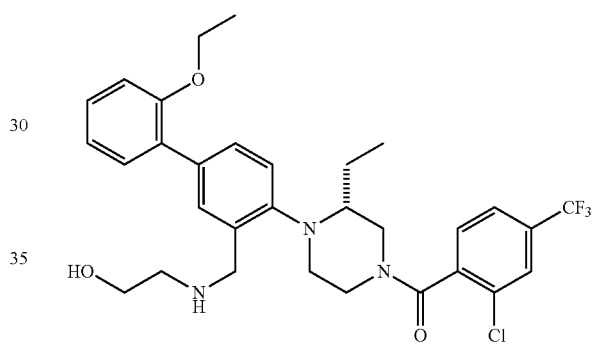

Step 13-1, preparation of tert-butyl (3R)-4-[2'-ethoxy-3-(methoxycarbonyl)-[1,1'-biphenyl]-4-yl]-3-ethylpiperazine-1-carboxylate: into a 8-mL pressure tube vessel, was placed tert-butyl (3R)-4-[4-bromo-2-(methoxycarbonyl)phenyl]-3-ethylpiperazine-1-carboxylate from Example 1, step 1.3 (80 mg, 0.19 mmol), (2-ethoxyphenyl)boronic acid (46.6 mg, 0.28 mmol), $Pd_2(dba)_3CHCl_3$ (19.4 mg, 0.02 mmol), P(t-Bu)$_3$.$HBF_4$ (5.4 mg, 0.02 mmol), $K_3PO_4$ (119.2 mg, 0.56 mmol), and toluene/$H_2O$ (1 mL/0.1 mL). The resulting solution was degassed for 5 min with $N_2$, sealed, and stirred at 70° C. for 2 hrs in an oil bath. The reaction was cooled to rt and concentrated under vacuum. The residue was applied onto a silica gel column eluting with ethyl acetate/petroleum ether (1:1). 80 mg (91%) of the desired product was isolated. LCMS (M+H)+=469.1.

Step 13-2, preparation of tert-butyl (3R)-4-[2'-ethoxy-3-(hydroxymethyl)-[1,1'-biphenyl]-4-yl]-3-ethylpiperazine-1-carboxylate: to a heterogenous solution of tert-butyl (3R)-4-[2'-ethoxy-3-(hydroxymethyl)-[1,1'-biphenyl]-4-yl]-3-ethylpiperazine-1-carboxylate (60 mg, 0.13 mmol) and $NiCl_2$ (16.6 mg, 0.13 mmol) in MeOH (1.0 mL) was added $NaBH_4$ (48.4 mg, 1.28 mmol, 10 eq.) at rt. The resulting mixture was stirred at 50° C. for 1 h. The reaction mixture was cooled to rt, diluted with $H_2O$, and extracted with ethyl acetate (3×). The combined organic layers were dried over anhydrous $Na_2SO_4$ and concentrated to afford 60 mg (~100%) of the desired product. LCMS (M+H)+=441.3.

Step 13-3, preparation of tert-butyl (3R)-4-{2'-ethoxy-3-formyl-[1,1'-biphenyl]-4-yl}-3-ethylpiperazine-1-carboxylate: a solution of tert-butyl (3R)-4-[2'-ethoxy-3-(hydroxymethyl)-[1,1'-biphenyl]-4-yl]-3-ethylpiperazine-1-carboxylate (90 mg, 0.2 mmol) and IBX (171.6 mg, 0.62 mmol) in ACN (2 mL) was stirred at rt for 1 h. After removal of the solids by filtration, the filtrate was concentrated under vacuum to afford the crude desired product (90 mg, ~100%), which was used in the next strp without further purification. LCMS (M+H)$^+$=439.3.

Step 13-4, preparation of tert-butyl (3R)-4-[3-({[2-(benzyloxy)ethyl]amino}methyl)-2'-ethoxy-[1,1'-biphenyl]-4-yl]-3-ethylpiperazine-1-carboxylate: to a solution of tert-butyl (3R)-4-{2'-ethoxy-3-formyl-[1,1'-biphenyl]-4-yl}-3-ethylpiperazine-1-carboxylate (30 mg, 0.07 mmol) and 2-(benzyloxy)ethan-1-amine (21 mg, 0.14 mmol) in DCM (2.0 mL) was added NaBH(OAc)$_3$ (44 mg, 0.21 mmol, 3 eq.). The resulting mixture was stirred at rt for 30 min and diluted with H$_2$O (20 mL). The resulting solution was extracted with EtOAc (3×). The combined organic layers were dried over anhydrous Na$_2$SO$_4$ and concentrated to afford the desired product (25 mg, 64%). LCMS (M+H)$^+$=574.4.

Step 13-5, preparation of [2-(benzyloxy)ethyl]({2'-ethoxy-4-[(2R)-2-ethylpiperazin-1-yl]-[1,1'-biphenyl]-3-yl}methyl)amine trifluoroacetate: to a solution of tert-butyl (3R)-4-[3-({[2-(benzyloxy)ethyl]amino}methyl)-2'-ethoxy-[1,1'-biphenyl]-4-yl]-3-ethylpiperazine-1-carboxylate (25 mg, 0.04 mmol) in DCM (2.0 mL) was added TFA (1 mL). The resulting mixture was stirred at rt for 1 h and concentrated under vacuum. This resulted in the desired product (25 mg, 98%) as TFA salt. LCMS (M+H)$^+$=474.3.

Step 13-6, preparation of [2-(benzyloxy)ethyl]({4-[(2R)-4-[2-chloro-4-(trifluoromethyl)benzoyl]-2-ethylpiperazin-1-yl]-2'-ethoxy-[1,1'-biphenyl]-3-yl}methyl)amine: to a solution of 2-chloro-4-(trifluoromethyl)benzoic acid (2 mg, 0.01 mmol, 0.3 eq.), HATU (5.7 mg, 0.01 mmol. 0.3 eq.) and [2-(benzyloxy)ethyl]({2'-ethoxy-4-[(2R)-2-ethylpiperazin-1-yl]-[1,1'-biphenyl]-3-yl}methyl)amine trifluoroacetate (17.5 mg, 0.03 mmol) in DMF (2 mL) was added DIEA (11.6 mg, 0.09 mmol, 3 eq.). The resulting mixture was stirred at rt for 1 h and diluted with H$_2$O (20 mL). The resulting solution was extracted with EtOAc (3×). The combined organic layers were dried over anhydrous Na$_2$SO$_4$ and concentrated. The residue was purified by a silica gel column chromatography eluting with DCM/MeOH (10/1) to afford the desired product (20 mg, 38%). LCMS (M+H)$^+$=680.2.

Step 13-7, preparation of 2-[({4-[(2R)-4-[2-chloro-4-(trifluoromethyl)benzoyl]-2-ethylpiperazin-1-yl]-2'-ethoxy-[1,1'-biphenyl]-3-yl}methyl)amino]ethan-1-ol trifluoroacetate: A solution of [2-(benzyloxy)ethyl]({4-[(2R)-4-[2-chloro-4-(trifluoromethyl)benzoyl]-2-ethylpiperazin-1-yl]-2'-ethoxy-[1,1'-biphenyl]-3-yl}methyl)amine (20 mg, 0.03 mmol) in TFA (1.0 mL) was stirred at 80° C. for 3 hrs. The resulting mixture was cooled to rt and concentrated under vacuum. The residue was purified by Prep-HPLC with the following conditions: SunFire Prep C18 OBD column; mobile phase, phase A: water (0.05% TFA); phase B: ACN (31% up to 45% in 6 min); flow rate: 20 mL/min; detector, 220 & 254 nm. 3.9 mg (19%) of the desired product was isolated as a TFA salt. LCMS (M+H)$^+$=590.2.

The following compounds were prepared similarly to Example 13 with appropriate substituting reagents and substrates at different steps. In some examples, an additional deprotection is not required in the final step.

| Compound no. | MS (M + H)$^+$ |
|---|---|
| 2-2 | 604.3 |
| 2-21 | 588.4 |

Example 14: N-(3-aminopropyl)-4-{4-[2-cyano-4-(trifluoromethyl)phenyl]piperazin-1-yl}-2'-ethoxy-[1,1'-biphenyl]-3-carboxamide (Compound 3-2)

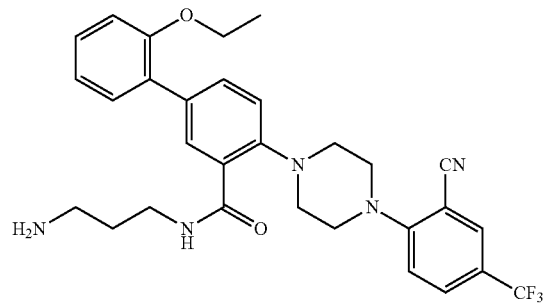 [SMILES: CCOc1ccccc1-c1ccc(N2CCN(c3ccc(C(F)(F)F)cc3C#N)CC2)c(C(=O)NCCCN)c1]

Step 14-1, preparation of tert-butyl 4-[4-bromo-2-(methoxycarbonyl)phenyl]piperazine-1-carboxylate: to a solution of tert-butyl piperazine-1-carboxylate (1.600 g, 8.588 mmol) and methyl 4-bromo-2-fluorobenzoate (1.000 g, 4.292 mmol) in DMSO (5 mL) was added DIEA (2.20 mL, 12.6 mmol). The mixture was heated at 130° C. for 1 day. The mixture was distributed between water and DCM and the organic layer was separated and concentrated. The residue was purified by C18 reversed phase column chromatography to give the title compound (0.5088 g, 30% yield) as a medium brown solid. MS (M+H)$^+$: 399.2. The hydrolyzed acid (0.7537 g, 46% yield) was also isolated as a light brown solid. LCMS (M+H)$^+$=385.3.

Step 14-2, preparation of methyl 5-bromo-2-(piperazin-1-yl)benzoate hydrochloride: to a solution of tert-butyl 4-[4-bromo-2-(methoxycarbonyl)phenyl]piperazine-1-carboxylate (508.8 mg, 1.274 mmol) in DCM (2 mL) was added 4N HCl in dioxane (2.0 mL, 8.0 mmol). The mixture was stirred at rt for 2 hrs. The mixture was concentrated to dryness to give the title compound as a light yellow solid. LCMS (M+H)$^+$=299.2.

Step 14-3, preparation of methyl 5-bromo-2-{4-[2-cyano-4-(trifluoromethyl)phenyl]piperazin-1-yl}benzoate: To a solution of methyl 5-bromo-2-(piperazin-1-yl)benzoate hydrochloride (0.4538 g, 1.352 mmol) and 2-fluoro-5-(trifluoromethyl)benzonitrile (353.0 mg, 1.867 mmol) in DMSO (3 mL) was added DIEA (0.81 mL, 4.7 mmol). The mixture was heated at 130° C. overnight. The mixture was purified by C18 reversed phase column chromatography to give the title compound (453 mg, 72% yield) as a yellow solid. LCMS (M+H)$^+$=468.3.

Step 14-4, preparation of 5-bromo-2-{4-[2-cyano-4-(trifluoromethyl)phenyl]piperazin-1-yl}benzoic acid: To a solution of methyl 5-bromo-2-{4-[2-cyano-4-(trifluoromethyl)phenyl]piperazin-1-yl}benzoate (453 mg, 0.967 mmol) in a mixed solvent of THF:MeOH:H$_2$O (6:2:2 mL) was added LiOH.H$_2$O (406 mg, 9.67 mmol). The mixture was stirred at rt for 4 hrs. After removal of volatile solvent, the aqueous residue was diluted with water and acidified with 1N HCl (aq) to pH 2-3. The solid was collected by vacuum filtration and washed with water and dried to give title compound (421 mg, 96% yield) as a yellow solid. LCMS (M+H)$^+$=454.1.

Step 14-5, preparation of tert-butyl N-{3-[(5-bromo-2-{4-[2-cyano-4-(trifluoromethyl)phenyl]piperazin-1-yl}phenyl)formamido]propyl}carbamate: To a solution of 5-bromo-2-{4-[2-cyano-4-(trifluoromethyl)phenyl]piperazin-1-yl}benzoic acid (201.9 mg, 0.4444 mmol) and HATU (220 mg, 0.579 mmol) in DMF (1 mL) was added DIEA (0.15 mL, 0.86 mmol). After stirring at RT for 5 min, the resulting solution was treated with tert-butyl N-(3-aminopropyl)carbamate (126.5 mg, 0.7262 mmol) and stirred at rt for 5 min. The reaction was purified by C18 reversed phase column chromatography to give the title compound (198.7 mg, 73% yield) as an off-white solid. LCMS (M+H)$^+$=610.3.

Step 14-6, preparation of tert-butyl N-{3-[(4-{4-[2-cyano-4-(trifluoromethyl)phenyl]piperazin-1-yl}-2'-ethoxy-[1,1'-biphenyl]-3-yl)formamido]propyl}carbamate: To a mixture of tert-butyl N-{3-[(5-bromo-2-{4-[2-cyano-4-(trifluoromethyl)phenyl]piperazin-1-yl}phenyl)formamido]propyl}carbamate (20.0 mg, 0.0328 mmol), 2-ethoxyphenylboronic acid (10.9 mg, 0.0657 mmol), Pd[t-Bu$_2$P(4-NMe$_2$C$_6$H$_4$)]$_2$Cl$_2$) (9.2 mg, 0.013 mmol), and K$_2$CO$_3$ (27.2 mg, 0.197 mmol) in a sealed tube was added dioxane (2 mL) and H$_2$O (0.2 mL). The resulting mixture was degassed with N2 for 10 min and stirred at 100° C. for 30 min. The mixture was concentrated and purified by C18 reversed phase column chromatography to give the title compound (18.5 mg, 87% yield) as a white solid. LCMS (M+H)$^+$=652.5.

Step 14-7, preparation of N-(3-aminopropyl)-4-{4-[2-cyano-4-(trifluoromethyl)phenyl]piperazin-1-yl}-2'-ethoxy-[1,1'-biphenyl]-3-carboxamide: to a solution of tert-butyl N-{3-[(4-{4-[2-cyano-4-(trifluoromethyl)phenyl]piperazin-1-yl}-2'-ethoxy-[1,1'-biphenyl]-3-yl)formamido]propyl}carbamate (18.5 mg, 0.0284 mmol) in DCM (0.1 mL) was added 4N HCl in dioxane (0.1 mL, 0.4 mmol). The mixture was stirred at rt for 30 min. The mixture was concentrated to dryness to give 1HCl salt of the title compound which was triturated with saturated NaHCO$_3$ (aq) to give the title compound (12.9 mg, 82% yield) as an off-white solid. LCMS (M+H)$^+$=552.2.

The following compounds were prepared similarly to Example 14 with appropriate substituting reagents and substrates at different steps:

| Compound no. | MS (M + H)$^+$ |
| --- | --- |
| 3-1 | 544.3 |

Example 15: 6-[(2R)-4-(2,4-dichlorobenzenesulfonyl)-2-ethylpiperazin-1-yl]-3-(2-ethoxypyridin-3-yl)-2-fluoro-N-[2-(methylamino)ethyl]benzamide (Compound 3-3)

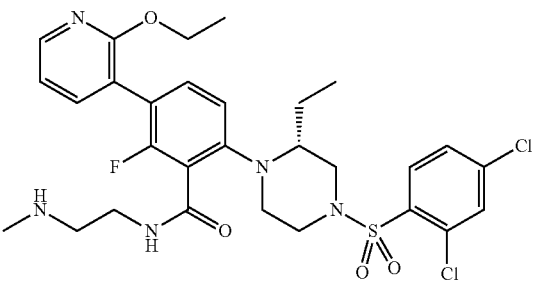 [SMILES: CCOc1ncccc1-c1ccc(N2CCN(S(=O)(=O)c3ccc(Cl)cc3Cl)C[C@H]2CC)c(C(=O)NCCNC)c1F]

Step 15-1, preparation of benzyl N-[2-([6-[(2R)-4-(2,4-dichlorobenzenesulfonyl)-2-ethylpiperazin-1-yl]-3-(2-ethoxypyridin-3-yl)-2-fluorophenyl]formamido)ethyl]-N-methylcarbamate: into a 8-mL vial, was placed benzyl N-(2-[[3-(2-ethoxypyridin-3-yl)-6-[(2R)-2-ethylpiperazin-1-yl]-2-fluorophenyl]formamido]ethyl)-N-methylcarbamate trifluoroacetate (30 mg, 0.027 mmol), which was prepared by a similar manner described in Example 4, step 1 & 2, TEA (8 mg, 0.079 mmol, 2.98 eq.), 2,4-dichlorobenzene-1-sulfonyl chloride (8 mg, 0.033 mmol, 1.23 eq.), and DCM (2 mL). The resulting solution was stirred for 2 hr at 25° C. The reaction was diluted with DCM (10 mL) and washed with H$_2$O (2×20 mL). The organic layer was dried over anhydrous sodium sulfate and concentrated under vacuum. This resulted in 20 mg (crude) of the title compound as off-white oil. LCMS (M+H)$^+$=772.2.

Step 15-2, preparation of 6-[(2R)-4-(2,4-dichlorobenzenesulfonyl)-2-ethylpiperazin-1-yl]-3-(2-ethoxypyridin-3-yl)-2-fluoro-N-[2-(methylamino)ethyl]benzamide: Into a 8-mL vial, was placed benzyl N-[2-([6-[(2R)-4-(2,4-dichlorobenzenesulfonyl)-2-ethylpiperazin-1-yl]-3-(2-ethoxypyridin-3-yl)-2-fluorophenyl]formamido)ethyl]-N-methylcarbamate (20 mg, 0.021 mmol) and trifluoroacetic acid (2 mL). The resulting solution was stirred for 3 hrs at 60° C., cooled to rt, and concentrated under vacuum. The residue was dissolved in DMF (4 mL) and purified by reverse phase HPLC resulting in 7.9 mg (56%) of the title compound as a formic acid salt. LCMS (M+H)$^+$=638.2

Example 16: (3R)—N-(2,4-dichlorophenyl)-4-[4-(2-ethoxypyridin-3-yl)-3-fluoro-2-{[2-(methylamino)ethyl]carbamoyl}phenyl]-3-ethylpiperazine-1-carboxamide (Compound 3-4)

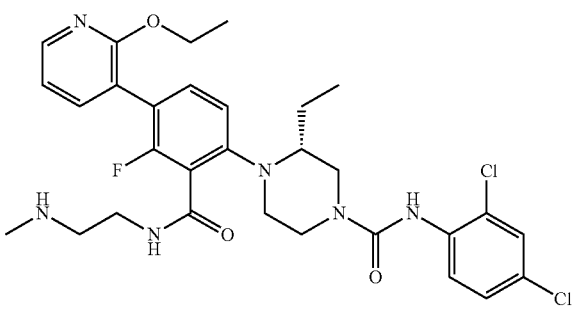 [SMILES: CCOc1ncccc1-c1ccc(N2CCN(C(=O)Nc3ccc(Cl)cc3Cl)C[C@H]2CC)c(C(=O)NCCNC)c1F]

Step 16-1, preparation of phenyl N-(2,4-dichlorophenyl) carbamate: Into a 8-mL vial, was placed 2,4-dichloroaniline (200 mg, 1.23 mmol) and THF (5 mL). The resulting solution was treated with NaH (59 mg, 1.47 mmol, 1.19 eq, 60% purity) and stirred for 20 min at 0° C. The reaction was treated with phenyl carbonochloridate (232 mg, 1.48 mmol, 1.2 eq.), stirred for an additional 3 hr at 0° C., and concentrated under vacuum. The residue was purified from a silica gel column chromatography eluting with ethyl acetate/petroleum ether (1:5). This resulted in 120 mg (34%) of the title compound as yellow oil. LCMS (M+H)$^+$=282.0.

Step 16-2, preparation of benzyl N-[2-([6-[(2R)-4-[(2,4-dichlorophenyl)carbamoyl]-2-ethylpiperazin-1-yl]-3-(2-ethoxypyridin-3-yl)-2-fluorophenyl]formamido)ethyl]-N-methylcarbamate: Into a 8-mL vial, was placed benzyl N-(2-[[3-(2-ethoxypyridin-3-yl)-6-[(2R)-2-ethylpiperazin-1-yl]-2-fluorophenyl]formamido]ethyl)-N-methylcarbamate trifluoroacetate (36 mg, 0.053 mmol), DCM (2 mL), TEA (16 mg, 0.158 mmol, 2.97 eq.), and phenyl N-(2,4-dichlorophenyl)carbamate (15 mg, 0.053 mmol). The resulting solution was stirred for 2 hrs at 25° C., diluted with DCM (10 mL), and washed with water (2×20 mL). The organic layer was dried over anhydrous sodium sulfate and concentrated under vacuum. This resulted in 30 mg (crude) of the title compound as yellow oil. LCMS (M+H)$^+$=751.2.

Step 16-3, preparation of (3R)—N-(2,4-dichlorophenyl)-4-[4-(2-ethoxypyridin-3-yl)-3-fluoro-2-[[2-(methylamino) ethyl]carbamoyl]phenyl]-3-ethylpiperazine-1-carboxamide: Into a 8-mL vial, was placed benzyl N-[2-([6-[(2R)-4-[(2,4-dichlorophenyl)carbamoyl]-2-ethylpiperazin-1-yl]-3-(2-ethoxypyridin-3-yl)-2-fluorophenyl]formamido)ethyl]-N-methylcarbamate (30 mg, 0.04 mmol) and TFA (2 mL). The resulting solution was stirred for 2 hrs at 60° C., cooled to rt, and concentrated under vacuum. The residue was dissolved in DMF (4 mL) and purified by Prep-HPLC with the following conditions (Prep-HPLC-013): Column, Atlantis Prep T3 OBD Column, 19*150 mm 5um; mobile phase, Water (0.1% FA) and ACN (24% PhaseB up to 53% in 6 min); 20 mL/min. Detector, UV 220, 254 nm. This resulted in 5.6 mg (21%) of the title compound as a formic acid salt. LCMS (M+H)$^+$=617.2.

Example 17: 5-[(2R)-4-[4-chloro-2-(trifluoromethyl) benzoyl]-2-ethylpiperazin-1-yl]-2'-ethoxy-N-[(3R)-1-methylpyrrolidin-3-yl]-[2,3'-bipyridine]-6-carboxamide (Compound 1-152)

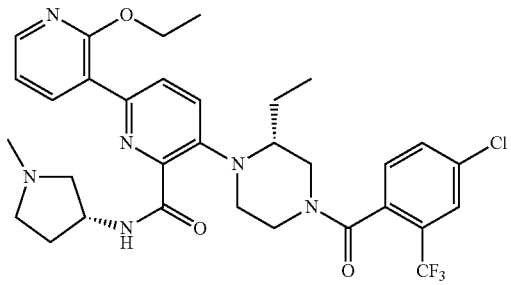 [SMILES: CCOc1ncccc1-c1ccc(N2CCN(C(=O)c3ccc(Cl)cc3C(F)(F)F)C[C@H]2CC)c(C(=O)N[C@@H]2CCN(C)C2)n1]

Step 17-1, preparation of 5-[(2R)-4-[4-chloro-2-(trifluoromethyl)benzoyl]-2-ethylpiperazin-1-yl]-2'-ethoxy-N-[(3R)-1-methylpyrrolidin-3-yl]-[2,3'-bipyridine]-6-carboxamide: to a solution of 5-[(2R)-4-[4-chloro-2-(trifluoromethyl)benzoyl]-2-ethylpiperazin-1-yl]-2'-ethoxy-[2,3'-bipyridine]-6-carboxylic acid from Example 9, step 5 (40 mg, 0.071 mmol) in ACN (0.5 mL) was added HATU (30 mg, 0.078 mmol, 1.1 eq.) and Et3N (19 µL, 2.0 eq.). The resulting solution was stirred at rt for 5 min and treated with (R)-1-methylpyrrolidin-3-ylamine (10.6 mg, 0.106 mmol, 1.5 eq.). The reaction was stirred at rt for 0.5 h. The crude reaction solution was purified by a C18 reversed phase column chromatography eluting with MeCN/water (5-100%). The combined pure fractions were neutralized with saturated NaHCO$_3$, removed volatile solvent, and extracted with DCM (3×). The combined organic layer was dried with anhydrous Na$_2$SO$_4$, concentrated and dried under high vacuum to give 25 mg (55%) of the title compound. LCMS (M+H)$^+$=645.5.

Example 18: 5-[(2R)-4-[4-chloro-2-(trifluoromethyl) benzoyl]-2-ethylpiperazin-1-yl]-2'-ethoxy-N-(1-methylazetidin-3-yl)-[2,3'-bipyridine]-6-carboxamide (Compound 1-212)

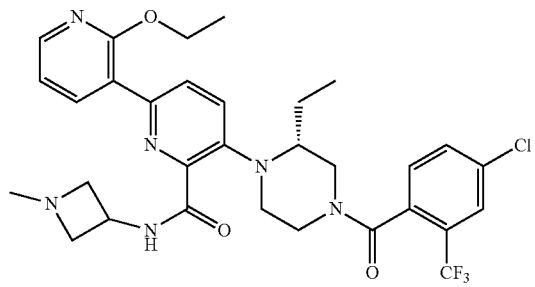 [SMILES: CCOc1ncccc1-c1ccc(N2CCN(C(=O)c3ccc(Cl)cc3C(F)(F)F)C[C@H]2CC)c(C(=O)NC2CN(C)C2)n1]

Step 18-1, preparation of 5-[(2R)-4-[4-chloro-2-(trifluoromethyl)benzoyl]-2-ethylpiperazin-1-yl]-2'-ethoxy-N-(1-methylazetidin-3-yl)-[2,3'-bipyridine]-6-carboxamide: the title compound was prepared by a similar manner described in Example 17 starting from 40 mg (0.071 mmol) of 5-[(2R)-4-[4-chloro-2-(trifluoromethyl)benzoyl]-2-ethylpiperazin-1-yl]-2'-ethoxy-[2,3'-bipyridine]-6-carboxylic acid. 20 mg (45%) of the title compound was isolated. LCMS (M+H)$^+$=631.4.

The following compounds were prepared similarly to Example 18 with appropriate substituting reagents and substrates at different steps:

| Compound no. | MS (M + H)$^+$ |
|---|---|
| 1-359 | 663.3 |
| 1-398 | 671.4 |

Example 19: 1-{2'-ethoxy-5-[(2R)-4-[6-ethoxy-2-(trifluoromethyl)pyridine-3-carbonyl]-2-ethylpiperazin-1-yl]-[2,3'-bipyridin]-6-yl}methanamine (Compound 2-30)

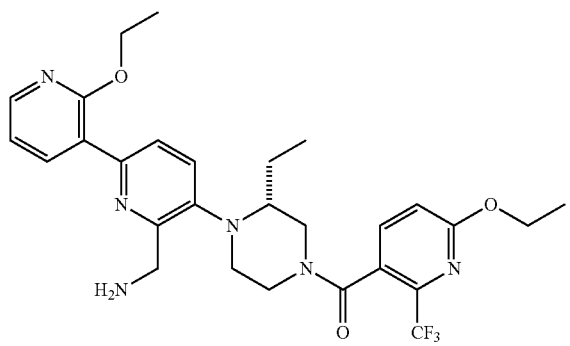 [SMILES: CCOc1ccc(C(=O)N2CCN(c3ccc(-c4cccnc4OCC)nc3CN)[C@H](CC)C2)c(C(F)(F)F)n1]

Step 19-1, preparation of 5-[(2R)-4-[6-chloro-2-(trifluoromethyl)pyridine-3-carbonyl]-2-ethylpiperazin-1-yl]-2'-ethoxy-[2,3'-bipyridine]-6-carbonitrile: to a DMF (3.0 mL) of 2'-ethoxy-5-[(2R)-2-ethylpiperazin-1-yl]-[2,3'-bipyridine]-6-carbonitrile (Step 9-3, 1.0 equiv, 0.26 mmol, 87 mg) was added DIPEA (2.5 equiv, 0.65 mmol, 0.1 mL), HATU (1.2 equiv, 0.39 mmol, 118 mg) and 6-chloro-2-(trifluoromethyl)pyridine-3-carboxylic acid (1.0 equiv, 0.26 mmol, 61 mg). The resulting mixture was stirred at rt for 0.5 h and LCMS showed complete consumption of starting material. The reaction solution was diluted with ethyl acetate (50 mL), washed with water and brine, dried with anhydrous $Na_2SO_4$, filtered and concentrated. The remaining residue was purified by silica gel chromatography eluting with EtOAc/hexane (0-50%) to afford 104 mg of the title compound. LCMS $(M+H)^+=545.3$.

Step 19-2, preparation of 2'-ethoxy-5-[(2R)-4-[6-ethoxy-2-(trifluoromethyl)pyridine-3-carbonyl]-2-ethylpiperazin-1-yl]-[2,3'-bipyridine]-6-carbonitrile: to an EtOH (0.5 mL) solution of 5-[(2R)-4-[6-chloro-2-(trifluoromethyl)pyridine-3-carbonyl]-2-ethylpiperazin-1-yl]-2'-ethoxy-[2,3'-bipyridine]-6-carbonitrile (1.0 equiv, 0.05 mmol, 28 mg) was added NaOEt (21% w/w in EtOH, 2.5 equiv, 0.13 mmol, 0.05 mL). The resulting mixture was heated at 70° C. for 0.5 h. The reaction solution was diluted with ethyl acetate (20 mL), washed with saturated $NH_4C_1$ and brine, dried with anhydrous $Na_2SO_4$, filtered and concentrated to afford 25 mg of crude product. This material was used for next step without purification. LCMS $(M+H)^+=555.2$.

Step 19-3, preparation of tert-butyl N-({2'-ethoxy-5-[(2R)-4-[6-ethoxy-2-(trifluoromethyl)pyridine-3-carbonyl]-2-ethylpiperazin-1-yl]-[2,3'-bipyridin]-6-yl}methyl)carbamate: to a MeOH (1.0 mL) solution of 2'-ethoxy-5-[(2R)-4-[6-ethoxy-2-(trifluoromethyl)pyridine-3-carbonyl]-2-ethylpiperazin-1-yl]-[2,3'-bipyridine]-6-carbonitrile (1.0 equiv, 0.05 mmol, 25 mg) was added $NiCl_2$ (0.5 equiv, 0.025 mmol, 3.3 mg) and di-tert-butyl dicarbonate (2.0 equiv, 0.10 mmol, 0.023 mL). At 0° C., $NaBH_4$ (7.0 equiv, 0.35 mmol, 13.5 mg) was added portion-wise and the resulting mixture was stirred at the same temperature for 0.5 h. The reaction mixture was filtered and filtrate was concentrated. The remaining residue was purified by silica gel chromatography eluting with EtOAc/hexane (0-50%) to afford 24 mg of the title compound. LCMS $(M+H)^+=659.4$.

Step 19-4, preparation of 1-{2'-ethoxy-5-[(2R)-4-[6-ethoxy-2-(trifluoromethyl)pyridine-3-carbonyl]-2-ethylpiperazin-1-yl]-[2,3'-bipyridin]-6-yl}methanamine: to a DCM (0.5 mL) of tert-butyl N-({2'-ethoxy-5-[(2R)-4-[6-ethoxy-2-(trifluoromethyl)pyridine-3-carbonyl]-2-ethylpiperazin-1-yl]-[2,3'-bipyridin]-6-yl}methyl)carbamate (1.0 equiv, 0.036 mmol, 24 mg) was added TFA (0.10 mL). The resulting mixture was stirred at ambient temperature for 0.5 h. The reaction solution was concentrated and the residue obtained was purified by C18 reversed-phase chromatography eluting with MeCN/water (5-50%). Pure fractions were combined, neutralized with saturated $NaHCO_3$ and NaCl, extracted with ethyl acetate and dried with $MgSO_4$. The organic layer was concentrated and dried under high vacuum to give 6 mg of the title compound. LCMS $(M+H)^+=559.2$ The following compounds were prepared similarly to Example 19 with appropriate substituting reagents and substrates at different steps:

| Compound no. | MS (M + H)+ |
| --- | --- |
| 2-31 | 545.4 |

Example 20: 5-[(2R)-4-[2-(difluoromethyl)-4-fluorobenzoyl]-2-ethylpiperazin-1-yl]-2'-ethoxy-N-[(3R)-1-methylpyrrolidin-3-yl]-[2,3'-bipyridine]-6-carboxamide (Compound 1-279)

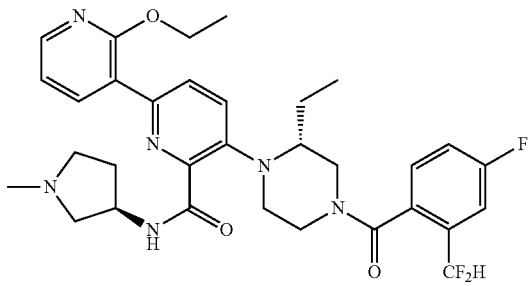 [SMILES: CCOc1ncccc1-c1ccc(N2CCN(C(=O)c3ccc(F)cc3C(F)F)C[C@H]2CC)c(C(=O)N[C@@H]2CCN(C)C2)n1]

Step 20-1, preparation of 2-(difluoromethyl)-4-fluorobenzoic acid: to a mixture of 4-fluoro-2-methylbenzoic acid (1.000 g, 6.49 mmol), Selectfluor (6.895 g, 19.46 mmol) and sodium persulfate (0.772 g, 3.24 mmol) under nitrogen was added MeCN (3.2 mL) and water (3.2 mL). The mixture was cooled to −78° C. under nitrogen and silver nitrate (110.2 mg, 0.649 mmol) was added. The frozen mixture was degassed under vacuum and charged with nitrogen (repeated 3×). The mixture was warmed to rt under nitrogen and then heated at 80° C. for 7 hrs. The reaction was not complete and thus more Selectfluor (2.298 g, 6.49 mmol), sodium persulfate (0.257 g, 1.08 mmol) and silver nitrate (36.7 mg, 0.216 mmol) were added under nitrogen and the reaction was continued to heat at 80° C. for 6 hrs. The mixture was filtered through Celite and rinsed with EtOAc. The filtrate was washed with saturated $NaHCO_3$ (aq) (5×25 mL). The combined basic aqueous solution was acidified with 1N HCl (aq) to pH 2-3 to form a solid. The solid was collected by vacuum filtration, washed with water and dried under vacuum to give the title compound (484.1 mg). The filtrate was extracted with EtOAc (1×) and the organic layer was concentrated and purified by C18 reversed phase column chromatography to give more product (314.4 mg). The reaction overall gave the title compound (798.5 mg, 4.20 mmol, 64.7% yield) as an off-white solid.

Step 20-2, preparation of tert-butyl (3R)-4-(2'-ethoxy-6-{[(3R)-1-methylpyrrolidin-3-yl]carbamoyl}-[2,3'-bipyridin]-5-yl)-3-ethylpiperazine-1-carboxylate: to a solution of 5-[(2R)-4-[(tert-butoxy)carbonyl]-2-ethylpiperazin-1-yl]-2'-ethoxy-[2,3'-bipyridine]-6-carboxylic acid (400 mg, 0.876 mmol) from Step 10-1 in DMF (2.0 mL) was added HATU (500 mg, 1.31 mmol), DIEA (0.46 mL, 2.63 mmol). After stirring at rt for 5 min, (3R)-1-methylpyrrolidin-3-amine (176 mg, 1.75 mmol) was added. The resulting mixture was stirred at rt for 10 min. The reaction mixture was purified by C18 reversed phase column chromatography to give the title compound (284.6 mg, 0.53 mmol, 60.3% yield) as a light brown solid. LCMS (M+H)$^+$=539.5.

Step 20-3, preparation of 2'-ethoxy-5-[(2R)-2-ethylpiperazin-1-yl]-N-[(3R)-1-methylpyrrolidin-3-yl]-[2,3'-bipyridine]-6-carboxamide tris(2,2,2-trifluoroacetate): to a solution of tert-butyl (3R)-4-(2'-ethoxy-6-{[(3R)-1-methylpyrrolidin-3-yl]carbamoyl}-[2,3'-bipyridin]-5-yl)-3-ethylpiperazine-1-carboxylate (268.8 mg, 0.50 mmol) in DCM (1.5 mL) was added TFA (0.76 mL). The resulting mixture was stirred at rt for 30 min and concentrated in vacuo to dryness to give the title compound (389.5 mg, 0.50 mmol, 100% yield) as a brown gum which was used in the next step without further purification. LCMS (M+H)$^+$=439.1.

Step 20-4, preparation of 5-[(2R)-4-[2-(difluoromethyl)-4-fluorobenzoyl]-2-ethylpiperazin-1-yl]-2'-ethoxy-N-[(3R)-1-methylpyrrolidin-3-yl]-[2,3'-bipyridine]-6-carboxamide: to a solution of 2-(difluoromethyl)-4-fluorobenzoic acid (142.3 mg, 0.75 mmol) in DMF (0.5 mL) was added HATU (265.6 mg, 0.70 mmol) and DIEA (0.26 mL, 1.50 mmol). After stirring at rt for 5 min, this HATU-activated solution was added to a solution of 2'-ethoxy-5-[(2R)-2-ethylpiperazin-1-yl]-N-[(3R)-1-methylpyrrolidin-3-yl]-[2,3'-bipyridine]-6-carboxamide tris(2,2,2-trifluoroacetate) (389.5 mg, 0.50 mmol) and DIEA (0.52 mL, 3.00 mmol) in DMF (0.5 mL). The resulting mixture was stirred at rt for 10 min. The reaction mixture was purified by C18 reversed phase column chromatography to give the title compound (245.0 mg, 0.40 mmol, 80.4% yield) as a light brown solid. LCMS (M+H)$^+$=611.3.

The following compounds were prepared similarly to Example 20 with appropriate substituting reagents and substrates at different steps:

| Compound no. | MS (M + H)$^+$ |
|---|---|
| 1-262 | 627.3 |
| 1-287 | 626.5 |
| 1-293 | 610.4 |

Example 21: 5-[(2R)-4-[2-(difluoromethyl)-4-fluorobenzoyl]-2-ethylpiperazin-1-yl]-2'-ethoxy-N-[(3R)-pyrrolidin-3-yl]-[2,3'-bipyridine]-6-carboxamide (Compound 1-278)

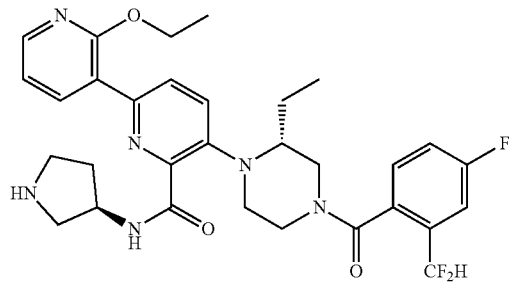 [SMILES: CCOc1ncccc1-c1ccc(N2CCN(C(=O)c3ccc(F)cc3C(F)F)C[C@H]2CC)c(C(=O)N[C@@H]2CCNC2)n1]

Step 21-1, preparation of tert-butyl (3R)-4-(6-{[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate: to a solution of 5-[(2R)-4-[(tert-butoxy)carbonyl]-2-ethylpiperazin-1-yl]-2'-ethoxy-[2,3'-bipyridine]-6-carboxylic acid (300 mg, 0.657 mmol) from Step 10-1 in DMF (1.0 mL) was added HATU (325 mg, 0.854 mmol), DIEA (0.23 mL, 1.3 mmol). After stirring at rt for 5 min, benzyl (3R)-3-aminopyrrolidine-1-carboxylate (217 mg, 0.986 mmol) was added. The resulting mixture was stirred at rt for 10 min. The reaction mixture was purified by C18 reversed phase column chromatography to give the title compound (270.8 mg, 0.411 mmol, 62.6% yield) as a brown solid. LCMS (M+H)$^+$=659.5.

Step 21-2, preparation of benzyl (3R)-3-{2'-ethoxy-5-[(2R)-2-ethylpiperazin-1-yl]-[2,3'-bipyridine]-6-amido}pyrrolidine-1-carboxylate bis(2,2,2-trifluoroacetate): to a solution of tert-butyl (3R)-4-(6-{[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate (90.0 mg, 0.137 mmol) in DCM (0.4 mL) was added TFA (0.2 mL). The resulting mixture was stirred at rt for 30 min and concentrated in vacuo to dryness to give the title compound (107 mg, 0.137 mmol, 100% yield) as a brown gum which was used in the next step without further purification. LCMS (M+H)$^+$=559.4.

Step 21-3, preparation of benzyl (3R)-3{5-[(2R)-4-[2-(difluoromethyl)-4-fluorobenzoyl]-2-ethylpiperazin-1-yl]-2'-ethoxy-[2,3'-bipyridine]-6-amido}pyrrolidine-1-carboxylate: to a solution of 2-(difluoromethyl)-4-fluorobenzoic acid (38.8 mg, 0.204 mmol) from Step 20-1 in DMF (0.2 mL) was added HATU (72.4 mg, 0.190 mmol) and DIEA (0.071 mL, 0.41 mmol). After stirring at rt for 5 min, this HATU-activated solution was added to a solution of benzyl (3R)-3-{2'-ethoxy-5-[(2R)-2-ethylpiperazin-1-yl]-[2,3'-bipyridine]-6-amido}pyrrolidine-1-carboxylate bis(2,2,2-trifluoroacetate) (107 mg, 0.136 mmol) and DIEA (0.14 mL, 0.80 mmol) in DMF (0.2 mL). The resulting mixture was stirred at rt for 10 min. The reaction mixture was purified by C18 reversed phase column chromatography to give the title compound (63.0 mg, 0.0862 mmol, 63.4% yield) as a light yellow solid. LCMS (M+H)$^+$=731.3.

Step 21-4, preparation of 5-[(2R)-4-[2-(difluoromethyl)-4-fluorobenzoyl]-2-ethylpiperazin-1-yl]-2'-ethoxy-N-[(3R)-pyrrolidin-3-yl]-[2,3'-bipyridine]-6-carboxamide: to benzyl (3R)-3{5-[(2R)-4-[2-(difluoromethyl)-4-fluorobenzoyl]-2-ethylpiperazin-1-yl]-2'-ethoxy-[2,3'-bipyridine]-6-amido}pyrrolidine-1-carboxylate (63.0 mg, 0.0862 mmol)

was added (methyl sulfanyl)benzene (0.050 mL) and TFA (0.25 mL). The resulting mixture was heated at 60° C. for 30 min. The reaction mixture was purified by C18 reversed phase column chromatography to give the title compound (39.9 mg, 0.0669 mmol, 77.6% yield) as an off-white solid. LCMS (M+H)⁺=597.4.

The following compounds were prepared similarly to Example 21 with appropriate substituting reagents and substrates at different steps:

| Compound no. | MS (M + H)⁺ |
|---|---|
| 1-265 | 613.3 |
| 1-288 | 612.1 |
| 1-292 | 596.4 |

Example 22: 2'-ethoxy-5-[(2R)-2-ethyl-4-[1-(trifluoromethyl)cyclopentanecarbonyl]piperazin-1-yl]-N-[(3R)-pyrrolidin-3-yl]-[2,3'-bipyridine]-6-carboxamide (Compound 1-263)

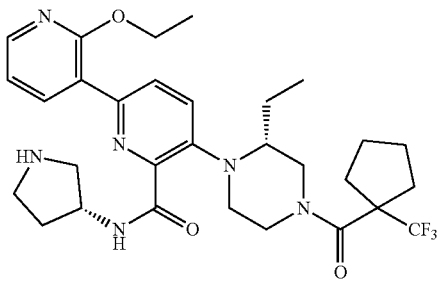 [SMILES: CCOc1ncccc1-c1ccc(N2CCN(C(=O)C3(C(F)(F)F)CCCC3)C[C@H]2CC)c(C(=O)N[C@@H]2CCNC2)n1]

Step 22-1, preparation of benzyl (3R)-3-{2'-ethoxy-5-[(2R)-2-ethylpiperazin-1-yl]-[2,3'-bipyridine]-6-amido}pyrrolidine-1-carboxylate: to a solution of tert-butyl (3R)-4-(6-{[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate from Example 21, step 1 (27 mg, 0.041 mmol) in DCM (0.4 mL) was added TFA (0.1 mL). The resulting solution was stirred at rt for 1 h and concentrated under vacuum to remove the volatile solvent. The residue was dissolved in ACN (0.3 mL) and neutralized with TEA (16 µL, 3 eq.), which was used in the next step without further purification. LCMS (M+H)⁺=559.3.

Step 22-2, preparation of benzyl (3R)-3-{2'-ethoxy-5-[(2R)-2-ethyl-4-[1-(trifluoromethyl)cyclopentanecarbonyl]piperazin-1-yl]-[2,3'-bipyridine]-6-amido}pyrrolidine-1-carboxylate: to a solution of 1-(trifluoromethyl)cyclopentane-1-carboxylic acid (11 mg, 0.06 mmol) in ACN (0.5 mL) was added HATU (22 mg, 0.06 mmol) and TEA (11 µL, 0.08 mmol). After stirring at rt for 5 min, the resulting solution was treated with benzyl (3R)-3-{2'-ethoxy-5-[(2R)-2-ethylpiperazin-1-yl]-[2,3'-bipyridine]-6-amido}pyrrolidine-1-carboxylate from step 1 (22 mg, 0.039 mmol). The reaction was stirred at rt for 30 min and directly purified by C18 reversed phase column chromatography to give the title compound (21 mg, 74% yield). LCMS (M+H)⁺= 723.8.

Step 22-3, preparation of 2'-ethoxy-5-[(2R)-2-ethyl-4-[1-(trifluoromethyl)cyclopentanecarbonyl]piperazin-1-yl]-N-[(3R)-pyrrolidin-3-yl]-[2,3'-bipyridine]-6-carboxamide: to a solution of benzyl (3R)-3-{2'-ethoxy-5-[(2R)-2-ethyl-4-[1-(trifluoromethyl)cyclopentanecarbonyl]piperazin-1-yl]-[2,3'-bipyridine]-6-amido}pyrrolidine-1-carboxylate (21 mg, 0.029 mmol) in TFA (0.5 mL) was added one drop of methyl(phenyl)sulfane. The resulting mixture was stirred at 60° C. for 1 hr and cooled to rt. After removal of the volatile solvent, the residue was purified by C18 reversed phase column chromatography to give the title compound (14 mg, 82% yield) as a white powder. LCMS (M+H)⁺=589.4.

The following compounds were prepared similarly to Example 22 with appropriate substituting reagents and substrates at different steps:

| Compound no. | MS (M + H)⁺ |
|---|---|
| 1-250 | 523.6 |
| 1-251 | 608.3 |
| 1-252 | 608.3 |
| 1-264 | 537.6 |
| 1-273 | 603.5 |
| 1-274 | 629.5 |
| 1-280 | 575.5 |
| 1-285 | 641.4 |
| 1-294 | 613.4 |
| 1-295 | 593.4 |
| 1-297 | 615.5 |
| 1-298 | 611.3 |
| 1-299 | 603.3 |
| 1-300 | 575.3 |
| 1-301 | 575.3 |
| 1-302 | 563.3 |
| 1-304 | 588.4 |
| 1-308 | 577.6 |
| 1-314 | 575.5 |
| 1-318 | 607.5 |
| 1-321 | 589.3 |
| 1-324 | 603.5 |
| 1-325 | 603.5 |
| 1-327 | 589.3 |
| 1-328 | 571.4 |
| 1-329 | 589.4 |
| 1-335 | 602.5 |
| 1-352 | 597.4 |
| 1-353 | 583.4 |
| 1-354 | 611.4 |
| 1-368 | 603.3 |

Example 23: 2'-ethoxy-5-[(2R)-2-ethyl-4-[1-(trifluoromethyl)cyclopentanecarbonyl]piperazin-1-yl]-N-[(3R)-1-methylpyrrolidin-3-yl]-[2,3'-bipyridine]-6-carboxamide (Compound 1-255)

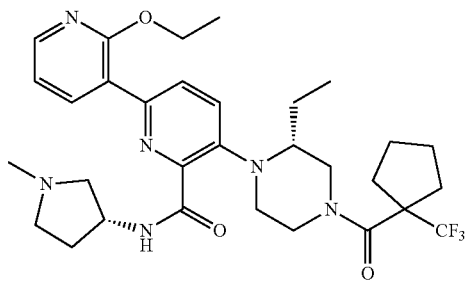 [SMILES: CCOc1ncccc1-c1ccc(N2CCN(C(=O)C3(C(F)(F)F)CCCC3)C[C@H]2CC)c(C(=O)N[C@@H]2CCN(C)C2)n1]

Step 23-1, preparation of 2'-ethoxy-5-[(2R)-2-ethyl-4-[1-(trifluoromethyl)cyclopentanecarbonyl]piperazin-1-yl]-N-[(3R)-1-methylpyrrolidin-3-yl]-[2,3'-bipyridine]-6-carboxamide: to a solution of 1-(trifluoromethyl)cyclopentane-1-carboxylic acid (13 mg, 0.071 mmol) in ACN (0.5 mL) was added HATU (27 mg, 0.071 mmol) and TEA (19 µL, 0.14 mmol). After stirring at rt for 5 min, the resulting solution was treated with neutral 2'-ethoxy-5-[(2R)-2-ethylpiperazin-1-yl]-N-[(3R)-1-methylpyrrolidin-3-yl]-[2,3'-bipyridine]-6-carboxamide from Example 20, step 3 (20 mg, 0.045 mmol). The reaction was stirred at rt for 30 min and directly purified by C18 reversed phase column chromatography to give the title compound (19 mg, 70% yield). LCMS (M+H)$^+$=603.6.

The following compounds were prepared similarly to Example 23 with appropriate substituting reagents and substrates at different steps. Some examples may require a reductive amination to introduce the tert-amine moiety in the final step:

| Compound no. | MS (M + H)$^+$ |
| --- | --- |
| 1-235 | 561.4 |
| 1-238 | 587.3 |
| 1-241 | 589.5 |
| 1-248 | 571.5 |
| 1-281 | 629.5 |
| 1-282 | 643.5 |
| 1-284 | 655.4 |
| 1-286 | 617.6 |
| 1-313 | 603.6 |
| 1-319 | 621.5 |
| 1-322 | 617.4 |
| 1-330 | 603.5 |
| 1-331 | 603.5 |
| 1-332 | 617.5 |
| 1-333 | 617.6 |
| 1-334 | 633.4 |
| 1-336 | 616.6 |
| 1-337 | 603.6 |
| 1-339 | 629.4 |
| 1-340 | 602.6 |
| 1-341 | 602.4 |
| 1-359 | 617.4 |
| 1-363 | 603.4 |
| 1-378 | 617.2 |
| 1-379 | 601.4 |
| 1-380 | 617.3 |
| 1-382 | 617.5 |
| 1-385 | 629.5 |
| 1-388 | 628.5 |
| 1-394 | 615.4 |
| 1-395 | 629.5 |
| 1-399 | 588.4 |
| 1-400 | 629.5 |
| 1-401 | 602.4 |
| 1-405 | 615.5 |
| 1-415 | 616.4 |
| 1-416 | 585.3 |
| 1-417 | 584.4 |

Example 24: 2'-ethoxy-5-[(2R)-2-ethyl-4-[1-(trifluoromethyl)cyclobutanecarbonyl]piperazin-1-yl]-N-[(3R)-1-methylpyrrolidin-3-yl]-[2,3'-bipyridine]-6-carboxamide (Compound 1-283)

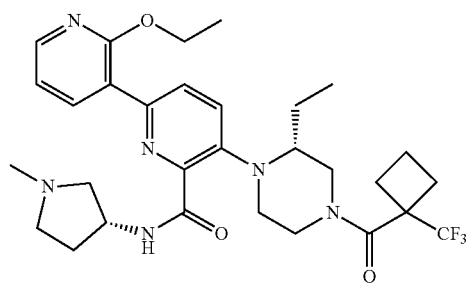 [SMILES: CCOc1ncccc1-c1ccc(N2CCN(C(=O)C3(C(F)(F)F)CCC3)C[C@H]2CC)c(C(=O)N[C@@H]2CCN(C)C2)n1]

Step 24-1, preparation of 2'-ethoxy-5-[(2R)-2-ethyl-4-[1-(trifluoromethyl)cyclobutanecarbonyl]piperazin-1-yl]-N-[(3R)-1-methylpyrrolidin-3-yl]-[2,3'-bipyridine]-6-carboxamide: to a solution of 1-(trifluoromethyl)cyclobutane-1-carboxylic acid (632 mg, 3.76 mmol) in DMF (5.0 mL) was added HATU (1.43 g, 3.76 mmol) and TEA (0.67 mL, 5.02 mmol). After stirring at rt for 5 min, the resulting solution was treated with 2'-ethoxy-5-[(2R)-2-ethylpiperazin-1-yl]-N-[(3R)-1-methylpyrrolidin-3-yl]-[2,3'-bipyridine]-6-carboxamide from Example 20, step 3 (1.10 g, 2.51 mmol). The reaction was stirred at rt for 30 min and directly purified by C18 reversed phase column chromatography to give the title compound (0.85 g, 58% yield). LCMS (M+H)$^+$=589.4.

The following compounds were prepared similarly to Example 24 with appropriate substituting reagents and substrates at different steps. Some examples may require a reductive amination to introduce the tert-amine moiety in the final step:

| Compound no. | MS (M + H)$^+$ |
| --- | --- |
| 1-344 | 588.4 |
| 1-349 | 602.5 |
| 1-358 | 597.2 |
| 1-364 | 589.4 |
| 1-371 | 633.4 |
| 1-390 | 589.4 |
| 1-411 | 615.4 |

Example 25: 6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide (Compound 1-374)

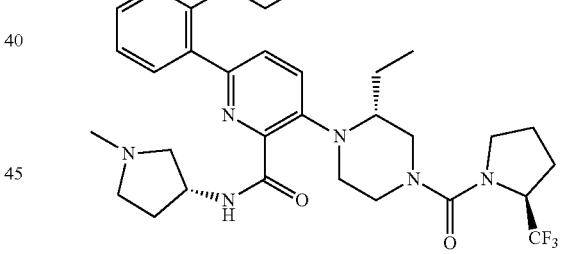

Step 25-1, preparation of tert-butyl (3R)-4-(6-bromo-2-cyanopyridin-3-yl)-3-ethylpiperazine-1-carboxylate: Into a 1000-mL round-bottom flask, was placed 6-bromo-3-fluoropicolinonitrile (50.0 g, 249 mmol), tert-butyl (R)-3-ethylpiperazine-1-carboxylate (59 g, 275 mmol), DIEA (97 g, 750 mmol), and DMSO (500 mL). The resulting reaction mixture was stirred for 24 hrs at 90° C. The reaction mixture was cooled to room temperature and quenched with water (1000 mL). The resulting solution was extracted with ethyl acetate (3×1000 mL). The organic layers were dried over anhydrous sodium sulfate and concentrated under vacuum. This resulted in the title compound (100 g, 66%) as a yellow oil. LCMS (M+H)$^+$=395.1.

Step 25-2, preparation of tert-butyl (3R)-4-[2-cyano-6-(2-ethoxyphenyl)pyridin-3-yl]-3-ethylpiperazine-1-carboxylate: Into a 250-mL round-bottom flask purged and maintained with an inert atmosphere of nitrogen, was placed tert-butyl (3R)-4-(6-bromo-2-cyanopyridin-3-yl)-3-ethylpiperazine-1-carboxylate (5.0 g, 13 mmol), (2-ethoxyphenyl)boronic acid (4.0 g, 26 mmol), potassium carbonate (5.0 g, 36 mmol), Pd(DtBPF)C$_2$ (0.4 g, 0.62 mmol), and dioxane/water (50 mL/5 mL). The resulting solution was stirred at 80° C. for 1 hour and cooled to rt. The inorganic solid was filtered off, and the filtrate was concentrated. The residue was purified from a silica gel column eluting with ethyl acetate/petroleum ether (1:3). This resulted in the title compound (4.0 g, 67%) as a yellowish oil. LCMS (M+H)$^+$=437.2.

Step 25-3, preparation of 3-[(2R)-4-[(tert-butoxy)carbonyl]-2-ethylpiperazin-1-yl]-6-(2-ethoxyphenyl)pyridine-2-carboxylic acid: Into a 250-mL round-bottom flask purged, was placed tert-butyl (3R)-4-[2-cyano-6-(2-ethoxyphenyl)pyridin-3-yl]-3-ethylpiperazine-1-carboxylate (4.0 g, 9.2 mmol), EtOH (40 mL), and water (40 mL). This resulting solution was treated with KOH (5.3 g, 94 mmol) at rt and then stirred at 100° C. for 50 hrs. The reaction was cooled to rt and concentrated to remove EtOH. The pH of aqueous layer was adjusted to 6-7 with 3N-HCl. The resulting solution was extracted with ethyl acetate (3×50 mL). The combined organic layers were washed with brine, dried over anhydrous sodium sulfate, and concentrated to afford the title compound (2.3 g, 55%) as a yellow solid. LCMS (M+H)$^+$=456.2.

Step 25-4, preparation of ethyl 6-(2-ethoxyphenyl)-3-[(2R)-2-ethylpiperazin-1-yl]pyridine-2-carboxylate: Into a 50-mL round-bottom flask, was placed 3-[(2R)-4-[(tert-butoxy)carbonyl]-2-ethylpiperazin-1-yl]-6-(2-ethoxyphenyl)pyridine-2-carboxylic acid (1.0 g, 2.2 mmol), EtOH (10 mL), and sulfuric acid (0.5 mL). The resulting reaction mixture was stirred at 80° C. for 3 hours and cooled to rt. The reaction was diluted with water (50 ml) and then adjusted to pH 6-7 with sodium bicarbonate. The resulting solution was extracted with EtOAc (3×10 mL). The combined organic layers were washed with brine, dried over anhydrous sodium sulfate, and concentrated under vacuum to afford the title compound (400 mg, 48%) as a yellow oil. LCMS (M+H)$^+$=384.2.

Step 25-5, preparation of ethyl 6-(2-ethoxyphenyl)-3-[(2R)-2-ethyl-4-[(2S)-2-(trifluoromethyl)pyrrolidine-1-carbonyl]piperazin-1-yl]pyridine-2-carboxylate: Into a 8-mL vial, was placed (S)-2-(trifluoromethyl)pyrrolidine (75 mg, 0.54 mmol), DIEA (210 mg, 1.62 mmol), and DCM (1 mL). The reaction mixture was cooled to 0° C. and treated with bis(trichloromethyl) carbonate (64 mg, 0.22 mmol). The resulting mixture was stirred at 0° C. for 3 hours, quenched with water (20 mL), and extracted with DCM (3×20 mL). The combined organic layers were dried over anhydrous sodium sulfate and concentrated under vacuum. The activated pyrrolidine was used in the next step directly without further purification. Ethyl 6-(2-ethoxyphenyl)-3-[(2R)-2-ethylpiperazin-1-yl]pyridine-2-carboxylate (210 mg, 5.43 mmol), the activated pyrrolidine described above, and potassium carbonate (750 mg, 5.43 mmol), and ACN (2 mL) were placed into a 8-mL vial. The resulting reaction mixture was stirred at 30° C. for 2 hours and cooled to room temperature. The crude product was purified by a reverse phase C18 column chromatography to afford the title compound (200 mg, 68%) as a yellow oil. LCMS (M+H)$^+$=549.4.

Step 25-6, preparation of 6-(2-ethoxyphenyl)-3-[(2R)-2-ethyl-4-[(2S)-2-(trifluoromethyl)pyrrolidine-1-carbonyl]piperazin-1-yl]pyridine-2-carboxylic acid: Into a 8-mL vial, was placed ethyl 6-(2-ethoxyphenyl)-3-[(2R)-2-ethyl-4-[(2S)-2-(trifluoromethyl)pyrrolidine-1-carbonyl]piperazin-1-yl]pyridine-2-carboxylate (200 mg, 0.365 mmol), LiOH (88 mg, 3.7 mmol), EtOH (2 mL), and water (1 mL). The resulting reaction mixture was stirred at 60° C. for 1 h and cooled to rt. The reaction was diluted with water (10 ml), and then adjusted to pH 6-7 with 3N-HCl. The resulting solution was extracted with EtOAc (3×10 mL). The combined organic layers were washed with brine, dried over anhydrous sodium sulfate, and concentrated to afford the title compound (170 mg, 90%) as a yellow oil. LCMS (M+H)$^+$=521.6.

Step 25-7, preparation of 6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide formate: Into a 50-mL round-bottom flask, was placed 6-(2-ethoxyphenyl)-3-[(2R)-2-ethyl-4-[(2S)-2-(trifluoromethyl)pyrrolidine-1-carbonyl]piperazin-1-yl]pyridine-2-carboxylic acid (80 mg, 0.15 mmol), HATU (58 mg, 0.15 mmol), DIEA (40 mg, 0.30 mmol), and DMF (1 mL). The resulting reaction mixture was stirred for 10 min at rt, and then treated with (R)-1-methylpyrrolidin-3-amine (20 mg, 0.20 mmol). The resulting reaction mixture was stirred at rt for 1 h. The crude product was purified by Prep-HPLC with the following conditions (Prep-HPLC-013): Column, Atlantis Prep T3 OBD Column, 19*150 mm 5 um; mobile phase, Water (0.1% FA) and ACN (30% Phase B up to 90% in 8 min); Total flow 20 mL/min. Detector, UV 220 nm. This resulted in the title compound (62 mg, 62%) as a white solid. LCMS (M+H)$^+$=603.4.

The following compounds were prepared similarly to Example 25 with appropriate substituting reagents and substrates at different steps. Some examples may require a chral separation to get optically pure compounds, but their absolute stereochemistries were not determined. In some examples, an additional deprotection is required in the final step:

| Compound no. | MS (M + H)$^+$ |
| --- | --- |
| 1-305 | 577.4 |
| 1-306 | 590.3 |
| 1-310 | 590.4 |
| 1-311 | 562.4 |
| 1-315 | 563.4 |
| 1-316 | 563.4 |
| 1-317 | 570.5 |
| 1-320 | 582.2 |
| 1-323 | 578.4 |
| 1-326 | 604.4 |
| 1-342 | 589.4 |
| 1-343 | 589.4 |
| 1-345 | 598.4 |
| 1-346 | 604.5 |
| 1-347 | 604.4 |
| 1-350 | 588.4 |
| 1-355 | 577.4 |
| 1-356 | 577.4 |
| 1-360 | 584.3 |
| 1-361 | 638.3 |
| 1-362 | 603.3 |
| 1-365 | 595.3 |
| 1-372 | 604.4 |
| 1-373 | 604.3 |
| 1-375 | 603.4 |
| 1-381 | 630.6 |
| 1-383 | 609.3 |
| 1-386 | 604.4 |
| 1-387 | 603.4 |

-continued

| Compound no. | MS (M + H)+ |
| --- | --- |
| 1-389 | 652.5 |
| 1-391 | 604.4 |
| 1-393 | 608.2 |
| 1-402 | 651.5 |
| 1-404 | 609.3 |
| 1-409 | 595.5 |
| 1-412 | 595.6 |
| 1-413 | 596.6 |
| 1-414 | 594.5 |
| 1-418 | 638.5 |
| 1-419 | 636.4 |
| 1-420 | 622.3 |
| 1-421 | 635.3 |
| 1-422 | 613.4 |
| 1-423 | 627.4 |
| 1-424 | 612.3 |
| 1-426 | 626.4 |
| 1-427 | 618.4 |
| 1-433 | 617.4 |
| 1-434 | 618.4 |
| 1-435 | 617.3 |

Example 26: 2'-ethoxy-5-[(2R)-2-ethyl-4-[1-(trifluoromethyl)cyclopentanecarbonyl]piperazin-1-yl]-N-[(3R)-1-[(5-methyl-2-oxo-2H-1,3-dioxol-4-yl)methyl]pyrrolidin-3-yl]-[2,3'-bipyridine]-6-carboxamide (Compound 1-307)

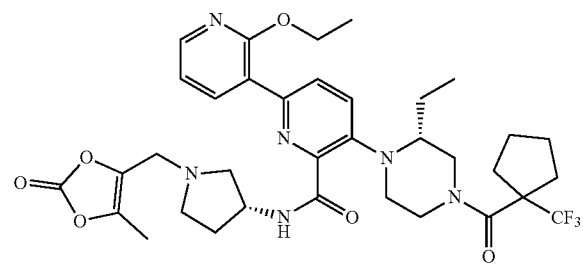 [SMILES: CCOc1ncccc1-c1ccc(N2CCN(C(=O)C3(C(F)(F)F)CCCC3)C[C@H]2CC)c(C(=O)N[C@@H]2CCN(Cc3oc(=O)oc3C)C2)n1]

Step 26-1, preparation of 2'-ethoxy-5-[(2R)-2-ethyl-4-[1-(trifluoromethyl)cyclopentanecarbonyl]piperazin-1-yl]-N-[(3R)-1-[(5-methyl-2-oxo-2H-1,3-dioxol-4-yl)methyl]pyrrolidin-3-yl]-[2,3'-bipyridine]-6-carboxamide: To a heterogeneous solution of Example 22 (50 mg, 0.085 mmol) and potassium hydrogen carbonate (10 mg, 0.10 mmol) in DMF (1.5 mL) was slowly added 4-(bromomethyl)-5-methyl-1,3-dioxol-2-one (20 mg, 0.10 mmol) at rt. The resulting reaction was stirred at rt for 16 hours. The inorganic solid was filtered off and then the filtrate was purified from a reverse phase C18 column chromatography to afford the title compound (18 mg, 30%). LCMS (M+H)+=701.4.

Example 27: (2S*)-1,1,1-trifluoro-3,3-dimethylbutan-2-yl (3R)-4-(2'-ethoxy-6-{[(3R)-pyrrolidin-3-yl]carbamoyl}-[2,3'-bipyridin]-5-yl)-3-ethylpiperazine-1-carboxylate (Compound 1-367) [*Absolute Stereochemistry not Determined]

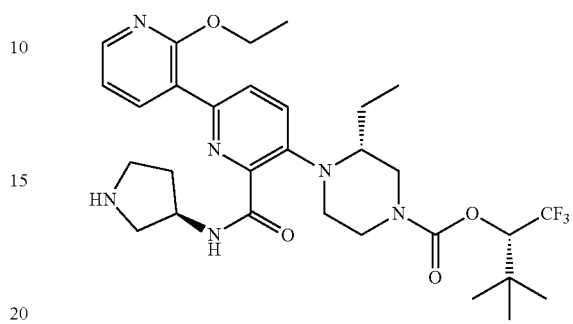

Step 27-1, preparation of (2S*)-1,1,1-trifluoro-3,3-dimethylbutan-2-yl 1H-imidazole-1-carboxylate: to a solution of 1,1,1-trifluoro-3,3-dimethylbutan-2-ol (100 mg, 0.640 mmol) in THF (3.0 mL) was added 1-(1H-imidazole-1-carbonyl)-1H-imidazole (156 mg, 0.961 mmol). The mixture was stirred at rt for 2.5 days. The mixture was concentrated to dryness and the residue was purified by silica gel column chromatography to give the racemic mixture of title compound (145 mg, 0.578 mmol, 90.3% yield) as a white solid. LCMS (M+H)+=251.1. The racemic mixture was purified by following conditions to give the enantiomerically pure title compound ($2^{nd}$ enantiomer: tentative assignment).
Chiral Resolution Conditions:
Column: normal phase Daicel Chiralpak ID column, 20 mm ID×250 mm L, 5 µm.particle size Gradient: isocratic 5% EtOH in Hexanes
Flow rate: 20 mL/min
Retention Times: $1^{st}$ enantiomer: 1.22 min (absolute stereochemistry not determined; tentatively assigned as compound 1-366); $2^{nd}$ enantiomer: 1.52 min (absolute stereochemistry not determined; tentatively assigned as compound 1-367).
Step 27-2, preparation of benzyl (3R)-3-{2'-ethoxy-5-[(2R)-2-ethylpiperazin-1-yl]-[2,3'-bipyridin]-6-amido}pyrrolidine-1-carboxylate: to a solution of tert-butyl (3R)-4-(6-{[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate (181 mg, 0.274 mmol) from Step 21-1 in DCM (0.7 mL) was added TFA (0.38 mL, 4.9 mmol). The resulting mixture was stirred at rt for 30 min and concentrated in vacuo to dryness. The crude TFA salt was neutralized with saturated NaHCO₃ (aq) to give the title compound (153 mg, 0.274 mmol, 100% yield) as a brown solid. LCMS (M+H)+=559.3.
Step 27-3, preparation of benzyl (2S*)-1,1,1-trifluoro-3,3-dimethylbutan-2-yl (3R)-4-(6-{_[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate: to a solution of benzyl (3R)-3-{2'-ethoxy-5-[(2R)-2-ethylpiperazin-1-yl]-[2,3'-bipyridin]-6-amido}pyrrolidine-1-carboxylate (110 mg, 0.197 mmol) in THF (5.0 mL) was added DIEA (0.270 mL, 1.55 mmol) and (2S)-1,1,1-trifluoro-3,3-dimmethylbutane-2-yl 1H-imidazole-1-carboxylate (75 mg, 0.30 mmol) in a sealed tube. The mixture was heated at 100° C. for 24 h. The mixture was concentrated to dryness and the residue was purified by C18 reversed phase column chromatography to give the title compound (120 mg, 0.162 mmol, 82.2% yield) as yellow oil. LCMS (M+H)⁺=741.4.

Step 27-4, preparation of (2S*)-1,1,1-trifluoro-3,3-dimethylbutane-2-yl (3R)-4-(2'-ethoxy-6-{[(3R)-pyrrolidin-3-yl]carbamoyl}-[2,3'-bipyridin]-5-yl)-3-ethylpiperazine-1-carboxylate formate: to benzyl (2S*)-1,1,1-trifluoro-3,3-dimethylbutane-2-yl (3R)-4-(6-{[(3R)-1-[(benzyloxy)carbonyl]pyrrolidin-3-yl]carbamoyl}-2'-ethoxy-[2,3'-bipyridin]-5-yl)-3-ethylpiperazine-1-carboxylate (120 mg, 0.162 mmol) was added TFA (2.0 mL). The resulting mixture was heated at 60° C. for 2 h. The reaction mixture was purified by C18 reversed phase column chromatography to give the title compound (72.0 mg, 0.110 mmol, 67.9% yield) as a white solid. LCMS (M+H)⁺=597.4.

The following compounds were prepared similarly to Example 27 with appropriate substituting reagents and substrates at different steps. Some examples' absolute stereochemistries were not determined. In some examples, an additional deprotection is not required in the final step:

| Compound no. | MS (M + H)⁺ |
| --- | --- |
| 1-309 | 579.4 |
| 1-312 | 607.3 |
| 1-338 | 590.4 |
| 1-348 | 606.3 |
| 1-351 | 627.3 |
| 1-366* | 607.4 |
| 1-369 | 619.3 |
| 1-377 | 627.2 |
| 1-396* | 621.4 |
| 1-403* | 647.4 |
| 1-407* | 606.3 |

*absolute stereochemistry not determined

Example 28: (2S*)-1,1,1-trifluoro-3,3-dimethylbutan-2-yl (3R)-4-(2'-ethoxy-6-{[(3R)-1-methylpyrrolidin-3-yl]carbamoyl}-[2,3'-bipyridin]-5-yl)-3-ethylpiperazine-1-carboxylate (Compound 1-392)
[*Absolute Stereochemistry not Determined]

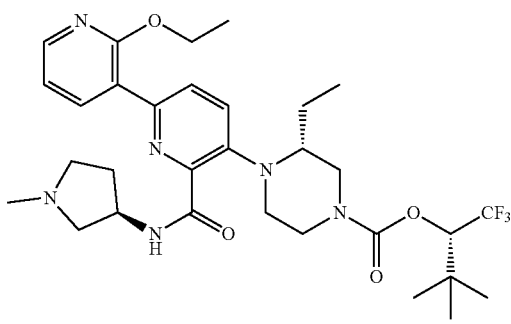 [SMILES: CCOc1ncccc1-c1ccc(N2CCN(C(=O)O[C@@H](C(C)(C)C)C(F)(F)F)C[C@H]2CC)c(C(=O)N[C@@H]2CCN(C)C2)n1]

Step 28-1, preparation of (2S*)-1,1,1-trifluoro-3,3-dimethylbutan-2-yl (3R)-4-(2'-ethoxy-6-{[(3R)-1-methylpyrrolidin-3-yl]carbamoyl}-[2,3'-bipyridin]-5-yl)-3-ethylpiperazine-1-carboxylate: to a solution of (2S)-1,1,1-trifluoro-3,3-dimethylbutane-2-yl (3R)-4-(2'-ethoxy-6-{[(3R)-pyrrolidin-3-yl]carbamoyl}-[2,3'-bipyridin]-5-yl)-3-ethylpiperazine-1-carboxylate formate (40.0 mg, 0.0613 mmol) in MeOH (3.0 mL) was added paraformaldehyde (38.5 mg) and sodium cyanoborohydride (38.5 mg, 0.613 mmol). The resulting mixture was stirred at rt for 1 h. The reaction mixture was quenched by TFA (0.1 mL) and re-basified with saturated NaHCO₃ (aq). The mixture was extracted with DCM and the organic layer was concentrated in vacuo to dryness. The residue was purified by C18 reversed phase column chromatography to give the title compound (26.1 mg, 0.0420 mmol, 68.5% yield) as an off-white solid. LCMS (M+H)⁺=621.5.

The following compounds were prepared similarly to Example 28 with appropriate substituting reagents and substrates at different steps. Some examples' absolute stereochemistries were not determined:

| Compound no. | MS (M + H)⁺ |
| --- | --- |
| 1-370 | 621.4 |
| 1-376 | 621.5 |
| 1-384 | 613.3 |
| 1-397 | 579.4 |
| 1-406* | 621.5 |
| 1-408 | 629.6 |

*absolute stereochemistry not determined

Example 29: 5-[(2R)-4-(7-cyano-5-fluoro-1H-indole-1-carbonyl)-2-ethylpiperazin-1-yl]-2'-ethoxy-N-[(3R)-1-methylpyrrolidin-3-yl]-[2,3'-bipyridine]-6-carboxamide (Compound 1-438)

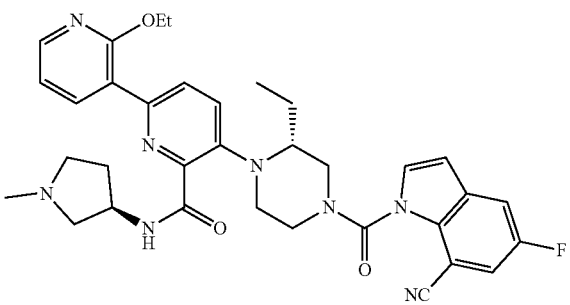 [SMILES: CCOc1ncccc1-c1ccc(N2CCN(C(=O)n3ccc4cc(F)cc(C#N)c43)C[C@H]2CC)c(C(=O)N[C@@H]2CCN(C)C2)n1]

Step 29-1, preparation of 5-fluoro-1H-indole-7-carbonitrile: to a mixture of 7-bromo-5-fluoro-1H-indole (920 mg, 4.30 mmol), dicyanozinc (1.514 g, 12.89 mmol) and Pd(PPh₃)₄ (993 mg, 0.860 mmol) in a sealed tube was added DMF (10 mL). Nitrogen (g) was bubbled through the reaction mixture. The resulting mixture was heated at 120° C. for 16 h. The mixture was quenched by water and extracted with DCM (3×). The combined organics were concentrated to dryness and the residue was purified by C18 reversed phase column chromatography to give the title compound (676 mg, 4.22 mmmol, 98% yield) as an off-white solid.

Step 29-2, preparation of 4-nitrophenyl 7-cyano-5-fluoro-1H-indole-1-carboxylate: to a suspension of 5-fluoro-1H-indole-7-carbonitrile (306 mg, 1.91 mmol) and 4-nitrophenyl carbonochloridate (463 mg, 2.30 mmol) in THF (20 mL) was added TEA (0.80 mL, 5.74 mmol) and DMAP (23.4 mg, 0.191 mmol). The resulting mixture was stirred at rt for 2 h but the reaction was not complete. More 4-nitrophenyl carbonochloridate (463 mg, 2.30 mmol) and triethylamine (0.80 mL, 5.73 mmol) were added and the reaction was continued for 2 h. The mixture was concentrated to dryness and the residue was purified by silica gel column chromatography to give the title compound (411 mg, 1.26 mmol, 66% yield) as an off-white solid.

Step 29-3, preparation of 5-[(2R)-4-(7-cyano-5-fluoro-1H-indole-1-carbonyl)-2-ethylpiperazin-1-yl]-2'-ethoxy-N-[(3R)-1-methylpyrrolidin-3-yl]-[2,3'-bipyridine]-6-carboxamide: to a solution of T-ethoxy-5-[(2R)-2-ethylpiperazin-1-yl]-N-[(3R)-1-methylpyrrolidin-3-yl]-[2,3'-bipyridine]-6-carboxamide from Example 20, Step 3 (50.0 mg, 0.114 mmol) and 4-nitrophenyl 7-cyano-5-fluoro-1H-indole-1-carboxylate (44.5 mg, 0.137 mmol) in MeCN (1 mL) was added DMAP (34.8 mg, 0.285 mmol). The mixture was heated at 50° C. for 1 h. The mixture was purified by C18 reversed phase column chromatography to give the title compound (14.5 mg, 0.023 mmol, 20% yield) as a light yellow solid. LCMS (M+H)$^+$=625.4.

The following compounds were prepared similarly to Example 29 with appropriate substituting reagents and substrates at different steps.

| Compound no. | MS (M + H)$^+$ |
|---|---|
| 1-425 | 634.1 |
| 1-428 | 616.2 |
| 1-429 | 607.4 |
| 1-430 | 633.3 |
| 1-431 | 615.2 |
| 1-432 | 606.3 |
| 1-436 | 650.5 |
| 1-437 | 649.4 |
| 1-439 | 624.3 |

Example 30: 5-[(2R)-4-[2-chloro-4-fluorobenzoyl]-2-ethylpiperazin-1-yl]-2'-ethoxy-N-[(3R)-1-methylpyrrolidin-3-yl]-[2,3'-bipyridine]-6-carboxamide (Compound 1-261)

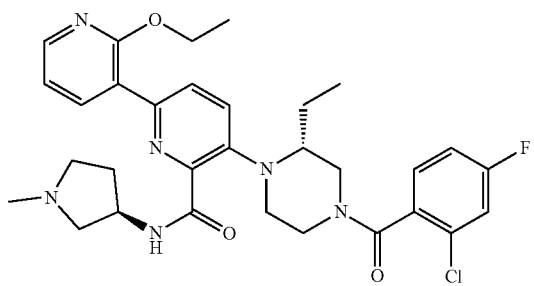 [SMILES: CCOc1ncccc1-c1ccc(N2CCN(C(=O)c3ccc(F)cc3Cl)C[C@H]2CC)c(C(=O)N[C@@H]2CCN(C)C2)n1]

Step 30-1, preparation of 5-[(2R)-4-[2-chloro-4-fluorobenzoyl]-2-ethylpiperazin-1-yl]-2'-ethoxy-N-[(3R)-1-methylpyrrolidin-3-yl]-[2,3'-bipyridine]-6-carboxamide: to a solution of 2-chloro-4-fluorobenzoic acid (35.9 mg, 0.206 mmol) and HATU (73.0 mg, 0.192 mmol) in DMF (0.2 mL) was added DIEA (0.072 mL, 0.41 mmol). After stirring at rt for 5 min, this HATU-activated solution was added to a solution of 2'-ethoxy-5-[(2R)-2-ethylpiperazin-1-yl]-N-[(3R)-1-methylpyrrolidin-3-yl]-[2,3'-bipyridine]-6-carboxamide tris(2,2,2-trifluoroacetate) from Example 20, Step 3 (107 mg, 0.137 mmol) and DIEA (0.072 mL, 0.41 mmol) in DMF (0.2 mL). The resulting mixture was stirred at rt for 10 min. The reaction mixture was purified by C18 reversed phase column chromatography to give the title compound (39.4 mg, 0.0645 mmol, 47% yield) as a light yellow solid. LCMS (M+H)$^+$=595.5.

Example 31: N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide (Compound 1-410)

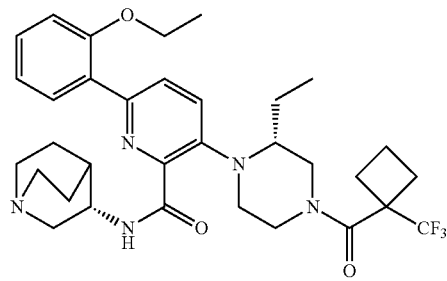 [SMILES: CCOc1ccccc1-c1ccc(N2CCN(C(=O)C3(C(F)(F)F)CCC3)C[C@H]2CC)c(C(=O)N[C@@H]2CN3CCC2CC3)n1]

Step 31-1, preparation of 6-(2-ethoxyphenyl)-3-[(2R)-2-ethyl-4-[1-(trifluoromethyl)cyclobutanecarbonyl]piperazin-1-yl]pyridine-2-carboxylic acid: to a solution of 3-[(2R)-4-[(tert-butoxy)carbonyl]-2-ethylpiperazin-1-yl]-6-(2-ethoxyphenyl)pyridine-2-carboxylic acid (450 mg, 0.98 mmol) from Example 25, step 3 in DCM (5.0 mL) was added TFA (1.14 mL, 14.8 mmol) at rt. The resulting solution was stirred at rt for 1 h and concentrated under vacuum to afford 6-(2-ethoxyphenyl)-3-[(2R)-2-ethylpiperazin-1-yl]pyridine-2-carboxylic acid. This residue was dissolved in ACN (2 mL) and neutralized with Et3N (~0.3 mL). The solution was used in the next HATU coupling step without further purification.

To a solution of 1-(trifluoromethyl)cyclobutane-1-carboxylic acid (332 mg, 1.98 mmol) in ACN (5 mL) was added HATU (751 mg, 1.98 mmol) and followed by Et3N (0.26 mL, 1.98 mmol) at rt. After stirring at rt for 5 min, this HATU-activated solution was treated with the solution of 6-(2-ethoxyphenyl)-3-[(2R)-2-ethylpiperazin-1-yl]pyridine-2-carboxylic acid described above. The resulting mixture was stirred at rt for 30 min and concentrated under vacuum. The residue was purified by C18 reversed phase column chromatography to give the title compound (290 mg, 58% yield). LCMS (M+H)$^+$=506.3.

Step 31-2, preparation of N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide: to a solution of 6-(2-ethoxyphenyl)-3-[(2R)-2-ethyl-4-[1-(trifluoromethyl)cyclobutanecarbonyl] piperazin-1-yl]pyridine-2-carboxylic acid (70 mg, 0.14 mmol) and HATU (58.0 mg, 0.15 mmol) in DMF (1.5 mL) was added Et3N (0.074 mL, 0.55 mmol). After stirring at rt for 5 min, the resulting solution was treated with (S)-quinuclidin-3-amine dihydrochloride (33 mg, 0.17 mmol). The resulting mixture was stirred at rt for 1 hr and directly purified by C18 reversed phase column chromatography to give the title compound (40 mg, 47% yield). LCMS (M+H)$^+$= 614.3.

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: MC2R Assays

Membrane Preparation:

Crude membrane fractions are prepared from CRE-bla-CHO-K1 cells stably expressing hMC2 receptor and hMRAP accessory protein (Thermo Fisher). The cells are grown to 85-100% confluence on standard tissue culture dishes in GlutaMax DMEM growth media (Gibco) with following additives: 10% dialyzed FBS (Gemini), 0.1 mM NEAA (Gibco), 25 mM HEPES (Gibco), 5 μg/mL blasticidin (Goldbio), 100 μg/mL zeocin (Invitrogen), 600 μg/mL hygromycin (Goldbio). To prepare membranes, cells are scraped and collected in 1× Dulbecco's phosphate buffered saline (Corning) and then pelleted at 1000 RPM's. The cell pellet is reconstituted in membrane preparation buffer (20 mM HEPES, 6 mM $MgCl_2$ and 1 mM EGTA, protease inhibitor tablets (Pierce) adjusted to pH 7.4), homogenized using a dounce homogenizer, and the resulting membrane fraction is pelleted by centrifugation at 12,000 RPM's. The membrane pellet is resuspended in membrane preparation buffer, snap freezed and stored at −80° C. for later use.

Binding Assay for hMC2 Antagonists Protocol:

The hMC2 membrane binding assay utilizes the following components: radiolabel [$^{125}$I]ACTH (1-39) Tyr23 (PerkinElmer), wheatgerm agglutinin coated PVT SPA beads (PerkinElmer), crude hMC2R membranes, and compounds. Briefly hMC2R membranes are incubated with SPA beads in binding assay buffer (50 mM HEPES, 5 mM $MgCl_2$, 1 mM $CaCl_2$), 0.2% BSA, protease inhibitor tablets (Pierce) adjusted to pH7.4) prior to assay initiation. A dose response of compound (the final concentration of compound are typically 0-10,000 nM), SPA membranes, and [$^{125}$I]ACTH (1-39) Tyr23 at a final concentration of 0.2 nM is plated in a 96-well assay plate and allowed to incubate 1.5 hours at room temperature. Assay plates are read using a Top Count NXT and $K_i$ values for compounds are determined using a GraphPad Prism 6 non-linear regression analysis.

Illustrative binding affinities of selective compounds are described in Table A. The potencies are divided into four criteria: +means that $K_i$ is between 1,000 nM and 10,000 nM; ++ means that $K_i$ is between 100 nM and 1,000 nM; +++ means $K_i$ is between 10 nM and 100 nM; ++++ means $K_i$ is below 10 nM.

TABLE A

| Compound No. | MC2R binding potency |
| --- | --- |
| 1-1 | +++ |
| 1-2 | ++++ |
| 1-3 | ++++ |
| 1-4 | +++ |
| 1-5 | +++ |
| 1-6 | +++ |
| 1-7 | +++ |
| 1-8 | +++ |
| 1-9 | +++ |
| 1-11 | +++ |
| 1-15 | ++++ |
| 1-16 | +++ |
| 1-17 | ++++ |
| 1-18 | ++++ |
| 1-19 | +++ |
| 1-20 | +++ |
| 1-23 | +++ |
| 1-24 | ++++ |
| 1-25 | ++++ |
| 1-26 | ++++ |
| 1-27 | ++++ |
| 1-32 | +++ |
| 1-33 | +++ |
| 1-34 | ++++ |
| 1-35 | ++++ |
| 1-36 | ++++ |
| 1-37 | ++++ |
| 1-38 | ++++ |
| 1-40 | ++++ |
| 1-41 | ++++ |
| 1-42 | ++++ |
| 1-43 | ++++ |
| 1-44 | ++++ |
| 1-45 | ++++ |
| 1-46 | ++++ |
| 1-47 | ++++ |
| 1-48 | ++++ |
| 1-49 | ++++ |
| 1-50 | ++++ |
| 1-51 | ++++ |
| 1-52 | ++++ |
| 1-54 | ++++ |
| 1-57 | ++++ |
| 1-58 | ++++ |
| 1-59 | ++++ |
| 1-60 | ++++ |
| 1-62 | ++++ |
| 1-67 | ++++ |
| 1-68 | ++++ |

TABLE A-continued

| Compound No. | MC2R binding potency |
|---|---|
| 1-69 | ++++ |
| 1-71 | ++++ |
| 1-72 | ++++ |
| 1-73 | ++++ |
| 1-76 | ++++ |
| 1-82 | ++++ |
| 1-84 | ++++ |
| 1-87 | ++++ |
| 1-88 | ++++ |
| 1-90 | ++++ |
| 1-91 | ++++ |
| 1-92 | ++++ |
| 1-93 | ++++ |
| 1-94 | ++++ |
| 1-95 | ++++ |
| 1-96 | ++++ |
| 1-97 | ++++ |
| 1-98 | ++++ |
| 1-99 | ++++ |
| 1-100 | ++++ |
| 1-101 | ++++ |
| 1-102 | ++++ |
| 1-104 | ++++ |
| 1-107 | ++++ |
| 1-108 | ++++ |
| 1-109 | ++++ |
| 1-110 | ++++ |
| 1-111 | ++++ |
| 1-112 | ++++ |
| 1-113 | ++++ |
| 1-114 | ++++ |
| 1-115 | ++++ |
| 1-116 | ++++ |
| 1-117 | ++++ |
| 1-123 | ++++ |
| 1-124 | ++++ |
| 1-125 | ++++ |
| 1-136 | ++++ |
| 1-137 | ++++ |
| 1-138 | ++++ |
| 1-142 | ++++ |
| 1-143 | ++++ |
| 1-148 | ++++ |
| 1-149 | ++++ |
| 1-150 | ++++ |
| 1-151 | ++++ |
| 1-152 | ++++ |
| 1-155 | ++++ |
| 1-156 | ++++ |
| 1-163 | ++++ |
| 1-164 | ++++ |
| 1-165 | ++++ |
| 1-167 | ++++ |
| 1-168 | ++++ |
| 1-169 | ++++ |
| 1-170 | ++++ |
| 1-171 | ++++ |
| 1-173 | ++++ |
| 1-174 | ++++ |
| 1-176 | ++++ |
| 1-177 | ++++ |
| 1-178 | ++++ |
| 1-181 | ++++ |
| 1-182 | ++++ |
| 1-183 | ++++ |
| 1-184 | ++++ |
| 1-187 | ++++ |
| 1-188 | ++++ |
| 1-189 | ++++ |
| 1-190 | ++++ |
| 1-198 | ++++ |
| 1-199 | ++++ |
| 1-200 | ++++ |
| 1-201 | ++++ |
| 1-202 | ++++ |
| 1-203 | ++++ |
| 1-206 | ++++ |
| 1-207 | ++++ |
| 1-208 | ++++ |
| 1-209 | ++++ |
| 1-210 | ++++ |
| 1-211 | ++++ |
| 1-212 | ++++ |
| 1-213 | ++++ |
| 1-214 | ++++ |
| 1-215 | ++++ |
| 1-216 | ++++ |
| 1-219 | ++++ |
| 1-220 | ++++ |
| 1-221 | ++++ |
| 1-222 | ++++ |
| 1-223 | ++++ |
| 1-224 | ++++ |
| 1-225 | ++++ |
| 1-226 | ++++ |
| 1-227 | ++++ |
| 1-228 | ++++ |
| 1-229 | ++++ |
| 1-230 | ++++ |
| 1-231 | ++++ |
| 1-232 | ++++ |
| 1-233 | ++++ |
| 1-234 | ++++ |
| 1-236 | ++++ |
| 1-237 | ++++ |
| 1-238 | ++++ |
| 1-239 | ++++ |
| 1-240 | ++++ |
| 1-241 | ++++ |
| 1-242 | ++++ |
| 1-243 | ++++ |
| 1-244 | ++++ |
| 1-245 | ++++ |
| 1-246 | ++++ |
| 1-247 | ++++ |
| 1-249 | ++++ |
| 1-253 | ++++ |
| 1-254 | ++++ |
| 1-255 | ++++ |
| 1-256 | ++++ |
| 1-257 | ++++ |
| 1-258 | ++++ |
| 1-259 | ++++ |
| 1-260 | ++++ |
| 1-261 | ++++ |
| 1-262 | ++++ |
| 1-263 | ++++ |
| 1-264 | ++++ |
| 1-265 | ++++ |
| 1-266 | ++++ |
| 1-267 | ++++ |
| 1-270 | ++++ |
| 1-271 | ++++ |
| 1-273 | ++++ |
| 1-274 | ++++ |
| 1-275 | ++++ |
| 1-276 | ++++ |
| 1-277 | ++++ |
| 1-278 | ++++ |
| 1-279 | ++++ |
| 1-280 | ++++ |
| 1-282 | ++++ |
| 1-283 | ++++ |
| 1-286 | ++++ |
| 1-287 | ++++ |
| 1-288 | ++++ |
| 1-289 | ++++ |
| 1-290 | ++++ |
| 1-291 | ++++ |
| 1-292 | ++++ |
| 1-293 | ++++ |
| 1-296 | ++++ |
| 1-297 | ++++ |
| 1-298 | ++++ |
| 1-299 | ++++ |
| 1-304 | ++++ |

TABLE A-continued

| Compound No. | MC2R binding potency |
|---|---|
| 1-305 | ++++ |
| 1-306 | ++++ |
| 1-312 | ++++ |
| 1-313 | ++++ |
| 1-314 | ++++ |
| 1-315 | ++++ |
| 1-320 | ++++ |
| 1-321 | ++++ |
| 1-324 | ++++ |
| 1-325 | ++++ |
| 1-326 | ++++ |
| 1-327 | ++++ |
| 1-328 | ++++ |
| 1-329 | ++++ |
| 1-330 | ++++ |
| 1-331 | ++++ |
| 1-332 | ++++ |
| 1-333 | ++++ |
| 1-334 | ++++ |
| 1-335 | ++++ |
| 1-336 | ++++ |
| 1-337 | ++++ |
| 1-338 | ++++ |
| 1-339 | ++++ |
| 1-340 | ++++ |
| 1-341 | ++++ |
| 1-342 | ++++ |
| 1-343 | ++++ |
| 1-344 | ++++ |
| 1-345 | ++++ |
| 1-346 | ++++ |
| 1-348 | ++++ |
| 1-349 | ++++ |
| 1-350 | ++++ |
| 1-351 | ++++ |
| 1-352 | ++++ |
| 1-353 | ++++ |
| 1-354 | ++++ |
| 1-356 | ++++ |
| 1-357 | ++++ |
| 1-358 | ++++ |
| 1-360 | ++++ |
| 1-361 | ++++ |
| 1-362 | ++++ |
| 1-363 | ++++ |
| 1-365 | ++++ |
| 1-367* | ++++ |
| 1-368 | ++++ |
| 1-371 | ++++ |
| 1-372 | ++++ |
| 1-373 | ++++ |
| 1-374 | ++++ |
| 1-375 | ++++ |
| 1-376 | ++++ |
| 1-377 | ++++ |
| 1-378 | ++++ |
| 1-380 | ++++ |
| 1-381 | ++++ |
| 1-382 | ++++ |
| 1-383 | ++++ |
| 1-385 | ++++ |
| 1-386 | +++ |
| 1-387 | ++++ |
| 1-388 | ++++ |
| 1-389 | ++++ |
| 1-390 | +++ |
| 1-391 | ++++ |
| 1-392* | ++++ |
| 1-393 | ++++ |
| 1-394 | ++++ |
| 1-395 | ++++ |
| 1-396* | ++++ |
| 1-397 | ++++ |
| 1-398 | ++++ |
| 1-399 | ++++ |
| 1-400 | ++++ |
| 1-401 | ++++ |
| 1-402 | ++++ |
| 1-403* | ++++ |
| 1-404 | ++++ |
| 1-405 | ++++ |
| 1-406* | ++++ |
| 1-407* | ++++ |
| 1-408 | ++++ |
| 1-409 | ++++ |
| 1-410 | ++++ |
| 1-411 | ++++ |
| 1-412 | ++++ |
| 1-413 | ++++ |
| 1-414 | ++++ |
| 1-415 | ++++ |
| 1-416 | ++++ |
| 1-417 | ++++ |
| 1-418 | ++++ |
| 1-419 | ++++ |
| 1-420 | ++++ |
| 1-421 | ++++ |
| 1-422 | ++++ |
| 1-423 | ++++ |
| 1-424 | ++++ |
| 1-425 | ++++ |
| 1-426 | ++++ |
| 1-427 | ++++ |
| 1-428 | ++++ |
| 1-429 | ++++ |
| 1-430 | ++++ |
| 1-431 | ++++ |
| 1-432 | ++++ |
| 1-433 | ++++ |
| 1-434 | ++++ |
| 1-435 | ++++ |
| 1-436 | ++++ |
| 1-437 | ++++ |
| 1-438 | ++++ |
| 1-439 | ++++ |
| 2-2 | ++++ |
| 2-3 | +++ |
| 2-13 | ++++ |
| 2-16 | ++++ |
| 2-20 | ++++ |
| 2-21 | ++++ |
| 2-25 | ++++ |
| 2-30 | ++++ |
| 2-31 | ++++ |

*absolute stereochemistry not determined

The examples and embodiments described herein are for illustrative purposes only and various modifications or changes suggested to persons skilled in the art are to be included within the spirit and purview of this application and scope of the appended claims.

What is claimed is:

1. A compound of Formula (IX), or a pharmaceutically acceptable salt, or solvate thereof:

Formula (IX)

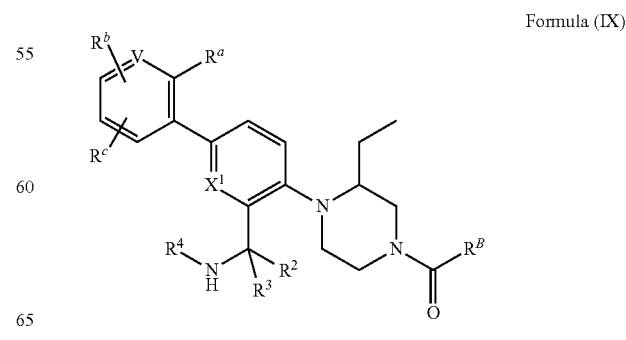

wherein:
V is CH;
$X^1$ is N;
$R^2$ and $R^3$ are hydrogen;
or $R^2$ and $R^3$ are taken together with the carbon atom to which they are attached to form —C(=O)—;
$R^a$ is —OCH$_2$CH$_3$;
$R^b$ and $R^c$ are hydrogen;
$R^B$ is
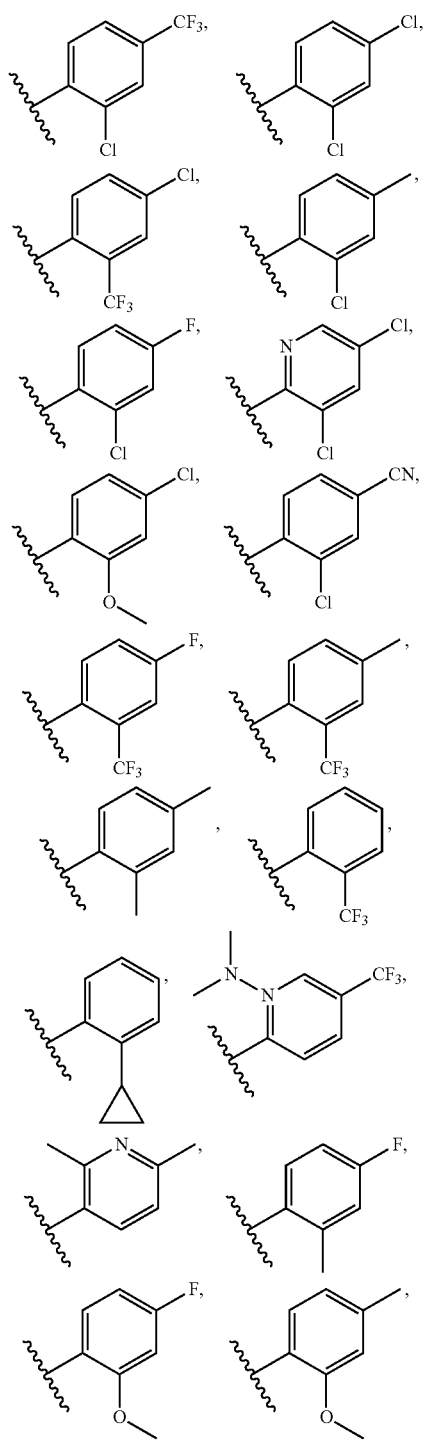
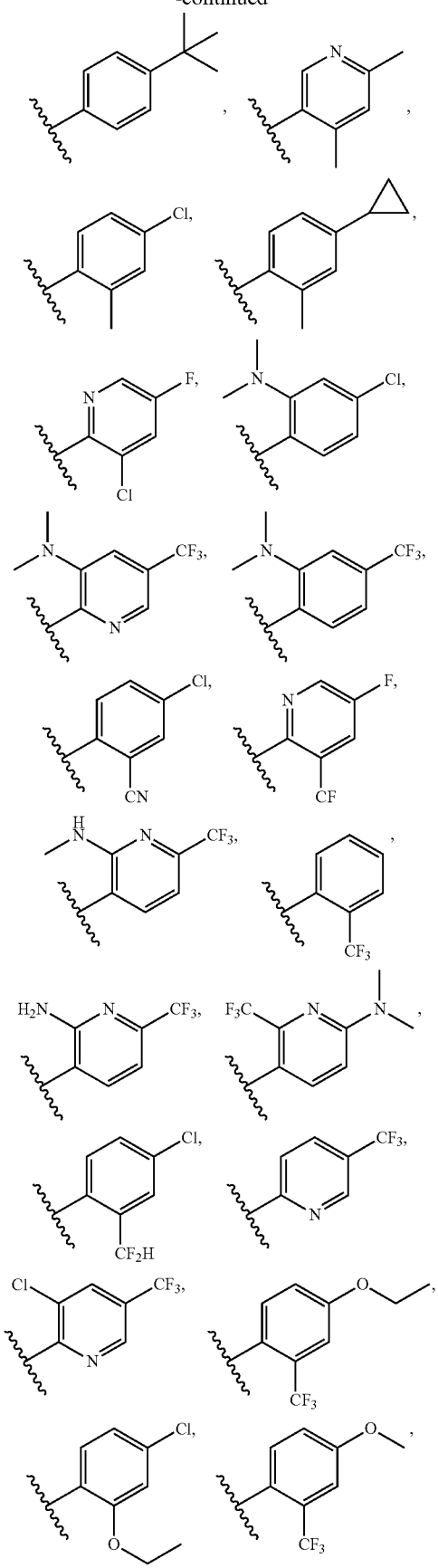

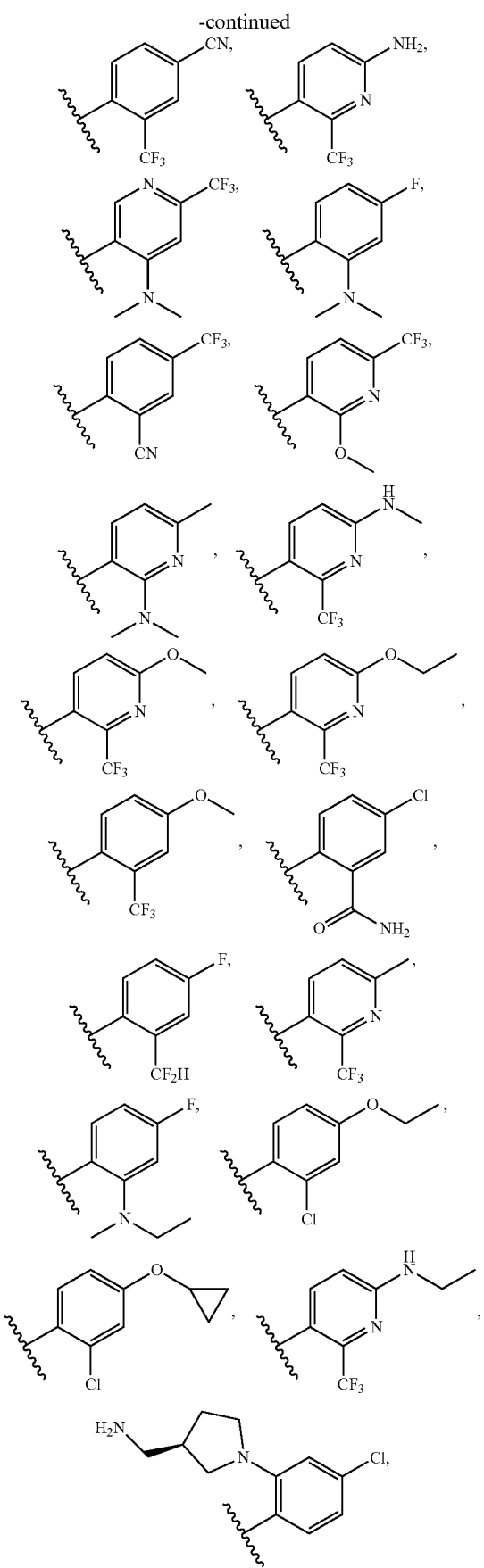
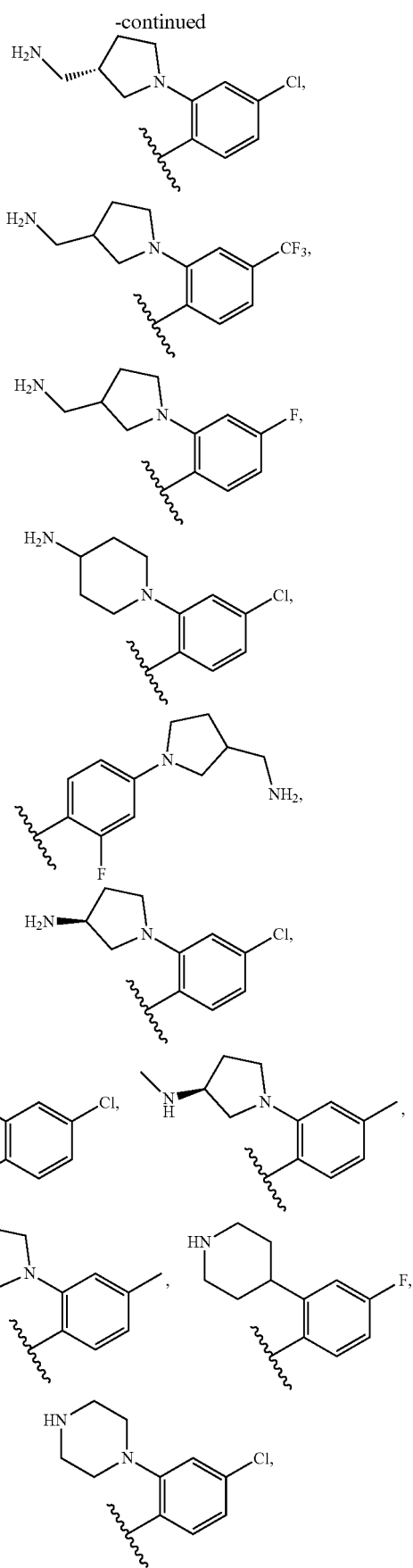

257 -continued

258 -continued

-continued
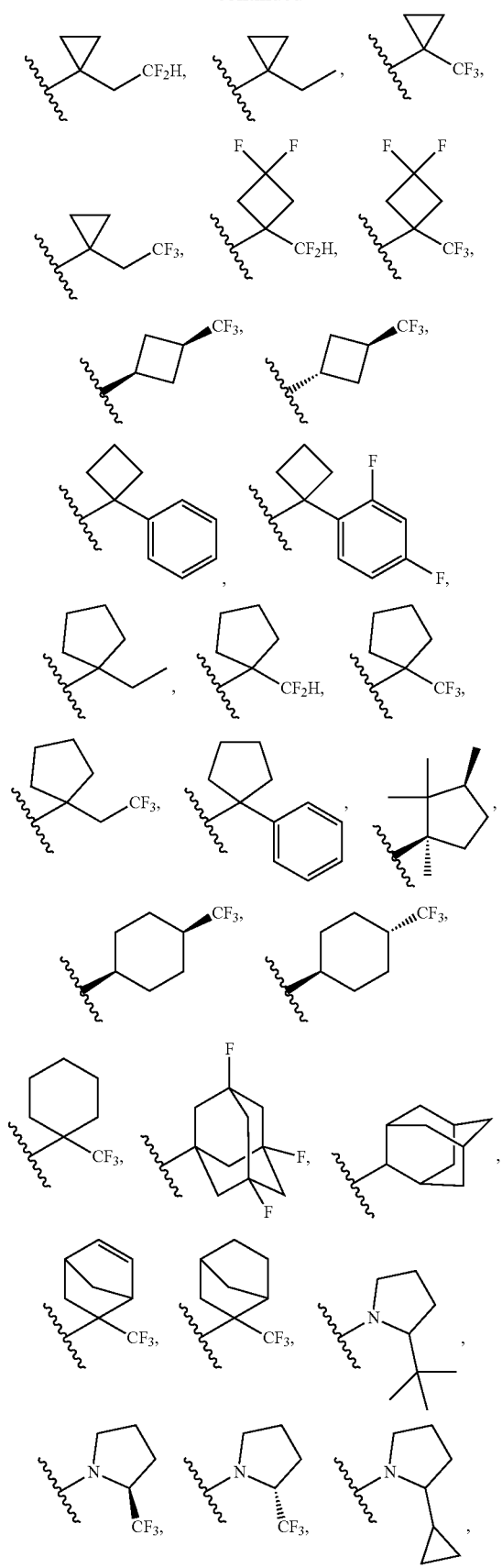
-continued
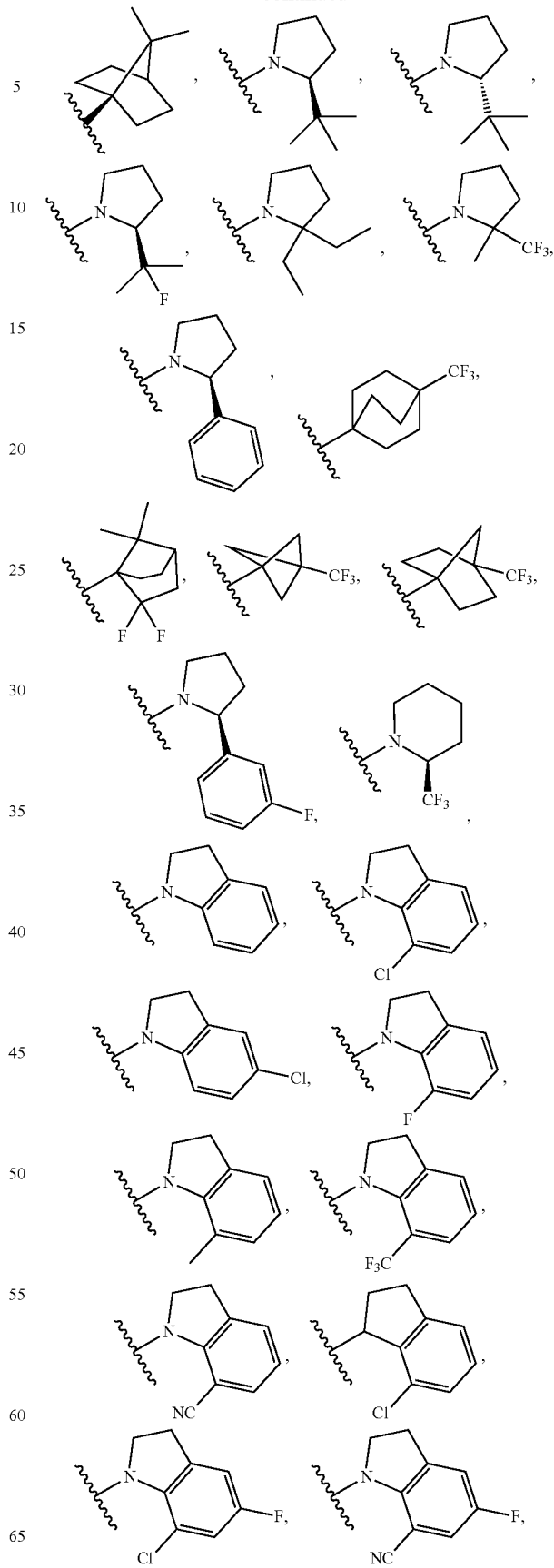

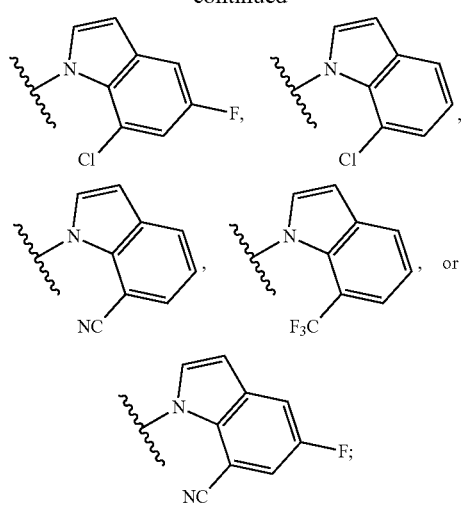
and
R[4] is
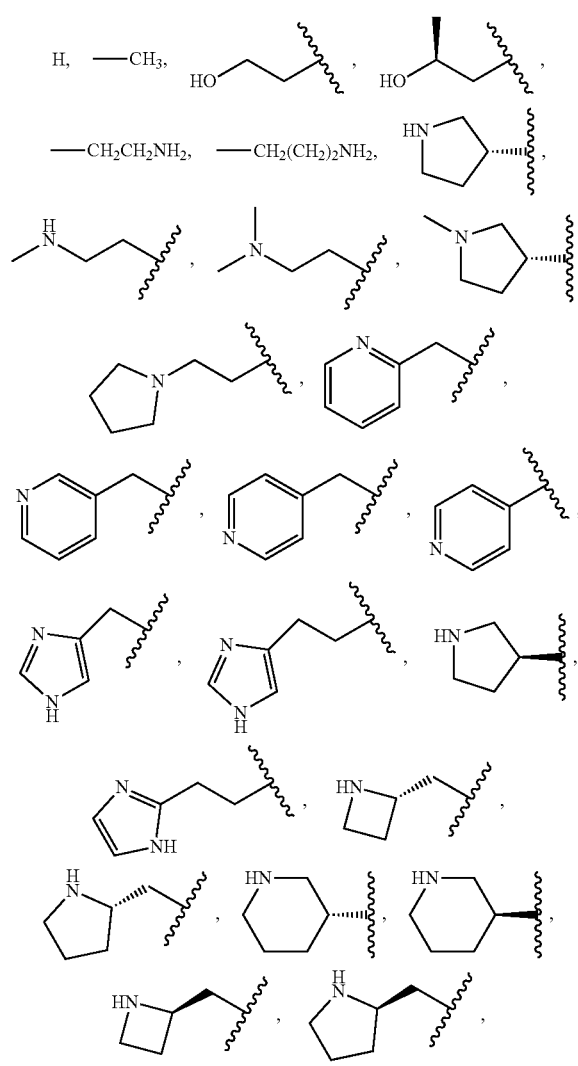
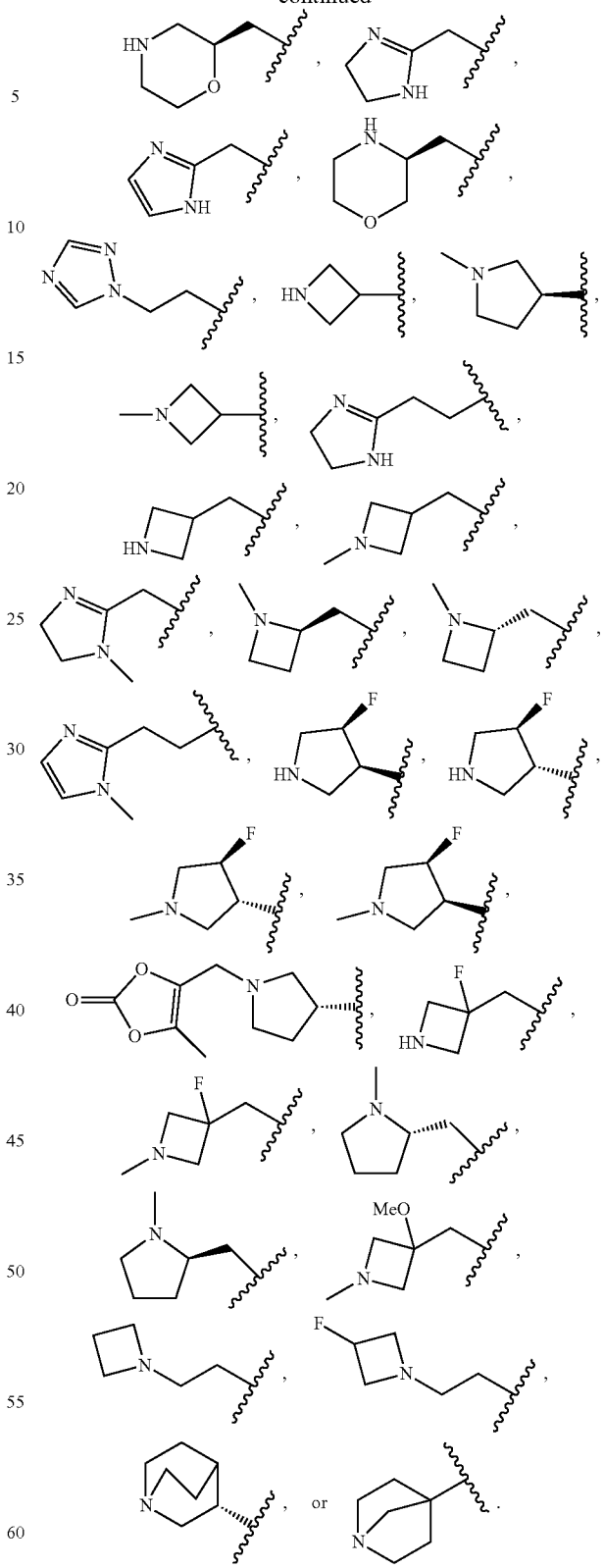
2. The compound of claim 1, or a pharmaceutically acceptable salt, or solvate thereof, wherein the compound of Formula (IX) has the structure of Formula (IXa), or a pharmaceutically acceptable salt, or solvate thereof:

Formula (IXa)

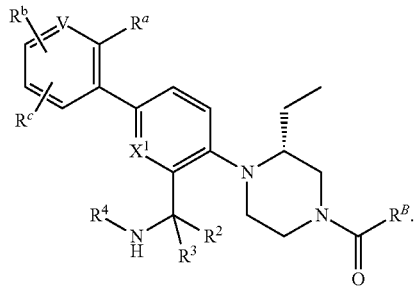

3. The compound of claim 2, or a pharmaceutically acceptable
salt, or solvate thereof, wherein:
$R^2$ and $R^3$ are hydrogen.

4. The compound of claim 2, or a pharmaceutically acceptable salt, or solvate thereof, wherein:
$R^2$ and $R^3$ are taken together with the carbon atom to which they are attached to form —C(=O)—.

5. The compound of claim 4, or a pharmaceutically acceptable salt, or solvate thereof, wherein:
$R^4$ is

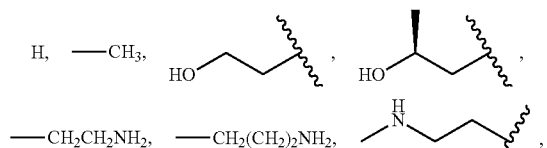

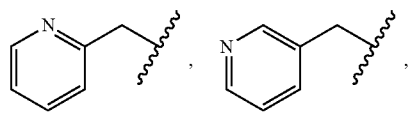

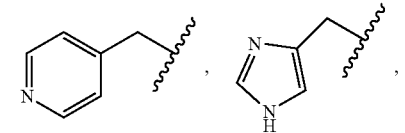

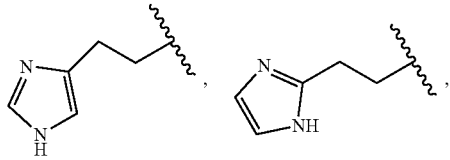

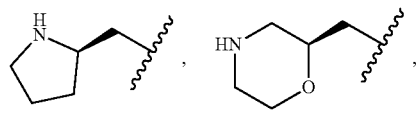

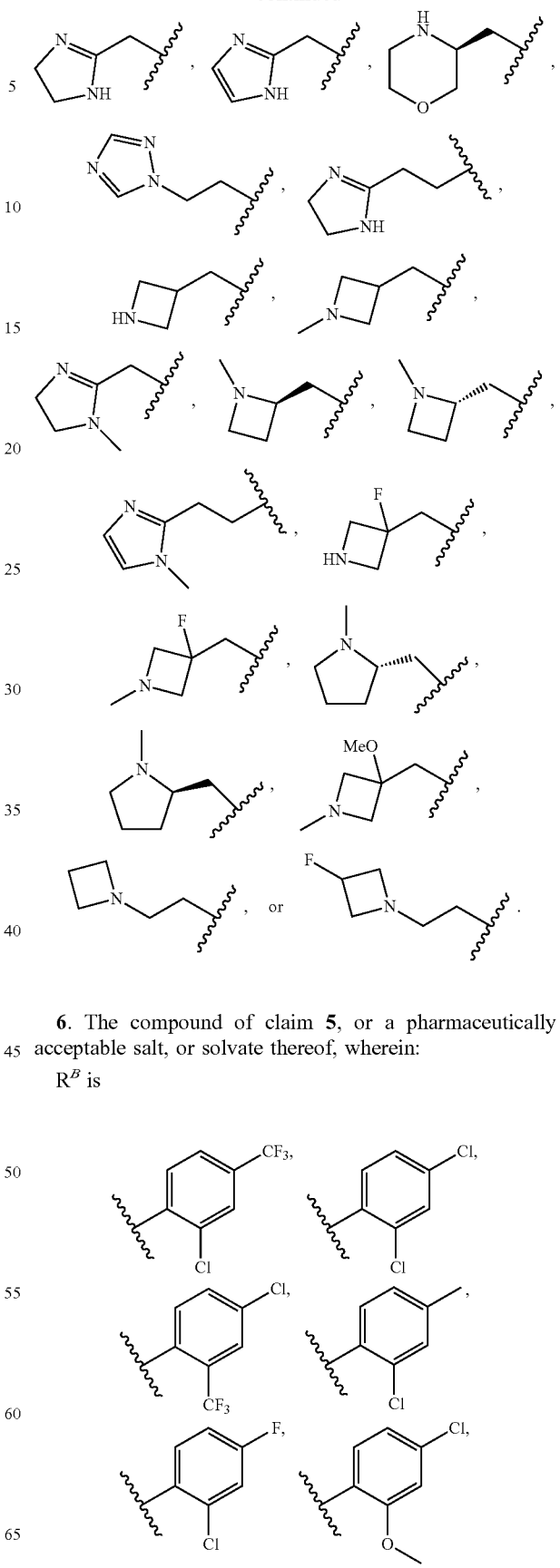

6. The compound of claim 5, or a pharmaceutically acceptable salt, or solvate thereof, wherein:
$R^B$ is 265
-continued
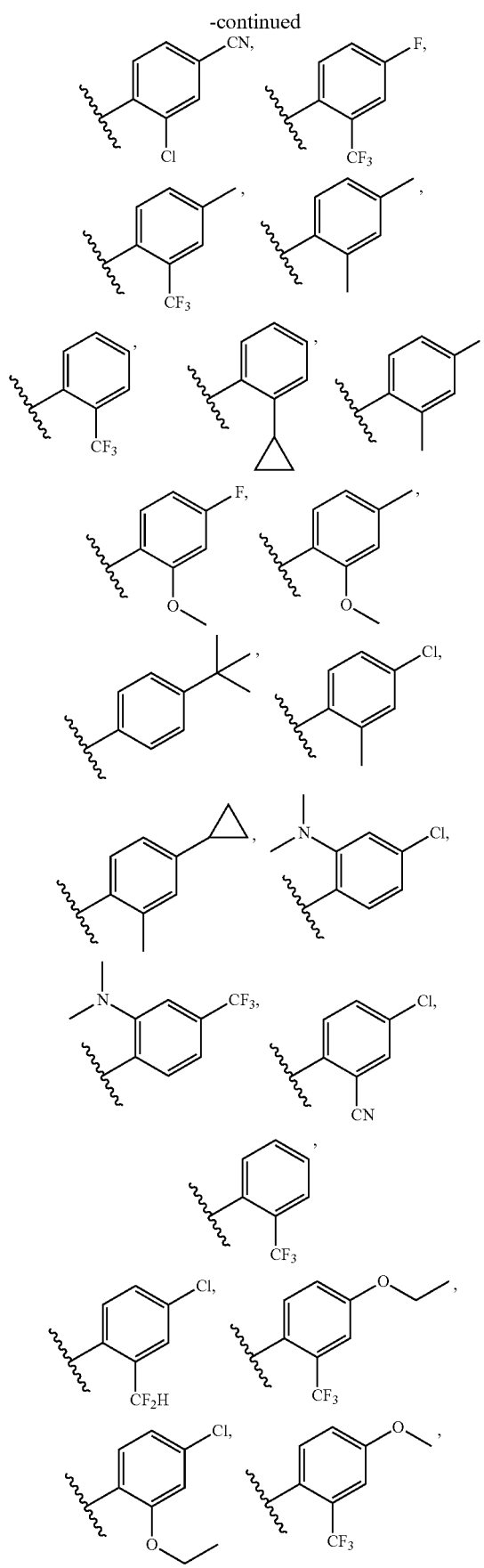
266
-continued
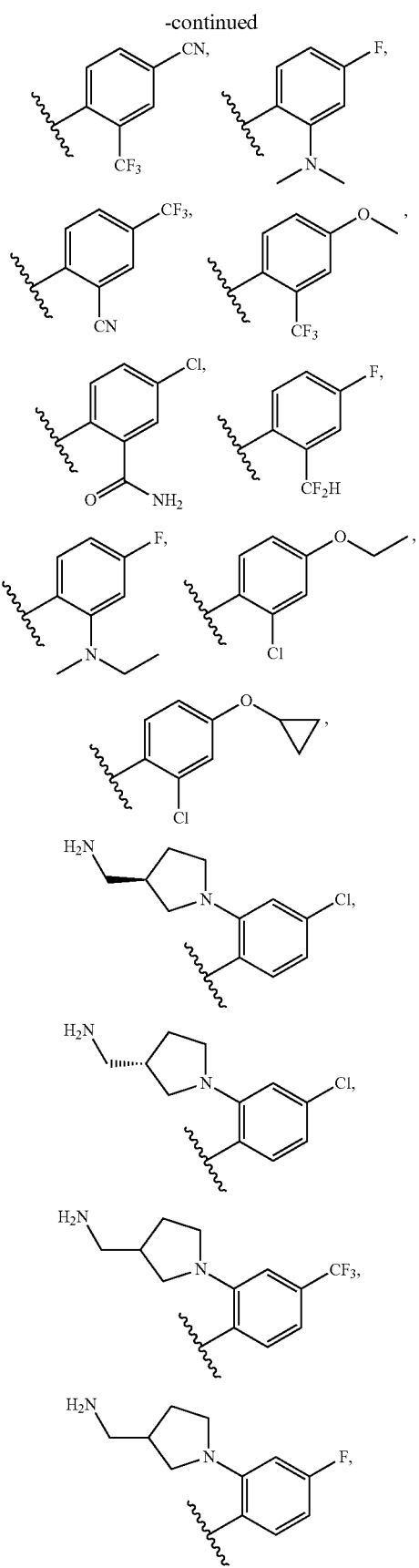

-continued
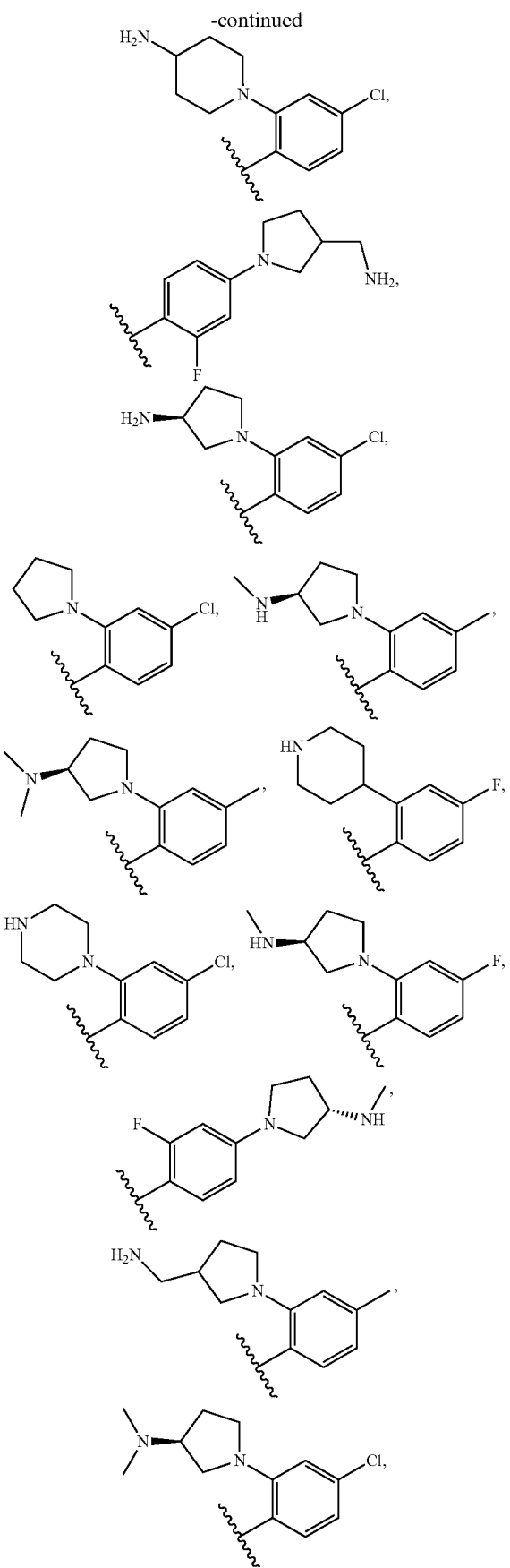
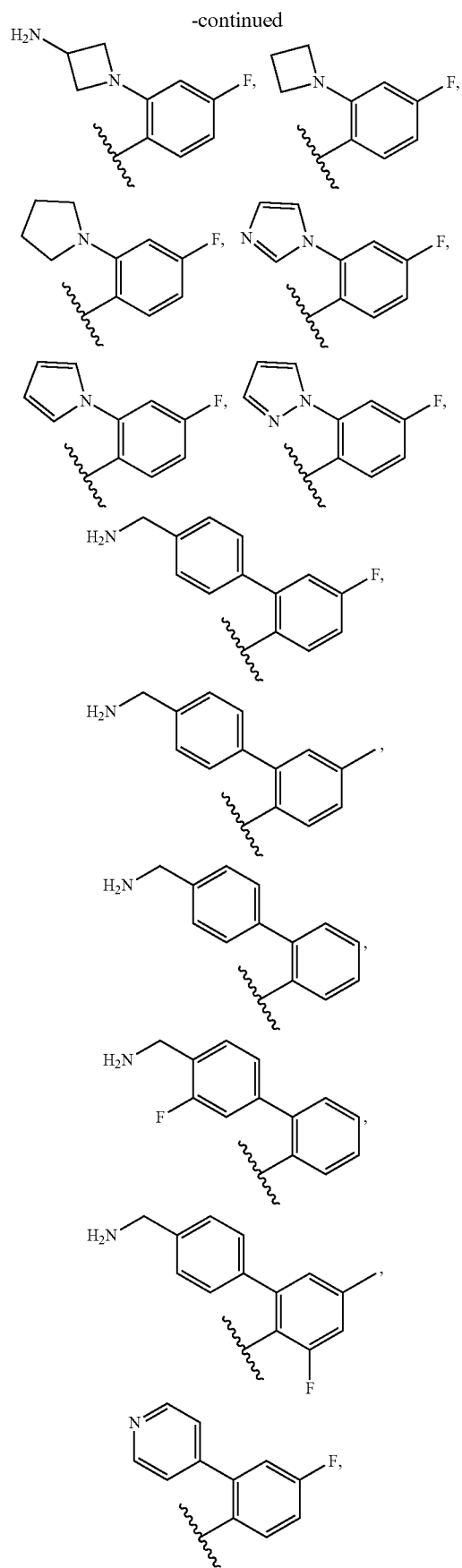

-continued
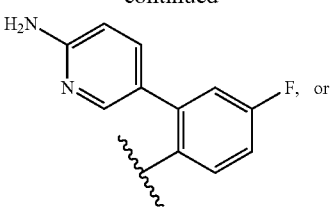
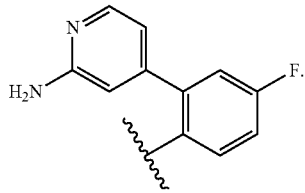 [SMILES: *c1ccc(F)cc1-c1ccnc(N)c1]
7. The compound of claim 5, or a pharmaceutically acceptable salt, or solvate thereof, wherein:
$R^B$ is
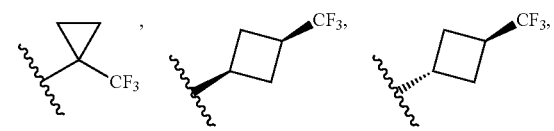
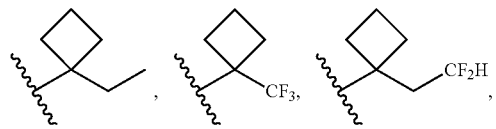
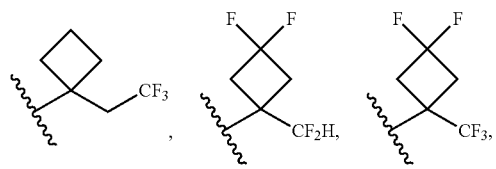
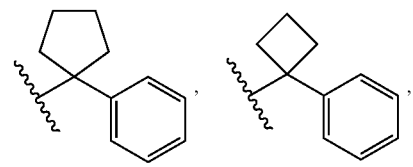
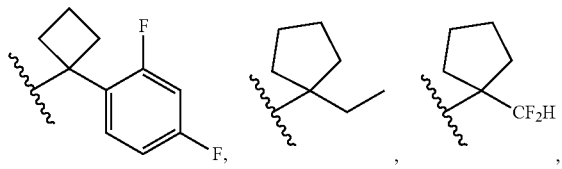
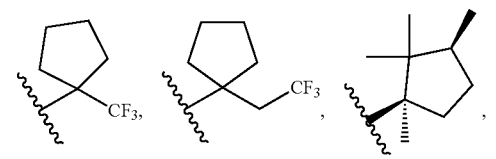
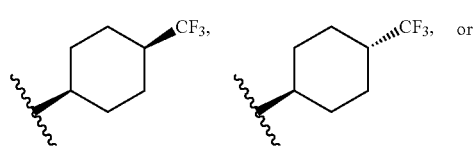
-continued
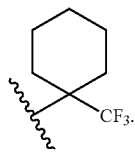
8. The compound of claim 5, or a pharmaceutically acceptable salt, or solvate thereof, wherein:
$R^B$ is
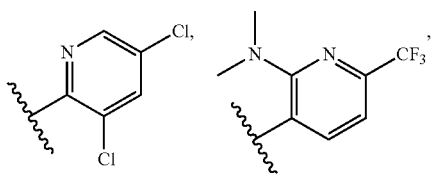
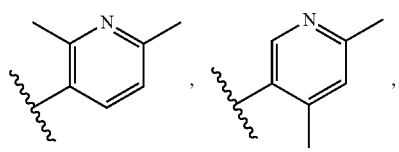
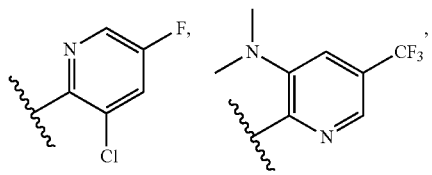
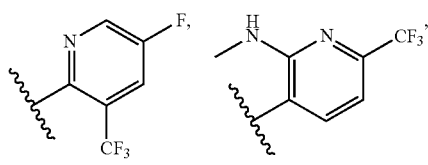
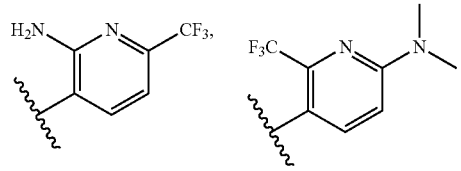
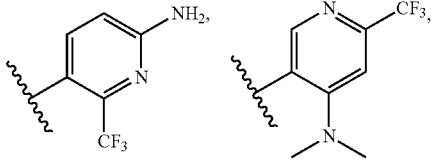
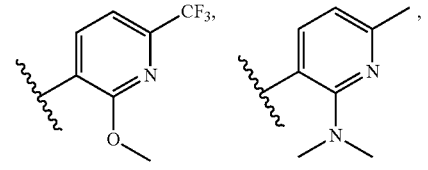

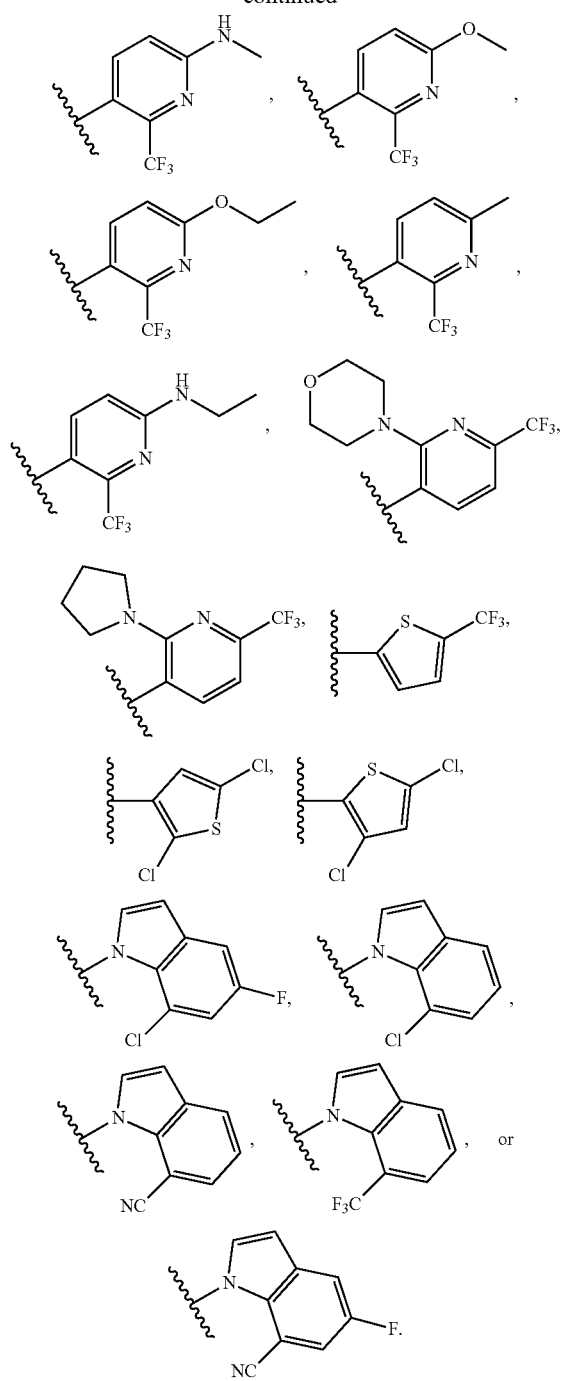
9. The compound of claim 5, or a pharmaceutically acceptable salt, or solvate thereof, wherein:
$R^B$ is
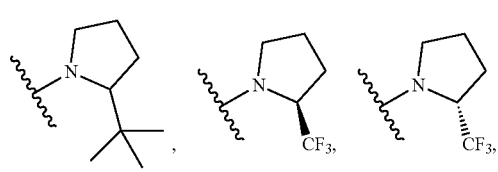
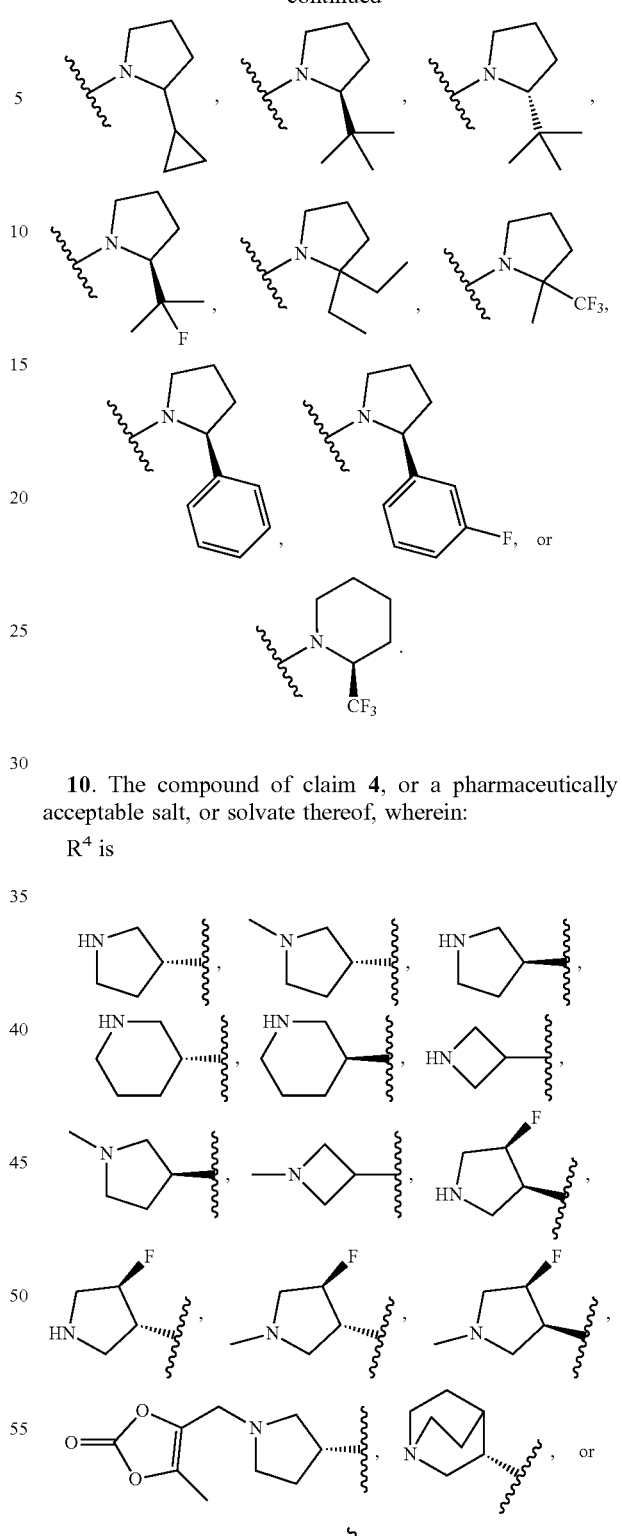
10. The compound of claim 4, or a pharmaceutically acceptable salt, or solvate thereof, wherein:
$R^4$ is
11. The compound of claim 10, or a pharmaceutically acceptable salt, or solvate thereof, wherein:

$R^B$ is
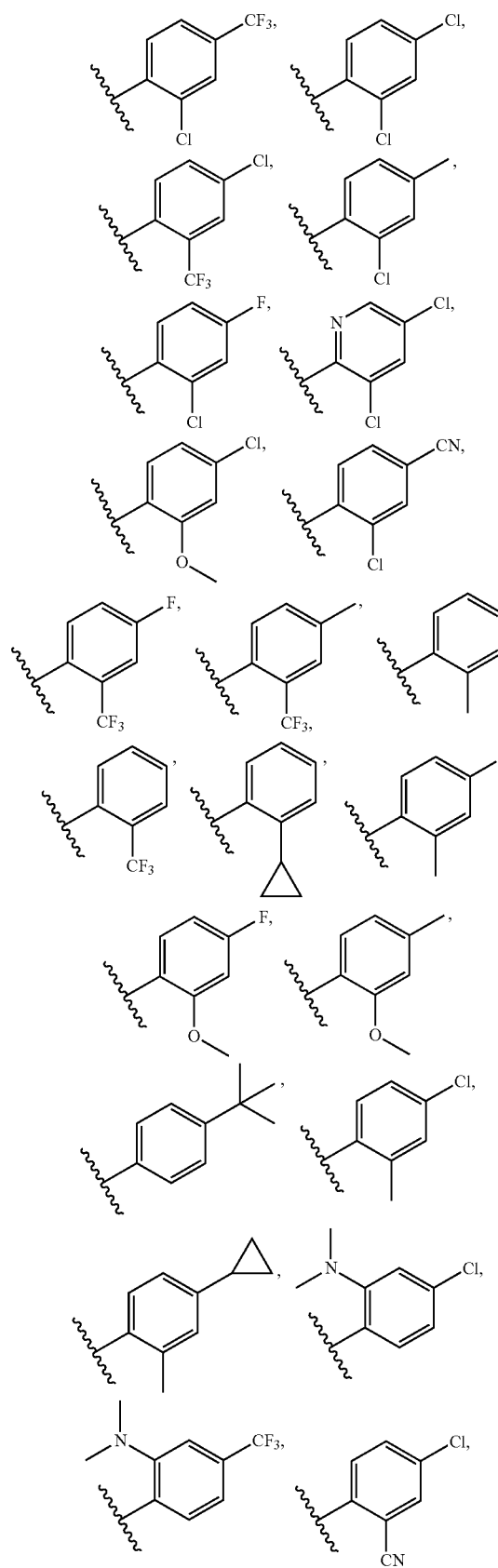
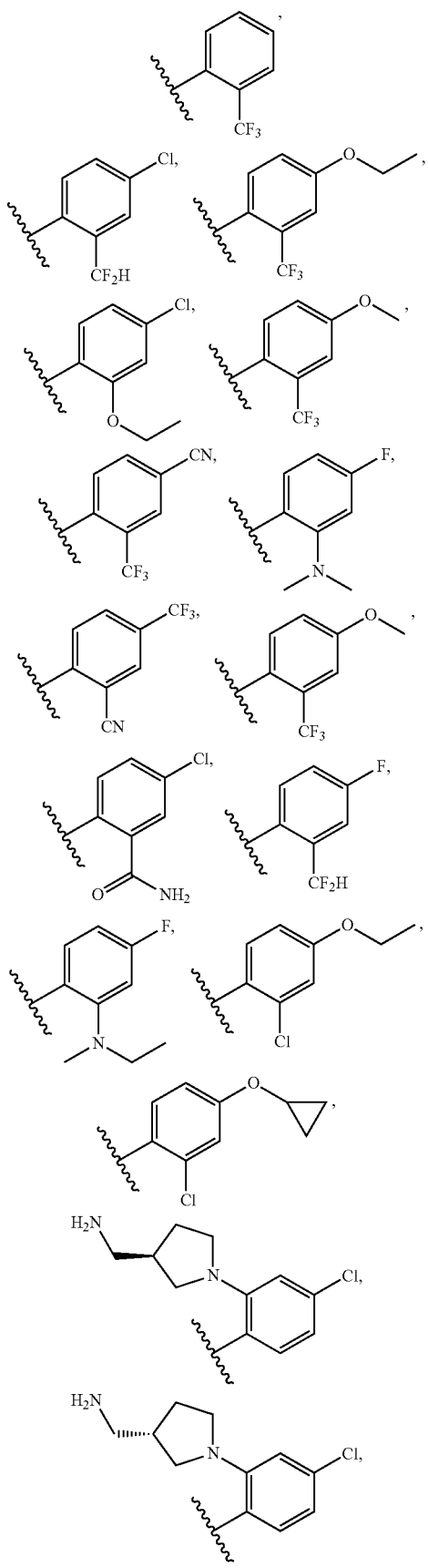

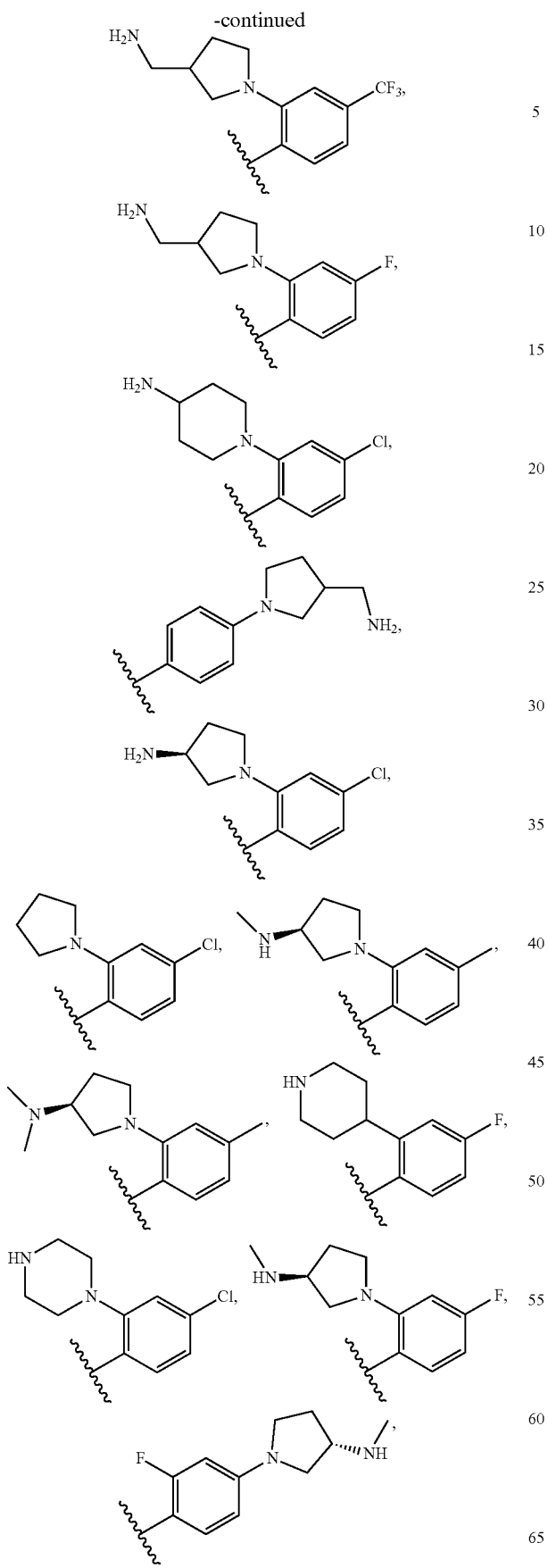
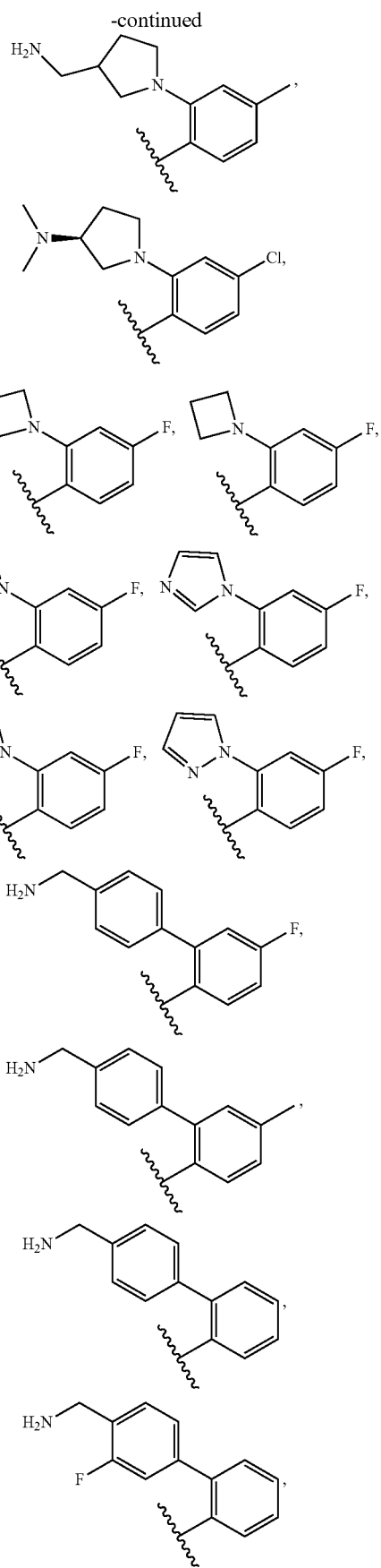

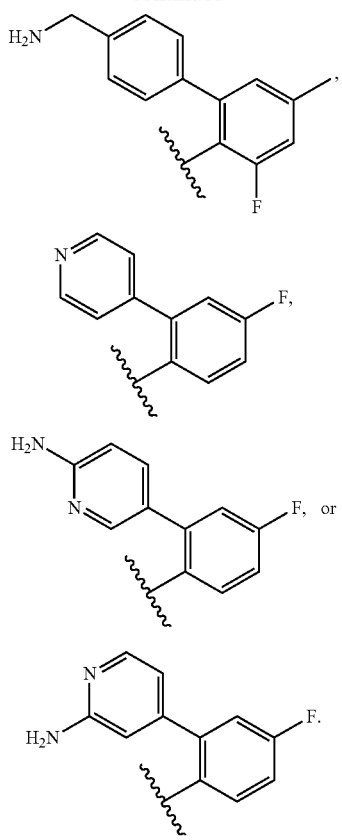
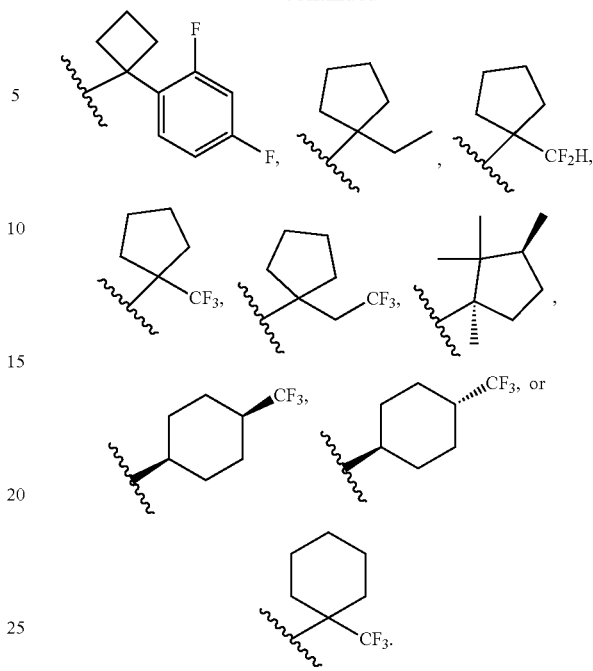
12. The compound of claim 10, or a pharmaceutically acceptable salt, or solvate thereof, wherein:
$R^B$ is
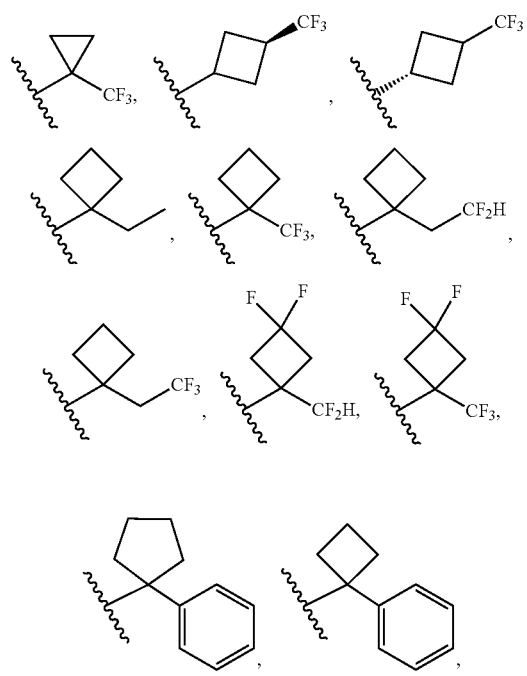
13. The compound of claim 10, or a pharmaceutically acceptable salt, or solvate thereof, wherein:
$R^B$ is
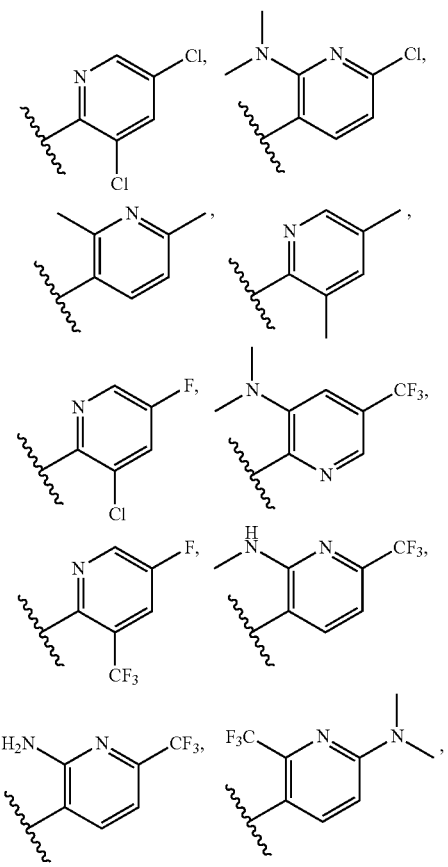

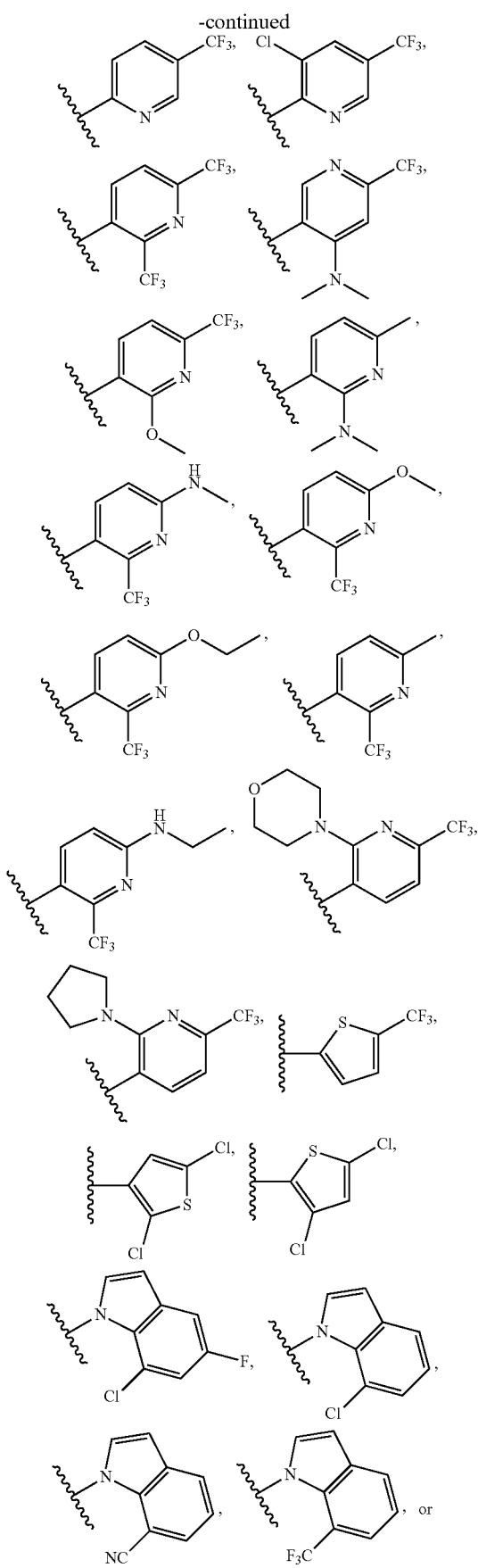
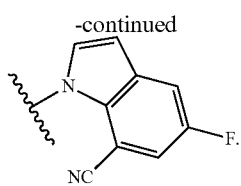

14. The compound of claim 10, or a pharmaceutically acceptable salt, or solvate thereof, wherein: $R^B$ is 15. A pharmaceutical composition comprising a compound of claim 1, or a pharmaceutically acceptable salt, or solvate thereof, and at least one pharmaceutically acceptable excipient.

16. A method of modulating melanocortin subtype-2 receptor (MC2R) activity in a mammal, comprising administering a compound of claim 1, or a pharmaceutically acceptable salt, or solvate thereof, to the mammal in need thereof.

17. A method of treating a disease or condition in a mammal that would benefit from the modulation of melanocortin subtype-2 receptor (MC2R) activity, comprising administering a compound of claim 1, or a pharmaceutically acceptable salt, or solvate thereof, to the mammal in need thereof, wherein the disease or condition comprises growth of fat pads in the collarbone, back of neck, face and trunk, excessive sweating, dilation of capillaries, thinning of the skin, muscle weakness, hirsutism, depression, anxiety, hypertension, osteoporosis, insulin resistance, hyperglycemia, heart disease, or combinations thereof.

18. The method of claim 17, wherein the disease or condition is Cushing's syndrome, Cushing's disease, ectopic ACTH syndrome, or congenital adrenal hyperplasia (CAH).

19. A compound that has the following structure, or a pharmaceutically acceptable salt, or solvate thereof:

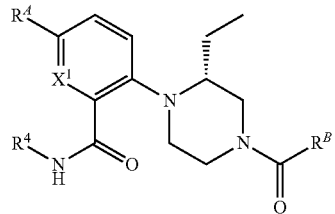

wherein:

X$^1$ is N;

R$^A$ is

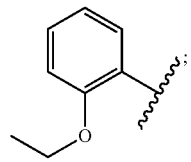 [SMILES: *c1ccccc1OCC]

R$^B$ is

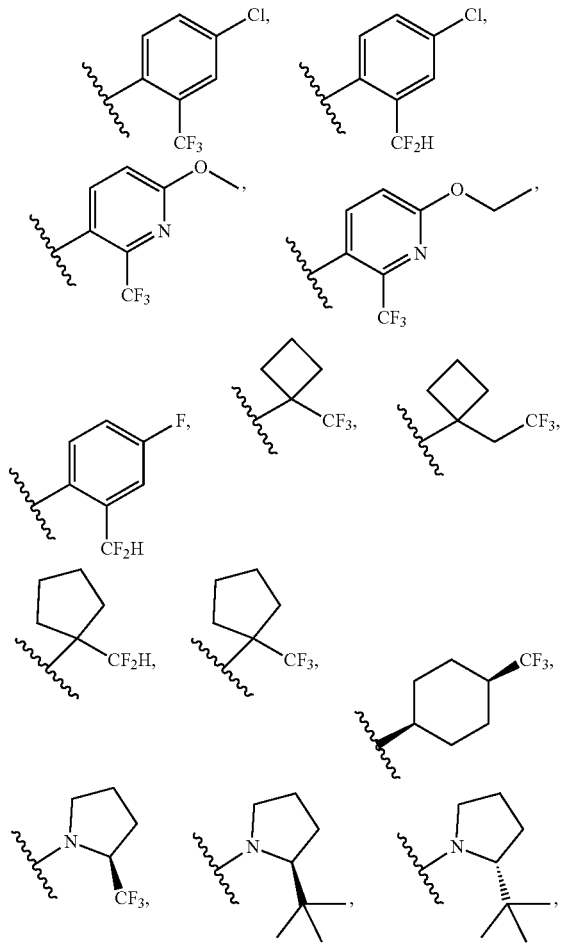

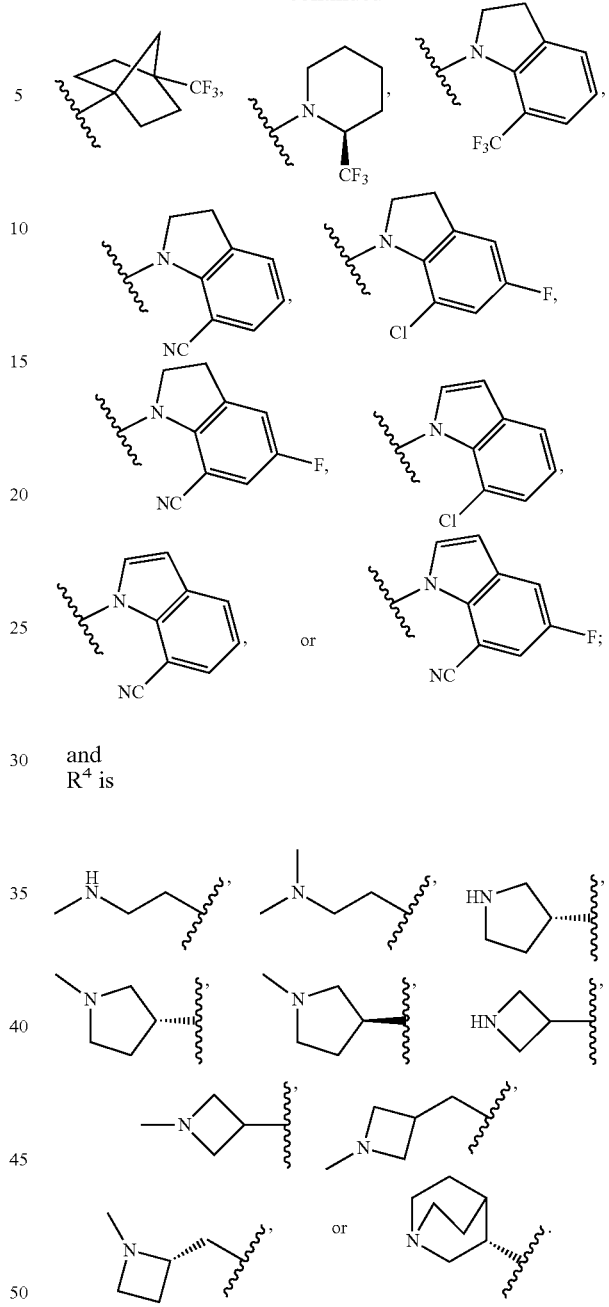

and
R$^4$ is

20. A compound that is:
3-[(2R)-4-[4-chloro-2-(trifluoromethyl) benzoyl]-2-ethylpiperazin-1-yl]-N-[2-(dimethylamino)ethyl]-6-(2-ethoxyphenyl)pyridine-2-carboxamide;
3-[(2R)-4-[4-chloro-2-(trifluoromethyl) benzoyl]-2-ethylpiperazin-1-yl]-6-(2-ethoxyphenyl)-N-[(3R)-1-methylpyrrolidin-3-yl]pyridine-2-carboxamide;
3-[(2R)-4-[4-chloro-2-(trifluoromethyl) benzoyl]-2-ethylpiperazin-1-yl]-6-(2-ethoxyphenyl)-N-[2-(methylamino)ethyl]pyridine-2-carboxamide;
3-[(2R)-4-[4-chloro-2-(trifluoromethyl) benzoyl]-2-ethylpiperazin-1-yl]-6-(2-ethoxyphenyl)-N-[(3R)-pyrrolidin-3-yl]pyridine-2-carboxamide;
N-(azetidin-3-yl)-3-[(2R)-4-[4-chloro-2-(trifluoromethyl)benzoyl]-2-ethylpiperazin-1-yl]-6-(2-ethoxyphenyl)pyridine-2-carboxamide;

3-[(2R)-4-[4-chloro-2-(trifluoromethyl) benzoyl]-2-ethylpiperazin-1-yl]-6-(2-ethoxyphenyl)-N-(1-methylazetidin-3-yl)pyridine-2-carboxamide;

6-(2-ethoxyphenyl)-3-[(2R)-2-ethyl-4-[6-methoxy-2-(trifluoromethyl)pyridine-3-carbonyl]piperazin-1-yl]-N-(1-methylazetidin-3-yl)pyridine-2-carboxamide;

3-[(2R)-4-[6-ethoxy-2-(trifluoromethyl) pyridine-3-carbonyl]-2-ethylpiperazin-1-yl]-6-(2-ethoxyphenyl)-N-(1-methylazetidin-3-yl)pyridine-2-carboxamide;

6-(2-ethoxyphenyl)-3-[2R)-2-ethyl-4-6[-methoxy-2-(trifluoromethyl)pyridine-3-carbonyl]piperazin-1-yl-]N-[(3R)-1-methylpyrrolidin-3-yl]pyridine-2-carboxamide;

6-(2-ethoxyphenyl)-3-[2R)-2-ethyl-4-6[-methoxy-2-(trifluoromethyl)pyridine-3-carbonyl]piperazin-1-yl]-N-[(3R)-pyrrolidin-3-yl]pyridine-2-carboxamide;

3-[(2R)-4-[4-chloro-2-(difluoromethyl) benzoyl]-2-ethylpiperazin-1-yl]-6-(2-ethoxyphenyl)-N-[(3R)-1-methylpyrrolidin-3-yl]pyridine-2-carboxamide;

3-[(2R)-4-[4-chloro-2-(difluoromethyl) benzoyl]-2-ethylpiperazin-1-yl]-6-(2-ethoxyphenyl)-N-[(3R)-pyrrolidin-3-yl]pyridine-2-carboxamide;

3-[(2R)-4-[2-(difluoromethyl)-4-fluorobenzoyl]-2-ethylpiperazin-1-yl]-6-(2-ethoxyphenyl)-N-[(3R)-pyrrolidin-3-yl]pyridine-2-carboxamide;

3-[(2R)-4-[2-(difluoromethyl)-4-fluorobenzoyl]-2-ethylpiperazin-1-yl]-6-(2-ethoxyphenyl)-N-[(3R)-1-methylpyrrolidin-3-yl]pyridine-2-carboxamide;

6-(2-ethoxyphenyl)-3-[(2R)-2-ethyl-4-[1-(trifluoromethyl)cyclopentanecarbonyl]piperazin-1-yl]-N-[(3R)-pyrrolidin-3-yl]pyridine-2-carboxamide;

3-[(2R)-4-(2-tert-butylpyrrolidine-1-carbonyl)-2-ethylpiperazin-1-yl]-6-(2-ethoxyphenyl)-N-[(3R)-pyrrolidin-3-yl]pyridine-2-carboxamide;

3-[(2R)-4-[(2S)-2-tert-butylpyrrolidine-1-carbonyl]-2-ethylpiperazin-1-yl]-6-(2-methoxyphenyl)-N-[(3R)-pyrrolidin-3-yl]pyridine-2-carboxamide;

3-[(2R)-4-[(2R)-2-tert-butylpyrrolidine-1-carbonyl]-2-ethylpiperazin-1-yl]-6-(2-methoxyphenyl)-N-[(3R)-pyrrolidin-3-yl]pyridine-2-carboxamide;

6-(2-ethoxyphenyl)-3-[(2R)-2-ethyl-4-[cis-4-(trifluoromethyl)cyclohexanecarbonyl]piperazin-1-yl]-N-[(3R)-pyrrolidin-3-yl]pyridine-2-carboxamide;

6-(2-ethoxyphenyl)-3-[(2R)-2-ethyl-4-[cis-4-(trifluoromethyl)cyclohexanecarbonyl]piperazin-1-yl]-N-[(3R)-1-methylpyrrolidin-3-yl]pyridine-2-carboxamide;

1-(trifluoromethyl)cyclobutyl (3R)-4-[6-(2-ethoxyphenyl)-2-{[(3R)-pyrrolidin-3-yl]carbamoyl}pyridin-3-yl]-3-ethylpiperazine-1-carboxylate;

6-(2-ethoxyphenyl)-3-[(2R)-2-ethyl-4-[1-(trifluoromethyl)cyclopentanecarbonyl]piperazin-1-yl]-N-[(1-methylazetidin-3-yl)methyl]pyridine-2-carboxamide;

6-(2-ethoxyphenyl)-3-[(2R)-2-ethyl-4-[1-(trifluoromethyl)cyclopentanecarbonyl]piperazin-1-yl]-N-[(3R)-1-methylpyrrolidin-3-yl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-[(3R)-pyrrolidin-3-yl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-[(3S)-pyrrolidin-3-yl]pyridine-2-carboxamide;

6-(2-ethoxyphenyl)-3-[(2R)-2-ethyl-4-[1-(trifluoromethyl)cyclobutanecarbonyl]piperazin-1-yl]-N-[(3R)-1-methylpyrrolidin-3-yl]pyridine-2-carboxamide;

1,1,1-trifluoro-3,3-dimethylbutan-2-yl (3R)-4-[6-(2-ethoxyphenyl)-2-{[(3R)-pyrrolidin-3-yl]carbamoyl}pyridin-3-yl]-3-ethylpiperazine-1-carboxylate;

6-(2-ethoxyphenyl)-3-[(2R)-2-ethyl-4-[1-(2,2,2-trifluoroethyl)cyclobutanecarbonyl]piperazin-1-yl]-N-[(3R)-1-methylpyrrolidin-3-yl]pyridine-2-carboxamide;

3-[(2R)-4-[(2S)-2-tert-butylpyrrolidine-1-carbonyl]-2-ethylpiperazin-1-yl]-6-(2-ethoxyphenyl)-N-[(3R)-pyrrolidin-3-yl]pyridine-2-carboxamide;

3-[(2R)-4-[(2R)-2-tert-butylpyrrolidine-1-carbonyl]-2-ethylpiperazin-1-yl]-6-(2-ethoxyphenyl)-N-[(3R)-pyrrolidin-3-yl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-[(1-methylazetidin-3-yl)methyl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-[(3S)-1-methylpyrrolidin-3-yl]pyridine-2-carboxamide;

6-(2-ethoxyphenyl)-3-[(2R)-2-ethyl-4-[(2S)-2-(trifluoromethyl)pyrrolidine-1-carbonyl]piperazin-1-yl]-N-{[(2S)-1-methylazetidin-2-yl]methyl}pyridine-2-carboxamide;

6-(2-ethoxyphenyl)-3-[(2R)-2-ethyl-4-[4-(trifluoromethyl)bicyclo[2.2.1]heptane-1-carbonyl]piperazin-1-yl]-N-[(3R)-1-methylpyrrolidin-3-yl]pyridine-2-carboxamide;

3-[(2R)-4-(7-cyano-2,3-dihydro-1H-indole-1-carbonyl)-2-ethylpiperazin-1-yl]-6-(2-ethoxyphenyl)-N-[(3R)-1-methylpyrrolidin-3-yl]pyridine-2-carboxamide;

6-(2-ethoxyphenyl)-3-[(2R)-2-ethyl-4-[1-(trifluoromethyl)cyclopentanecarbonyl]piperazin-1-yl]-N-(1-methylazetidin-3-yl)pyridine-2-carboxamide;

6-(2-ethoxyphenyl)-3-[(2R)-2-ethyl-4-[1-(trifluoromethyl)cyclopentanecarbonyl]piperazin-1-yl]-N-[(3S)-1-methylpyrrolidin-3-yl]pyridine-2-carboxamide;

6-(2-ethoxyphenyl)-3-[(2R)-2-ethyl-4-[7-(trifluoromethyl)-2,3-dihydro-1H-indol e-1-carbonyl]piperazin-1-yl]-N-[(3S)-1-methylpyrrolidin-3-yl]pyridine-2-carboxamide;

(2S)-1,1,1-trifluoro-3,3-dimethylbutan-2-yl(3R)-4-(2'-ethoxy-6-{[(3R)-1-methylpyrrolidin-3-yl]carbamoyl}-[2,3'-bipyridin]-5-yl)-3-ethylpiperazine-1-carboxylate;

N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide;

6-(2-ethoxyphenyl)-3-[(2R)-2-ethyl-4-[(2S)-2-(2-fluoropropan-2-yl)pyrrolidine-1-carbonyl]piperazin-1-yl]-N-[(3R)-1-methylpyrrolidin-3-yl]pyridine-2-carboxamide;

3-[(2R)-4-(7-cyano-2,3-dihydro-1H-indole-1-carbonyl)-2-ethylpiperazin-1-yl]-6-(2-ethoxyphenyl)-N-(1-methylazetidin-3-yl)pyridine-2-carboxamide;

3-[(2R)-4-[1-(difluoromethyl)cyclopentanecarbonyl]-2-ethylpiperazin-1-yl]-6-(2-ethoxyphenyl)-N-[(3R)-1-methylpyrrolidin-3-yl]pyridine-2-carboxamide;

3-[(2R)-4-(7-chloro-5-fluoro-2,3-dihydro-1H-indole-1-carbonyl)-2-ethylpiperazin-1-yl]-6-(2-ethoxyphenyl)-N-[(3S)-1-methylpyrrolidin-3-yl]pyridine-2-carboxamide;

3-[(2R)-4-(7-cyano-5-fluoro-2,3-dihydro-1H-indole-1-carbonyl)-2-ethylpiperazin -1-yl]-6-(2-ethoxyphenyl)-N-(1-methylazetidin-3-yl)pyridine-2-carboxamide;

3-[(2R)-4-(7-cyano-5-fluoro-2,3-dihydro-1H-indole-1-carbonyl)-2-ethylpiperazin-1-yl]-6-(2-ethoxyphenyl)-N-[(3S)-1-methylpyrrolidin-3-yl]pyridine-2-carboxamide;

3-[(2R)-4-(7-chloro-5-fluoro-1H-indole-1-carbonyl)-2-ethylpiperazin-1-yl]-6-(2-ethoxyphenyl)-N-[(3R)-1-methylpyrrolidin-3-yl]pyridine-2-carboxamide;

3-[(2R)-4-(7-chloro-1H-indole-1-carbonyl)-2-ethylpiperazin-1-yl]-6-(2-ethoxyphenyl)-N-[(3R)-1-methylpyrrolidin-3-yl]pyridine-2-carboxamide;

3-[(2R)-4-(7-cyano-1H-indole-1-carbonyl)-2-ethylpiperazin-1-yl]-6-(2-ethoxyphenyl)-N-[(3R)-1-methylpyrrolidin-3-yl]pyridine-2-carboxamide;

6-(2-ethoxyphenyl)-3-[(2R)-2-ethyl-4-[(2S)-2-(trifluoromethyl)piperidine-1-carbonyl]piperazin-1-yl]-N-[(3R)-1-methylpyrrolidin-3-yl]pyridine-2-carboxamide;

6-(2-ethoxyphenyl)-3-[(2R)-2-ethyl-4-[(2S)-2-(trifluoromethyl)piperidine-1-carbonyl]piperazin-1-yl]-N-[(3S)-1-methylpyrrolidin-3-yl]pyridine-2-carboxamide;

6-(2-ethoxyphenyl)-3-[(2R)-2-ethyl-4-[7-(trifluoromethyl)-1H-indole-1-carbonyl]piperazin-1-yl]-N-[(3R)-1-methylpyrrolidin-3-yl]pyridine-2-carboxamide;

3-[(2R)-4-(7-cyano-5-fluoro-1H-indole-1-carbonyl)-2-ethylpiperazin-1-yl]-6-(2-ethoxyphenyl) -N-[(3R)-1-methylpyrrolidin-3-yl]pyridine-2-carboxamide;

or a pharmaceutically acceptable salt, or solvate thereof.

21. A compound that is: 3-[(2R)-4-[4-chloro-2-(trifluoromethyl)benzoyl]-2-ethylpiperazin-1-yl]-N-[2-(dimethylamino)ethyl]-6-(2-ethoxyphenyl)pyridine-2-carboxamide; or a pharmaceutically acceptable salt, or solvate thereof.

22. A pharmaceutical composition comprising a compound of claim 21, or a pharmaceutically acceptable salt, or solvate thereof, and at least one pharmaceutically acceptable excipient.

23. A method of treating Cushing's syndrome, Cushing's disease, ectopic ACTH syndrome, or congenital adrenal hyperplasia (CAH) in a mammal comprising administering a compound of claim 21, or a pharmaceutically acceptable salt, or solvate thereof, to the mammal in need thereof.

24. A compound that is: 6-(2-ethoxyphenyl)-3-[(2R)-2-ethyl-4-[1-(trifluoromethyl)cyclobutanecarbonyl]piperazin-1-yl]-N-[(3R)-1-methylpyrrolidin-3-yl]pyridine-2-carboxamide; or a pharmaceutically acceptable salt, or solvate thereof.

25. A pharmaceutical composition comprising a compound of claim 24, or a pharmaceutically acceptable salt, or solvate thereof, and at least one pharmaceutically acceptable excipient.

26. A method of treating Cushing's syndrome, Cushing's disease, ectopic ACTH syndrome, or congenital adrenal hyperplasia (CAH) in a mammal comprising administering a compound of claim 24, or a pharmaceutically acceptable salt, or solvate thereof, to the mammal in need thereof.

27. A compound that is: 6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide; or a pharmaceutically acceptable salt, or solvate thereof.

28. A pharmaceutical composition comprising a compound of claim 27, or a pharmaceutically acceptable salt, or solvate thereof, and at least one pharmaceutically acceptable excipient.

29. A method of treating Cushing's syndrome, Cushing's disease, ectopic ACTH syndrome, or congenital adrenal hyperplasia (CAH) in a mammal comprising administering a compound of claim 27, or a pharmaceutically acceptable salt, or solvate thereof, to the mammal in need thereof.

30. A compound that is: N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide; or a pharmaceutically acceptable salt, or solvate thereof.

31. A pharmaceutical composition comprising a compound of claim 30, or a pharmaceutically acceptable salt, or solvate thereof, and at least one pharmaceutically acceptable excipient.

32. A method of treating Cushing's syndrome, Cushing's disease, ectopic ACTH syndrome, or congenital adrenal hyperplasia (CAH) in a mammal comprising administering a compound of claim 30, or a pharmaceutically acceptable salt, or solvate thereof, to the mammal in need thereof.

33. The compound of claim 21 that is 3-[(2R)-4-[4-chloro-2-(trifluoromethyl)benzoyl]-2-ethylpiperazin-1-yl]-N-[2-(dimethylamino)ethyl]-6-(2-ethoxyphenyl)pyridine-2-carboxamide, or a pharmaceutically acceptable salt thereof 34. The compound of claim 24 that is 6-(2-ethoxyphenyl)-3-[(2R)-2-ethyl-4-[1-(trifluoromethyl)cyclobutanecarbonyl]piperazin-1-yl]-N-[(3R)-1-methylpyrrolidin-3-yl]pyridine-2-carboxamide, or a pharmaceutically acceptable salt thereof.

35. The compound of claim 27 that is 6-(2-ethoxyphenyl)-3-[(2R)-2-ethyl-4-[(2S)-2-(trifluoromethyl)pyrrolidine-1-carbonyl]piperazin-1-yl]-N-[(3R)-1-methylpyrrolidin-3-yl]pyridine-2-carboxamide, or a pharmaceutically acceptable salt thereof.

36. The compound of claim 30 that is N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide, or a pharmaceutically acceptable salt thereof.

* * * * *

UNITED STATES PATENT AND TRADEMARK OFFICE
CERTIFICATE OF CORRECTION

PATENT NO. : 11,566,015 B2
APPLICATION NO. : 17/170396
DATED : January 31, 2023
INVENTOR(S) : Sangdon Han et al.

Page 1 of 2

It is certified that error appears in the above-identified patent and that said Letters Patent is hereby corrected as shown below:

In the Specification

• Column 1, Lines 22-24:
"This invention was made with government support under DK115245 awarded by the National Institutes of Health. The government has certain rights in the invention." should read --This invention was made with government support under grant number DK115245 awarded by the National Institutes of Health. The government has certain rights in the invention.--.

In the Claims

• Claim 1, Column 253, Lines 48-53:

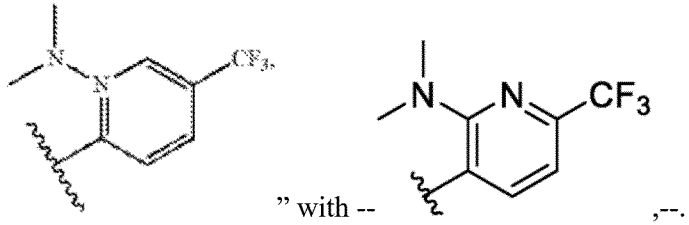

Please replace " " with -- ,--.

• Claim 11, Column 275, Lines 24-31:

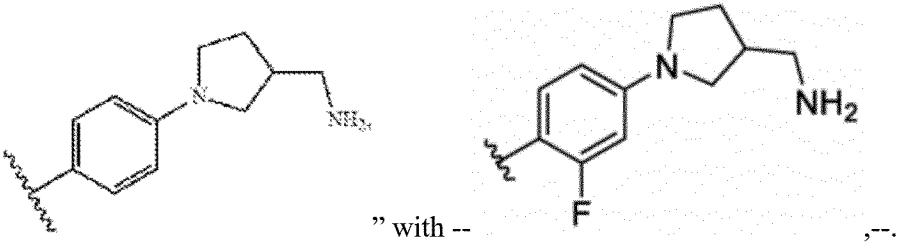

Please replace " " with -- ,--.

• Claim 12, Column 277, Lines 41-45:

Signed and Sealed this
Thirty-first Day of December, 2024

Derrick Brent
*Acting Director of the United States Patent and Trademark Office*

CERTIFICATE OF CORRECTION (continued)
U.S. Pat. No. 11,566,015 B2

Please replace "  " with -- --.

• Claim 13, Column 278, Lines 34-41:

Please replace " 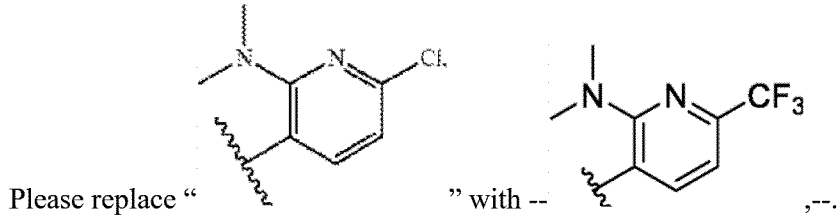 " with -- ,--.